US011549117B2

(12) United States Patent
Kim et al.

(10) Patent No.: US 11,549,117 B2
(45) Date of Patent: Jan. 10, 2023

(54) MARKER COMPOSITION FOR SELECTING LIVING MODIFIED ORGANISM, LIVING MODIFIED ORGANISM, AND TRANSFORMATION METHOD

(71) Applicant: INDUSTRY-ACADEMIC COOPERATION FOUNDATION GYEONGSANG NATIONAL UNIVERSITY, Gyeongsangnam-do (KR)

(72) Inventors: Seon Won Kim, Gyeongsangnam-do (KR); Hyo Jung Han, Gyeongsangnam-do (KR); Sin Young Kim, Gyeongsangnam-do (KR); Ji Bin Park, Busan (KR)

(73) Assignee: INDUSTRY-ACADEMIC COOPERATION FOUNDATION GYEONGSANG NATIONAL UNIVERSITY, Gyeongsangnam-Do (KR)

( * ) Notice: Subject to any disclaimer, the term of this patent is extended or adjusted under 35 U.S.C. 154(b) by 9 days.

(21) Appl. No.: 16/612,918

(22) PCT Filed: May 11, 2018

(86) PCT No.: PCT/KR2018/005425
§ 371 (c)(1),
(2) Date: Nov. 12, 2019

(87) PCT Pub. No.: WO2018/208116
PCT Pub. Date: Nov. 15, 2018

(65) Prior Publication Data

US 2020/0199602 A1 Jun. 25, 2020

(30) Foreign Application Priority Data

May 11, 2017 (KR) ........................ 10-2017-0058829
May 11, 2018 (KR) ........................ 10-2018-0054080

(51) Int. Cl.
*C12N 15/63* (2006.01)
*C12N 15/70* (2006.01)
(Continued)

(52) U.S. Cl.
CPC ............... *C12N 15/70* (2013.01); *C12N 1/20* (2013.01); *C12N 15/63* (2013.01); *C12N 15/746* (2013.01); *C12P 5/002* (2013.01); *C12P 7/02* (2013.01)

(58) Field of Classification Search
None
See application file for complete search history.

(56) References Cited

U.S. PATENT DOCUMENTS

2007/0087425 A1 4/2007 Ohto
2008/0274523 A1* 11/2008 Renninger ................ C12P 7/04
435/157

(Continued)

FOREIGN PATENT DOCUMENTS

KR 10-2006-0040494 A 5/2006
KR 10-2009-0078113 A 7/2009

(Continued)

OTHER PUBLICATIONS

European Search Report For EP20180799253.2 dated Jan. 27, 2021 from European patent office in a counterpart European patent application.

(Continued)

*Primary Examiner* — Richard C Ekstrom
(74) *Attorney, Agent, or Firm* — Pleechae IP, LLC

(57) ABSTRACT

A marker composition for selecting a living modified organism allows transformation and the production of a target product without antibiotics or antibiotic resistance genes. The marker composition for selecting a living modified organism may basically prevent problems caused by the use
(Continued)

of antibiotics and antibiotic resistance genes and produce a target product at a high yield.

22 Claims, 13 Drawing Sheets

Specification includes a Sequence Listing.

(51) Int. Cl.

| | |
|---|---|
| ***C12N 15/74*** | (2006.01) |
| ***C12N 1/20*** | (2006.01) |
| ***C12P 5/00*** | (2006.01) |
| ***C12P 7/02*** | (2006.01) |

(56) References Cited

U.S. PATENT DOCUMENTS

2015/0218590 A1 8/2015 Mcauliffe
2020/0199602 A1* 6/2020 Kim ........................ C12P 5/002

FOREIGN PATENT DOCUMENTS

| | | | |
|---|---|---|---|
| KR | 10-1190255 | B1 | 10/2012 |
| KR | 10-2016-0045001 | A | 4/2016 |
| WO | WO 2013/019051 | A2 | 2/2013 |
| WO | WO 2014/100726 | A2 | 6/2014 |

OTHER PUBLICATIONS

International Search Report for PCT/KR2018/005425 dated Aug. 16, 2018.

Paola Maura Tricarico et al., "Mevalonate Pathway Blockade, Mitochondrial Dysfunction and Autophagy: A Possible Link" International Journal of Molecular Sciences, vol. 16, No. 7, pp. 16067-16084, 2015.

Notice of Allowance dated Mar. 25, 2020 from Korean Patent Office in a counterpart Korean Patent Application No. 10-2018-0054080 (all the cited references are listed in this IDS.) (English translation is also submitted herewith.).

Hyun Sook Lee et al., "The Complete Genome Sequence of Thermococcus onnurineus NA1 Reveals a Mixed Heterotrophic and Carboxydotrophic Metabolism", Journal of Bacteriology, vol. 190 (22), pp. 7491-7499, Nov. 2008.

* cited by examiner

SEQUENCE LISTING

<160> NUMBER OF SEQ ID NOS: 143

<210> SEQ ID NO 1
<211> LENGTH: 46
<212> TYPE: DNA
<213> ORGANISM: Artificial Sequence
<220> FEATURE:
<223> OTHER INFORMATION: SN12Didi-F

<400> SEQUENCE: 1
gcgaattcag gaggtaataa tatgacaaaa aaagttggtg tcggtc 46

<210> SEQ ID NO 2
<211> LENGTH: 39
<212> TYPE: DNA
<213> ORGANISM: Artificial Sequence
<220> FEATURE:
<223> OTHER INFORMATION: SN12Didi-R

<400> SEQUENCE: 2
cgcctgcagg ttatttaagc tgggtaaatg cagataatc 39

<210> SEQ ID NO 3
<211> LENGTH: 74
<212> TYPE: DNA
<213> ORGANISM: Artificial Sequence
<220> FEATURE:
<223> OTHER INFORMATION: IS poxB-Ptrc-F

<400> SEQUENCE: 3
gatgaactaa acttgttacc gttatcacat tcaggagatg gagaaccatg gtttgacagc 60
ttatcatcga ctgc 74

<210> SEQ ID NO 4
<211> LENGTH: 70
<212> TYPE: DNA
<213> ORGANISM: Artificial Sequence
<220> FEATURE:
<223> OTHER INFORMATION: KO poxB -R

<400> SEQUENCE: 4
ccttattatg acgggaaatg ccaccctttt taccttagcc agtttgtttt tgtaggctgg 60
agctgcttcg 70

<210> SEQ ID NO 5
<211> LENGTH: 74
<212> TYPE: DNA
<213> ORGANISM: Artificial Sequence
<220> FEATURE:
<223> OTHER INFORMATION: IS ldhA-Ptrc-F

<400> SEQUENCE: 5
atttttagta gcttaaatgt gattcaacat cactggagaa agtcttatga gtttgacagc 60
ttatcatcga ctgc 74

<210> SEQ ID NO 6
<211> LENGTH: 70
<212> TYPE: DNA
<213> ORGANISM: Artificial Sequence
<220> FEATURE:
<223> OTHER INFORMATION: KO ldhA-R

<400> SEQUENCE: 6
ctcccctgga atgcagggga gcggcaagat taaaccagtt cgttcgggca tgtaggctgg 60
agctgcttcg 70

<210> SEQ ID NO 7
<211> LENGTH: 74
<212> TYPE: DNA
<213> ORGANISM: Artificial Sequence
<220> FEATURE:
<223> OTHER INFORMATION: IS adhE-Ptrc-F

<400> SEQUENCE: 7
cgagcagatg atttactaaa aaagtttaac attatcagga gagcattatg gtttgacagc 60
ttatcatcga ctgc 74

<210> SEQ ID NO 8
<211> LENGTH: 70
<212> TYPE: DNA

<213> ORGANISM: Artificial Sequence
<220> FEATURE:
<223> OTHER INFORMATION: KO adhE-R

<400> SEQUENCE: 8
ccgtttatgt tgccagacag cgctactgat taagcggatt ttttcgcttt tgtaggctgg 60
agctgcttcg 70

<210> SEQ ID NO 9
<211> LENGTH: 74
<212> TYPE: DNA
<213> ORGANISM: Artificial Sequence
<220> FEATURE:
<223> OTHER INFORMATION: IS atoDA-Ptrc-F

<400> SEQUENCE: 9
ctattgcctg actgtaccca caacggtgta tgcaagaggg ataaaaaatg gtttgacagc 60
ttatcatcga ctgc 74

<210> SEQ ID NO 10
<211> LENGTH: 70
<212> TYPE: DNA
<213> ORGANISM: Artificial Sequence
<220> FEATURE:
<223> OTHER INFORMATION: KO atoDA-R

<400> SEQUENCE: 10
acgcgtcata aaacgcgata tgcgaccaat cataaatcac cccgttgcgt tgtaggctgg 60
agctgcttcg 70

<210> SEQ ID NO 11
<211> LENGTH: 22
<212> TYPE: DNA
<213> ORGANISM: Artificial Sequence
<220> FEATURE:
<223> OTHER INFORMATION: KOpoxBCF-F

<400> SEQUENCE: 11
ttacgtactg gcctgctcct gc 22

<210> SEQ ID NO 12
<211> LENGTH: 22
<212> TYPE: DNA
<213> ORGANISM: Artificial Sequence
<220> FEATURE:
<223> OTHER INFORMATION: KOpoxBCF-R

<400> SEQUENCE: 12
gtcgggtaac ggtatcactg cg 22

<210> SEQ ID NO 13
<211> LENGTH: 20
<212> TYPE: DNA
<213> ORGANISM: Artificial Sequence
<220> FEATURE:
<223> OTHER INFORMATION: KOldhACF-F

<400> SEQUENCE: 13
tcatcagcag cgtcaacggc 20

<210> SEQ ID NO 14
<211> LENGTH: 20
<212> TYPE: DNA
<213> ORGANISM: Artificial Sequence
<220> FEATURE:
<223> OTHER INFORMATION: KOldhACF-R

<400> SEQUENCE: 14
cgctggtcac gggcttaccg 20

<210> SEQ ID NO 15
<211> LENGTH: 20
<212> TYPE: DNA
<213> ORGANISM: Artificial Sequence
<220> FEATURE:
<223> OTHER INFORMATION: KOadhECF-F

<400> SEQUENCE: 15
ccgcactgac tatactctcg 20

<210> SEQ ID NO 16
<211> LENGTH: 20
<212> TYPE: DNA
<213> ORGANISM: Artificial Sequence
<220> FEATURE:
<223> OTHER INFORMATION: KOadhECF-R

<400> SEQUENCE: 16
tgatcggcat tgcccagaag 20

<210> SEQ ID NO 17
<211> LENGTH: 22
<212> TYPE: DNA
<213> ORGANISM: Artificial Sequence
<220> FEATURE:
<223> OTHER INFORMATION: KOatoDACF-F

<400> SEQUENCE: 17
ctggcgaggt aaaaacagcc cc 22

<210> SEQ ID NO 18
<211> LENGTH: 22
<212> TYPE: DNA
<213> ORGANISM: Artificial Sequence
<220> FEATURE:
<223> OTHER INFORMATION: KOatoDACF-R

<400> SEQUENCE: 18
aagcgcgatc acgaatgtta gc 22

<210> SEQ ID NO 19
<211> LENGTH: 65
<212> TYPE: DNA
<213> ORGANISM: Artificial Sequence
<220> FEATURE:
<223> OTHER INFORMATION: KO dxr-F

<400> SEQUENCE: 19
ggctggcggc gttttgcttt ttattctgtc tcaactctgg atgtttcatg ggggatccgt 60
cgacc 65

<210> SEQ ID NO 20
<211> LENGTH: 70
<212> TYPE: DNA
<213> ORGANISM: Artificial Sequence
<220> FEATURE:
<223> OTHER INFORMATION: KO dxr-R

<400> SEQUENCE: 20

-continued tagcgcgact ctctgtagcc ggattatcct cagcttgcga gacgcatcac tgtaggctgg 60
agctgcttcg 70

<210> SEQ ID NO 21
<211> LENGTH: 24
<212> TYPE: DNA
<213> ORGANISM: Artificial Sequence
<220> FEATURE:
<223> OTHER INFORMATION: KOdxrCF-F

<400> SEQUENCE: 21
ctgtgtgtga ctgtctggtc tgac 24

<210> SEQ ID NO 22
<211> LENGTH: 27
<212> TYPE: DNA
<213> ORGANISM: Artificial Sequence
<220> FEATURE:
<223> OTHER INFORMATION: KOdxrCF-R

<400> SEQUENCE: 22
catctgtaaa gtaaagttcg gcatagg 27

<210> SEQ ID NO 23
<211> LENGTH: 20
<212> TYPE: DNA
<213> ORGANISM: Artificial Sequence
<220> FEATURE:
<223> OTHER INFORMATION: dxrCF-R

<400> SEQUENCE: 23
ccattttgct caaggtcagc 20

<210> SEQ ID NO 24
<211> LENGTH: 70
<212> TYPE: DNA
<213> ORGANISM: Artificial Sequence
<220> FEATURE:
<223> OTHER INFORMATION: KO dxs-F

<400> SEQUENCE: 24
tttcttaagc atagcaggag tggagtaggg attatgccag ccaggccttg caattcgatg 60
gggatccgtc 70

<210> SEQ ID NO 25
<211> LENGTH: 70
<212> TYPE: DNA
<213> ORGANISM: Artificial Sequence
<220> FEATURE:
<223> OTHER INFORMATION: KO dxs-R

<400> SEQUENCE: 25
gtattaatag gcccctgatg agttttgata ttgccaaata cccgaccctg tgtaggctgg 60
agctgcttcg 70

<210> SEQ ID NO 26
<211> LENGTH: 17
<212> TYPE: DNA
<213> ORGANISM: Artificial Sequence
<220> FEATURE:
<223> OTHER INFORMATION: KOdxsCF-F

<400> SEQUENCE: 26
ggaaacgcga aggtcgg 17

<210> SEQ ID NO 27
<211> LENGTH: 20
<212> TYPE: DNA
<213> ORGANISM: Artificial Sequence
<220> FEATURE:
<223> OTHER INFORMATION: KOdxsCF-R

<400> SEQUENCE: 27
gcggactaca tcatccagcg 20

<210> SEQ ID NO 28
<211> LENGTH: 20
<212> TYPE: DNA
<213> ORGANISM: Artificial Sequence
<220> FEATURE:
<223> OTHER INFORMATION: KmCF-F

<400> SEQUENCE: 28
ccttgctcct gccgagaaag 20

<210> SEQ ID NO 29
<211> LENGTH: 23
<212> TYPE: DNA
<213> ORGANISM: Artificial Sequence
<220> FEATURE:
<223> OTHER INFORMATION: dCmp(NA)-F

<400> SEQUENCE: 29
tttttttaag gcagttattg gtg 23

<210> SEQ ID NO 30
<211> LENGTH: 20
<212> TYPE: DNA
<213> ORGANISM: Artificial Sequence
<220> FEATURE:
<223> OTHER INFORMATION: dCmp(NA)-R

<400> SEQUENCE: 30
agcttcctta gctcctgaaa 20

<210> SEQ ID NO 31
<211> LENGTH: 20
<212> TYPE: DNA
<213> ORGANISM: Artificial Sequence
<220> FEATURE:
<223> OTHER INFORMATION: ddxs(RET)-F

<400> SEQUENCE: 31
gtacccagct tggctgtttt 20

<210> SEQ ID NO 32
<211> LENGTH: 20
<212> TYPE: DNA
<213> ORGANISM: Artificial Sequence
<220> FEATURE:
<223> OTHER INFORMATION: ddxs(RET)-R

<400> SEQUENCE: 32
catggtgaat tcctcctgct 20

<210> SEQ ID NO 33
<211> LENGTH: 32
<212> TYPE: DNA
<213> ORGANISM: Artificial Sequence
<220> FEATURE:

-continued

<223> OTHER INFORMATION: P1mvaE-F

<400> SEQUENCE: 33
ttgcggccgc gctgttgaca attaatcatc cg 32

<210> SEQ ID NO 34
<211> LENGTH: 30
<212> TYPE: DNA
<213> ORGANISM: Artificial Sequence
<220> FEATURE:
<223> OTHER INFORMATION: P1mvaE-R

<400> SEQUENCE: 34
ttctcgagcc tgaaacggct acctaatgtg 30

<210> SEQ ID NO 35
<211> LENGTH: 29
<212> TYPE: DNA
<213> ORGANISM: Artificial Sequence
<220> FEATURE:
<223> OTHER INFORMATION: dAmp(RET)-F

<400> SEQUENCE: 35
cccaagcttc gtcagacccc gtagaaaag 29

<210> SEQ ID NO 36
<211> LENGTH: 23
<212> TYPE: DNA
<213> ORGANISM: Artificial Sequence
<220> FEATURE:
<223> OTHER INFORMATION: RET-R

<400> SEQUENCE: 36
cctcgagtta tcaggcgatt ttc 23

<210> SEQ ID NO 37
<211> LENGTH: 21
<212> TYPE: DNA
<213> ORGANISM: Artificial Sequence
<220> FEATURE:
<223> OTHER INFORMATION: RET-F

<400> SEQUENCE: 37
gcctgataac tcgaggaggt a 21

<210> SEQ ID NO 38
<211> LENGTH: 31
<212> TYPE: DNA
<213> ORGANISM: Artificial Sequence
<220> FEATURE:
<223> OTHER INFORMATION: dAmp(RET)-R

<400> SEQUENCE: 38
cccaagcttt gagcggatac atatttgaat g 31

<210> SEQ ID NO 39
<211> LENGTH: 32
<212> TYPE: DNA
<213> ORGANISM: Artificial Sequence
<220> FEATURE:
<223> OTHER INFORMATION: dxr_1-F

<400> SEQUENCE: 39
aaaagatctg tgtggaattg tgagcggata ac 32

<210> SEQ ID NO 40
<211> LENGTH: 30
<212> TYPE: DNA
<213> ORGANISM: Artificial Sequence
<220> FEATURE:
<223> OTHER INFORMATION: dxr_1-R

<400> SEQUENCE: 40
aaaactcgag tagatcagct tgcgagacgc 30

<210> SEQ ID NO 41
<211> LENGTH: 32
<212> TYPE: DNA
<213> ORGANISM: Artificial Sequence
<220> FEATURE:
<223> OTHER INFORMATION: dxs_1-F

<400> SEQUENCE: 41
aaaagatctg tgtggaattg tgagcggata ac 32

<210> SEQ ID NO 42
<211> LENGTH: 29
<212> TYPE: DNA
<213> ORGANISM: Artificial Sequence
<220> FEATURE:
<223> OTHER INFORMATION: dxs_1-R

<400> SEQUENCE: 42
aaaactcgag ttatgccagc caggccttg 29

<210> SEQ ID NO 43
<211> LENGTH: 46
<212> TYPE: DNA
<213> ORGANISM: Artificial Sequence
<220> FEATURE:
<223> OTHER INFORMATION: idi-f

<400> SEQUENCE: 43
acggatcctg aggaggtaac gtatgcaaac ggaacacgtc atttta 46

<210> SEQ ID NO 44
<211> LENGTH: 42
<212> TYPE: DNA
<213> ORGANISM: Artificial Sequence
<220> FEATURE:
<223> OTHER INFORMATION: idi-r

<400> SEQUENCE: 44
tatcgtcgac tctaagatct tatttaagct gggtaaatgc ag 42

<210> SEQ ID NO 45
<211> LENGTH: 32
<212> TYPE: DNA
<213> ORGANISM: Artificial Sequence
<220> FEATURE:
<223> OTHER INFORMATION: dxr_3-F

<400> SEQUENCE: 45
aaagtcgacg tgtggaattg tgagcggata ac 32

<210> SEQ ID NO 46
<211> LENGTH: 30
<212> TYPE: DNA
<213> ORGANISM: Artificial Sequence
<220> FEATURE:
<223> OTHER INFORMATION: dxr_3-R

<400> SEQUENCE: 46
ttaaaagctt tagatcagct tgcgagacgc 30

<210> SEQ ID NO 47
<211> LENGTH: 32
<212> TYPE: DNA
<213> ORGANISM: Artificial Sequence
<220> FEATURE:
<223> OTHER INFORMATION: dxs_2-F

<400> SEQUENCE: 47
aaaactcgag tgtggaattg tgagcggata ac 32

<210> SEQ ID NO 48
<211> LENGTH: 28
<212> TYPE: DNA
<213> ORGANISM: Artificial Sequence
<220> FEATURE:
<223> OTHER INFORMATION: dxs_2-R

<400> SEQUENCE: 48
aaaagatctt tatgccagcc aggccttg 28

<210> SEQ ID NO 49
<211> LENGTH: 30
<212> TYPE: DNA
<213> ORGANISM: Artificial Sequence
<220> FEATURE:
<223> OTHER INFORMATION: dmvaE-F

<400> SEQUENCE: 49
aaaagatctc attaggtagc cgtttcaggc 30

<210> SEQ ID NO 50
<211> LENGTH: 38
<212> TYPE: DNA
<213> ORGANISM: Artificial Sequence
<220> FEATURE:
<223> OTHER INFORMATION: dmvaE-R

<400> SEQUENCE: 50
aaaagatctt tctcgagact ccatggtctg tttcctcg 38

<210> SEQ ID NO 51
<211> LENGTH: 32
<212> TYPE: DNA
<213> ORGANISM: Artificial Sequence
<220> FEATURE:
<223> OTHER INFORMATION: dxr_2-F

<400> SEQUENCE: 51
cccagtactg tgtggaattg tgagcggata ac 32

<210> SEQ ID NO 52
<211> LENGTH: 29
<212> TYPE: DNA
<213> ORGANISM: Artificial Sequence
<220> FEATURE:
<223> OTHER INFORMATION: dxr_2-R

<400> SEQUENCE: 52
cccgctagct agatcagctt gcgagacgc 29

<210> SEQ ID NO 53
<211> LENGTH: 27

<212> TYPE: DNA
<213> ORGANISM: Artificial Sequence
<220> FEATURE:
<223> OTHER INFORMATION: RET_2-F

<400> SEQUENCE: 53
cccgctagca cagaatttgc ctggcgg 27

<210> SEQ ID NO 54
<211> LENGTH: 31
<212> TYPE: DNA
<213> ORGANISM: Artificial Sequence
<220> FEATURE:
<223> OTHER INFORMATION: RET_2-R

<400> SEQUENCE: 54
cccagtactc atgcctgcag ttaacgatga g 31

<210> SEQ ID NO 55
<211> LENGTH: 22
<212> TYPE: DNA
<213> ORGANISM: Artificial Sequence
<220> FEATURE:
<223> OTHER INFORMATION: mvaA u/s-Fwd

<400> SEQUENCE: 55
ccagcttcaa ccattaatga ag 22

<210> SEQ ID NO 56
<211> LENGTH: 53
<212> TYPE: DNA
<213> ORGANISM: Artificial Sequence
<220> FEATURE:
<223> OTHER INFORMATION: mvaA u/s-Rev

<400> SEQUENCE: 56
caggctatta ttttctcaaa ttttttagtt aaaatttttt tctcatattt ccc 53

<210> SEQ ID NO 57
<211> LENGTH: 51
<212> TYPE: DNA
<213> ORGANISM: Artificial Sequence
<220> FEATURE:
<223> OTHER INFORMATION: mvaA d/s-Fwd

<400> SEQUENCE: 57
gggaaatatg agaaaaaaat tttaactaaa aaatttgaga aaataatagc c 51

<210> SEQ ID NO 58
<211> LENGTH: 19
<212> TYPE: DNA
<213> ORGANISM: Artificial Sequence
<220> FEATURE:
<223> OTHER INFORMATION: mvaA d/s-Rev

<400> SEQUENCE: 58
gaatgacgag tggatcacc 19

<210> SEQ ID NO 59
<211> LENGTH: 24
<212> TYPE: DNA
<213> ORGANISM: Artificial Sequence
<220> FEATURE:
<223> OTHER INFORMATION: mvaA ex-Fwd

<400> SEQUENCE: 59

-continued ccattaatga agtttgtggt tcag 24

<210> SEQ ID NO 60
<211> LENGTH: 21
<212> TYPE: DNA
<213> ORGANISM: Artificial Sequence
<220> FEATURE:
<223> OTHER INFORMATION: mvaA ex-Rev

<400> SEQUENCE: 60
cccttacatc ctctgtctca c 21

<210> SEQ ID NO 61
<211> LENGTH: 21
<212> TYPE: DNA
<213> ORGANISM: Artificial Sequence
<220> FEATURE:
<223> OTHER INFORMATION: pORI19-Rev

<400> SEQUENCE: 61
taccgagctc gaattcactg g 21

<210> SEQ ID NO 62
<211> LENGTH: 20
<212> TYPE: DNA
<213> ORGANISM: Artificial Sequence
<220> FEATURE:
<223> OTHER INFORMATION: pORI19-Fwd

<400> SEQUENCE: 62
atcctctaga gtcgacctgc 20

<210> SEQ ID NO 63
<211> LENGTH: 21
<212> TYPE: DNA
<213> ORGANISM: Artificial Sequence
<220> FEATURE:
<223> OTHER INFORMATION: DCO-Fwd

<400> SEQUENCE: 63
cgccttaaga acaccagtcg g 21

<210> SEQ ID NO 64
<211> LENGTH: 19
<212> TYPE: DNA
<213> ORGANISM: Artificial Sequence
<220> FEATURE:
<223> OTHER INFORMATION: DCO-Rev

<400> SEQUENCE: 64
gctctccgta ggtcatggc 19

<210> SEQ ID NO 65
<211> LENGTH: 22
<212> TYPE: DNA
<213> ORGANISM: Artificial Sequence
<220> FEATURE:
<223> OTHER INFORMATION: SCO u/s-Rev

<400> SEQUENCE: 65
acaatttcac acaggaaaca gc 22

<210> SEQ ID NO 66
<211> LENGTH: 21
<212> TYPE: DNA
<213> ORGANISM: Artificial Sequence
<220> FEATURE:
<223> OTHER INFORMATION: SCO u/s-Fwd

<400> SEQUENCE: 66
cccccattaa gtgccgagtg c 21

<210> SEQ ID NO 67
<211> LENGTH: 52
<212> TYPE: DNA
<213> ORGANISM: Artificial Sequence
<220> FEATURE:
<223> OTHER INFORMATION: mvaA-Fwd

<400> SEQUENCE: 67
cgcggatcca ggaggtaata aatatgagaa aaaaatttta tcaaatgtcg cc 52

<210> SEQ ID NO 68
<211> LENGTH: 39
<212> TYPE: DNA
<213> ORGANISM: Artificial Sequence
<220> FEATURE:
<223> OTHER INFORMATION: mvaA-Rev

<400> SEQUENCE: 68
gtctagatta ttttctcaaa ttttttagta aattttggg 39

<210> SEQ ID NO 69
<211> LENGTH: 42
<212> TYPE: DNA
<213> ORGANISM: Artificial Sequence
<220> FEATURE:
<223> OTHER INFORMATION: EGFP-Fwd

<400> SEQUENCE: 69
cgcgtcgaca ggaggtaata aatatggtga gcaagggcga gg 42

<210> SEQ ID NO 70
<211> LENGTH: 31
<212> TYPE: DNA
<213> ORGANISM: Artificial Sequence
<220> FEATURE:
<223> OTHER INFORMATION: EGFP-Rev

<400> SEQUENCE: 70
ggcatgctta cttgtacagc tcgtccatgc c 31

<210> SEQ ID NO 71
<211> LENGTH: 2999
<212> TYPE: DNA
<213> ORGANISM: Artificial Sequence
<220> FEATURE:
<223> OTHER INFORMATION: pSTV28

<400> SEQUENCE: 71
cgtatggcaa tgaaagacgg tgagctggtg atatgggata gtgttcaccc ttgttacacc 60
gttttccatg agcaaactga aacgttttca tcgctctgga gtgaatacca cgacgatttc 120
cggcagtttc tacacatata ttcgcaagat gtggcgtgtt acggtgaaaa cctggcctat 180
ttccctaaag ggtttattga gaatatgttt ttcgtctcag ccaatccctg ggtgagtttc 240
accagttttg atttaaacgt ggccaatatg gacaacttct tcgcccccgt tttcaccatg 300
ggcaaatatt atacgcaagg cgacaaggtg ctgatgccgc tggcgattca ggttcatcat 360
gccgtttgtg atggcttcca tgtcggcaga atgcttaatg aattacaaca gtactgcgat 420

-continued

```
gagtggcagg gcggggcgta atttttttaa ggcagttatt ggtgccctta aacgcctggt    480
gctacgcctg aataagtgat aataagcgga tgaatggcag aaattcgaaa gcaaattcga    540
cccggtcgtc ggttcagggc agggtcgtta aatagccgct tatgtctatt gctggtttac    600
cggtttattg actaccggaa gcagtgtgac cgtgtgcttc tcaaatgcct gaggccagtt    660
tgctcaggct ctccccgtgg aggtaataat tgacgatatg atcatttatt ctgcctccca    720
gagcctgata aaaacggtta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg   1020
ctcatggcgt tccaatacgc aaaccgcctc tccccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgaat   1260
tcgagctcgg tacccgggga tcctctagag tcgacctgca ggcatgcaag cttggcactg   1320
gccgtcgttt tacaacgtcg tgactgggaa aaccctggcg ttacccaact taatcgcctt   1380
gcagcacatc ccccttttcgc cagctggcgt aatagcgaag aggcccgcac cgatcgccct   1440
tcccaacagt tgcgcagcct gaatggcgaa tgagcttatc gatgataagc tgtcaaacat   1500
gagaattaca acttatatcg tatggggctg acttcaggtg ctacatttga agagataaat   1560
tgcactgaaa tctagaaata ttttatctga ttaataagat gatcttcttg agatcgtttt   1620
ggtctgcgcg taatctcttg ctctgaaaac gaaaaaaccg ccttgcaggg cggtttttcg   1680
aaggttctct gagctaccaa ctctttgaac cgaggtaact ggcttggagg agcgcagtca   1740
ccaaaacttg tcctttcagt ttagccttaa ccggcgcatg acttcaagac taactcctct   1800
aaatcaatta ccagtggctg ctgccagtgg tgcttttgca tgtctttccg ggttggactc   1860
aagacgatag ttaccggata aggcgcagcg gtcggactga acggggggtt cgtgcataca   1920
gtccagcttg gagcgaactg cctacccgga actgagtgtc aggcgtggaa tgagacaaac   1980
gcggccataa cagcggaatg acaccggtaa accgaaaggc aggaacagga gagcgcacga   2040
gggagccgcc aggggaaacg cctggtatct ttatagtcct gtcgggtttc gccaccactg   2100
atttgagcgt cagatttcgt gatgcttgtc aggggggcgg agcctatgga aaaacggctt   2160
tgccgcggcc ctctcacttc cctgttaagt atcttcctgg catcttccag gaaatctccg   2220
ccccgttcgt aagccatttc cgctcgccgc agtcgaacga ccgagcgtag cgagtcagtg   2280
agcgaggaag cggaatatat cctgtatcac atattctgct gacgcaccgg tgcagccttt   2340
tttctcctgc cacatgaagc acttcactga caccctcatc agtgccaaca tagtaagcca   2400
gtatacactc cgctagcgct gatgtccggc ggtgcttttg ccgttacgca ccaccccgtc   2460
agtagctgaa caggagggac agctgataga aacagaagcc actggagcac ctcaaaaaca   2520
ccatcataca ctaaatcagt aagttggcag catcacccga cgcactttgc gccgaataaa   2580
tacctgtgac ggaagatcac ttcgcagaat aaataaatcc tggtgtccct gttgataccg   2640
ggaagccctg ggccaacttt tggcgaaaat gagacgttga tcggcacgta agaggttcca   2700
actttcacca taatgaaata agatcactac cgggcgtatt ttttgagtta tcgagatttt   2760
caggagctaa ggaagctaaa atggagaaaa aaatcactgg atataccacc gttgatatat   2820
```

cccaatggca tcgtaaagaa cattttgagg catttcagtc agttgctcaa tgtacctata 2880
accagaccgt tcagctggat attacggcct ttttaaagac cgtaaagaaa aataagcaca 2940
agttttatcc ggcctttatt cacattcttg cccgcctgat gaatgctcat ccggaattt 2999

<210> SEQ ID NO 72
<211> LENGTH: 4176
<212> TYPE: DNA
<213> ORGANISM: Artificial Sequence
<220> FEATURE:
<223> OTHER INFORMATION: pTrc99A

<400> SEQUENCE: 72
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagaccatgg aattcgagct cggtacccgg ggatcctcta 300
gagtcgacct gcaggcatgc aagcttggct gttttggcgg atgagagaag attttcagcc 360
tgatacagat taaatcagaa cgcagaagcg gtctgataaa acagaatttg cctggcggca 420
gtagcgcggt ggtcccacct gaccccatgc cgaactcaga agtgaaacgc cgtagcgccg 480
atggtagtgt ggggtctccc catgcgagag tagggaactg ccaggcatca aataaaacga 540
aaggctcagt cgaaagactg ggcctttcgt tttatctgtt gtttgtcggt gaacgctctc 600
ctgagtagga caaatccgcc gggagcggat ttgaacgttg cgaagcaacg gcccggaggg 660
tggcgggcag gacgcccgcc ataaactgcc aggcatcaaa ttaagcagaa ggccatcctg 720
acggatggcc tttttgcgtt tctacaaact ctttttgttt atttttctaa atacattcaa 780
atatgtatcc gctcatgaga caataaccct gataaatgct tcaataatat tgaaaaagga 840
agagtatgag tattcaacat ttccgtgtcg cccttattcc cttttttgcg gcattttgcc 900
ttcctgtttt tgctcaccca gaaacgctgg tgaaagtaaa agatgctgaa gatcagttgg 960
gtgcacgagt gggttacatc gaactggatc tcaacagcgg taagatcctt gagagttttc 1020
gccccgaaga acgttttcca atgatgagca cttttaaagt tctgctatgt ggcgcggtat 1080
tatcccgtgt tgacgccggg caagagcaac tcggtcgccg catacactat tctcagaatg 1140
acttggttga gtactcacca gtcacagaaa agcatcttac ggatggcatg acagtaagag 1200
aattatgcag tgctgccata accatgagtg ataacactgc ggccaactta cttctgacaa 1260
cgatcggagg accgaaggag ctaaccgctt ttttgcacaa catgggggat catgtaactc 1320
gccttgatcg ttgggaaccg gagctgaatg aagccatacc aaacgacgag cgtgacacca 1380
cgatgcctac agcaatggca acaacgttgc gcaaactatt aactggcgaa ctacttactc 1440
tagcttcccg gcaacaatta atagactgga tggaggcgga taaagttgca ggaccacttc 1500
tgcgctcggc ccttccggct ggctggttta ttgctgataa atctggagcc ggtgagcgtg 1560
ggtctcgcgg tatcattgca gcactggggc cagatggtaa gccctcccgt atcgtagtta 1620
tctacacgac ggggagtcag gcaactatgg atgaacgaaa tagacagatc gctgagatag 1680
gtgcctcact gattaagcat tggtaactgt cagaccaagt ttactcatat atactttaga 1740
ttgatttaaa acttcatttt taatttaaaa ggatctaggt gaagatcctt tttgataatc 1800
tcatgaccaa aatcccttaa cgtgagtttt cgttccactg agcgtcagac cccgtagaaa 1860

-continued

```
agatcaaagg atcttcttga gatccttttt ttctgcgcgt aatctgctgc ttgcaaacaa   1920
aaaaaccacc gctaccagcg gtggtttgtt tgccggatca agagctacca actctttttc   1980
cgaaggtaac tggcttcagc agagcgcaga taccaaatac tgtccttcta gtgtagccgt   2040
agttaggcca ccacttcaag aactctgtag caccgcctac atacctcgct ctgctaatcc   2100
tgttaccagt ggctgctgcc agtggcgata agtcgtgtct taccgggttg gactcaagac   2160
gatagttacc ggataaggcg cagcggtcgg gctgaacggg gggttcgtgc acacagccca   2220
gcttggagcg aacgacctac accgaactga gatacctaca gcgtgagcta tgagaaagcg   2280
ccacgcttcc cgaagggaga aaggcggaca ggtatccggt aagcggcagg gtcggaacag   2340
gagagcgcac gagggagctt ccagggggaa acgcctggta tctttatagt cctgtcgggt   2400
ttcgccacct ctgacttgag cgtcgatttt tgtgatgctc gtcagggggg cggagcctat   2460
ggaaaaacgc cagcaacgcg gcctttttac ggttcctggc cttttgctgg ccttttgctc   2520
acatgttctt tcctgcgtta tcccctgatt ctgtggataa ccgtattacc gcctttgagt   2580
gagctgatac cgctcgccgc agccgaacga ccgagcgcag cgagtcagtg agcgaggaag   2640
cggaagagcg cctgatgcgg tattttctcc ttacgcatct gtgcggtatt tcacaccgca   2700
tatggtgcac tctcagtaca atctgctctg atgccgcata gttaagccag tatacactcc   2760
gctatcgcta cgtgactggg tcatggctgc gccccgacac ccgccaacac ccgctgacgc   2820
gccctgacgg gcttgtctgc tcccggcatc cgcttacaga caagctgtga ccgtctccgg   2880
gagctgcatg tgtcagaggt tttcaccgtc atcaccgaaa cgcgcgaggc agcagatcaa   2940
ttcgcgcgcg aaggcgaagc ggcatgcatt tacgttgaca ccatcgaatg gtgcaaaacc   3000
tttcgcggta tggcatgata gcgcccggaa gagagtcaat tcagggtggt gaatgtgaaa   3060
ccagtaacgt tatacgatgt cgcagagtat gccggtgtct cttatcagac cgtttcccgc   3120
gtggtgaacc aggccagcca cgtttctgcg aaaacgcggg aaaaagtgga agcggcgatg   3180
gcggagctga attacattcc caaccgcgtg gcacaacaac tggcgggcaa acagtcgttg   3240
ctgattggcg ttgccacctc cagtctggcc ctgcacgcgc cgtcgcaaat tgtcgcggcg   3300
attaaatctc gcgccgatca actgggtgcc agcgtggtgg tgtcgatggt agaacgaagc   3360
ggcgtcgaag cctgtaaagc ggcggtgcac aatcttctcg cgcaacgcgt cagtgggctg   3420
atcattaact atccgctgga tgaccaggat gccattgctg tggaagctgc ctgcactaat   3480
gttccggcgt tatttcttga tgtctctgac cagacaccca tcaacagtat tattttctcc   3540
catgaagacg gtacgcgact gggcgtggag catctggtcg cattgggtca ccagcaaatc   3600
gcgctgttag cgggcccatt aagttctgtc tcggcgcgtc tgcgtctggc tggctggcat   3660
aaatatctca ctcgcaatca aattcagccg atagcggaac gggaaggcga ctggagtgcc   3720
atgtccggtt ttcaacaaac catgcaaatg ctgaatgagg gcatcgttcc cactgcgatg   3780
ctggttgcca acgatcagat ggcgctgggc gcaatgcgcg ccattaccga gtccgggctg   3840
cgcgttggtg cggatatctc ggtagtggga tacgacgata ccgaagacag ctcatgttat   3900
atcccgccgt taaccaccat caaacaggat tttcgcctgc tggggcaaac cagcgtggac   3960
cgcttgctgc aactctctca gggccaggcg gtgaagggca atcagctgtt gcccgtctca   4020
ctggtgaaaa gaaaaaccac cctggcgccc aatacgcaaa ccgcctctcc ccgcgcgttg   4080
gccgattcat taatgcagct ggcacgacag gtttcccgac tggaaagcgg gcagtgagcg   4140
caacgcaatt aatgtgagtt agcgcgaatt gatctg                             4176
```

-continued

<210> SEQ ID NO 73
<211> LENGTH: 4620
<212> TYPE: DNA
<213> ORGANISM: Artificial Sequence
<220> FEATURE:
<223> OTHER INFORMATION: pTFKC(DPB)

<400> SEQUENCE: 73
atcgtagtta tctacacgac ggggagtcag gcaactatgg atgaacgaaa tagacagatc 60
gctgagatag gtgcctcact gattaagcat tggtaactgt cagaccaagt ttactcatat 120
atactttaga ttgatttaaa acttcatttt taatttaaaa ggatctaggt gaagatcctt 180
tttgataatc tcatgaccaa aatcccttaa cgtgagtttt cgttccactg agcgtcagac 240
cccgtagaaa agatcaaagg atcttcttga gatccttttt ttctgcgcgt aatctgctgc 300
ttgcaaacaa aaaaaccacc gctaccagcg gtggtttgtt tgccggatca agagctacca 360
actctttttc cgaaggtaac tggcttcagc agagcgcaga taccaaatac tgtccttcta 420
gtgtagccgt agttaggcca ccacttcaag aactctgtag caccgcctac atacctcgct 480
ctgctaatcc tgttaccagt ggctgctgcc agtggcgata agtcgtgtct taccgggttg 540
gactcaagac gatagttacc ggataaggcg cagcggtcgg gctgaacggg gggttcgtgc 600
acacagccca gcttggagcg aacgacctac accgaactga gatacctaca gcgtgagcta 660
tgagaaagcg ccacgcttcc cgaagggaga aaggcggaca ggtatccggt aagcggcagg 720
gtcggaacag gagagcgcac gagggagctt ccagggggaa acgcctggta tctttatagt 780
cctgtcgggt ttcgccacct ctgacttgag cgtcgatttt tgtgatgctc gtcagggggg 840
cggagcctat ggaaaaacgc cagcaacgcg gcctttttac ggttcctggc cttttgctgg 900
ccttttgctc acatgtgttt gacagcttat catcgactgc acggtgcacc aatgcttctg 960
gcgtcaggca gccatcggaa gctgtggtat ggctgtgcag gtcgtaaatc actgcataat 1020
tcgtgtcgct caaggcgcac tcccgttctg gataatgttt tttgcgccga catcataacg 1080
gttctggcaa atattctgaa atgagctgtt gacaattaat catccggctc gtataatgtg 1140
tggtcacaca ggaaacagac catggaattc gagctcggta cccggggatc ctctagagtc 1200
gacctgcagg catgcaagct tggctgtttt ggcggatgag agaagatttt cagcctgata 1260
cagattaaat cagaacgcag aagcggtctg ataaaacaga atttgcctgg cggcagtagc 1320
gcggtggtcc cacctgaccc catgccgaac tcagaagtga aacgccgtag cgccgatggt 1380
agtgtggggt ctccccatgc gagagtaggg aactgccagg catcaaataa aacgaaaggc 1440
tcagtcgaaa gactgggcct ttcgttttat ctgttgtttg tcggtgaacg ctctcctgag 1500
taggacaaat ccgccgggag cggatttgaa cgttgcgaag caacggcccg gagggtggcg 1560
ggcaggacgc ccgccataaa ctgccaggca tcaaattaag cagaaggcca tcctgacgga 1620
tggccttttt gcgtttctac aaactctttt tgtttatttt tctaaataca ttcaaatatg 1680
tatccgctca tgagacaata acccgataat tcgatgggga tccgtcgacc tgcagttcga 1740
agttcctatt ctctagaaag tataggaact tcagagcgct tttgaagctc acgctgccgc 1800
aagcactcag ggcgcaaggg ctgctaaagg aagcggaaca cgtagaaagc cagtccgcag 1860
aaacggtgct gaccccggat gaatgtcagc tactgggcta tctggacaag ggaaaacgca 1920
agcgcaaaga gaaagcaggt agcttgcagt gggcttacat ggcgatagct agactgggcg 1980
gttttatgga cagcaagcga accggaattg ccagctgggg cgccctctgg taaggttggg 2040
aagccctgca aagtaaactg gatggctttc ttgccgccaa ggatctgatg gcgcagggga 2100

-continued

```
tcaagatctg atcaagagac aggatgagga tcgtttcgca tgattgaaca agatggattg   2160
cacgcaggtt ctccggccgc ttgggtggag aggctattcg gctatgactg ggcacaacag   2220
acaatcggct gctctgatgc cgccgtgttc cggctgtcag cgcaggggcg cccggttctt   2280
tttgtcaaga ccgacctgtc cggtgccctg aatgaactgc aggacgaggc agcgcggcta   2340
tcgtggctgg ccacgacggg cgttccttgc gcagctgtgc tcgacgttgt cactgaagcg   2400
ggaagggact ggctgctatt gggcgaagtg ccggggcagg atctcctgtc atctcacctt   2460
gctcctgccg agaaagtatc catcatggct gatgcaatgc ggcggctgca tacgcttgat   2520
ccggctacct gcccattcga ccaccaagcg aaacatcgca tcgagcgagc acgtactcgg   2580
atggaagccg gtcttgtcga tcaggatgat ctggacgaag agcatcaggg gctcgcgcca   2640
gccgaactgt tcgccaggct caaggcgcgc atgcccgacg gcgaggatct cgtcgtgacc   2700
catggcgatg cctgcttgcc gaatatcatg gtggaaaatg gccgcttttc tggattcatc   2760
gactgtggcc ggctgggtgt ggcggaccgc tatcaggaca tagcgttggc tacccgtgat   2820
attgctgaag agcttggcgg cgaatgggct gaccgcttcc tcgtgcttta cggtatcgcc   2880
gctcccgatt cgcagcgcat cgccttctat cgccttcttg acgagttctt ctaataaggg   2940
gatcttgaag ttcctattcc gaagttccta ttctctagaa agtataggaa cttcgaagca   3000
gctccagcct acaaggaggt aataaatatg atcaagctta tcgataccgt cgacctcgag   3060
ggggggcccg gtacccaatt cgccctatag tgagtcgtat tacgcgcgct cactggccgt   3120
cgttttacaa cgtcgtgact gggaaaaccc tggcgttacc caacttaatc gccttgcagc   3180
acatccccct ttcgccagct ggcgtaatag cgaagaggcc cgcaccgatc gcccttccca   3240
acagttgcgc agcctgaatg gcgaatggga cgcgccctgt agcggcgcat taagcgcggc   3300
gggtgtggtg gttacgcgca gcgtgaccgc tacacttgcc agcgccctag cgcccgctcc   3360
tttcgctttc ttcccttcct ttctcgccac gttcgccggc tttccccgtc aagctctaaa   3420
tcgggggctc cctttagggt tccgatttag tgctttacgg cacctcgacc ccaaaaaact   3480
tgattagggt gatggttcac gtagtgggcc atcgccctga tagacggttt ttcgcccttt   3540
gacgttggag tccacgttct ttaatagtgg actcttgttc caaactggaa caacactcaa   3600
ccctatctcg gtctattctt ttgatttata agggattttg ccgatttcgg cctattggtt   3660
aaaaaatgag ctgatttaac aaaaatttaa cgcgaatttt aacaaaatat taacgcttac   3720
aatttaggtg gcacttttcg gggaaatgtg cgcggaaccc ctatttgttt atttttctaa   3780
atacattcaa atatgtatcc gctcatgaga caataaccct gataaatgct tcaataatat   3840
tgaaaaagga agagtatgag tattcaacat ttccgtgtcg cccttattcc cttttttgcg   3900
gcattttgcc ttcctgtttt tgctcaccca gaaacgctgg tgaaagtaaa agatgctgaa   3960
gatcagttgg gtgcacgagt gggttacatc gaactggatc tcaacagcgg taagatcctt   4020
gagagttttc gccccgaaga acgttttcca atgatgagca cttttaaagt tctgctatgt   4080
ggcgcggtat tatcccgtat tgacgccggg caagagcaac tcggtcgccg catacactat   4140
tctcagaatg acttggttga gtactcacca gtcacagaaa agcatcttac ggatggcatg   4200
acagtaagag aattatgcag tgctgccata accatgagtg ataacactgc ggccaactta   4260
cttctgacaa cgatcggagg accgaaggag ctaaccgctt ttttgcacaa catgggggat   4320
catgtaactc gccttgatcg ttgggaaccg gagctgaatg aagccatacc aaacgacgag   4380
cgtgacacca cgatgcctgt agcaatggca acaacgttgc gcaaactatt aactggcgaa   4440
ctacttactc tagcttcccg gcaacaatta atagactgga tggaggcgga taaagttgca   4500
```

ggaccacttc tgcgctcggc ccttccggct ggctggttta ttgctgataa atctggagcc 4560
ggtgagcgtg ggtctcgcgg tatcattgca gcactggggc cagatggtaa gccctcccgt 4620

<210> SEQ ID NO 74
<211> LENGTH: 4335
<212> TYPE: DNA
<213> ORGANISM: Artificial Sequence
<220> FEATURE:
<223> OTHER INFORMATION: pTFCC(DPB)

<400> SEQUENCE: 74
gtggcacttt tcggggaaat gtgcgcggaa cccctatttg tttatttttc taaatacatt 60
caaatatgta tccgctcatg agacaataac cctgataaat gcttcaataa tattgaaaaa 120
ggaagagtat gagtattcaa catttccgtg tcgcccttat tccctttttt gcggcatttt 180
gccttcctgt ttttgctcac ccagaaacgc tggtgaaagt aaaagatgct gaagatcagt 240
tgggtgcacg agtgggttac atcgaactgg atctcaacag cggtaagatc cttgagagtt 300
ttcgccccga agaacgtttt ccaatgatga gcacttttaa agttctgcta tgtggcgcgg 360
tattatcccg tattgacgcc gggcaagagc aactcggtcg ccgcatacac tattctcaga 420
atgacttggt tgagtactca ccagtcacag aaaagcatct tacggatggc atgacagtaa 480
gagaattatg cagtgctgcc ataaccatga gtgataacac tgcggccaac ttacttctga 540
caacgatcgg aggaccgaag gagctaaccg cttttttgca caacatgggg gatcatgtaa 600
ctcgccttga tcgttgggaa ccggagctga atgaagccat accaaacgac gagcgtgaca 660
ccacgatgcc tgtagcaatg gcaacaacgt tgcgcaaact attaactggc gaactactta 720
ctctagcttc ccggcaacaa ttaatagact ggatggaggc ggataaagtt gcaggaccac 780
ttctgcgctc ggcccttccg gctggctggt ttattgctga taaatctgga gccggtgagc 840
gtgggtctcg cggtatcatt gcagcactgg ggccagatgg taagccctcc cgtatcgtag 900
ttatctacac gacggggagt caggcaacta tggatgaacg aaatagacag atcgctgaga 960
taggtgcctc actgattaag cattggtaac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgtcctt ctagtgtagc 1320
cgtagttagg ccaccacttc aagaactctg tagcaccgcc tacatacctc gctctgctaa 1380
tcctgttacc agtggctgct gccagtggcg ataagtcgtg tcttaccggg ttggactcaa 1440
gacgatagtt accggataag gcgcagcggt cgggctgaac ggggggttcg tgcacacagc 1500
ccagcttgga gcgaacgacc tacaccgaac tgagatacct acagcgtgag ctatgagaaa 1560
gcgccacgct tcccgaaggg agaaaggcgg acaggtatcc ggtaagcggc agggtcggaa 1620
caggagagcg cacgagggag cttccagggg gaaacgcctg gtatctttat agtcctgtcg 1680
ggtttcgcca cctctgactt gagcgtcgat ttttgtgatg ctcgtcaggg gggcggagcc 1740
tatggaaaaa cgccagcaac gcggcctttt tacggttcct ggccttttgc tggccttttg 1800
ctcacatgtg tttgacagct tatcatcgac tgcacggtgc accaatgctt ctggcgtcag 1860
gcagccatcg gaagctgtgg tatggctgtg caggtcgtaa atcactgcat aattcgtgtc 1920

-continued

```
gctcaaggcg cactcccgtt ctggataatg tttttgcgc cgacatcata acggttctgg   1980
caaatattct gaaatgagct gttgacaatt aatcatccgg ctcgtataat gtgtggtcac   2040
acaggaaaca gaccatggaa ttcgagctcg gtacccgggg atcctctaga gtcgacctgc   2100
aggcatgcaa gcttggctgt tttggcggat gagagaagat tttcagcctg atacagatta   2160
aatcagaacg cagaagcggt ctgataaaac agaatttgcc tggcggcagt agcgcggtgg   2220
tcccacctga ccccatgccg aactcagaag tgaaacgccg tagcgccgat ggtagtgtgg   2280
ggtctcccca tgcgagagta gggaactgcc aggcatcaaa taaaacgaaa ggctcagtcg   2340
aaagactggg cctttcgttt tatctgttgt ttgtcggtga acgctctcct gagtaggaca   2400
aatccgccgg gagcggattt gaacgttgcg aagcaacggc ccggagggtg gcgggcagga   2460
cgcccgccat aaactgccag gcatcaaatt aagcagaagg ccatcctgac ggatggcctt   2520
tttgcgtttc tacaaactct tttgtttat ttttctaaat acattcaaat atgtatccgc   2580
tcatgagaca ataacccgat aattcgatca tatgaatatc ctccttagtt cctattccga   2640
agttcctatt ctctagaaag tataggaact tcggcgcgcc tacctgtgac ggaagatcac   2700
ttcgcagaat aaataaatcc tggtgtccct gttgataccg ggaagccctg ggccaacttt   2760
tggcgaaaat gagacgttga tcggcacgta agaggttcca actttcacca taatgaaata   2820
agatcactac cgggcgtatt ttttgagttg tcgagatttt caggagctaa ggaagctaaa   2880
atggagaaaa aaatcactgg atataccacc gttgatatat cccaatggca tcgtaaagaa   2940
cattttgagg catttcagtc agttgctcaa tgtacctata accagaccgt tcagctggat   3000
attacggcct ttttaaagac cgtaaagaaa aataagcaca agttttatcc ggcctttatt   3060
cacattcttg cccgcctgat gaatgctcat ccggaattac gtatggcaat gaaagacggt   3120
gagctggtga tatgggatag tgttcaccct tgttacaccg ttttccatga gcaaactgaa   3180
acgttttcat cgctctggag tgaataccac gacgatttcc ggcagtttct acacatatat   3240
tcgcaagatg tggcgtgtta cggtgaaaac ctggcctatt tccctaaagg gtttattgag   3300
aatatgtttt tcgtctcagc caatccctgg gtgagtttca ccagttttga tttaaacgtg   3360
gccaatatgg acaacttctt cgcccccgtt ttcaccatgg gcaaatatta tacgcaaggc   3420
gacaaggtgc tgatgccgct ggcgattcag gttcatcatg ccgtttgtga tggcttccat   3480
gtcggcagat gcttaatgaa tacaacagta ctgcgatgag tggcagggcg gggcgtaagg   3540
cgcgccattt aaatgaagtt cctattccga agttcctatt ctctagaaag tataggaact   3600
tcgaagcagc tccagcctac aaggaggtaa taaatatgat caagcttatc gataccgtcg   3660
acctcgaggg ggggcccggt acccaattcg ccctatagtg agtcgtatta cgcgcgctca   3720
ctggccgtcg ttttacaacg tcgtgactgg gaaaaccctg gcgttaccca acttaatcgc   3780
cttgcagcac atcccccttt cgccagctgg cgtaatagcg aagaggcccg caccgatcgc   3840
ccttcccaac agttgcgcag cctgaatggc gaatgggacg cgccctgtag cggcgcatta   3900
agcgcggcgg gtgtggtggt tacgcgcagc gtgaccgcta cacttgccag cgccctagcg   3960
cccgctcctt tcgctttctt cccttccttt ctcgccacgt tcgccggctt tccccgtcaa   4020
gctctaaatc gggggctccc tttagggttc cgatttagtg ctttacggca cctcgacccc   4080
aaaaaacttg attagggtga tggttcacgt agtgggccat cgccctgata gacggttttt   4140
cgccctttga cgttggagtc cacgttcttt aatagtggac tcttgttcca aactggaaca   4200
acactcaacc ctatctcggt ctattctttt gatttataag ggattttgcc gatttcggcc   4260
tattggttaa aaaatgagct gatttaacaa aaatttaacg cgaattttaa caaaatatta   4320
```

-continued acgcttacaa tttag 4335

<210> SEQ ID NO 75
<211> LENGTH: 9497
<212> TYPE: DNA
<213> ORGANISM: Artificial Sequence
<220> FEATURE:
<223> OTHER INFORMATION: pCP20

<400> SEQUENCE: 75
gaattccgga tgagcattca tcaggcgggc aagaatgtga ataaaggccg gataaaactt 60
gtgcttattt ttctttacgg tctttaaaaa ggccgtaata tccagctgaa cggtctggtt 120
ataggtacat tgagcaactg actgaaatgc ctcaaaatgt tctttacgat gccattggga 180
tatatcaacg gtggtatatc cagtgatttt tttctccatt ttagcttcct tagctcctga 240
aaatctcgat aactcaaaaa atacgcccgg tagtgatctt atttcattat ggtgaaagtt 300
ggaacctctt acgtgccgat caacgtctca ttttcgccaa aagttggccc agggcttccc 360
ggtatcaaca gggacaccag gatttattta ttctgcgaag tgatcttccg tcacaggtat 420
ttattcggcg caaagtgcgt cgggtgatgc tgccaactta ctgatttagt gtatgatggt 480
gtttttgagg tgctccagtg gcttctgttt ctatcagctg tccctcctgt tcagctactg 540
acggggtggt gcgtaacggc aaaagcaccg ccggacatca gcgcctgtag tgccatttac 600
ccccattcac tgccagagcc gtgagcgcag cgaactgaat gtcacgaaaa agacagcgac 660
tcaggtgcct gatggtcgga gacaaaagga atattcagcg atttgcccga gcttgcgagg 720
gtgctactta agcctttagg gttttaaggt ctgttttgta gaggagcaaa cagcgtttgc 780
gacatccttt tgtaatactg cggaactgac taaagtagtg agttatacac agggctggga 840
tctattcttt ttatcttttt ttattctttc tttattctat aaattataac cacttgaata 900
taaacaaaaa aaacacacaa aggtctagcg gaatttacag agggtctagc agaatttaca 960
agttttccag caaaggtcta gcagaattta cagataccca caactcaaag gaaaaggact 1020
agtaattatc attgactagc ccatctcaat tggtatagtg attaaaatca cctagaccaa 1080
ttgagatgta tgtctgaatt agttgttttc aaagcaaatg aactagcgat tagtcgctat 1140
gacttaacgg agcatgaaac caagctaatt ttatgctgtg tggcactact caaccccacg 1200
attgaaaacc ctacaaggaa agaacggacg gtatcgttca cttataacca atacgttcag 1260
atgatgaaca tcagtaggga aaatgcttat ggtgtattag ctaaagcaac cagagagctg 1320
atgacgagaa ctgtggaaat caggaatcct ttggttaaag gctttgagat tttccagtgg 1380
acaaactatg ccaagttctc aagcgaaaaa ttagaattag tttttagtga agagatattg 1440
ccttatcttt tccagttaaa aaaattcata aaatataatc tggaacatgt taagtctttt 1500
gaaaacaaat actctatgag gatttatgag tggttattaa aagaactaac acaaaagaaa 1560
actcacaagg caaatataga gattagcctt gatgaattta agttcatgtt aatgcttgaa 1620
aataactacc atgagtttaa aaggcttaac caatgggttt tgaaaccaat aagtaaagat 1680
ttaaacactt acagcaatat gaaattggtg gttgataagc gaggccgccc gactgatacg 1740
ttgattttcc aagttgaact agatagacaa atggatctcg taaccgaact tgagaacaac 1800
cagataaaaa tgaatggtga caaaatacca acaaccatta catcagattc ctacctacgt 1860
aacggactaa gaaaaacact acacgatgct ttaactgcaa aaattcagct caccagtttt 1920
gaggcaaaat ttttgagtga catgcaaagt aagcatgatc tcaatggttc gttctcatgg 1980

-continued

```
ctcacgcaaa aacaacgaac cacactagag aacatactgg ctaaatacgg aaggatctga   2040
ggttcttatg gctcttgtat ctatcagtga agcatcaaga ctaacaaaca aaagtagaac   2100
aactgttcac cgttagatat caaagggaaa actgtccata tgcacagatg aaaacggtgt   2160
aaaaaagata gatacatcag agcttttacg agtttttggt gcatttaaag ctgttcacca   2220
tgaacagatc gacaatgtaa cagatgaaca gcatgtaaca cctaatagaa caggtgaaac   2280
cagtaaaaca aagcaactag aacatgaaat tgaacacctg agacaacttg ttacagctca   2340
acagtcacac atagacagcc tgaaacaggc gatgctgctt atcgaatcaa agctgccgac   2400
aacacgggag ccagtgacgc ctcccgtggg gaaaaaatca tggcaattct ggaagaaaat   2460
agcgcctgtt tcgtttcagg caggttatca gggagtgtca gcgtcctgcg gttctccggg   2520
gcgttcgggt catgcagccc gtaatggtga tttaacagcg tctgccaagc atcaattcta   2580
ggcctgtctg cgcggtcgta gtacggctgg aggcgttttc cggtctgtag ctccatgttc   2640
ggaatgacaa aattcagctc aagccgtccc ttgtcctggt gctccaccca caggatgctg   2700
tactgatttt tttcgagacc gggcatcagt acacgctcaa agctcgccat cactttttca   2760
cgtcctcccg gcggcagctc cttctccgcg aacgacagaa caccggacgt gtatttcttc   2820
gcaaatggcg tggcatcgat gagttcccgg acttcttccg gattaccctg aagcaccgtt   2880
gcgccttcgc ggttacgctc cctccccagc aggtaatcaa ccggaccact gccaccacct   2940
tttcccctgg catgaaattt aactatcatc ccgcgccccc tgttccctga cagccagacg   3000
cagccggcgc agctcatccc cgatggccat cagtgcggcc accacctgaa cccggtcacc   3060
ggaagaccac tgcccgctgt tcaccttacg ggctgtctga ttcaggttat ttccgatggc   3120
ggccagctga cgcagtaacg gcggtgccag tgtcggcagt tttccggaac gggcaaccgg   3180
ctcccccagg cagacccgcc gcatccatac cgccagttgt ttaccctcac agcgttcaag   3240
taaccgggca tgttcatcat cagtaacccg tattgtgagc atcctctcgc gtttcatcgg   3300
tatcattacc ccatgaacag aaatccccct tacacggagg catcagtgac taaacggggt   3360
ctgacgctca gtggaacgaa aactcacgtt aagggatttt ggtcatgaga ttatcaaaaa   3420
ggatcttcac ctagatcctt ttaaattaaa aatgaagttt taaatcaatc taaagtatat   3480
atgagtaaac ttggtctgac agttaccaat gcttaatcag tgaggcacct atctcagcga   3540
tctgtctatt tcgttcatcc atagttgcct gactccccgt cgtgtagata actacgatac   3600
gggagggctt accatctggc cccagtgctg caatgatacc gcgagaccca cgctcaccgg   3660
ctccagattt atcagcaata aaccagccag ccggaagggc cgagcgcaga agtggtcctg   3720
caactttatc cgcctccatc cagtctatta attgttgccg ggaagctaga gtaagtagtt   3780
cgccagttaa tagtttgcgc aacgttgttg ccattgctgc aggcatcgtg gtgtcacgct   3840
cgtcgtttgg tatggcttca ttcagctccg gttcccaacg atcaaggcga gttacatgat   3900
cccccatgtt gtgcaaaaaa gcggttagct ccttcggtcc tccgatcgtt gtcagaagta   3960
agttggccgc agtgttatca ctcatggtta tggcagcact gcataattct cttactgtca   4020
tgccatccgt aagatgcttt tctgtgactg gtgagtactc aaccaagtca ttctgagaat   4080
agtgtatgcg gcgaccgagt tgctcttgcc cggcgtcaac acgggataat accgcgccac   4140
atagcagaac tttaaaagtg ctcatcattg gaaaacgttc ttcggggcga aaactctcaa   4200
ggatcttacc gctgttgaga tccagttcga tgtaacccac tcgtgcaccc aactgatctt   4260
cagcatcttt tactttcacc agcgtttctg ggtgagcaaa aacaggaagg caaaatgccg   4320
caaaaaaggg aataagggcg acacggaaat gttgaatact catactcttc ctttttcaat   4380
```

```
attattgaag catttatcag ggttattgtc tcatgagcgg atacatattt gaatgtattt   4440
agaaaaataa acaaataggg gttccgcgca catttccccg aaaagtgcca cctgacgtct   4500
aagaaaccat tattatcatg acattaacct ataaaaatag gcgtatcacg aggccctttc   4560
gtcttcaaga attttataaa ccgtggagcg ggcaatactg agctgatgag caatttccgt   4620
tgcaccagtg cccttctgat gaagcgtcag cacgacgttc ctgtccacgg tacgcctgcg   4680
gccaaatttg attcctttca gctttgcttc ctgtcggccc tcattcgtgc gctctaggat   4740
cctctacgcc ggacgcatcg tggccggcat caccggcgct gaggtctgcc tcgtgaagaa   4800
ggtgttgctg actcatacca ggcctgaatc gccccatcat ccagccagaa agtgagggag   4860
ccacggttga tgagagcttt gttgtaggtg gaccagttgg tgattttgaa cttttgcttt   4920
gccacggaac ggtctgcgtt gtcgggaaga tgcgtgatct gatccttcaa ctcagcaaaa   4980
gttcgattta ttcaacaaag ccgccgtccc gtcaagtcag cgtaatgctc tgccagtgtt   5040
acaaccaatt aaccaattct gattagaaaa actcatcgag catcaaatga aactgcaatt   5100
tattcatatc aggattatca ataccatatt tttgaaaaag ccgtttctgt aatgaaggag   5160
aaaactcacc gaggcagttc cataggatgg caagatcctg gtatcggtct gcgattccga   5220
ctcgtccaac atcaatacaa cctattaatt tcccctcgtc aaaaataagg ttatcaagtg   5280
agaaatcacc atgagtgacg actgaatccg gtgagaatgg caaaagcttc tagaggatcc   5340
ccctagagaa taggaacttc ggaataggaa cttcaaagcg tttccgaaaa cgagcgcttc   5400
cgaaaatgca acgcgagctg cgcacataca gctcactgtt cacgtcgcac ctatatctgc   5460
gtgttgcctg tatatatata tacatgagaa gaacggcata gtgcgtgttt atgcttaaat   5520
gcgtacttat atgcgtctat ttatgtagga tgaaaggtag tctagtacct cctgtgatat   5580
tatcccattc catgcggggt atcgtatgct tccttcagca ctaccettta gctgttctat   5640
atgctgccac tcctcaattg gattagtctc atccttcaat gctatcattt cctttgatat   5700
tggatcatat gcatagtacc gagaaactag tgcgaagtag tgatcaggta ttgctgttat   5760
ctgatgagta tacgttgtcc tggccacggc agaagcacgc ttatcgctcc aatttcccac   5820
aacattagtc aactccgtta ggcccttcat tgaaagaaat gaggtcatca aatgtcttcc   5880
aatgtgagat tttgggccat tttttatagc aaagattgaa taaggcgcat ttttcttcaa   5940
agctttattg tacgatctga ctaagttatc ttttaataat tggtattcct gtttattgct   6000
tgaagaattg ccggtcctat ttactcgttt taggactggt tcagaattcc tcaaaaattc   6060
atccaaatat acaagtggat cgatcctacc ccttgcgcta aagaagtata tgtgcctact   6120
aacgcttgtc tttgtctctg tcactaaaca ctggattatt actcccagat acttattttg   6180
gactaattta aatgatttcg gatcaacgtt cttaatatcg ctgaatcttc cacaattgat   6240
gaaagtagct aggaagagga attggtataa agtttttgtt tttgtaaatc tcgaagtata   6300
ctcaaacgaa tttagtattt tctcagtgat ctcccagatg ctttcaccct cacttagaag   6360
tgctttaagc atttttttac tgtggctatt tcccttatct gcttcttccg atgattcgaa   6420
ctgtaattgc aaactactta caatatcagt gatatcagat tgatgttttt gtccatagta   6480
aggaataatt gtaaattccc aagcaggaat caatttcttt aatgaggctt ccagaattgt   6540
tgctttttgc gtcttgtatt taaactggag tgatttattg acaatatcga aactcagcga   6600
attgcttatg atagtattat agctcatgaa tgtggctctc ttgattgctg ttccgttatg   6660
tgtaatcatc caacataaat aggttagttc agcagcacat aatgctattt tctcacctga   6720
```

-continued aggtctttca aacctttcca caaactgacg aacaagcacc ttaggtggtg ttttacataa 6780
tataccaaat tgtggcatac aacctcctta gtacatgcaa ccattatcac cgccagaggt 6840
aaaatagtca acacgcacgg tgttagatat ttatcccttg cggtgataga tttaacgtat 6900
gagcacaaaa aagaaaccat taacacaaga gcagcttgag gacgcacgtc gccttaaagc 6960
aatttatgaa aaaaagaaaa atgaacttgg cttatcccag gaatctgtcg cagacaagat 7020
ggggatgggg cagtcaggcg ttggtgcttt atttaatggc atcaatgcat taaatgctta 7080
taacgccgca ttgcttacaa aaattctcaa agttagcgtt gaagaattta gcccttcaat 7140
cgccagagaa atctacgaga tgtatgaagc ggttagtatg cagccgtcac ttagaagtga 7200
gtatgagtac cctgtttttt ctcatgttca ggcagggatg ttctcaccta agcttagaac 7260
ctttaccaaa ggtgatgcgg agagatgggt aagcacaacc aaaaaagcca gtgattctgc 7320
attctggctt gaggttgaag gtaattccat gaccgcacca acaggctcca agccaagctt 7380
tcctgacgga atgttaattc tcgttgaccc tgagcaggct gttgagccag gtgatttctg 7440
catagccaga cttggggggtg atgagtttac cttcaagaaa ctgatcaggg atagcggtca 7500
ggtgttttta caaccactaa acccacagta cccaatgatc ccatgcaatg agagttgttc 7560
cgttgtgggg aaagttatcg ctagtcagtg gcctgaagag acgtttggct gatcggcaag 7620
gtgttctggt cggcgcatag ctgataacaa ttgagcaaga atcttcatcg aattagggga 7680
attttcactc ccctcagaac ataacatagt aaatggattg aattatgaag aatggttttt 7740
atgcgactta ccgcagcaaa aataaaggga aagataagcg ctcaataaac ctgtctgttt 7800
tccttaattc tctgctggct gataatcatc acctgcaggt tggctccaat tatttgtata 7860
ttcataaaat cgagcttatg catttctttc cagacttgtt caacaggcca gccattacgc 7920
tcgtcatcaa aatcactcgc atcaaccaaa ccgttattca ttcgtgattg cgcctgagcg 7980
agacgaaata cgcgatcgct gttaaaagga caattacaaa caggaatcga atgcaaccgg 8040
cgcaggaaca ctgccagcgc atcaacaata ttttcacctg aatcaggata ttcttctaat 8100
acctggaatg ctgttttccc ggggatcgca gtggtgagta accatgcatc atcaggagta 8160
cggataaaat gcttgatggt cggaagaggc ataaattccg tcagccagtt tagtctgacc 8220
atctcatctg taacatcatt ggcaacgcta cctttgccat gtttcagaaa caactctggc 8280
gcatcgggct tcccatacaa tcgatagatt gtcgcacctg attgcccgac attatcgcga 8340
gcccatttat acccatataa atcagcatcc atgttggaat ttaatcgcgg cctcgagcaa 8400
gacgtttccc gttgaatatg gctcataaca ccccttgtat tactgtttat gtaagcagac 8460
agttttattg ttcatgatga tatattttta tcttgtgcaa tgtaacatca gagattttga 8520
gacacaacgt ggctttgttg aataaatcga acttttgctg agttgaagga tcagatcacg 8580
catcttcccg acaacgcaga ccgttccgtg gcaaagcaaa agttcaaaat caccaactgg 8640
tccacctaca acaaagctct catcaaccgt ggctccctca ctttctggct ggatgatggg 8700
gcgattcagg cctggtatga gtcagcaaca ccttcttcac gaggcagacc tcagcgctaa 8760
ccgtttttat caggctctgg gaggcagaat aaatgatcat atcgtcaatt attacctcca 8820
cggggagagc ctgagcaaac tggcctcagg catttgagaa gcacacggtc acactgcttc 8880
cggtagtcaa taaaccggta aaccagcaat agacataagc ggctatttaa cgaccctgcc 8940
ctgaaccgac gaccgggtcg aatttgcttt cgaatttctg ccattcatcc gcttattatc 9000
acttattcag gcgtagcacc aggcgtttaa gggcaccaat aactgcctta aaaaaattac 9060
gccccgccct gccactcatc gcagtactgt tgtaattcat taagcattct gccgacatgg 9120

-continued aagccatcac agacggcatg atgaacctga atcgccagcg gcatcagcac cttgtcgcct 9180
tgcgtataat atttgcccat ggtgaaaacg ggggcgaaga agttgtccat attggccacg 9240
tttaaatcaa aactggtgaa actcacccag ggattggctg agacgaaaaa catattctca 9300
ataaaccctt tagggaaata ggccaggttt tcaccgtaac acgccacatc ttgcgaatat 9360
atgtgtagaa actgccggaa atcgtcgtgg tattcactcc agagcgatga aaacgtttca 9420
gtttgctcat ggaaaacggt gtaacaaggg tgaacactat cccatatcac cagctcaccg 9480
tctttcattg ccatacg 9497

<210> SEQ ID NO 76
<211> LENGTH: 6329
<212> TYPE: DNA
<213> ORGANISM: Artificial Sequence
<220> FEATURE:
<223> OTHER INFORMATION: pKD46

<400> SEQUENCE: 76
catcgattta ttatgacaac ttgacggcta catcattcac tttttcttca caaccggcac 60
ggaactcgct cgggctggcc ccggtgcatt ttttaaatac ccgcgagaaa tagagttgat 120
cgtcaaaacc aacattgcga ccgacggtgg cgataggcat ccgggtggtg ctcaaaagca 180
gcttcgcctg gctgatacgt tggtcctcgc gccagcttaa gacgctaatc cctaactgct 240
ggcggaaaag atgtgacaga cgcgacggcg acaagcaaac atgctgtgcg acgctggcga 300
tatcaaaatt gctgtctgcc aggtgatcgc tgatgtactg acaagcctcg cgtacccgat 360
tatccatcgg tggatggagc gactcgttaa tcgcttccat gcgccgcagt aacaattgct 420
caagcagatt tatcgccagc agctccgaat agcgcccttc cccttgcccg gcgttaatga 480
tttgcccaaa caggtcgctg aaatgcggct ggtgcgcttc atccgggcga aagaaccccg 540
tattggcaaa tattgacggc cagttaagcc attcatgcca gtaggcgcgc ggacgaaagt 600
aaacccactg gtgataccat tcgcgagcct ccggatgacg accgtagtga tgaatctctc 660
ctggcgggaa cagcaaaata tcacccggtc ggcaaacaaa ttctcgtccc tgatttttca 720 ccacccccctg accgcgaatg gtgagattga gaatataacc tttcattccc agcggtcggt 780
cgataaaaaa atcgagataa ccgttggcct caatcggcgt taaacccgcc accagatggg 840
cattaaacga gtatcccggc agcaggggat cattttgcgc ttcagccata cttttcatac 900
tcccgccatt cagagaagaa accaattgtc catattgcat cagacattgc cgtcactgcg 960
tcttttactg gctcttctcg ctaaccaaac cggtaacccc gcttattaaa agcattctgt 1020
aacaaagcgg gaccaaagcc atgacaaaaa cgcgtaacaa aagtgtctat aatcacggca 1080
gaaaagtcca cattgattat ttgcacggcg tcacactttg ctatgccata gcatttttat 1140
ccataagatt agcggatcct acctgacgct ttttatcgca actctctact gtttctccat 1200
acccgttttt ttgggaattc gagctctaag gaggttataa aaaatggata ttaatactga 1260
aactgagatc aagcaaaagc attcactaac cccctttcct gttttcctaa tcagcccggc 1320
atttcgcggg cgatattttc acagctattt caggagttca gccatgaacg cttattacat 1380
tcaggatcgt cttgaggctc agagctgggc gcgtcactac cagcagctcg cccgtgaaga 1440
gaaagaggca gaactggcag acgacatgga aaaaggcctg ccccagcacc tgtttgaatc 1500
gctatgcatc gatcatttgc aacgccacgg ggccagcaaa aaatccatta cccgtgcgtt 1560
tgatgacgat gttgagtttc aggagcgcat ggcagaacac atccggtaca tggttgaaac 1620

-continued

```
cattgctcac caccaggttg atattgattc agaggtataa aacgaatgag tactgcactc   1680
gcaacgctgg ctgggaagct ggctgaacgt gtcggcatgg attctgtcga cccacaggaa   1740
ctgatcacca ctcttcgcca gacggcattt aaaggtgatg ccagcgatgc gcagttcatc   1800
gcattactga tcgttgccaa ccagtacggc cttaatccgt ggacgaaaga aatttacgcc   1860
tttcctgata agcagaatgg catcgttccg gtggtgggcg ttgatggctg gtcccgcatc   1920
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacggggcc gtggcagtcg   2100
catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
gctcttggat tcctgaaaca gaaagccgca gagcagaagg tggcagcatg acaccggaca   2460
ttatcctgca gcgtaccggg atcgatgtga gagctgtcga acagggggat gatgcgtggc   2520
acaaattacg gctcggcgtc atcaccgctt cagaagttca caacgtgata gcaaaacccc   2580
gctccggaaa gaagtggcct gacatgaaaa tgtcctactt ccacaccctg cttgctgagg   2640
tttgcaccgg tgtggctccg gaagttaacg ctaaagcact ggcctgggga aaacagtacg   2700
agaacgacgc cagaaccctg tttgaattca cttccggcgt gaatgttact gaatccccga   2760
tcatctatcg cgacgaaagt atgcgtaccg cctgctctcc cgatggttta tgcagtgacg   2820
gcaacggcct tgaactgaaa tgcccgttta cctcccggga tttcatgaag ttccggctcg   2880
gtggtttcga ggccataaag tcagcttaca tggcccaggt gcagtacagc atgtgggtga   2940
cgcgaaaaaa tgcctggtac tttgccaact atgacccgcg tatgaagcgt gaaggcctgc   3000
attatgtcgt gattgagcgg gatgaaaagt acatggcgag ttttgacgag atcgtgccgg   3060
agttcatcga aaaaatggac gaggcactgg ctgaaattgg ttttgtattt ggggagcaat   3120
ggcgatgacg catcctcacg ataatatccg ggtaggcgca atcactttcg tctactccgt   3180
tacaaagcga ggctgggtat ttcccggcct ttctgttatc cgaaatccac tgaaagcaca   3240
gcggctggct gaggagataa ataataaacg aggggctgta tgcacaaagc atcttctgtt   3300
gagttaagaa cgagtatcga gatggcacat agccttgctc aaattggaat caggtttgtg   3360
ccaataccag tagaaacaga cgaagaatcc atgggtatgg acagttttcc ctttgatatg   3420
taacggtgaa cagttgttct acttttgttt gttagtcttg atgcttcact gatagataca   3480
agagccataa gaacctcaga tccttccgta tttagccagt atgttctcta gtgtggttcg   3540
ttgtttttgc gtgagccatg agaacgaacc attgagatca tacttacttt gcatgtcact   3600
caaaaatttt gcctcaaaac tggtgagctg aatttttgca gttaaagcat cgtgtagtgt   3660
ttttcttagt ccgttacgta ggtaggaatc tgatgtaatg gttgttggta ttttgtcacc   3720
attcattttt atctggttgt tctcaagttc ggttacgaga tccatttgtc tatctagttc   3780
aacttggaaa atcaacgtat cagtcgggcg gcctcgctta tcaaccacca atttcatatt   3840
gctgtaagtg tttaaatctt tacttattgg tttcaaaacc cattggttaa gccttttaaa   3900
ctcatggtag ttattttcaa gcattaacat gaacttaaat tcatcaaggc taatctctat   3960
atttgccttg tgagttttct tttgtgttag ttcttttaat aaccactcat aaatcctcat   4020
```

-continued agagtatttg ttttcaaaag acttaacatg ttccagatta tattttatga atttttttaa 4080
ctggaaaaga taaggcaata tctcttcact aaaaactaat tctaattttt cgcttgagaa 4140
cttggcatag tttgtccact ggaaaatctc aaagccttta accaaaggat tcctgatttc 4200
cacagttctc gtcatcagct ctctggttgc tttagctaat acaccataag cattttccct 4260
actgatgttc atcatctgag cgtattggtt ataagtgaac gataccgtcc gttctttcct 4320
tgtagggttt tcaatcgtgg ggttgagtag tgccacacag cataaaatta gcttggtttc 4380
atgctccgtt aagtcatagc gactaatcgc tagttcattt gctttgaaaa caactaattc 4440
agacatacat ctcaattggt ctaggtgatt ttaatcacta taccaattga gatgggctag 4500
tcaatgataa ttactagtcc ttttcctttg agttgtgggt atctgtaaat tctgctagac 4560
ctttgctgga aaacttgtaa attctgctag accctctgta aattccgcta gacctttgtg 4620
tgtttttttt gtttatattc aagtggttat aatttataga ataaagaaag aataaaaaaa 4680
gataaaaaga atagatccca gccctgtgta taactcacta ctttagtcag ttccgcagta 4740
ttacaaaagg atgtcgcaaa cgctgtttgc tcctctacaa aacagacctt aaaaccctaa 4800
aggcttaagt agcaccctcg caagctcggt tgcggccgca atcgggcaaa tcgctgaata 4860
ttccttttgt ctccgaccat caggcacctg agtcgctgtc tttttcgtga cattcagttc 4920
gctgcgctca cggctctggc agtgaatggg ggtaaatggc actacaggcg ccttttatgg 4980
attcatgcaa ggaaactacc cataatacaa gaaaagcccg tcacgggctt ctcagggcgt 5040
tttatggcgg gtctgctatg tggtgctatc tgactttttg ctgttcagca gttcctgccc 5100
tctgatttc cagtctgacc acttcggatt atcccgtgac aggtcattca gactggctaa 5160
tgcacccagt aaggcagcgg tatcatcaac ggggtctgac gctcagtgga acgaaaactc 5220
acgttaaggg attttggtca tgagattatc aaaaaggatc ttcacctaga tccttttaaa 5280
ttaaaaatga agttttaaat caatctaaag tatatatgag taaacttggt ctgacagtta 5340
ccaatgctta atcagtgagg cacctatctc agcgatctgt ctatttcgtt catccatagt 5400
tgcctgactc cccgtcgtgt agataactac gatacgggag ggcttaccat ctggccccag 5460
tgctgcaatg ataccgcgag acccacgctc accggctcca gatttatcag caataaacca 5520
gccagccgga agggccgagc gcagaagtgg tcctgcaact ttatccgcct ccatccagtc 5580
tattaattgt tgccgggaag ctagagtaag tagttcgcca gttaatagtt tgcgcaacgt 5640
tgttgccatt gctacaggca tcgtggtgtc acgctcgtcg tttggtatgg cttcattcag 5700
ctccggttcc caacgatcaa ggcgagttac atgatccccc atgttgtgca aaaaagcggt 5760
tagctccttc ggtcctccga tcgttgtcag aagtaagttg gccgcagtgt tatcactcat 5820
ggttatggca gcactgcata attctcttac tgtcatgcca tccgtaagat gcttttctgt 5880
gactggtgag tactcaacca agtcattctg agaatagtgt atgcggcgac cgagttgctc 5940
ttgcccggcg tcaatacggg ataataccgc gccacatagc agaactttaa aagtgctcat 6000
cattggaaaa cgttcttcgg ggcgaaaact ctcaaggatc ttaccgctgt tgagatccag 6060
ttcgatgtaa cccactcgtg cacccaactg atcttcagca tcttttactt tcaccagcgt 6120
ttctgggtga gcaaaaacag gaaggcaaaa tgccgcaaaa aagggaataa gggcgacacg 6180
gaaatgttga atactcatac tcttcctttt tcaatattat tgaagcattt atcagggtta 6240
ttgtctcatg agcggataca tatttgaatg tatttagaaa aataaacaaa taggggttcc 6300
gcgcacattt ccccgaaaag tgccacctg 6329

<210> SEQ ID NO 77
<211> LENGTH: 6738
<212> TYPE: DNA
<213> ORGANISM: Artificial Sequence
<220> FEATURE:
<223> OTHER INFORMATION: pT-ispA-STS

<400> SEQUENCE: 77

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggagg taataaatat ggaattcatg gactttccgc agcaactcga    300
agcctgcgtt aagcaggcca accaggcgct gagccgtttt atcgccccac tgccctttca    360
gaacactccc gtggtcgaaa ccatgcagta tggcgcatta ttaggtggta agcgcctgcg    420
acctttcctg gtttatgcca ccggtcatat gttcggcgtt agcacaaaca cgctggacgc    480
acccgctgcc gccgttgagt gtatccacgc ttactcatta attcatgatg atttaccggc    540
aatggatgat gacgatctgc gtcgcggttt gccaacctgc catgtgaagt ttggcgaagc    600
aaacgcgatt ctcgctggcg acgctttaca aacgctggcg ttctcgattt taagcgatgc    660
cgatatgccg gaagtgtcgg accgcgacag aatttcgatg atttctgaac tggcgagcgc    720
cagtggtatt gccggaatgt gcggtggtca ggcattagat ttagacgcgg aaggcaaaca    780
cgtacctctg gacgcgcttg agcgtattca tcgtcataaa accggcgcat tgattcgcgc    840
cgccgttcgc cttggtgcat taagcgccgg agataaagga cgtcgtgctc tgccggtact    900
cgacaagtat gcagagagca tcggccttgc cttccaggtt caggatgaca tcctggatgt    960
ggtgggagat actgcaacgt tgggaaaacg ccagggtgcc gaccagcaac ttggtaaaag   1020
tacctaccct gcacttctgg gtcttgagca agcccggaag aaagcccggg atctgatcga   1080
cgatgcccgt cagtcgctga aacaactggc tgaacagtca ctcgatacct cggcactgga   1140
agcgctagcg gactacatca tccagcgtaa taaataagga tccaaaaagg aggtaataaa   1200
ccatgtcaac tcaacaagtt tcatcagaga acattgttcg taacgctgcg aatttccatc   1260
ctaatatatg gggaaaccat ttcctcacat gtccttctca gacgattgat agttggactc   1320
aacagcacca caaagaactg aaagaagagg tgaggaaaat gatggtgtct gatgcaaata   1380
aacctgccca gagattgcgc ttgattgata ctgtccaaag gctaggtgtg gcttaccact   1440
ttgaaaagga gattgatgat gcattggaga aaataggtca tgaccctttt gatgataaag   1500
atgatctcta cattgtctct ctttgttttc gattgctgag gcagcatgga attaagatat   1560
catgtgatgt gtttgagaag tttaaagatg acgatggaaa attcaaggca tcattgatga   1620
atgatgttca aggcatgcta agtttatatg aggcagcaca cctagccatt cacggagaag   1680
atattttaga tgaagcaatt gttttcacga ccactcacct taagtcaacg gtatctaatt   1740
ctcctgtaaa ctctactttt gctgaacaaa tacgtcattc tctcagagtt cctctccgta   1800
aagctgtacc taggttagag tcgaggtatt tcttggatat ctattcaaga gatgatttgc   1860
acgataaaac tttgctcaat ttcgcaaagt tagactttaa tatactacaa gcaatgcacc   1920
agaaggaagc aagtgagatg accaggtggt ggagagattt tgacttcctt aaaaagctgc   1980
cttatataag agacagagtc gtggagctat atttttggat tctggtggga gtgtcttatc   2040
agcccaaatt cagcactggt agaatttttt tgtccaaaat aatatgcctt gagaccctcg   2100
```

-continued

```
tagatgatac atttgacgcc tacggtactt ttgacgagct cgcaatcttt actgaagcag   2160
ttacaagatg ggaccttggc cacagagatg cactaccaga atacatgaaa ttcattttca   2220
agacactcat tgatgtctac agtgaagctg agcaagaact ggcaaaggaa gggagatcat   2280
acagcataca ctatgcaata cgatcgttcc aagaactagt tatgaagtac ttctgcgaag   2340
ccaagtggtt aaataaaggt tatgttccga gcctggacga ttataaatca gtttcattaa   2400
gaagtatcgg tttttaccg atagcggtag cttccttcgt tttcatgggt gatattgcaa   2460
ctaaggaggt ctttgaatgg gaaatgaata accctaagat cataatagcc gcagaaacga   2520
ttttcagatt cctggatgac atagcaggcc ataggtttga gcaaaagaga gaacatagtc   2580
catcagctat tgaatgctac aagaatcaac atggagtgtc tgaggaagag gcagttaaag   2640
cgttgtcgtt agaagttgct aatagttgga aagatataaa tgaggagctg cttctcaacc   2700
caatggctat tcctttacct ctgcttcagg tgattcttga tctctcacgt tcggccgatt   2760
ttatgtacgg taatgctcaa gatcgcttca cgcattcaac gatgatgaaa gaccaagttg   2820
atttggtgct gaaggacccc gttaagcttg acgattaaag atctgtcgac ctgcaggcat   2880
gcaagcttgg ctgttttggc ggatgagaga agattttcag cctgatacag attaaatcag   2940
aacgcagaag cggtctgata aaacagaatt tgcctggcgg cagtagcgcg gtggtcccac   3000
ctgaccccat gccgaactca gaagtgaaac gccgtagcgc cgatggtagt gtggggtctc   3060
cccatgcgag agtagggaac tgccaggcat caaataaaac gaaaggctca gtcgaaagac   3120
tgggcctttc gttttatctg ttgtttgtcg gtgaacgctc tcctgagtag gacaaatccg   3180
ccgggagcgg atttgaacgt tgcgaagcaa cggcccggag ggtggcgggc aggacgcccg   3240
ccataaactg ccaggcatca aattaagcag aaggccatcc tgacggatgg cctttttgcg   3300
tttctacaaa ctctttttgt ttatttttct aaatacattc aaatatgtat ccgctcatga   3360
gacaataacc ctgataaatg cttcaataat attgaaaaag gaagagtatg agtattcaac   3420
atttccgtgt cgcccttatt cccttttttg cggcattttg ccttcctgtt tttgctcacc   3480
cagaaacgct ggtgaaagta aaagatgctg aagatcagtt gggtgcacga gtgggttaca   3540
tcgaactgga tctcaacagc ggtaagatcc ttgagagttt tcgccccgaa gaacgttttc   3600
caatgatgag cacttttaaa gttctgctat gtggcgcggt attatcccgt gttgacgccg   3660
ggcaagagca actcggtcgc cgcatacact attctcagaa tgacttggtt gagtactcac   3720
cagtcacaga aaagcatctt acggatggca tgacagtaag agaattatgc agtgctgcca   3780
taaccatgag tgataacact gcggccaact tacttctgac aacgatcgga ggaccgaagg   3840
agctaaccgc ttttttgcac aacatggggg atcatgtaac tcgccttgat cgttgggaac   3900
cggagctgaa tgaagccata ccaaacgacg agcgtgacac cacgatgcct acagcaatgg   3960
caacaacgtt gcgcaaacta ttaactggcg aactacttac tctagcttcc cggcaacaat   4020
taatagactg gatggaggcg gataaagttg caggaccact tctgcgctcg gcccttccgg   4080
ctggctggtt tattgctgat aaatctggag ccggtgagcg tgggtctcgc ggtatcattg   4140
cagcactggg gccagatggt aagccctccc gtatcgtagt tatctacacg acggggagtc   4200
aggcaactat ggatgaacga aatagacaga tcgctgagat aggtgcctca ctgattaagc   4260
attggtaact gtcagaccaa gtttactcat atatacttta gattgattta aaacttcatt   4320
tttaatttaa aaggatctag gtgaagatcc tttttgataa tctcatgacc aaaatccctt   4380
aacgtgagtt ttcgttccac tgagcgtcag accccgtaga aaagatcaaa ggatcttctt   4440
```

-continued

```
gagatccttt ttttctgcgc gtaatctgct gcttgcaaac aaaaaaacca ccgctaccag   4500
cggtggtttg tttgccggat caagagctac caactctttt tccgaaggta actggcttca   4560
gcagagcgca gataccaaat actgtccttc tagtgtagcc gtagttaggc caccacttca   4620
agaactctgt agcaccgcct acatacctcg ctctgctaat cctgttacca gtggctgctg   4680
ccagtggcga taagtcgtgt cttaccgggt tggactcaag acgatagtta ccggataagg   4740
cgcagcggtc gggctgaacg gggggttcgt gcacacagcc cagcttggag cgaacgacct   4800
acaccgaact gagataccta cagcgtgagc tatgagaaag cgccacgctt cccgaaggga   4860
gaaaggcgga caggtatccg gtaagcggca gggtcggaac aggagagcgc acgagggagc   4920
ttccaggggg aaacgcctgg tatctttata gtcctgtcgg gtttcgccac ctctgacttg   4980
agcgtcgatt tttgtgatgc tcgtcagggg ggcggagcct atggaaaaac gccagcaacg   5040
cggccttttt acggttcctg gccttttgct ggccttttgc tcacatgttc tttcctgcgt   5100
tatcccctga ttctgtggat aaccgtatta ccgcctttga gtgagctgat accgctcgcc   5160
gcagccgaac gaccgagcgc agcgagtcag tgagcgagga agcggaagag cgcctgatgc   5220
ggtattttct ccttacgcat ctgtgcggta tttcacaccg catatggtgc actctcagta   5280
caatctgctc tgatgccgca tagttaagcc agtatacact ccgctatcgc tacgtgactg   5340
ggtcatggct gcgccccgac acccgccaac acccgctgac gcgccctgac gggcttgtct   5400
gctcccggca tccgcttaca gacaagctgt gaccgtctcc gggagctgca tgtgtcagag   5460
gttttcaccg tcatcaccga aacgcgcgag gcagcagatc aattcgcgcg cgaaggcgaa   5520
gcggcatgca tttacgttga caccatcgaa tggtgcaaaa cctttcgcgg tatggcatga   5580
tagcgcccgg aagagagtca attcagggtg gtgaatgtga aaccagtaac gttatacgat   5640
gtcgcagagt atgccggtgt ctcttatcag accgtttccc gcgtggtgaa ccaggccagc   5700
cacgtttctg cgaaaacgcg ggaaaaagtg gaagcggcga tggcggagct gaattacatt   5760
cccaaccgcg tggcacaaca actggcgggc aaacagtcgt tgctgattgg cgttgccacc   5820
tccagtctgg ccctgcacgc gccgtcgcaa attgtcgcgg cgattaaatc tcgcgccgat   5880
caactgggtg ccagcgtggt ggtgtcgatg gtagaacgaa gcggcgtcga agcctgtaaa   5940
gcggcggtgc acaatcttct cgcgcaacgc gtcagtgggc tgatcattaa ctatccgctg   6000
gatgaccagg atgccattgc tgtggaagct gcctgcacta atgttccggc gttatttctt   6060
gatgtctctg accagacacc catcaacagt attattttct cccatgaaga cggtacgcga   6120
ctgggcgtgg agcatctggt cgcattgggt caccagcaaa tcgcgctgtt agcgggccca   6180
ttaagttctg tctcggcgcg tctgcgtctg gctggctggc ataaatatct cactcgcaat   6240
caaattcagc cgatagcgga acgggaaggc gactggagtg ccatgtccgg ttttcaacaa   6300
accatgcaaa tgctgaatga gggcatcgtt cccactgcga tgctggttgc caacgatcag   6360
atggcgctgg gcgcaatgcg cgccattacc gagtccgggc tgcgcgttgg tgcggatatc   6420
tcggtagtgg gatacgacga taccgaagac agctcatgtt atatcccgcc gttaaccacc   6480
atcaaacagg attttcgcct gctggggcaa accagcgtgg accgcttgct gcaactctct   6540
cagggccagg cggtgaaggg caatcagctg ttgcccgtct cactggtgaa aagaaaaacc   6600
accctggcgc ccaatacgca aaccgcctct ccccgcgcgt tggccgattc attaatgcag   6660
ctggcacgac aggtttcccg actggaaagc gggcagtgag cgcaacgcaa ttaatgtgag   6720
ttagcgcgaa ttgatctg                                                 6738
```

-continued

<210> SEQ ID NO 78
<211> LENGTH: 13899
<212> TYPE: DNA
<213> ORGANISM: Artificial Sequence
<220> FEATURE:
<223> OTHER INFORMATION: pTAS-NA

<400> SEQUENCE: 78
gatcctacct gacgcttttt atcgcaactc tctactgttt ctccataccc gtttttttgg 60
gctagcagga ggaattcacc atggtaccaa tgacaaaaaa agttggtgtc ggtcaggcac 120
atagtaagat aattttaata ggggaacatg cggtcgttta cggttatcct gccatttccc 180
tgcctctttt ggaggtggag gtgacctgta aggtagttcc tgcagagagt ccttggcgcc 240
tttatgagga ggataccttg tccatggcgg tttatgcctc actggagtat ttgaatatca 300
cagaagcctg cattcgttgt gagattgact cggctatccc tgagaaacgg gggatgggtt 360
cgtcagcggc tatcagcata gcggccattc gtgcagtatt tgactactat caggctgatc 420
tgcctcatga tgtactagaa atcttggtca atcgagctga aatgattgcc catatgaatc 480
ctagtggttt ggatgctaag acctgtctta gtgaccaacc tattcgcttt atcaagaacg 540
taggatttac agaacttgag atggatttat ccgcctattt ggtgattgcc gatacgggtg 600
tttatggtca tactcgtgaa gccatccaag tggttcaaaa taagggcaag gatgccctac 660
cgtttttgca tgccttggga gaattaaccc agcaagcaga agttgcgatt tcacaaaaag 720
atgctgaagg actgggacaa atcctcagtc aagcgcattt acatttaaaa gaaattggag 780
tcagtagccc tgaggcagac tttttggttg aaacgactct tagccatggt gctctgggtg 840
ccaagatgag cggtggtggg ctaggaggtt gtatcatagc cttggtaacc aatttgacac 900
acgcacaaga actagcagaa agattagaag agaaaggagc tgttcagaca tggatagaga 960
gcctgtaaca gtacgttcct acgcaaatat tgctattatc aaatattggg gaaagaaaaa 1020
agaaaaagag atggtgcctg ctactagcag tatttctcta actttggaaa atatgtatac 1080
agagacgacc ttgtcgcctt taccagccaa tgtaacagct gacgaatttt acatcaatgg 1140
tcagctacaa aatgaggtcg agcatgccaa gatgagtaag attattgacc gttatcgtcc 1200
agctggtgag ggctttgtcc gtatcgatac tcaaaacaat atgcctacgg cagcgggcct 1260
gtcctcaagt tctagtggtt tgtccgccct ggtcaaggct tgtaatgctt atttcaagct 1320
tggattggat agaagtcagt tggcacagga agccaaattt gcctcaggct cttcttctcg 1380
gagtttttat ggaccactag gagcctggga taaggatagt ggagaaattt accctgtaga 1440
gacagacttg aaactagcta tgattatgtt ggtgctagag gacaagaaaa aaccaatctc 1500
tagccgtgac gggatgaaac tttgtgtgga aacctcgacg acttttgacg actgggttcg 1560
tcagtctgag aaggactatc aggatatgct gatttatctc aaggaaaatg attttgccaa 1620
gattggagaa ttaacggaga aaaatgctct ggctatgcat gctacgacaa agactgctag 1680
tccagccttt tcttatctga cggatgcctc ttatgaggct atggcctttg ttcgccagct 1740
tcgtgagaaa ggagaggcct gctactttac catggatgct ggtcccaatg ttaaggtctt 1800
ctgtcaggag aaagacttgg agcatttgtc agaaattttc ggtcagcgtt atcgcttgat 1860
tgtgtcaaaa acaaaggatt tgagtcaaga tgattgctgt taaaacttgc ggaaaactct 1920
attgggcagg tgaatatgct attttagagc cagggcagtt agctttgata aaggatattc 1980
ccatctatat gagggctgag attgcttttt ctgacagcta ccgtatctat tcagatatgt 2040
ttgatttcgc agtggactta aggcccaatc ctgactacag cttgattcaa gaaacgattg 2100

-continued

```
ctttgatggg agacttcctc gctgttcgcg gtcagaattt aagacctttt tccctaaaaa   2160
tctgtggcaa aatggaacga gaagggaaaa agtttggtct aggttctagt ggcagcgtcg   2220
ttgtcttggt tgtcaaggct ttactggctc tctataatct ttcggttgat cagaatctct   2280
tgttcaagct gactagcgct gtcttgctca agcgaggaga caatggttcc atgggcgacc   2340
ttgcctgtat tgtggcagag gatttggttc tttaccagtc atttgatcgc cagaaggcgg   2400
ctgcttggtt agaagaagaa aacttggcga cagttctgga gcgtgattgg ggattttta   2460
tctcacaagt gaaaccaact ttagaatgtg atttcttagt gggatggacc aaggaagtgg   2520
ctgtatcgag tcacatggtc cagcaaatca agcaaaatat caatcaaaat tttttaagtt   2580
cctcaaaaga aacggtggtt tctttggtcg aagccttgga gcaggggaaa gccgaaaaag   2640
ttatcgagca agtagaagta gccagcaagc ttttagaagg cttgagtaca gatatttaca   2700
cgcctttgct tagacagttg aaagaagcca gtcaagattt gcaggccgtt gccaagagta   2760
gtggtgctgg tggtggtgac tgtggcatcg ccctgagttt tgatgcgcaa tcttctcgaa   2820
acactttaaa aaatcgttgg gccgatctgg ggattgagct cttatatcaa gaaaggatag   2880
gacatgacga caaatcgtaa tctagccccg ggaggagaga aattatgcaa acggaacacg   2940
tcattttatt gaatgcacag ggagttccca cgggtacgct ggaaaagtat gccgcacaca   3000
cggcagacac ccgcttacat ctcgcgttct ccagttggct gtttaatgcc aaaggacaat   3060
tattagttac ccgccgcgca ctgagcaaaa aagcatggcc tggcgtgtgg actaactcgg   3120
tttgtgggca cccacaactg ggagaaagca acgaagacgc agtgatccgc cgttgccgtt   3180
atgagcttgg cgtggaaatt acgcctcctg aatctatcta tcctgacttt cgctaccgcg   3240
ccaccgatcc gagtggcatt gtggaaaatg aagtgtgtcc ggtatttgcc gcacgcacca   3300
ctagtgcgtt acagatcaat gatgatgaag tgatggatta tcaatggtgt gatttagcag   3360
atgtattaca cggtattgat gccacgccgt gggcgttcag tccgtggatg gtgatgcagg   3420
cgacaaatcg cgaagccaga aaacgattat ctgcatttac ccagcttaaa taagcatgca   3480
ctagagtcga ggaaacagac catggagttg aaaacagtag ttattattga tgcattacga   3540
acaccaattg gaaaatataa aggcagctta agtcaagtaa gtgccgtaga cttaggaaca   3600
catgttacaa cacaactttt aaaaagacat tccactattt ctgaagaaat tgatcaagta   3660
atctttggaa atgttttaca agctggaaat ggccaaaatc ccgcacgaca aatagcaata   3720
aacagcggtt tatctcatga aattcccgca atgacagtta atgaggtctg cggatcagga   3780
atgaaggccg ttattttggc gaaacaattg attcaattag gagaagcgga agttttaatt   3840
gctggcggga ttgagaatat gtcccaagca cctaaattac aacgatttaa ttacgaaaca   3900
gaaagctatg atgcgccttt ttctagtatg atgtacgatg ggttaacgga tgcctttagt   3960
ggtcaagcaa tgggcttaac tgctgaaaat gtggccgaaa agtatcatgt aactagagaa   4020
gagcaagatc aattttctgt acattcacaa ttaaaagcag ctcaagcaca agcagaaggg   4080
atattcgctg acgaaatagc cccattagaa gtatcaggaa cgcttgtgga gaaagatgaa   4140
gggattcgcc ctaattcgag cgttgagaag ctaggaacgc ttaaaacagt ttttaaagaa   4200
gacggtactg taacagcagg gaatgcatca accattaatg atggggcttc tgctttgatt   4260
attgcttcac aagaatatgc cgaagcacac ggtcttcctt atttagctat tattcgagac   4320
agtgtggaag tcggtattga tccagcctat atgggaattt cgccgattaa agccattcaa   4380
aaactgttag cgcgcaatca acttactacg gaagaaattg atctgtatga aatcaacgaa   4440
gcatttgcag caacttcaat cgtggtccaa agagaactgg ctttaccaga ggaaaaggtc   4500
```

-continued

```
aacatttatg gtggcggtat ttcattaggt catgcgattg gtgccacagg tgctcgttta   4560
ttaacgagtt taagttatca attaaatcaa aaagaaaaga aatatggagt ggcttcttta   4620
tgtatcggcg gtggcttagg actcgctatg ctactagaga gacctcagca aaaaaaaaac   4680
agccgatttt atcaaatgag tcctgaggaa cgcctggctt ctcttcttaa tgaaggccag   4740
atttctgctg atacaaaaaa agaatttgaa aatacggctt tatcttcgca gattgccaat   4800
catatgattg aaaatcaaat cagtgaaaca gaagtgccga tgggcgttgg cttacattta   4860
acagtggacg aaactgatta tttggtacca atggcgacag aagagccctc agtgattgcg   4920
gctttgagta atggtgcaaa aatagcacaa ggatttaaaa cagtgaatca acaacgttta   4980
atgcgtggac aaatcgtttt ttacgatgtt gcagacgccg agtcattgat tgatgaacta   5040
caagtaagag aaacggaaat tttcaacaa gcagagttaa gttatccatc tatcgttaaa    5100
cgcggcggcg gcttaagaga tttgcaatat cgtgcttttg atgaatcatt tgtatctgtc   5160
gactttttag tagatgttaa ggatgcaatg ggggcaaata tcgttaacgc tatgttggaa   5220
ggtgtggccg agttgttccg tgaatggttt gcggagcaaa agattttatt cagtatttta   5280
agtaattatg ccacggagtc ggttgttacg atgaaaacgg ctattccagt ttcacgttta   5340
agtaagggga gcaatggccg ggaaattgct gaaaaaattg ttttagcttc acgctatgct   5400
tcattagatc cttatcgggc agtcacgcat aacaaaggga tcatgaatgg cattgaagct   5460
gtcgttttag ctacaggaaa tgatacacgc gctgttagcg cttcttgtca tgcttttgcg   5520
gtgaaggaag gtcgctacca aggtttgact agttggacgc tggatggcga acaactaatt   5580
ggtgaaattt cagttccgct tgcgttagcc acggttggcg gtgccacaaa agtcttacct   5640
aaatctcaag cagctgctga tttgttagca gtgacggatg caaaagaact aagtcgagta   5700
gtagcggctg ttggtttggc acaaaattta gcggcgttac gggccttagt ctctgaagga   5760
attcaaaaag gacacatggc tctacaagca cgttctttag cgatgacggt cggagctact   5820
ggtaaagaag ttgaggcagt cgctcaacaa ttaaaacgtc aaaaaacgat gaaccaagac   5880
cgagccttgg ctattttaaa tgatttaaga aaacaataaa aaaacagttc agcagaaatt   5940
attctgctga actgtttttt ttcacattag gtagccgttt caggccacga gctcaggagt   6000
taaagaaatg acaattggga ttgataaaat tagttttttt gtgccccctt attatattga   6060
tatgacggca ctggctgaag ccagaaatgt agaccctgga aaatttcata ttggtattgg   6120
gcaagaccaa atggcggtga acccaatcag ccaagatatt gtgacatttg cagccaatgc   6180
cgcagaagcg atcttgacca aagaagataa agaggccatt gatatggtga ttgtcgggac   6240
tgagtccagt atcgatgagt caaaagcggc cgcagttgtc ttacatcgtt taatggggat   6300
tcaacctttc gctcgctctt tcgaaatcaa ggaagcttgt tacggagcaa cagcaggctt   6360
acagttagct aagaatcacg tagccttaca tccagataaa aaagtcttgg ttgtagcagc   6420
agatattgca aaatatggat taaattctgg cggtgagcct acacaaggag ctggggcggt   6480
tgcaatgtta gttgctagtg aaccgcgcat cttggcttta aaagaggata atgtgatgct   6540
gacgcaagat atctatgact tttggcgtcc aacaggccat ccgtatccta tggtcgatgg   6600
tcctttgtca aacgaaacct acatccaatc ttttgcccaa gtctgggatg aacataaaaa   6660
aagaaccggt cttgattttg cagattatga tgctttagcg ttccatattc cttacacaaa   6720
aatgggcaaa aaagccttat tagcaaaaat ctccgaccaa actgaagcag aacaggaacg   6780
aattttagcc cgttatgaag aaagcatcat ctatagtcgt cgcgtaggaa acttgtatac   6840
```

-continued

```
gggttcactt tatctgggac tcatttccct tttagaaaat gcaacgactt taaccgcagg   6900
caatcaaatt gggttattca gttatggttc tggtgctgtc gctgaatttt tcactggtga   6960
attagtagct ggttatcaaa atcatttaca aaaagaaact catttagcac tgctagataa   7020
tcggacagaa ctttctatcg ctgaatatga agccatgttt gcagaaactt tagacacaga   7080
tattgatcaa acgttagaag atgaattaaa atatagtatt tctgctatta ataataccgt   7140
tcgctcttat cgaaactaac tgcagcctcg acctgcaggc atgcaagctt ggctgttttg   7200
gcggatgaga gaagattttc agcctgatac agattaaatc agaacgcaga agcggtctga   7260
taaaacagaa tttgcctggc ggcagtagcg cggtggtccc acctgacccc atgccgaact   7320
cagaagtgaa acgccgtagc gccgatggta gtgtggggtc tccccatgcg agagtaggga   7380
actgccaggc atcaaataaa acgaaaggct cagtcgaaag actgggcctt tcgttttatc   7440
tgttgtttgt cggtgaacgc tctcctgagt aggacaaatc cgccgggagc ggatttgaac   7500
gttgcgaagc aacggcccgg agggtggcgg gcaggacgcc cgccataaac tgccaggcat   7560
caaattaagc agaaggccat cctgacggat ggcctttttg cgtttctaca aactcttttt   7620
gtttattttt ctaaatacat tcaaatatgt atccgctcat gagacaataa ccctgataaa   7680
tgcttcaata atattgaaaa aggaagagta tgagtattca acatttccgt gtcgccctta   7740
ttcccttttt tgcggcattt tgccttcctg tttttgctca cccagaaacg ctggtgaaag   7800
taaaagatgc tgaagatcag ttgggtgcac gagtgggtta catcgaactg gatctcaaca   7860
gcggtaagat ccttgagagt tttcgccccg aagaacgttt tccaatgatg agcactttta   7920
aagttctgct atgtggcgcg gtattatccc gtgttgacgc cgggcaagag caactcggtc   7980
gccgcataca ctattctcag aatgacttgg ttgagtactc accagtcaca gaaaagcatc   8040
ttacggatgg catgacagta agagaattat gcagtgctgc cataaccatg agtgataaca   8100
ctgcggccaa cttacttctg acaacgatcg gaggaccgaa ggagctaacc gcttttttgc   8160
acaacatggg ggatcatgta actcgccttg atcgttggga accggagctg aatgaagcca   8220
taccaaacga cgagcgtgac accacgatgc ctacagcaat ggcaacaacg ttgcgcaaac   8280
tattaactgg cgaactactt actctagctt cccggcaaca attaatagac tggatggagg   8340
cggataaagt tgcaggacca cttctgcgct cggcccttcc ggctggctgg tttattgctg   8400
ataaatctgg agccggtgag cgtgggtctc gcggtatcat tgcagcactg gggccagatg   8460
gtaagccctc ccgtatcgta gttatctaca cgacggggag tcaggcaact atggatgaac   8520
gaaatagaca gatcgctgag ataggtgcct cactgattaa gcattggtaa ctgtcagacc   8580
aagtttactc atatatactt tagattgatt taaaacttca tttttaattt aaaaggatct   8640
aggtgaagat cctttttgat aatctcatga ccaaaatccc ttaacgtgag ttttcgttcc   8700
actgagcgtc agaccccgta gaaaagatca aaggatcttc ttgagatcct ttttttctgc   8760
gcgtaatctg ctgcttgcaa acaaaaaaac caccgctacc agcggtggtt tgtttgccgg   8820
atcaagagct accaactctt tttccgaagg taactggctt cagcagagcg cagataccaa   8880
atactgtcct tctagtgtag ccgtagttag gccaccactt caagaactct gtagcaccgc   8940
ctacatacct cgctctgcta atcctgttac cagtggctgc tgccagtggc gataagtcgt   9000
gtcttaccgg gttggactca agacgatagt taccggataa ggcgcagcgg tcgggctgaa   9060
cggggggttc gtgcacacag cccagcttgg agcgaacgac ctacaccgaa ctgagatacc   9120
tacagcgtga gctatgagaa agcgccacgc ttcccgaagg gagaaaggcg gacaggtatc   9180
cggtaagcgg cagggtcgga acaggagagc gcacgaggga gcttccaggg ggaaacgcct   9240
```

-continued

```
ggtatcttta tagtcctgtc gggtttcgcc acctctgact tgagcgtcga tttttgtgat   9300
gctcgtcagg ggggcggagc ctatggaaaa acgccagcaa cgcggccttt ttacggttcc   9360
tggccttttg ctggcctttt gctcacatgt tctttcctgc gttatcccct gattctgtgg   9420
ataaccgtat taccgccttt gagtgagctg ataccgctcg ccgcagccga acgaccgagc   9480
gcagcgagtc agtgagcgag gaagcggaag agcgcctgat gcggtatttt ctccttacgc   9540
atctgtgcgg tatttcacac cgcatatggt gcactctcag tacaatctgc tctgatgccg   9600
catagttaag ccagtataca ctccgctatc gctacgtgac tgggtcatgg ctgcgccccg   9660
acacccgcca acacccgctg acgcgccctg acgggcttgt ctgctcccgg catccgctta   9720
cagacaagct gtgaccgtct ccgggagctg catgtgtcag aggttttcac cgtcatcacc   9780
gaaacgcgcg aggcagcaga tcaattcgcg cgcgaaggcg aagcggcatg catttacgtt   9840
gacaccatcg aatggtgcaa aacctttcgc ggtatggcat gatagcgccc ggaagagagt   9900
caattcaggg tggtgaatgt gaaaccagta acgttatacg atgtcgcaga gtatgccggt   9960
gtctcttatc agaccgtttc ccgcgtggtg aaccaggcca gccacgtttc tgcgaaaacg  10020
cgggaaaaag tggaagcggc gatggcggag ctgaattaca ttcccaaccg cgtggcacaa  10080
caactggcgg gcaaacagtc gttgctgatt ggcgttgcca cctccagtct ggccctgcac  10140
gcgccgtcgc aaattgtcgc ggcgattaaa tctcgcgccg atcaactggg tgccagcgtg  10200
gtggtgtcga tggtagaacg aagcggcgtc gaagcctgta aagcggcggt gcacaatctt  10260
ctcgcgcaac gcgtcagtgg gctgatcatt aactatccgc tggatgacca ggatgccatt  10320
gctgtggaag ctgcctgcac taatgttccg gcgttatttc ttgatgtctc tgaccagaca  10380
cccatcaaca gtattatttt ctcccatgaa gacggtacgc gactgggcgt ggagcatctg  10440
gtcgcattgg gtcaccagca aatcgcgctg ttagcgggcc cattaagttc tgtctcggcg  10500
cgtctgcgtc tggctggctg gcataaatat ctcactcgca atcaaattca gccgatagcg  10560
gaacgggaag gcgactggag tgccatgtcc ggttttcaac aaaccatgca aatgctgaat  10620
gagggcatcg ttcccactgc gatgctggtt gccaacgatc agatggcgct gggcgcaatg  10680
cgcgccatta ccgagtccgg gctgcgcgtt ggtgcggata tctcggtagt gggatacgac  10740
gataccgaag acagctcatg ttatatcccg ccgttaacca ccatcaaaca ggattttcgc  10800
ctgctggggc aaaccagcgt ggaccgcttg ctgcaactct ctcagggcca ggcggtgaag  10860
ggcaatcagc tgttgcccgt ctcactggtg aaaagaaaaa ccaccctggc gcccaatacg  10920
caaaccgcct ctccccgcgc gttggccgat tcattaatgc agctggcacg acaggtttcc  10980
cgactggaaa gcgggcagtg agcgcaacgc aattaatgtg agttagcgcg aattgatctg  11040
gtttgacagc ttatcatcga ctgcacggtg caccaatgct tctggcgtca ggcagccatc  11100
ggaagctgtg gtatggctgt gcaggtcgta aatcactgca taattcgtgt cgctcaaggc  11160
gcactcccgt tctggataat gtttttttgcg ccgacatcat aacggttctg gcaaatattc  11220
tgaaatgagc tgttgacaat taatcatccg gctcgtataa tgtgtggaat tgtgagcgga  11280
taacaatttc acacaggagg taataaatat ggaattcatg gactttccgc agcaactcga  11340
agcctgcgtt aagcaggcca accaggcgct gagccgtttt atcgccccac tgccctttca  11400
gaacactccc gtggtcgaaa ccatgcagta tggcgcatta ttaggtggta agcgcctgcg  11460
acctttcctg gtttatgcca ccggtcatat gttcggcgtt agcacaaaca cgctggacgc  11520
acccgctgcc gccgttgagt gtatccacgc ttactcatta attcatgatg atttaccggc  11580
```

-continued

```
aatggatgat gacgatctgc gtcgcggttt gccaacctgc catgtgaagt ttggcgaagc  11640
aaacgcgatt ctcgctggcg acgctttaca aacgctggcg ttctcgattt taagcgatgc  11700
cgatatgccg gaagtgtcgg accgcgacag aatttcgatg atttctgaac tggcgagcgc  11760
cagtggtatt gccggaatgt gcggtggtca ggcattagat ttagacgcgg aaggcaaaca  11820
cgtacctctg gacgcgcttg agcgtattca tcgtcataaa accggcgcat tgattcgcgc  11880
cgccgttcgc cttggtgcat taagcgccgg agataaagga cgtcgtgctc tgccggtact  11940
cgacaagtat gcagagagca tcggccttgc cttccaggtt caggatgaca tcctggatgt  12000
ggtgggagat actgcaacgt tgggaaaacg ccagggtgcc gaccagcaac ttggtaaaag  12060
tacctaccct gcacttctgg gtcttgagca agcccggaag aaagcccggg atctgatcga  12120
cgatgcccgt cagtcgctga aacaactggc tgaacagtca ctcgatacct cggcactgga  12180
agcgctagcg gactacatca tccagcgtaa taaataagga tccaaaaagg aggtaataaa  12240
ccatgtcaac tcaacaagtt tcatcagaga acattgttcg taacgctgcg aatttccatc  12300
ctaatatatg ggaaaccat ttcctcacat gtccttctca gacgattgat agttggactc  12360
aacagcacca caaagaactg aaagaagagg tgaggaaaat gatggtgtct gatgcaaata  12420
aacctgccca gagattgcgc ttgattgata ctgtccaaag gctaggtgtg gcttaccact  12480
ttgaaaagga gattgatgat gcattggaga aaataggtca tgaccctttt gatgataaag  12540
atgatctcta cattgtctct ctttgttttc gattgctgag gcagcatgga attaagatat  12600
catgtgatgt gtttgagaag tttaaagatg acgatggaaa attcaaggca tcattgatga  12660
atgatgttca aggcatgcta agtttatatg aggcagcaca cctagccatt cacggagaag  12720
atattttaga tgaagcaatt gttttcacga ccactcacct taagtcaacg gtatctaatt  12780
ctcctgtaaa ctctactttt gctgaacaaa tacgtcattc tctcagagtt cctctccgta  12840
aagctgtacc taggttagag tcgaggtatt tcttggatat ctattcaaga gatgatttgc  12900
acgataaaac tttgctcaat ttcgcaaagt tagactttaa tatactacaa gcaatgcacc  12960
agaaggaagc aagtgagatg accaggtggt ggagagattt tgacttcctt aaaaagctgc  13020
cttatataag agacagagtc gtggagctat atttttggat tctggtggga gtgtcttatc  13080
agcccaaatt cagcactggt agaatttttt tgtccaaaat aatatgcctt gagaccctcg  13140
tagatgatac atttgacgcc tacggtactt ttgacgagct cgcaatcttt actgaagcag  13200
ttacaagatg ggaccttggc cacagagatg cactaccaga atacatgaaa ttcattttca  13260
agacactcat tgatgtctac agtgaagctg agcaagaact ggcaaaggaa gggagatcat  13320
acagcataca ctatgcaata cgatcgttcc aagaactagt tatgaagtac ttctgcgaag  13380
ccaagtggtt aaataaaggt tatgttccga gcctggacga ttataaatca gtttcattaa  13440
gaagtatcgg tttttaccg atagcggtag cttccttcgt tttcatgggt gatattgcaa  13500
ctaaggaggt ctttgaatgg gaaatgaata accctaagat cataatagcc gcagaaacga  13560
ttttcagatt cctggatgac atagcaggcc ataggtttga gcaaaagaga gaacatagtc  13620
catcagctat tgaatgctac aagaatcaac atggagtgtc tgaggaagag gcagttaaag  13680
cgttgtcgtt agaagttgct aatagttgga aagatataaa tgaggagctg cttctcaacc  13740
caatggctat tcctttacct ctgcttcagg tgattcttga tctctcacgt tcggccgatt  13800
ttatgtacgg taatgctcaa gatcgcttca cgcattcaac gatgatgaaa gaccaagttg  13860
atttggtgct gaaggacccc gttaagcttg acgattaaa                         13899
```

<210> SEQ ID NO 79
<211> LENGTH: 10342
<212> TYPE: DNA
<213> ORGANISM: Artificial Sequence
<220> FEATURE:
<223> OTHER INFORMATION: pSNAK

<400> SEQUENCE: 79
gcgcaacgca attaatgtga gttagctcac tcattaggca ccccaggctt tacactttat 60
gcttccggct cgtatgttgt gtggaattgt gagcggataa caatttcaca caggaaacag 120
ctatgaccat gattacgaat tcgagctcgg tacccgggga tcctacctga cgctttttat 180
cgcaactctc tactgtttct ccatacccgt ttttttgggc tagcaggagg aattcaccat 240
ggtaccaatg acaaaaaaag ttggtgtcgg tcaggcacat agtaagataa ttttaatagg 300
ggaacatgcg gtcgtttacg gttatcctgc catttccctg cctcttttgg aggtggaggt 360
gacctgtaag gtagttcctg cagagagtcc ttggcgcctt tatgaggagg ataccttgtc 420
catggcggtt tatgcctcac tggagtattt gaatatcaca gaagcctgca ttcgttgtga 480
gattgactcg gctatccctg agaaacgggg gatgggttcg tcagcggcta tcagcatagc 540
ggccattcgt gcagtatttg actactatca ggctgatctg cctcatgatg tactagaaat 600
cttggtcaat cgagctgaaa tgattgccca tatgaatcct agtggtttgg atgctaagac 660
ctgtcttagt gaccaaccta ttcgctttat caagaacgta ggatttacag aacttgagat 720
ggatttatcc gcctatttgg tgattgccga tacgggtgtt tatggtcata ctcgtgaagc 780
catccaagtg gttcaaaata agggcaagga tgccctaccg tttttgcatg ccttgggaga 840
attaacccag caagcagaag ttgcgatttc acaaaaagat gctgaaggac tgggacaaat 900
cctcagtcaa gcgcatttac atttaaaaga aattggagtc agtagccctg aggcagactt 960
tttggttgaa acgactctta gccatggtgc tctgggtgcc aagatgagcg gtggtgggct 1020
aggaggttgt atcatagcct tggtaaccaa tttgacacac gcacaagaac tagcagaaag 1080
attagaagag aaaggagctg ttcagacatg gatagagagc ctgtaacagt acgttcctac 1140
gcaaatattg ctattatcaa atattgggga aagaaaaaag aaaaagagat ggtgcctgct 1200
actagcagta tttctctaac tttggaaaat atgtatacag agacgacctt gtcgccttta 1260
ccagccaatg taacagctga cgaattttac atcaatggtc agctacaaaa tgaggtcgag 1320
catgccaaga tgagtaagat tattgaccgt tatcgtccag ctggtgaggg ctttgtccgt 1380
atcgatactc aaaacaatat gcctacggca gcgggcctgt cctcaagttc tagtggtttg 1440
tccgccctgg tcaaggcttg taatgcttat ttcaagcttg gattggatag aagtcagttg 1500
gcacaggaag ccaaatttgc ctcaggctct tcttctcgga gtttttatgg accactagga 1560
gcctgggata aggatagtgg agaaatttac cctgtagaga cagacttgaa actagctatg 1620
attatgttgg tgctagagga caagaaaaaa ccaatctcta gccgtgacgg gatgaaactt 1680
tgtgtggaaa cctcgacgac ttttgacgac tgggttcgtc agtctgagaa ggactatcag 1740
gatatgctga tttatctcaa ggaaaatgat tttgccaaga ttggagaatt aacggagaaa 1800
aatgctctgg ctatgcatgc tacgacaaag actgctagtc cagccttttc ttatctgacg 1860
gatgcctctt atgaggctat ggcctttgtt cgccagcttc gtgagaaagg agaggcctgc 1920
tactttacca tggatgctgg tcccaatgtt aaggtcttct gtcaggagaa agacttggag 1980
catttgtcag aaattttcgg tcagcgttat cgcttgattg tgtcaaaaac aaaggatttg 2040
agtcaagatg attgctgtta aaacttgcgg aaaactctat tgggcaggtg aatatgctat 2100

-continued

```
tttagagcca gggcagttag ctttgataaa ggatattccc atctatatga gggctgagat   2160
tgctttttct gacagctacc gtatctattc agatatgttt gatttcgcag tggacttaag   2220
gcccaatcct gactacagct tgattcaaga aacgattgct ttgatgggag acttcctcgc   2280
tgttcgcggt cagaatttaa gacctttttc cctaaaaatc tgtggcaaaa tggaacgaga   2340
agggaaaaag tttggtctag gttctagtgg cagcgtcgtt gtcttggttg tcaaggcttt   2400
actggctctc tataatcttt cggttgatca gaatctcttg ttcaagctga ctagcgctgt   2460
cttgctcaag cgaggagaca atggttccat gggcgacctt gcctgtattg tggcagagga   2520
tttggttctt taccagtcat ttgatcgcca gaaggcggct gcttggttag aagaagaaaa   2580
cttggcgaca gttctggagc gtgattgggg atttttttatc tcacaagtga aaccaacttt   2640
agaatgtgat ttcttagtgg gatggaccaa ggaagtggct gtatcgagtc acatggtcca   2700
gcaaatcaag caaaatatca atcaaaattt tttaagttcc tcaaaagaaa cggtggtttc   2760
tttggtcgaa gccttggagc aggggaaagc cgaaaaagtt atcgagcaag tagaagtagc   2820
cagcaagctt ttagaaggct tgagtacaga tatttacacg cctttgctta gacagttgaa   2880
agaagccagt caagatttgc aggccgttgc caagagtagt ggtgctggtg gtggtgactg   2940
tggcatcgcc ctgagttttg atgcgcaatc ttctcgaaac actttaaaaa atcgttgggc   3000
cgatctgggg attgagctct tatatcaaga aaggatagga catgacgaca aatcgtaatc   3060
tagccccggg aggagagaaa ttatgcaaac ggaacacgtc attttattga atgcacaggg   3120
agttcccacg ggtacgctgg aaaagtatgc cgcacacacg gcagacaccc gcttacatct   3180
cgcgttctcc agttggctgt ttaatgccaa aggacaatta ttagttaccc gccgcgcact   3240
gagcaaaaaa gcatggcctg gcgtgtggac taactcggtt tgtgggcacc cacaactggg   3300
agaaagcaac gaagacgcag tgatccgccg ttgccgttat gagcttggcg tggaaattac   3360
gcctcctgaa tctatctatc ctgactttcg ctaccgcgcc accgatccga gtggcattgt   3420
ggaaaatgaa gtgtgtccgg tatttgccgc acgcaccact agtgcgttac agatcaatga   3480
tgatgaagtg atggattatc aatggtgtga tttagcagat gtattacacg gtattgatgc   3540
cacgccgtgg gcgttcagtc cgtggatggt gatgcaggcg acaaatcgcg aagccagaaa   3600
acgattatct gcatttaccc agcttaaata agcatgcact agagtcgagg aaacagacca   3660
tggagttgaa aacagtagtt attattgatg cattacgaac accaattgga aaatataaag   3720
gcagcttaag tcaagtaagt gccgtagact taggaacaca tgttacaaca caacttttaa   3780
aaagacattc cactatttct gaagaaattg atcaagtaat ctttggaaat gttttacaag   3840
ctggaaatgg ccaaaatccc gcacgacaaa tagcaataaa cagcggttta tctcatgaaa   3900
ttcccgcaat gacagttaat gaggtctgcg gatcaggaat gaaggccgtt attttggcga   3960
aacaattgat tcaattagga gaagcggaag ttttaattgc tggcgggatt gagaatatgt   4020
cccaagcacc taaattacaa cgatttaatt acgaaacaga aagctatgat gcgccttttt   4080
ctagtatgat gtacgatggg ttaacggatg cctttagtgg tcaagcaatg ggcttaactg   4140
ctgaaaatgt ggccgaaaag tatcatgtaa ctagagaaga gcaagatcaa ttttctgtac   4200
attcacaatt aaaagcagct caagcacaag cagaagggat attcgctgac gaaatagccc   4260
cattagaagt atcaggaacg cttgtggaga aagatgaagg gattcgccct aattcgagcg   4320
ttgagaagct aggaacgctt aaaacagttt ttaaagaaga cggtactgta acagcaggga   4380
atgcatcaac cattaatgat ggggcttctg ctttgattat tgcttcacaa gaatatgccg   4440
aagcacacgg tcttccttat ttagctatta ttcgagacag tgtggaagtc ggtattgatc   4500
```

cagcctatat gggaatttcg ccgattaaag ccattcaaaa actgttagcg cgcaatcaac 4560
ttactacgga agaaattgat ctgtatgaaa tcaacgaagc atttgcagca acttcaatcg 4620
tggtccaaag agaactggct ttaccagagg aaaaggtcaa catttatggt ggcggtattt 4680
cattaggtca tgcgattggt gccacaggtg ctcgtttatt aacgagttta agttatcaat 4740
taaatcaaaa agaaaagaaa tatggagtgg cttctttatg tatcggcggt ggcttaggac 4800
tcgctatgct actagagaga cctcagcaaa aaaaaaacag ccgattttat caaatgagtc 4860
ctgaggaacg cctggcttct cttcttaatg aaggccagat ttctgctgat acaaaaaaag 4920
aatttgaaaa tacggcttta tcttcgcaga ttgccaatca tatgattgaa aatcaaatca 4980
gtgaaacaga agtgccgatg ggcgttggct tacatttaac agtggacgaa actgattatt 5040
tggtaccaat ggcgacagaa gagccctcag tgattgcggc tttgagtaat ggtgcaaaaa 5100
tagcacaagg atttaaaaca gtgaatcaac aacgtttaat gcgtggacaa atcgtttttt 5160
acgatgttgc agacgccgag tcattgattg atgaactaca agtaagagaa acggaaattt 5220
ttcaacaagc agagttaagt tatccatcta tcgttaaacg cggcggcggc ttaagagatt 5280
tgcaatatcg tgcttttgat gaatcatttg tatctgtcga ctttttagta gatgttaagg 5340
atgcaatggg ggcaaatatc gttaacgcta tgttggaagg tgtggccgag ttgttccgtg 5400
aatggtttgc ggagcaaaag attttattca gtattttaag taattatgcc acggagtcgg 5460
ttgttacgat gaaaacggct attccagttt cacgtttaag taaggggagc aatggccggg 5520
aaattgctga aaaaattgtt ttagcttcac gctatgcttc attagatcct tatcgggcag 5580
tcacgcataa caaagggatc atgaatggca ttgaagctgt cgttttagct acaggaaatg 5640
atacacgcgc tgttagcgct tcttgtcatg cttttgcggt gaaggaaggt cgctaccaag 5700
gtttgactag ttggacgctg gatggcgaac aactaattgg tgaaatttca gttccgcttg 5760
cgttagccac ggttggcggt gccacaaaag tcttacctaa atctcaagca gctgctgatt 5820
tgttagcagt gacggatgca aaagaactaa gtcgagtagt agcggctgtt ggtttggcac 5880
aaaatttagc ggcgttacgg gccttagtct ctgaaggaat tcaaaaagga cacatggctc 5940
tacaagcacg ttctttagcg atgacggtcg gagctactgg taaagaagtt gaggcagtcg 6000
ctcaacaatt aaaacgtcaa aaaacgatga accaagaccg agccttggct attttaaatg 6060
atttaagaaa acaataaaaa aacagttcag cagaaattat tctgctgaac tgtttttttt 6120
cacattaggt agccgtttca ggccacgagc tcaggagtta aagaaatgac aattgggatt 6180
gataaaatta gtttttttgt gcccccttat tatattgata tgacggcact ggctgaagcc 6240
agaaatgtag accctggaaa atttcatatt ggtattgggc aagaccaaat ggcggtgaac 6300
ccaatcagcc aagatattgt gacatttgca gccaatgccg cagaagcgat cttgaccaaa 6360
gaagataaag aggccattga tatggtgatt gtcgggactg agtccagtat cgatgagtca 6420
aaagcggccg cagttgtctt acatcgttta atggggattc aacctttcgc tcgctctttc 6480
gaaatcaagg aagcttgtta cggagcaaca gcaggcttac agttagctaa gaatcacgta 6540
gccttacatc cagataaaaa agtcttggtt gtagcagcag atattgcaaa atatggatta 6600
aattctggcg gtgagcctac acaaggagct ggggcggttg caatgttagt tgctagtgaa 6660
ccgcgcatct tggctttaaa agaggataat gtgatgctga cgcaagatat ctatgacttt 6720
tggcgtccaa caggccatcc gtatcctatg gtcgatggtc ctttgtcaaa cgaaacctac 6780
atccaatctt ttgcccaagt ctgggatgaa cataaaaaaa gaaccggtct tgattttgca 6840
gattatgatg ctttagcgtt ccatattcct tacacaaaaa tgggcaaaaa agccttatta 6900
gcaaaaatct ccgaccaaac tgaagcagaa caggaacgaa ttttagcccg ttatgaagaa 6960
agcatcatct atagtcgtcg cgtaggaaac ttgtatacgg gttcacttta tctgggactc 7020
atttcccttt tagaaaatgc aacgacttta accgcaggca atcaaattgg gttattcagt 7080
tatggttctg gtgctgtcgc tgaatttttc actggtgaat tagtagctgg ttatcaaaat 7140
catttacaaa aagaaactca tttagcactg ctagataatc ggacagaact ttctatcgct 7200
gaatatgaag ccatgtttgc agaaacttta gacacagata ttgatcaaac gttagaagat 7260
gaattaaaat atagtatttc tgctattaat aataccgttc gctcttatcg aaactaactg 7320
cagcctcgac ctgcaggcat gcaagcttgg cactggccgt cgttttacaa cgtcgtgact 7380
gggaaaaccc tggcgttacc caacttaatc gccttgcagc acatccccct ttcgccagct 7440
ggcgtaatag cgaagaggcc cgcaccgatc gcccttccca acagttgcgc agcctgaatg 7500
gcgaatgagc ttatcgatga taagctgtca aacatgagaa ttacaactta tatcgtatgg 7560
ggctgacttc aggtgctaca tttgaagaga taaattgcac tgaaatctag aaatatttta 7620
tctgattaat aagatgatct tcttgagatc gttttggtct gcgcgtaatc tcttgctctg 7680
aaaacgaaaa aaccgccttg cagggcggtt tttcgaaggt tctctgagct accaactctt 7740
tgaaccgagg taactggctt ggaggagcgc agtcaccaaa acttgtcctt tcagtttagc 7800
cttaaccggc gcatgacttc aagactaact cctctaaatc aattaccagt ggctgctgcc 7860
agtggtgctt ttgcatgtct ttccgggttg gactcaagac gatagttacc ggataaggcg 7920
cagcggtcgg actgaacggg gggttcgtgc atacagtcca gcttggagcg aactgcctac 7980
ccggaactga gtgtcaggcg tggaatgaga caaacgcggc cataacagcg gaatgacacc 8040
ggtaaaccga aaggcaggaa caggagagcg cacgagggag ccgccagggg aaacgcctgg 8100
tatctttata gtcctgtcgg gtttcgccac cactgatttg agcgtcagat ttcgtgatgc 8160
ttgtcagggg ggcggagcct atggaaaaac ggctttgccg cggccctctc acttccctgt 8220
taagtatctt cctggcatct tccaggaaat ctccgccccg ttcgtaagcc atttccgctc 8280
gccgcagtcg aacgaccgag cgtagcgagt cagtgagcga ggaagcggaa tatatcctgt 8340
atcacatatt ctgctgacgc accggtgcag cctttttttct cctgccacat gaagcacttc 8400
actgacaccc tcatcagtgc caacatagta agccagtata cactccgcta gcgctgatgt 8460
ccggcggtgc ttttgccgtt acgcaccacc ccgtcagtag ctgaacagga gggacagctg 8520
atagaaacag aagccactgg agcacctcaa aaacaccatc atacactaaa tcagtaagtt 8580
ggcagcatca cccgacgcac tttgcgccga ataaatacct gtgacggaag atcacttcgc 8640
agaataaata aatcctggtg tccctgttga taccgggaag ccctgggcca acttttggcg 8700
aaaatgagac gttgatcggc acgtaagagg ttccaacttt caccataatg aaataagatc 8760
actaccgggc gtattttttg agttatcgag attttcagga gctaaggaag ctaaaatgag 8820
ccatattcaa cgggaaacgt cttgctctag gccgcgatta aattccaaca tggatgctga 8880
tttatatggg tataaatggg ctcgcgataa tgtcgggcaa tcaggtgcga caatctatcg 8940
attgtatggg aagcccgatg cgccagagtt gtttctgaaa catggcaaag gtagcgttgc 9000
caatgatgtt acagatgaga tggtcagact aaactggctg acggaattta tgcctcttcc 9060
gaccatcaag cattttatcc gtactcctga tgatgcatgg ttactcacca ctgcgatccc 9120
cgggaaaaca gcattccagg tattagaaga atatcctgat tcaggtgaaa atattgttga 9180
tgcgctggca gtgttcctgc gccggttgca ttcgattcct gtttgtaatt gtccttttaa 9240

```
cagcgatcgc gtatttcgtc tcgctcaggc gcaatcacga atgaataacg gtttggttga   9300

tgcgagtgat tttgatgacg agcgtaatgg ctggcctgtt gaacaagtct ggaaagaaat   9360

gcataaactt ttgccattct caccggattc agtcgtcact catggtgatt tctcacttga   9420

taaccttatt tttgacgagg ggaaattaat aggttgtatt gatgttggac gagtcggaat   9480

cgcagaccga taccaggatc ttgccatcct atggaactgc ctcggtgagt tttctccttc   9540

attacagaaa cggctttttc aaaaatatgg tattgataat cctgatatga ataaattgca   9600

gtttcatttg atgctcgatg agtttttcta aagtactgcg atgagtggca gggcggggcg   9660

taattttttt aaggcagtta ttggtgccct taaacgcctg gtgctacgcc tgaataagtg   9720

ataataagcg gatgaatggc agaaattcga aagcaaattc gacccggtcg tcggttcagg   9780

gcagggtcgt taaatagccg cttatgtcta ttgctggttt accggtttat tgactaccgg   9840

aagcagtgtg accgtgtgct tctcaaatgc ctgaggccag tttgctcagg ctctccccgt   9900

ggaggtaata attgacgata tgatcattta ttctgcctcc cagagcctga taaaaacggt   9960

tagcgcttcg ttaatacaga tgtaggtgtt ccacagggta gccagcagca tcctgcgatg  10020

cagatccgga acataatggt gcagggcgct tgtttcggcg tgggtatggt ggcaggcccc  10080

gtggccgggg gactgttggg cgctgccggc acctgtccta cgagttgcat gataaagaag  10140

acagtcataa gtgcggcgac gatagtcatg ccccgcgccc accggaagga gctaccggac  10200

agcggtgcgg actgttgtaa ctcagaataa gaaatgaggc cgctcatggc gttccaatac  10260

gcaaaccgcc tctccccgcg cgttggccga ttcattaatg cagctggcac gacaggtttc  10320

ccgactggaa agcgggcagt ga                                           10342
```

<210> SEQ ID NO 80
<211> LENGTH: 9081
<212> TYPE: DNA
<213> ORGANISM: Artificial Sequence
<220> FEATURE:
<223> OTHER INFORMATION: pSNAK(-E)

<400> SEQUENCE: 80

```
aacgctatgt tggaaggtgt ggccgagttg ttccgtgaat ggtttgcgga gcaaaagatt     60

ttattcagta ttttaagtaa ttatgccacg gagtcggttg ttacgatgaa aacggctatt    120

ccagtttcac gtttaagtaa ggggagcaat ggccgggaaa ttgctgaaaa aattgtttta    180

gcttcacgct atgcttcatt agatccttat cgggcagtca cgcataacaa agggatcatg    240

aatggcattg aagctgtcgt tttagctaca ggaaatgata cacgcgctgt tagcgcttct    300

tgtcatgctt ttgcggtgaa ggaaggtcgc taccaaggtt tgactagttg gacgctggat    360

ggcgaacaac taattggtga aatttcagtt ccgcttgcgt tagccacggt tggcggtgcc    420

acaaaagtct tacctaaatc tcaagcagct gctgatttgt tagcagtgac ggatgcaaaa    480

gaactaagtc gagtagtagc ggctgttggt ttggcacaaa atttagcggc gttacgggcc    540

ttagtctctg aaggaattca aaaaggacac atggctctac aagcacgttc tttagcgatg    600

acggtcggag ctactggtaa agaagttgag gcagtcgctc aacaattaaa acgtcaaaaa    660

acgatgaacc aagaccgagc cttggctatt ttaaatgatt taagaaaaca ataaaaaaac    720

agttcagcag aaattattct gctgaactgt ttttttcac attaggtagc cgtttcaggc    780

cacgagctca ggagttaaag aaatgacaat tgggattgat aaaaattagtt tttttgtgcc    840

cccttattat attgatatga cggcactggc tgaagccaga aatgtagacc ctggaaaatt    900
```

-continued

```
tcatattggt attgggcaag accaaatggc ggtgaaccca atcagccaag atattgtgac    960
atttgcagcc aatgccgcag aagcgatctt gaccaaagaa gataaagagg ccattgatat   1020
ggtgattgtc gggactgagt ccagtatcga tgagtcaaaa gcggccgcag ttgtcttaca   1080
tcgtttaatg gggattcaac ctttcgctcg ctctttcgaa atcaaggaag cttgttacgg   1140
agcaacagca ggcttacagt tagctaagaa tcacgtagcc ttacatccag ataaaaaagt   1200
cttggttgta gcagcagata ttgcaaaata tggattaaat tctggcggtg agcctacaca   1260
aggagctggg gcggttgcaa tgttagttgc tagtgaaccg cgcatcttgg ctttaaaaga   1320
ggataatgtg atgctgacgc aagatatcta tgacttttgg cgtccaacag gccatccgta   1380
tcctatggtc gatggtcctt tgtcaaacga aacctacatc caatcttttg cccaagtctg   1440
ggatgaacat aaaaaaagaa ccggtcttga ttttgcagat tatgatgctt tagcgttcca   1500
tattccttac acaaaaatgg gcaaaaaagc cttattagca aaaatctccg accaaactga   1560
agcagaacag gaacgaattt tagcccgtta tgaagaaagc atcatctata gtcgtcgcgt   1620
aggaaacttg tatacgggtt cactttatct gggactcatt tccctttag aaaatgcaac    1680
gactttaacc gcaggcaatc aaattgggtt attcagttat ggttctggtg ctgtcgctga   1740
atttttcact ggtgaattag tagctggtta tcaaaatcat ttacaaaaag aaactcattt   1800
agcactgcta gataatcgga cagaactttc tatcgctgaa tatgaagcca tgtttgcaga   1860
aactttagac acagatattg atcaaacgtt agaagatgaa ttaaaatata gtatttctgc   1920
tattaataat accgttcgct cttatcgaaa ctaactgcag cctcgacctg caggcatgca   1980
agcttggcac tggccgtcgt tttacaacgt cgtgactggg aaaaccctgg cgttacccaa   2040
cttaatcgcc ttgcagcaca tccccctttc gccagctggc gtaatagcga agaggcccgc   2100
accgatcgcc cttcccaaca gttgcgcagc ctgaatggcg aatgagctta tcgatgataa   2160
gctgtcaaac atgagaatta caacttatat cgtatggggc tgacttcagg tgctacattt   2220
gaagagataa attgcactga aatctagaaa tattttatct gattaataag atgatcttct   2280
tgagatcgtt ttggtctgcg cgtaatctct tgctctgaaa acgaaaaaac cgccttgcag   2340
ggcggttttt cgaaggttct ctgagctacc aactctttga accgaggtaa ctggcttgga   2400
ggagcgcagt caccaaaact tgtcctttca gtttagcctt aaccggcgca tgacttcaag   2460
actaactcct ctaaatcaat taccagtggc tgctgccagt ggtgcttttg catgtctttc   2520
cgggttggac tcaagacgat agttaccgga taaggcgcag cggtcggact gaacgggggg   2580
ttcgtgcata cagtccagct tggagcgaac tgcctacccg gaactgagtg tcaggcgtgg   2640
aatgagacaa acgcggccat aacagcggaa tgacaccggt aaaccgaaag gcaggaacag   2700
gagagcgcac gagggagccg ccaggggaaa cgcctggtat ctttatagtc ctgtcgggtt   2760
tcgccaccac tgatttgagc gtcagatttc gtgatgcttg tcaggggggc ggagcctatg   2820
gaaaaacggc tttgccgcgg ccctctcact tccctgttaa gtatcttcct ggcatcttcc   2880
aggaaatctc cgccccgttc gtaagccatt tccgctcgcc gcagtcgaac gaccgagcgt   2940
agcgagtcag tgagcgagga agcggaatat atcctgtatc acatattctg ctgacgcacc   3000
ggtgcagcct tttttctcct gccacatgaa gcacttcact gacaccctca tcagtgccaa   3060
catagtaagc cagtatacac tccgctagcg ctgatgtccg gcggtgcttt tgccgttacg   3120
caccaccccg tcagtagctg aacaggaggg acagctgata gaaacagaag ccactggagc   3180
acctcaaaaa caccatcata cactaaatca gtaagttggc agcatcaccc gacgcacttt   3240
gcgccgaata aatacctgtg acggaagatc acttcgcaga ataaataaat cctggtgtcc   3300
```

ctgttgatac cgggaagccc tgggccaact tttggcgaaa atgagacgtt gatcggcacg 3360
taagaggttc caactttcac cataatgaaa taagatcact accgggcgta tttttttgagt 3420 tatcgagatt ttcaggagct aaggaagcta aaatgagcca tattcaacgg gaaacgtctt 3480
gctctaggcc gcgattaaat tccaacatgg atgctgattt atatgggtat aaatgggctc 3540
gcgataatgt cgggcaatca ggtgcgacaa tctatcgatt gtatgggaag cccgatgcgc 3600
cagagttgtt tctgaaacat ggcaaaggta gcgttgccaa tgatgttaca gatgagatgg 3660
tcagactaaa ctggctgacg gaatttatgc ctcttccgac catcaagcat tttatccgta 3720
ctcctgatga tgcatggtta ctcaccactg cgatccccgg gaaaacagca ttccaggtat 3780
tagaagaata tcctgattca ggtgaaaata ttgttgatgc gctggcagtg ttcctgcgcc 3840
ggttgcattc gattcctgtt tgtaattgtc cttttaacag cgatcgcgta tttcgtctcg 3900
ctcaggcgca atcacgaatg aataacggtt tggttgatgc gagtgatttt gatgacgagc 3960
gtaatggctg gcctgttgaa caagtctgga aagaaatgca taaacttttg ccattctcac 4020
cggattcagt cgtcactcat ggtgatttct cacttgataa ccttattttt gacgagggga 4080
aattaatagg ttgtattgat gttggacgag tcggaatcgc agaccgatac caggatcttg 4140
ccatcctatg gaactgcctc ggtgagtttt ctccttcatt acagaaacgg ctttttcaaa 4200
aatatggtat tgataatcct gatatgaata aattgcagtt tcatttgatg ctcgatgagt 4260
ttttctaaag tactgcgatg agtggcaggg cggggcgtaa tttttttaag gcagttattg 4320
gtgcccttaa acgcctggtg ctacgcctga ataagtgata ataagcggat gaatggcaga 4380
aattcgaaag caaattcgac ccggtcgtcg gttcagggca gggtcgttaa atagccgctt 4440
atgtctattg ctggtttacc ggtttattga ctaccggaag cagtgtgacc gtgtgcttct 4500
caaatgcctg aggccagttt gctcaggctc tccccgtgga ggtaataatt gacgatatga 4560
tcatttattc tgcctcccag agcctgataa aaacggttag cgcttcgtta atacagatgt 4620
aggtgttcca cagggtagcc agcagcatcc tgcgatgcag atccggaaca taatggtgca 4680
gggcgcttgt ttcggcgtgg gtatggtggc aggccccgtg gccgggggac tgttgggcgc 4740
tgccggcacc tgtcctacga gttgcatgat aaagaagaca gtcataagtg cggcgacgat 4800
agtcatgccc cgcgcccacc ggaaggagct accggacagc ggtgcggact gttgtaactc 4860
agaataagaa atgaggccgc tcatggcgtt ccaatacgca aaccgcctct ccccgcgcgt 4920
tggccgattc attaatgcag ctggcacgac aggtttcccg actggaaagc gggcagtgag 4980
cgcaacgcaa ttaatgtgag ttagctcact cattaggcac cccaggcttt acactttatg 5040
cttccggctc gtatgttgtg tggaattgtg agcggataac aatttcacac aggaaacagc 5100
tatgaccatg attacgaatt cgagctcggt acccggggat cctacctgac gctttttatc 5160
gcaactctct actgtttctc catacccgtt tttttgggct agcaggagga attcaccatg 5220
gtaccaatga caaaaaaagt tggtgtcggt caggcacata gtaagataat tttaataggg 5280
gaacatgcgg tcgtttacgg ttatcctgcc atttccctgc ctcttttgga ggtggaggtg 5340
acctgtaagg tagttcctgc agagagtcct tggcgccttt atgaggagga taccttgtcc 5400
atggcggttt atgcctcact ggagtatttg aatatcacag aagcctgcat tcgttgtgag 5460
attgactcgg ctatccctga gaaacggggg atgggttcgt cagcggctat cagcatagcg 5520
gccattcgtg cagtatttga ctactatcag gctgatctgc ctcatgatgt actagaaatc 5580
ttggtcaatc gagctgaaat gattgcccat atgaatccta gtggtttgga tgctaagacc 5640

-continued

```
tgtcttagtg accaacctat tcgctttatc aagaacgtag gatttacaga acttgagatg   5700
gatttatccg cctatttggt gattgccgat acgggtgttt atggtcatac tcgtgaagcc   5760
atccaagtgg ttcaaaataa gggcaaggat gccctaccgt ttttgcatgc cttgggagaa   5820
ttaacccagc aagcagaagt tgcgatttca caaaaagatg ctgaaggact gggacaaatc   5880
ctcagtcaag cgcatttaca tttaaaagaa attggagtca gtagccctga ggcagacttt   5940
ttggttgaaa cgactcttag ccatggtgct ctgggtgcca agatgagcgg tggtgggcta   6000
ggaggttgta tcatagcctt ggtaaccaat ttgacacacg cacaagaact agcagaaaga   6060
ttagaagaga aaggagctgt tcagacatgg atagagagcc tgtaacagta cgttcctacg   6120
caaatattgc tattatcaaa tattggggaa agaaaaaaga aaaagagatg gtgcctgcta   6180
ctagcagtat ttctctaact ttggaaaata tgtatacaga gacgaccttg tcgcctttac   6240
cagccaatgt aacagctgac gaattttaca tcaatggtca gctacaaaat gaggtcgagc   6300
atgccaagat gagtaagatt attgaccgtt atcgtccagc tggtgagggc tttgtccgta   6360
tcgatactca aaacaatatg cctacggcag cgggcctgtc ctcaagttct agtggtttgt   6420
ccgccctggt caaggcttgt aatgcttatt tcaagcttgg attggataga agtcagttgg   6480
cacaggaagc caaatttgcc tcaggctctt cttctcggag tttttatgga ccactaggag   6540
cctgggataa ggatagtgga gaaatttacc ctgtagagac agacttgaaa ctagctatga   6600
ttatgttggt gctagaggac aagaaaaaac caatctctag ccgtgacggg atgaaacttt   6660
gtgtggaaac ctcgacgact tttgacgact gggttcgtca gtctgagaag gactatcagg   6720
atatgctgat ttatctcaag gaaaatgatt ttgccaagat tggagaatta acggagaaaa   6780
atgctctggc tatgcatgct acgacaaaga ctgctagtcc agccttttct tatctgacgg   6840
atgcctctta tgaggctatg gcctttgttc gccagcttcg tgagaaagga gaggcctgct   6900
actttaccat ggatgctggt cccaatgtta aggtcttctg tcaggagaaa gacttggagc   6960
atttgtcaga aattttcggt cagcgttatc gcttgattgt gtcaaaaaca aaggatttga   7020
gtcaagatga ttgctgttaa aacttgcgga aaactctatt gggcaggtga atatgctatt   7080
ttagagccag ggcagttagc tttgataaag gatattccca tctatatgag ggctgagatt   7140
gctttttctg acagctaccg tatctattca gatatgtttg atttcgcagt ggacttaagg   7200
cccaatcctg actacagctt gattcaagaa acgattgctt tgatgggaga cttcctcgct   7260
gttcgcggtc agaatttaag acctttttcc ctaaaaatct gtggcaaaat ggaacgagaa   7320
gggaaaaagt ttggtctagg ttctagtggc agcgtcgttg tcttggttgt caaggcttta   7380
ctggctctct ataatctttc ggttgatcag aatctcttgt tcaagctgac tagcgctgtc   7440
ttgctcaagc gaggagacaa tggttccatg ggcgaccttg cctgtattgt ggcagaggat   7500
ttggttcttt accagtcatt tgatcgccag aaggcggctg cttggttaga agaagaaaac   7560
ttggcgacag ttctggagcg tgattgggga tttttttatct cacaagtgaa accaacttta   7620
gaatgtgatt tcttagtggg atggaccaag gaagtggctg tatcgagtca catggtccag   7680
caaatcaagc aaaatatcaa tcaaaatttt ttaagttcct caaaagaaac ggtggtttct   7740
ttggtcgaag ccttggagca ggggaaagcc gaaaaagtta tcgagcaagt agaagtagcc   7800
agcaagcttt tagaaggctt gagtacagat atttacacgc ctttgcttag acagttgaaa   7860
gaagccagtc aagatttgca ggccgttgcc aagagtagtg gtgctggtgg tggtgactgt   7920
ggcatcgccc tgagttttga tgcgcaatct tctcgaaaca ctttaaaaaa tcgttgggcc   7980
gatctgggga ttgagctctt atatcaagaa aggataggac atgacgacaa atcgtaatct   8040
```

agccccggga ggagagaaat tatgcaaacg gaacacgtca ttttattgaa tgcacaggga 8100
gttcccacgg gtacgctgga aaagtatgcc gcacacacgg cagacacccg cttacatctc 8160
gcgttctcca gttggctgtt taatgccaaa ggacaattat tagttacccg ccgcgcactg 8220
agcaaaaaag catggcctgg cgtgtggact aactcggttt gtgggcaccc acaactggga 8280
gaaagcaacg aagacgcagt gatccgccgt tgccgttatg agcttggcgt ggaaattacg 8340
cctcctgaat ctatctatcc tgactttcgc taccgcgcca ccgatccgag tggcattgtg 8400
gaaaatgaag tgtgtccggt atttgccgca cgcaccacta gtgcgttaca gatcaatgat 8460
gatgaagtga tggattatca atggtgtgat ttagcagatg tattacacgg tattgatgcc 8520
acgccgtggg cgttcagtcc gtggatggtg atgcaggcga caaatcgcga agccagaaaa 8580
cgattatctg catttaccca gcttaaataa gcatgcacta gagtcgagga aacagaccat 8640
ggagttgaaa acagtagtta ttattgatgc attacgaaca ccaattggaa aatataaagg 8700
cagcttaagt caagtaagtg ccgtagactt aggaacacat gttacaacac aacttttaaa 8760
aagacattcc actatttctg aagaaattga tcaagtaatc tttggaaatg ttttacaagc 8820
tggaaatggc caaaatcccg cacgacaaat agcaataaac agcggtttat ctcatgaaat 8880
tcccgcaatg acagttaatg aggtctgcgg atcaggaatg aaggccgtta ttttggcgaa 8940
acaattgatt caattaggag aagcggaagt tttaattgct ggcgggattg agaatatgtc 9000
ccaagcacct aaattacaac gatttaatta cgaaacagaa agctatgatg cgcctttttc 9060
tagtatgatg tacgatgggt t 9081

<210> SEQ ID NO 81
<211> LENGTH: 8230
<212> TYPE: DNA
<213> ORGANISM: Artificial Sequence
<220> FEATURE:
<223> OTHER INFORMATION: pSNA(-E)free

<400> SEQUENCE: 81
tttttttaag gcagttattg gtgcccttaa acgcctggtg ctacgcctga ataagtgata 60
ataagcggat gaatggcaga aattcgaaag caaattcgac ccggtcgtcg gttcagggca 120
gggtcgttaa atagccgctt atgtctattg ctggtttacc ggtttattga ctaccggaag 180
cagtgtgacc gtgtgcttct caaatgcctg aggccagttt gctcaggctc tccccgtgga 240
ggtaataatt gacgatatga tcatttattc tgcctcccag agcctgataa aaacggttag 300
cgcttcgtta atacagatgt aggtgttcca cagggtagcc agcagcatcc tgcgatgcag 360
atccggaaca taatggtgca gggcgcttgt ttcggcgtgg gtatggtggc aggccccgtg 420
gccgggggac tgttgggcgc tgccggcacc tgtcctacga gttgcatgat aaagaagaca 480
gtcataagtg cggcgacgat agtcatgccc cgcgcccacc ggaaggagct accggacagc 540
ggtgcggact gttgtaactc agaataagaa atgaggccgc tcatggcgtt ccaatacgca 600
aaccgcctct ccccgcgcgt tggccgattc attaatgcag ctggcacgac aggtttcccg 660
actggaaagc gggcagtgag cgcaacgcaa ttaatgtgag ttagctcact cattaggcac 720
cccaggcttt acactttatg cttccggctc gtatgttgtg tggaattgtg agcggataac 780
aatttcacac aggaaacagc tatgaccatg attacgaatt cgagctcggt acccggggat 840
cctacctgac gctttttatc gcaactctct actgtttctc catacccgtt tttttgggct 900
agcaggagga attcaccatg gtaccaatga caaaaaaagt tggtgtcggt caggcacata 960

-continued

```
gtaagataat tttaataggg gaacatgcgg tcgtttacgg ttatcctgcc atttccctgc   1020
ctcttttgga ggtggaggtg acctgtaagg tagttcctgc agagagtcct tggcgccttt   1080
atgaggagga taccttgtcc atggcggttt atgcctcact ggagtatttg aatatcacag   1140
aagcctgcat tcgttgtgag attgactcgg ctatccctga gaaacggggg atgggttcgt   1200
cagcggctat cagcatagcg gccattcgtg cagtatttga ctactatcag gctgatctgc   1260
ctcatgatgt actagaaatc ttggtcaatc gagctgaaat gattgcccat atgaatccta   1320
gtggtttgga tgctaagacc tgtcttagtg accaacctat tcgctttatc aagaacgtag   1380
gatttacaga acttgagatg gatttatccg cctatttggt gattgccgat acgggtgttt   1440
atggtcatac tcgtgaagcc atccaagtgg ttcaaaataa gggcaaggat gccctaccgt   1500
ttttgcatgc cttgggagaa ttaacccagc aagcagaagt tgcgatttca caaaaagatg   1560
ctgaaggact gggacaaatc ctcagtcaag cgcatttaca tttaaaagaa attggagtca   1620
gtagccctga ggcagacttt ttggttgaaa cgactcttag ccatggtgct ctgggtgcca   1680
agatgagcgg tggtgggcta ggaggttgta tcatagcctt ggtaaccaat ttgacacacg   1740
cacaagaact agcagaaaga ttagaagaga aaggagctgt tcagacatgg atagagagcc   1800
tgtaacagta cgttcctacg caaatattgc tattatcaaa tattggggaa agaaaaaaga   1860
aaaagagatg gtgcctgcta ctagcagtat ttctctaact ttggaaaata tgtatacaga   1920
gacgaccttg tcgcctttac cagccaatgt aacagctgac gaattttaca tcaatggtca   1980
gctacaaaat gaggtcgagc atgccaagat gagtaagatt attgaccgtt atcgtccagc   2040
tggtgagggc tttgtccgta tcgatactca aaacaatatg cctacggcag cgggcctgtc   2100
ctcaagttct agtggtttgt ccgccctggt caaggcttgt aatgcttatt tcaagcttgg   2160
attggataga agtcagttgg cacaggaagc caaatttgcc tcaggctctt cttctcggag   2220
tttttatgga ccactaggag cctgggataa ggatagtgga gaaatttacc ctgtagagac   2280
agacttgaaa ctagctatga ttatgttggt gctagaggac aagaaaaaac caatctctag   2340
ccgtgacggg atgaaacttt gtgtggaaac ctcgacgact tttgacgact gggttcgtca   2400
gtctgagaag gactatcagg atatgctgat ttatctcaag gaaaatgatt ttgccaagat   2460
tggagaatta acggagaaaa atgctctggc tatgcatgct acgacaaaga ctgctagtcc   2520
agccttttct tatctgacgg atgcctctta tgaggctatg gcctttgttc gccagcttcg   2580
tgagaaagga gaggcctgct actttaccat ggatgctggt cccaatgtta aggtcttctg   2640
tcaggagaaa gacttggagc atttgtcaga aattttcggt cagcgttatc gcttgattgt   2700
gtcaaaaaca aaggatttga gtcaagatga ttgctgttaa aacttgcgga aaactctatt   2760
gggcaggtga atatgctatt ttagagccag ggcagttagc tttgataaag gatattccca   2820
tctatatgag ggctgagatt gctttttctg acagctaccg tatctattca gatatgtttg   2880
atttcgcagt ggacttaagg cccaatcctg actacagctt gattcaagaa acgattgctt   2940
tgatgggaga cttcctcgct gttcgcggtc agaatttaag acctttttcc ctaaaaatct   3000
gtggcaaaat ggaacgagaa gggaaaaagt ttggtctagg ttctagtggc agcgtcgttg   3060
tcttggttgt caaggcttta ctggctctct ataatctttc ggttgatcag aatctcttgt   3120
tcaagctgac tagcgctgtc ttgctcaagc gaggagacaa tggttccatg ggcgaccttg   3180
cctgtattgt ggcagaggat ttggttcttt accagtcatt tgatcgccag aaggcggctg   3240
cttggttaga agaagaaaac ttggcgacag ttctggagcg tgattgggga tttttttatct  3300
cacaagtgaa accaacttta gaatgtgatt tcttagtggg atggaccaag gaagtggctg   3360
```

```
tatcgagtca catggtccag caaatcaagc aaaatatcaa tcaaaatttt ttaagttcct   3420
caaaagaaac ggtggtttct ttggtcgaag ccttggagca ggggaaagcc gaaaaagtta   3480
tcgagcaagt agaagtagcc agcaagcttt tagaaggctt gagtacagat atttacacgc   3540
ctttgcttag acagttgaaa gaagccagtc aagatttgca ggccgttgcc aagagtagtg   3600
gtgctggtgg tggtgactgt ggcatcgccc tgagttttga tgcgcaatct tctcgaaaca   3660
ctttaaaaaa tcgttgggcc gatctgggga ttgagctctt atatcaagaa aggataggac   3720
atgacgacaa atcgtaatct agccccggga ggagagaaat tatgcaaacg gaacacgtca   3780
ttttattgaa tgcacaggga gttcccacgg gtacgctgga aaagtatgcc gcacacacgg   3840
cagacacccg cttacatctc gcgttctcca gttggctgtt taatgccaaa ggacaattat   3900
tagttacccg ccgcgcactg agcaaaaaag catggcctgg cgtgtggact aactcggttt   3960
gtgggcaccc acaactggga gaaagcaacg aagacgcagt gatccgccgt tgccgttatg   4020
agcttggcgt ggaaattacg cctcctgaat ctatctatcc tgactttcgc taccgcgcca   4080
ccgatccgag tggcattgtg gaaaatgaag tgtgtccggt atttgccgca cgcaccacta   4140
gtgcgttaca gatcaatgat gatgaagtga tggattatca atggtgtgat ttagcagatg   4200
tattacacgg tattgatgcc acgccgtggg cgttcagtcc gtggatggtg atgcaggcga   4260
caaatcgcga agccagaaaa cgattatctg catttaccca gcttaaataa gcatgcacta   4320
gagtcgagga aacagaccat ggagttgaaa acagtagtta ttattgatgc attacgaaca   4380
ccaattggaa aatataaagg cagcttaagt caagtaagtg ccgtagactt aggaacacat   4440
gttacaacac aacttttaaa aagacattcc actatttctg aagaaattga tcaagtaatc   4500
tttggaaatg ttttacaagc tggaaatggc caaaatcccg cacgacaaat agcaataaac   4560
agcggtttat ctcatgaaat tcccgcaatg acagttaatg aggtctgcgg atcaggaatg   4620
aaggccgtta ttttggcgaa acaattgatt caattaggag aagcggaagt tttaattgct   4680
ggcgggattg agaatatgtc ccaagcacct aaattacaac gatttaatta cgaaacagaa   4740
agctatgatg cgcctttttc tagtatgatg tacgatgggt taacgctatg ttggaaggtg   4800
tggccgagtt gttccgtgaa tggtttgcgg agcaaaagat tttattcagt attttaagta   4860
attatgccac ggagtcggtt gttacgatga aaacggctat tccagtttca cgtttaagta   4920
aggggagcaa tggccgggaa attgctgaaa aaattgtttt agcttcacgc tatgcttcat   4980
tagatcctta tcgggcagtc acgcataaca aagggatcat gaatggcatt gaagctgtcg   5040
ttttagctac aggaaatgat acacgcgctg ttagcgcttc ttgtcatgct tttgcggtga   5100
aggaaggtcg ctaccaaggt ttgactagtt ggacgctgga tggcgaacaa ctaattggtg   5160
aaatttcagt tccgcttgcg ttagccacgg ttggcggtgc cacaaaagtc ttacctaaat   5220
ctcaagcagc tgctgatttg ttagcagtga cggatgcaaa agaactaagt cgagtagtag   5280
cggctgttgg tttggcacaa aatttagcgg cgttacgggc cttagtctct gaaggaattc   5340
aaaaaggaca catggctcta caagcacgtt ctttagcgat gacggtcgga gctactggta   5400
aagaagttga ggcagtcgct caacaattaa aacgtcaaaa aacgatgaac caagaccgag   5460
ccttggctat tttaaatgat ttaagaaaac aataaaaaaa cagttcagca gaaattattc   5520
tgctgaactg ttttttttca cattaggtag ccgtttcagg ccacgagctc aggagttaaa   5580
gaaatgacaa ttgggattga taaaattagt ttttttgtgc cccttatta tattgatatg   5640
acggcactgg ctgaagccag aaatgtagac cctggaaaat ttcatattgg tattgggcaa   5700
```

-continued

```
gaccaaatgg cggtgaaccc aatcagccaa gatattgtga catttgcagc caatgccgca   5760
gaagcgatct tgaccaaaga agataaagag gccattgata tggtgattgt cgggactgag   5820
tccagtatcg atgagtcaaa agcggccgca gttgtcttac atcgtttaat ggggattcaa   5880
cctttcgctc gctctttcga aatcaaggaa gcttgttacg gagcaacagc aggcttacag   5940
ttagctaaga atcacgtagc cttacatcca gataaaaaag tcttggttgt agcagcagat   6000
attgcaaaat atggattaaa ttctggcggt gagcctacac aaggagctgg ggcggttgca   6060
atgttagttg ctagtgaacc gcgcatcttg gctttaaaag aggataatgt gatgctgacg   6120
caagatatct atgacttttg gcgtccaaca ggccatccgt atcctatggt cgatggtcct   6180
ttgtcaaacg aaacctacat ccaatctttt gcccaagtct gggatgaaca taaaaaaaga   6240
accggtcttg attttgcaga ttatgatgct ttagcgttcc atattcctta cacaaaaatg   6300
ggcaaaaaag ccttattagc aaaaatctcc gaccaaactg aagcagaaca ggaacgaatt   6360
ttagcccgtt atgaagaaag catcatctat agtcgtcgcg taggaaactt gtatacgggt   6420
tcactttatc tgggactcat ttccctttta gaaaatgcaa cgactttaac cgcaggcaat   6480
caaattgggt tattcagtta tggttctggt gctgtcgctg aatttttcac tggtgaatta   6540
gtagctggtt atcaaaatca tttacaaaaa gaaactcatt tagcactgct agataatcgg   6600
acagaacttt ctatcgctga atatgaagcc atgtttgcag aaactttaga cacagatatt   6660
gatcaaacgt tagaagatga attaaaatat agtatttctg ctattaataa taccgttcgc   6720
tcttatcgaa actaactgca gcctcgacct gcaggcatgc aagcttggca ctggccgtcg   6780
ttttacaacg tcgtgactgg gaaaaccctg gcgttaccca acttaatcgc cttgcagcac   6840
atcccccttt cgccagctgg cgtaatagcg aagaggcccg caccgatcgc ccttcccaac   6900
agttgcgcag cctgaatggc gaatgagctt atcgatgata agctgtcaaa catgagaatt   6960
acaacttata tcgtatgggg ctgacttcag gtgctacatt tgaagagata aattgcactg   7020
aaatctagaa atattttatc tgattaataa gatgatcttc ttgagatcgt tttggtctgc   7080
gcgtaatctc ttgctctgaa aacgaaaaaa ccgccttgca gggcggtttt tcgaaggttc   7140
tctgagctac caactctttg aaccgaggta actggcttgg aggagcgcag tcaccaaaac   7200
ttgtcctttc agtttagcct taaccggcgc atgacttcaa gactaactcc tctaaatcaa   7260
ttaccagtgg ctgctgccag tggtgctttt gcatgtcttt ccgggttgga ctcaagacga   7320
tagttaccgg ataaggcgca gcggtcggac tgaacggggg gttcgtgcat acagtccagc   7380
ttggagcgaa ctgcctaccc ggaactgagt gtcaggcgtg gaatgagaca aacgcggcca   7440
taacagcgga atgacaccgg taaaccgaaa ggcaggaaca ggagagcgca cgagggagcc   7500
gccaggggaa acgcctggta tctttatagt cctgtcgggt ttcgccacca ctgatttgag   7560
cgtcagattt cgtgatgctt gtcagggggg cggagcctat ggaaaaacgg ctttgccgcg   7620
gccctctcac ttccctgtta agtatcttcc tggcatcttc caggaaatct ccgccccgtt   7680
cgtaagccat ttccgctcgc cgcagtcgaa cgaccgagcg tagcgagtca gtgagcgagg   7740
aagcggaata tatcctgtat cacatattct gctgacgcac cggtgcagcc tttttctcc    7800
tgccacatga agcacttcac tgacaccctc atcagtgcca acatagtaag ccagtataca   7860
ctccgctagc gctgatgtcc ggcggtgctt ttgccgttac gcaccacccc gtcagtagct   7920
gaacaggagg gacagctgat agaaacagaa gccactggag cacctcaaaa acaccatcat   7980
acactaaatc agtaagttgg cagcatcacc cgacgcactt tgcgccgaat aaatacctgt   8040
gacggaagat cacttcgcag aataaataaa tcctggtgtc cctgttgata ccgggaagcc   8100
```

ctgggccaac ttttggcgaa aatgagacgt tgatcggcac gtaagaggtt ccaactttca 8160
ccataatgaa ataagatcac taccgggcgt attttttgag ttatcgagat tttcaggagc 8220
taaggaagct 8230

<210> SEQ ID NO 82
<211> LENGTH: 6678
<212> TYPE: DNA
<213> ORGANISM: Artificial Sequence
<220> FEATURE:
<223> OTHER INFORMATION: pTEFAmvaE

<400> SEQUENCE: 82
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagaccatgg ggctgcagga attcgatgcc atggagttga 300
aaacagtagt tattattgat gcattacgaa caccaattgg aaaatataaa ggcagcttaa 360
gtcaagtaag tgccgtagac ttaggaacac atgttacaac acaactttta aaaagacatt 420
ccactatttc tgaagaaatt gatcaagtaa tctttggaaa tgttttacaa gctggaaatg 480
gccaaaatcc cgcacgacaa atagcaataa acagcggttt gtctcatgaa attcccgcaa 540
tgacggttaa tgaggtctgc ggatcaggaa tgaaggccgt tattttggcg aaacaattga 600
ttcaattagg agaagcggaa gttttaattg ctggcgggat tgagaatatg tcccaagcac 660
ctaaattaca acgttttaat tacgaaacag aaagctacga tgcgcctttt tctagtatga 720
tgtatgatgg attaacggat gcctttagtg gtcaggcaat gggcttaact gctgaaaatg 780
tggccgaaaa gtatcatgta actagagaag agcaagatca attttctgta cattcacaat 840
taaaagcagc tcaagcacaa gcagaaggga tattcgctga cgaaatagcc ccattagaag 900
tatcaggaac gcttgtggag aaagatgaag ggattcgccc taattcgagc gttgagaagc 960
taggaacgct taaaacagtt tttaaagaag acggtactgt aacagcaggg aatgcatcaa 1020
ccattaatga tggggcttct gctttgatta ttgcttcaca agaatatgcc gaagcacacg 1080
gtcttcctta tttagctatt attcgagaca gtgtggaagt cggtattgat ccagcctata 1140
tgggaatttc gccgattaaa gccattcaaa aactgttagc gcgcaatcaa cttactacgg 1200
aagaaattga tctgtatgaa atcaacgaag catttgcagc aacttcaatc gtggtccaaa 1260
gagaactggc tttaccagag gaaaaggtca acatttatgg tggcggtatt tcattaggtc 1320
atgcgattgg tgccacaggt gctcgtttat taacgagttt aagttatcaa ttaaatcaaa 1380
aagaaaagaa atatggagtg gcttctttat gtatcggcgg tggcttagga ctcgctatgc 1440
tactagagag acctcagcaa aaaaaaaaca gccgatttta tcaaatgagt cctgaggaac 1500
gcctggcttc tcttcttaat gaaggccaga tttctgctga tacaaaaaaa gaatttgaaa 1560
atacggcttt atcttcgcag attgccaatc atatgattga aaatcaaatc agtgaaacag 1620
aagtgccgat gggcgttggc ttacatttaa cagtggacga aactgattat ttggtaccaa 1680
tggcgacaga agagccctca gttattgcgg ctttgagtaa tggtgcaaaa atagcacaag 1740
gatttaaaac agtgaatcaa caacgcttaa tgcgtggaca aatcgttttt tacgatgttg 1800
cagatcccga gtcattgatt gataaactac aagtaagaga agcggaagtt tttcaacaag 1860

-continued

```
cagagttaag ttatccatct atcgttaaac ggggcggcgg cttaagagat ttgcaatatc   1920
gtacttttga tgaatcattt gtatctgtcg actttttagt agatgttaag gatgcaatgg   1980
gggcaaatat cgttaacgct atgttggaag gtgtggccga gttgttccgt gaatggtttg   2040
cggagcaaaa gattttattc agtattttaa gtaattatgc cacggagtcg gttgttacga   2100
tgaaaacggc tattccagtt tcacgtttaa gtaaggggag caatggccgg gaaattgctg   2160
aaaaaattgt tttagcttca cgctatgctt cattagatcc ttatcgggca gtcacgcata   2220
acaaaggaat catgaatggc attgaagctg tagttttagc tacaggaaat gatacacgcg   2280
ctgttagcgc ttcttgtcat gcttttgcgg tgaaggaagg tcgctaccaa ggcttgacta   2340
gttggacgct ggatggcgaa caactaattg gtgaaatttc agttccgctt gctttagcca   2400
cggttggcgg tgccacaaaa gtcttaccta aatctcaagc agctgctgat ttgttagcag   2460
tgacggatgc aaaagaacta agtcgagtag tagcggctgt tggtttggca caaaatttag   2520
cggcgttacg ggccttagtc tctgaaggaa ttcaaaaagg acacatggct ctacaagcac   2580
gttctttagc gatgacggtc ggagctactg gtaaagaagt tgaggcagtc gctcaacaat   2640
taaaacgtca aaaaacgatg aaccaagacc gagccatggc tattttaaat gatttaagaa   2700
aacaataaaa aaacagttca gcagaaatta ttctgctgaa ctattttttt tcacattagg   2760
tagccgtttc aggccacgag ctcggtaccc ggggatcctc tagagtcgac ctgcaggcat   2820
gcaagcttgg ctgttttggc ggatgagaga agattttcag cctgatacag attaaatcag   2880
aacgcagaag cggtctgata aaacagaatt tgcctggcgg cagtagcgcg gtggtcccac   2940
ctgaccccat gccgaactca gaagtgaaac gccgtagcgc cgatggtagt gtggggtctc   3000
cccatgcgag agtagggaac tgccaggcat caaataaaac gaaaggctca gtcgaaagac   3060
tgggcctttc gttttatctg ttgtttgtcg gtgaacgctc tcctgagtag gacaaatccg   3120
ccgggagcgg atttgaacgt tgcgaagcaa cggcccggag ggtggcgggc aggacgcccg   3180
ccataaactg ccaggcatca aattaagcag aaggccatcc tgacggatgg cctttttgcg   3240
tttctacaaa ctctttttgt ttatttttct aaatacattc aaatatgtat ccgctcatga   3300
gacaataacc ctgataaatg cttcaataat attgaaaaag gaagagtatg agtattcaac   3360
atttccgtgt cgcccttatt cccttttttg cggcattttg ccttcctgtt tttgctcacc   3420
cagaaacgct ggtgaaagta aaagatgctg aagatcagtt gggtgcacga gtgggttaca   3480
tcgaactgga tctcaacagc ggtaagatcc ttgagagttt tcgccccgaa gaacgttttc   3540
caatgatgag cacttttaaa gttctgctat gtggcgcggt attatcccgt gttgacgccg   3600
ggcaagagca actcggtcgc cgcatacact attctcagaa tgacttggtt gagtactcac   3660
cagtcacaga aaagcatctt acggatggca tgacagtaag agaattatgc agtgctgcca   3720
taaccatgag tgataacact gcggccaact tacttctgac aacgatcgga ggaccgaagg   3780
agctaaccgc ttttttgcac aacatggggg atcatgtaac tcgccttgat cgttgggaac   3840
cggagctgaa tgaagccata ccaaacgacg agcgtgacac cacgatgcct acagcaatgg   3900
caacaacgtt gcgcaaacta ttaactggcg aactacttac tctagcttcc cggcaacaat   3960
taatagactg gatggaggcg gataaagttg caggaccact tctgcgctcg gcccttccgg   4020
ctggctggtt tattgctgat aaatctggag ccggtgagcg tgggtctcgc ggtatcattg   4080
cagcactggg gccagatggt aagccctccc gtatcgtagt tatctacacg acggggagtc   4140
aggcaactat ggatgaacga aatagacaga tcgctgagat aggtgcctca ctgattaagc   4200
attggtaact gtcagaccaa gtttactcat atatacttta gattgattta aaacttcatt   4260
```

```
tttaatttaa aaggatctag gtgaagatcc tttttgataa tctcatgacc aaaatccctt   4320
aacgtgagtt ttcgttccac tgagcgtcag accccgtaga aaagatcaaa ggatcttctt   4380
gagatccttt ttttctgcgc gtaatctgct gcttgcaaac aaaaaaacca ccgctaccag   4440
cggtggtttg tttgccggat caagagctac caactctttt tccgaaggta actggcttca   4500
gcagagcgca gataccaaat actgtccttc tagtgtagcc gtagttaggc caccacttca   4560
agaactctgt agcaccgcct acatacctcg ctctgctaat cctgttacca gtggctgctg   4620
ccagtggcga taagtcgtgt cttaccgggt tggactcaag acgatagtta ccggataagg   4680
cgcagcggtc gggctgaacg gggggttcgt gcacacagcc cagcttggag cgaacgacct   4740
acaccgaact gagataccta cagcgtgagc tatgagaaag cgccacgctt cccgaaggga   4800
gaaaggcgga caggtatccg gtaagcggca gggtcggaac aggagagcgc acgagggagc   4860
ttccaggggg aaacgcctgg tatctttata gtcctgtcgg gtttcgccac ctctgacttg   4920
agcgtcgatt tttgtgatgc tcgtcagggg ggcggagcct atggaaaaac gccagcaacg   4980
cggccttttt acggttcctg gccttttgct ggccttttgc tcacatgttc tttcctgcgt   5040
tatcccctga ttctgtggat aaccgtatta ccgcctttga gtgagctgat accgctcgcc   5100
gcagccgaac gaccgagcgc agcgagtcag tgagcgagga agcggaagag cgcctgatgc   5160
ggtattttct ccttacgcat ctgtgcggta tttcacaccg catatggtgc actctcagta   5220
caatctgctc tgatgccgca tagttaagcc agtatacact ccgctatcgc tacgtgactg   5280
ggtcatggct gcgccccgac acccgccaac acccgctgac gcgccctgac gggcttgtct   5340
gctcccggca tccgcttaca gacaagctgt gaccgtctcc gggagctgca tgtgtcagag   5400
gttttcaccg tcatcaccga aacgcgcgag gcagcagatc aattcgcgcg cgaaggcgaa   5460
gcggcatgca tttacgttga caccatcgaa tggtgcaaaa cctttcgcgg tatggcatga   5520
tagcgcccgg aagagagtca attcagggtg gtgaatgtga aaccagtaac gttatacgat   5580
gtcgcagagt atgccggtgt ctcttatcag accgtttccc gcgtggtgaa ccaggccagc   5640
cacgtttctg cgaaaacgcg ggaaaaagtg gaagcggcga tggcggagct gaattacatt   5700
cccaaccgcg tggcacaaca actggcgggc aaacagtcgt tgctgattgg cgttgccacc   5760
tccagtctgg ccctgcacgc gccgtcgcaa attgtcgcgg cgattaaatc tcgcgccgat   5820
caactgggtg ccagcgtggt ggtgtcgatg gtagaacgaa gcggcgtcga agcctgtaaa   5880
gcggcggtgc acaatcttct cgcgcaacgc gtcagtgggc tgatcattaa ctatccgctg   5940
gatgaccagg atgccattgc tgtggaagct gcctgcacta atgttccggc gttatttctt   6000
gatgtctctg accagacacc catcaacagt attattttct cccatgaaga cggtacgcga   6060
ctgggcgtgg agcatctggt cgcattgggt caccagcaaa tcgcgctgtt agcgggccca   6120
ttaagttctg tctcggcgcg tctgcgtctg gctggctggc ataaatatct cactcgcaat   6180
caaattcagc cgatagcgga acgggaaggc gactggagtg ccatgtccgg ttttcaacaa   6240
accatgcaaa tgctgaatga gggcatcgtt cccactgcga tgctggttgc caacgatcag   6300
atggcgctgg gcgcaatgcg cgccattacc gagtccgggc tgcgcgttgg tgcggatatc   6360
tcggtagtgg gatacgacga taccgaagac agctcatgtt atatcccgcc gttaaccacc   6420
atcaaacagg attttcgcct gctggggcaa accagcgtgg accgcttgct gcaactctct   6480
cagggccagg cggtgaaggg caatcagctg ttgcccgtct cactggtgaa aagaaaaacc   6540
accctggcgc ccaatacgca aaccgcctct ccccgcgcgt tggccgattc attaatgcag   6600
```

-continued ctggcacgac aggtttcccg actggaaagc gggcagtgag cgcaacgcaa ttaatgtgag 6660
ttagcgcgaa ttgatctg 6678

<210> SEQ ID NO 83
<211> LENGTH: 13288
<212> TYPE: DNA
<213> ORGANISM: Artificial Sequence
<220> FEATURE:
<223> OTHER INFORMATION: pT-DHBSRYbbO

<400> SEQUENCE: 83
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagaccatgg aattctacgt actagtgaat tcaggaggta 300
ataaatatgg gtctgatgct gattgattgg tgtgcactgg ctctggttgt tttcattggc 360
ctgccgcacg gcgcgctgga tgctgccatt tctttttcta tgatctcttc tgcaaaacgc 420
attgctcgtc tggctggtat tctgctgatc tatctgctgc tggcgaccgc gttcttcctg 480
atctggtatc agctgccagc gtttagcctg ctgatcttcc tgctgatctc cattatccac 540
tttggtatgg cagacttcaa cgcgtcccca agcaaactga aatggccgca tatcatcgcc 600
cacggcggtg ttgttactgt ttggctgccg ctgatccaga aaaacgaagt aactaaactg 660
tttagcatcc tgactaacgg tccgactccg atcctgtggg acatcctgct gatttcttc 720 ctgtgttggt ctattggcgt gtgtctgcac acgtacgaaa ccctgcgctc taaacattac 780
aacatcgcct ttgaactgat cggtctgatt ttcctggcgt ggtatgcgcc gcctctggtt 840
acgtttgcca cttacttctg cttcattcat tcccgtcgcc acttctcctt tgtgtggaag 900
cagctgcaac acatgtcttc caaaaagatg atgattggca gcgcgattat cctgtcctgt 960
acctcttggc tgatcggcgg tggtatctat ttcttcctga actccaaaat gatcgcctct 1020
gaggctgcgc tgcagactgt gttcatcggt ctggcggcac tgaccgtgcc gcacatgatt 1080
ctgatcgact tcatcttccg tccgcactct tcccgtatca aatcaaaaa ctaattaatt 1140 aaaggaggta ataatatgac tcataaagca acggagatcc tgacaggtaa agttatgcaa 1200
aaatcggtct taattaccgg atgttccagt ggaattggcc tggaaagcgc gctcgaatta 1260
aaacgccagg gttttcatgt gctggcaggt tgccggaaac cggatgatgt tgagcgcatg 1320
aacagcatgg gatttaccgg cgtgttgatc gatctggatt caccagaaag tgttgatcgc 1380
gcagccgacg aggtgatcgc cctgaccgat aattgtctgt atgggatctt taacaatgcc 1440
ggattcggca tgtatggccc cctttccacc atcagccgtg cgcagatgga acagcagttt 1500
tccgccaact ttttcggcgc acaccagctc accatgcgcc tgttacccgc gatgttaccg 1560
cacggtgaag ggcgtattgt gatgacatca tcggtgatgg gattaatctc cacgccgggt 1620
cgtggcgctt acgcggccag taaatatgcg ctggaggcgt ggtcagatgc actgcgcatg 1680
gagctgcgcc acagcggaat taaagtcagc ctgatcgaac ccggtcccat tcgtactcgc 1740
ttcaccgaca acgtcaacca gacgcaaagt gataaaccag tcgaaaatcc cggcatcgcc 1800
gcccgcttta cgttgggacc ggaagcggtg gtggacaaag tacgccatgc ttttattagc 1860
gagaagccga agatgcgcta tccggtgacg ctggtgacct gggcggtaat ggtgcttaag 1920
cgcctgctgc cggggcgcgt gatggacaaa atattgcagg ggtaactagt aggaggtaat 1980

```
aaatatggtg agtggcagta aagcgggcgt ttcgcctcat cgcgaaatag aagtaatgag   2040
acaatccatt gacgatcacc tggctggcct gttacctgaa accgacagcc aggatatcgt   2100
cagccttgcg atgcgtgaag gcgtcatggc acccggtaaa cggatccgtc cgctgctgat   2160
gctgctggcc gcccgcgacc tccgctacca gggcagtatg cctacgctgc tcgatctcgc   2220
ctgcgccgtt gaactgaccc ataccgcgtc gctgatgctc gacgacatgc cctgcatgga   2280
caacgccgag ctgcgccgcg gtcagcccac tacccacaaa aaatttggtg agagcgtggc   2340
gatccttgcc tccgttgggc tgctctctaa agcctttggt ctgatcgccg ccaccggcga   2400
tctgccgggg gagaggcgtg cccaggcggt caacgagctc tctaccgccg tgggcgtgca   2460
gggcctggta ctggggcagt ttcgcgatct taacgatgcc gccctcgacc gtacccctga   2520
cgctatcctc agcaccaacc acctcaagac cggcattctg ttcagcgcga tgctgcagat   2580
cgtcgccatt gcttccgcct cgtcgccgag cacgcgagag acgctgcacg ccttcgccct   2640
cgacttcggc caggcgtttc aactgctgga cgatctgcgt gacgatcacc cggaaaccgg   2700
taaagatcgc aataaggacg cgggaaaatc gacgctggtc aaccggctgg gcgcagacgc   2760
ggcccggcaa aagctgcgcg agcatattga ttccgccgac aaacacctca cttttgcctg   2820
tccgcagggc ggcgccatcc gacagtttat gcatctgtgg tttggccatc accttgccga   2880
ctggtcaccg gtcatgaaaa tcgcctgata actcgaggag gtataaagga tgaaaaaaac   2940
cgttgtgatt ggcgcaggct ttggtggcct ggcgctggcg attcgcctgc aggcggcagg   3000
gatcccaacc gtactgctgg agcagcggga caagcccggc ggtcgggcct acgtctggca   3060
tgaccagggc tttacctttg acgccgggcc gacggtgatc accgatccta ccgcgcttga   3120
ggcgctgttc accctggccg gcaggcgcat ggaggattac gtcaggctgc tgccggtaaa   3180
acccttctac cgactctgct gggagtccgg gaagaccctc gactatgcta acgacagcgc   3240
cgagcttgag gcgcagatta cccagttcaa cccccgcgac gtcgagggct accggcgctt   3300
tctggcttac tcccaggcgg tattccagga gggatatttg cgcctcggca gcgtgccgtt   3360
cctctctttt cgcgacatgc tgcgcgccgg gccgcagctg cttaagctcc aggcgtggca   3420
gagcgtctac cagtcggttt cgcgctttat tgaggatgag catctgcggc aggccttctc   3480
gttccactcc ctgctggtag gcggcaaccc cttcaccacc tcgtccatct acaccctgat   3540
ccacgccctt gagcgggagt ggggggtctg gttccctgag ggcggcaccg gggcgctggt   3600
gaacggcatg gtgaagctgt ttaccgatct gggcggggag atcgaactca acgcccgggt   3660
cgaagagctg gtggtggccg ataaccgcgt aagccaggtc cggctggcgg atggtcggat   3720
ctttgacacc gacgccgtag cctcgaacgc tgacgtggtg aacacctata aaaagctgct   3780
cggccaccat ccggtggggc agaagcgggc ggcagcgctg gagcgcaaga gcatgagcaa   3840
ctcgctgttt gtgctctact tcggcctgaa ccagcctcat tcccagctgg cgcaccatac   3900
catctgtttt ggtccccgct accgggagct gatcgacgag atctttaccg gcagcgcgct   3960
ggcggatgac ttctcgctct acctgcactc gccctgcgtg accgatccct cgctcgcgcc   4020
tcccggctgc gccagcttct acgtgctggc cccggtgccg catcttggca acgcgccgct   4080
ggactgggcg caggaggggc cgaagctgcg cgaccgcatc tttgactacc ttgaagagcg   4140
ctatatgccc ggcctgcgta gccagctggt gacccagcgg atctttaccc cggcagactt   4200
ccacgacacg ctggatgcgc atctgggatc ggccttctcc atcgagccgc tgctgaccca   4260
aagcgcctgg ttccgcccgc acaaccgcga cagcgacatt gccaacctct acctggtggg   4320
```

-continued

```
cgcaggtact caccctgggg cgggcattcc tggcgtagtg gcctcggcga aagccaccgc   4380
cagcctgatg attgaggatc tgcaatgagc caaccgccgc tgcttgacca cgccacgcag   4440
accatggcca acggctcgaa aagttttgcc accgctgcga agctgttcga cccggccacc   4500
cgccgtagcg tgctgatgct ctacacctgg tgccgccact gcgatgacgt cattgacgac   4560
cagacccacg gcttcgccag cgaggccgcg gcggaggagg aggccaccca gcgcctggcc   4620
cggctgcgca cgctgaccct ggcggcgttt gaaggggccg agatgcagga tccggccttc   4680
gctgcctttc aggaggtggc gctgacccac ggtattacgc cccgcatggc gctcgatcac   4740
ctcgacggct ttgcgatgga cgtggctcag acccgctatg tcacctttga ggatacgctg   4800
cgctactgct atcacgtggc gggcgtggtg ggtctgatga tggccagggt gatgggcgtg   4860
cgggatgagc gggtgctgga tcgcgcctgc gatctggggc tggccttcca gctgacgaat   4920
atcgcccggg atattattga cgatgcggct attgaccgct gctatctgcc cgccgagtgg   4980
ctgcaggatg ccgggctgac cccggagaac tatgccgcgc gggagaatcg ggccgcgctg   5040
gcgcgggtgg cggagcggct tattgatgcc gcagagccgt actacatctc ctcccaggcc   5100
gggctacacg atctgccgcc gcgctgcgcc tgggcgatcg ccaccgcccg cagcgtctac   5160
cgggagatcg gtattaaggt aaaagcggcg ggaggcagcg cctgggatcg ccgccagcac   5220
accagcaaag gtgaaaaaat tgccatgctg atggcggcac cggggcaggt tattcgggcg   5280
aagacgacga gggtgacgcc gcgtccggcc ggtctttggc agcgtcccgt ttagtaatct   5340
agaggaggta ataaaatatg cttcgttcgt tgctcagagg cctcacgcat atcccccgcg   5400
tgaactccgc ccagcagccc agctgtgcac acgcgcgact ccagtttaag ctcaggagca   5460
tgcagatgac gctcatgcag cccagcatct cagccaatct gtcgcgcgcc gaggaccgca   5520
cagaccacat gaggggtgca agcacctggg caggcgggca gtcgcaggat gagctgatgc   5580
tgaaggacga gtgcatcttg gtggatgttg aggacaacat cacaggccat gccagcaagc   5640
tggagtgtca caagttccta ccacatcagc ctgcaggcct gctgcaccgg gccttctctg   5700
tgttcctgtt tgacgatcag gggcgactgc tgctgcaaca gcgtgcacgc tcaaaaatca   5760
ccttcccaag tgtgtggacg aacacctgct gcagccaccc tttacatggg cagaccccag   5820
atgaggtgga ccaactaagc caggtggccg acggaacagt acctggcgca aaggctgctg   5880
ccatccgcaa gttggagcac gagctgggga taccagcgca ccagctgccg gcaagcgcgt   5940
ttcgcttcct cacgcgtttg cactactgtg ccgcggacgt gcagccagct gcgacacaat   6000
cagcgctctg ggcgagcac gaaatggact acatcttgtt catccgggcc aacgtcacct   6060
tggcgcccaa ccctgacgag gtggacgaag tcaggtacgt gacgcaagag gagctgcggc   6120
agatgatgca gccggacaac gggctgcaat ggtcgccgtg gtttcgcatc atcgccgcgc   6180
gcttccttga gcgttggtgg gctgacctgg acgcggccct aaacactgac aaacacgagg   6240
attggggaac ggtgcatcac atcaacgaag cgtgataagc ggccgcgtcg acaggaggag   6300
cggctatgca accgcattat gatctgattc tcgtgggggc tggactcgcg aatggcctta   6360
tcgccctgcg tcttcagcag cagcaacctg atatgcgtat tttgcttatc gacgccgcac   6420
cccaggcggg cgggaatcat acgtggtcat ttcaccacga tgatttgact gagagccaac   6480
atcgttggat agctccgctg gtggttcatc actggcccga ctatcaggta cgctttccca   6540
cacgccgtcg taagctgaac agcggctact tttgtattac ttctcagcgt ttcgctgagg   6600
ttttacagcg acagtttggc ccgcacttgt ggatggatac cgcggtcgca gaggttaatg   6660
cggaatctgt tcggttgaaa aagggtcagg ttatcggtgc ccgcgcggtg attgacgggc   6720
```

```
ggggttatgc ggcaaattca gcactgagcg tgggcttcca ggcgtttatt ggccaggaat   6780
ggcgattgag ccacccgcat ggtttatcgt ctcccattat catggatgcc acggtcgatc   6840
agcaaaatgg ttatcgcttc gtgtacagcc tgccgctctc gccgaccaga ttgttaattg   6900
aagacacgca ctatattgat aatgcgacat tagatcctga atgcgcgcgg caaaatattt   6960
gcgactatgc cgcgcaacag ggttggcagc ttcagacact gctgcgagaa gaacagggcg   7020
ccttacccat tactctgtcg ggcaatgccg acgcattctg gcagcagcgc cccctggcct   7080
gtagtggatt acgtgccggt ctgttccatc ctaccaccgg ctattcactg ccgctggcgg   7140
ttgccgtggc cgaccgcctg agtgcacttg atgtctttac gtcggcctca attcaccatg   7200
ccattacgca ttttgcccgc gagcgctggc agcagcaggg ctttttccgc atgctgaatc   7260
gcatgctgtt tttagccgga cccgccgatt cacgctggcg ggttatgcag cgtttttatg   7320
gtttacctga agatttaatt gcccgttttt atgcgggaaa actcacgctg accgatcggc   7380
tacgtattct gagcggcaag ccgcctgttc cggtattagc agcattgcaa gccattatga   7440
cgactcatcg ttaactgcag gcatgcaagc tggggatcct acctgacgct ttttatcgca   7500
actctctact gtttctccat acccgttttt ttgggctagc aggaggaatt caccatggaa   7560
ttcatgagtt ttgatattgc caaataccecg accctggcac tggtcgactc cacccaggag   7620
ttacgactgt tgccgaaaga gagtttaccg aaactctgcg acgaactgcg ccgctattta   7680
ctcgacagcg tgagccgttc cagcgggcac ttcgcctccg ggctgggcac ggtcgaactg   7740
accgtggcgc tgcactatgt ctacaacacc ccgtttgacc aattgatttg ggatgtgggg   7800
catcaggctt atccgcataa aattttgacc ggacgccgcg acaaaatcgg caccatccgt   7860
cagaaaggcg gtctgcaccc gttcccgtgg cgcggcgaaa gcgaatatga cgtattaagc   7920
gtcgggcatt catcaacctc catcagtgcc ggaattggta ttgcggttgc tgccgaaaaa   7980
gaaggcaaaa atcgccgcac cgtctgtgtc attggcgatg gcgcgattac cgcaggcatg   8040
gcgtttgaag cgatgaatca cgcgggcgat atccgtcctg atatgctggt gattctcaac   8100
gacaatgaaa tgtcgatttc cgaaaatgtc ggcgcgctca acaaccatct ggcacagctg   8160
ctttccggta agctttactc ttcactgcgc gaaggcggga aaaaagtttt ctctggcgtg   8220
ccgccaatta aagagctgct caaacgcacc gaagaacata ttaaaggcat ggtagtgcct   8280
ggcacgttgt ttgaagagct gggctttaac tacatcggcc cggtggacgg tcacgatgtg   8340
ctggggctta tcaccacgct aaagaacatg cgcgacctga aaggcccgca gttcctgcat   8400
atcatgacca aaaaaggtcg tggttatgaa ccggcagaaa aagacccgat cactttccac   8460
gccgtgccta aatttgatcc ctccagcggt tgtttgccga aaagtagcgg cggtttgccg   8520
agctattcaa aaatctttgg cgactggttg tgcgaaacgg cagcgaaaga caacaagctg   8580
atggcgatta ctccggcgat gcgtgaaggt tccggcatgg tcgagttttc acgtaaattc   8640
ccggatcgct acttcgacgt ggcaattgcc gagcaacacg cggtgacctt tgctgcgggt   8700
ctggcgattg gtgggtacaa acccattgtc gcgatttact ccactttcct gcaacgcgcc   8760
tatgatcagg tgctgcatga cgtggcgatt caaaagcttc cggtcctgtt cgccatcgac   8820
cgcgcgggca ttgttggtgc tgacggtcaa acccatcagg gtgcttttga tctctcttac   8880
ctgcgctgca taccggaaat ggtcattatg accccgagcg atgaaaacga atgtcgccag   8940
atgctctata ccggctatca ctataacgat ggcccgtcag cggtgcgcta cccgcgtggc   9000
aacgcggtcg gcgtggaact gacgccgctg gaaaaactac caattggcaa aggcattgtg   9060
```

```
aagcgtcgtg gcgagaaact ggcgatcctt aactttggta cgctgatgcc agaagcggcg   9120
aaagtcgccg aatcgctgaa cgccacgctg gtcgatatgc gttttgtgaa accgcttgat   9180
gaagcgttaa ttctggaaat ggccgccagc catgaagcgc tggtcaccgt agaagaaaac   9240
gccattatgg gcggcgcagg cagcggcgtg aacgaagtgc tgatggccca tcgtaaacca   9300
gtacccgtgc tgaacattgg cctgccggac ttctttattc cgcaaggaac tcaggaagaa   9360
atgcgcgccg aactcggcct cgatgccgct ggtatggaag ccaaaatcaa ggcctggctg   9420
gcataaggta cccagcttgg ctgttttggc ggatgagaga agattttcag cctgatacag   9480
attaaatcag aacgcagaag cggtctgata aaacagaatt tgcctggcgg cagtagcgcg   9540
gtggtcccac ctgaccccat gccgaactca gaagtgaaac gccgtagcgc cgatggtagt   9600
gtggggtctc cccatgcgag agtagggaac tgccaggcat caaataaaac gaaaggctca   9660
gtcgaaagac tgggcctttc gttttatctg ttgtttgtcg gtgaacgctc tcctgagtag   9720
gacaaatccg ccgggagcgg atttgaacgt tgcgaagcaa cggcccggag ggtggcgggc   9780
aggacgcccg ccataaactg ccaggcatca aattaagcag aaggccatcc tgacggatgg   9840
cctttttgcg tttctacaaa ctctttttgt ttatttttct aaatacattc aaatatgtat   9900
ccgctcatga gacaataacc ctgataaatg cttcaataat attgaaaaag gaagagtatg   9960
agtattcaac atttccgtgt cgcccttatt cccttttttg cggcattttg ccttcctgtt  10020
tttgctcacc cagaaacgct ggtgaaagta aaagatgctg aagatcagtt gggtgcacga  10080
gtgggttaca tcgaactgga tctcaacagc ggtaagatcc ttgagagttt tcgccccgaa  10140
gaacgttttc caatgatgag cacttttaaa gttctgctat gtggcgcggt attatcccgt  10200
gttgacgccg ggcaagagca actcggtcgc cgcatacact attctcagaa tgacttggtt  10260
gagtactcac cagtcacaga aaagcatctt acggatggca tgacagtaag agaattatgc  10320
agtgctgcca taaccatgag tgataacact gcggccaact tacttctgac aacgatcgga  10380
ggaccgaagg agctaaccgc ttttttgcac aacatggggg atcatgtaac tcgccttgat  10440
cgttgggaac cggagctgaa tgaagccata ccaaacgacg agcgtgacac cacgatgcct  10500
acagcaatgg caacaacgtt gcgcaaacta ttaactggcg aactacttac tctagcttcc  10560
cggcaacaat taatagactg gatggaggcg gataaagttg caggaccact tctgcgctcg  10620
gcccttccgg ctggctggtt tattgctgat aaatctggag ccggtgagcg tgggtctcgc  10680
ggtatcattg cagcactggg gccagatggt aagccctccc gtatcgtagt tatctacacg  10740
acggggagtc aggcaactat ggatgaacga aatagacaga tcgctgagat aggtgcctca  10800
ctgattaagc attggtaact gtcagaccaa gtttactcat atatacttta gattgattta  10860
aaacttcatt tttaatttaa aaggatctag gtgaagatcc tttttgataa tctcatgacc  10920
aaaatccctt aacgtgagtt ttcgttccac tgagcgtcag accccgtaga aaagatcaaa  10980
ggatcttctt gagatccttt ttttctgcgc gtaatctgct gcttgcaaac aaaaaaacca  11040
ccgctaccag cggtggtttg tttgccggat caagagctac caactctttt tccgaaggta  11100
actggcttca gcagagcgca gataccaaat actgtccttc tagtgtagcc gtagttaggc  11160
caccacttca agaactctgt agcaccgcct acatacctcg ctctgctaat cctgttacca  11220
gtggctgctg ccagtggcga taagtcgtgt cttaccgggt tggactcaag acgatagtta  11280
ccggataagg cgcagcggtc gggctgaacg gggggttcgt gcacacagcc cagcttggag  11340
cgaacgacct acaccgaact gagataccta cagcgtgagc tatgagaaag cgccacgctt  11400
cccgaaggga gaaaggcgga caggtatccg gtaagcggca gggtcggaac aggagagcgc  11460
```

```
acgagggagc ttccaggggg aaacgcctgg tatctttata gtcctgtcgg gtttcgccac  11520
ctctgacttg agcgtcgatt tttgtgatgc tcgtcagggg ggcggagcct atggaaaaac  11580
gccagcaacg cggccttttt acggttcctg gccttttgct ggccttttgc tcacatgttc  11640
tttcctgcgt tatcccctga ttctgtggat aaccgtatta ccgcctttga gtgagctgat  11700
accgctcgcc gcagccgaac gaccgagcgc agcgagtcag tgagcgagga agcggaagag  11760
cgcctgatgc ggtattttct ccttacgcat ctgtgcggta tttcacaccg catatggtgc  11820
actctcagta caatctgctc tgatgccgca tagttaagcc agtatacact ccgctatcgc  11880
tacgtgactg ggtcatggct gcgccccgac acccgccaac acccgctgac gcgccctgac  11940
gggcttgtct gctcccggca tccgcttaca gacaagctgt gaccgtctcc gggagctgca  12000
tgtgtcagag gttttcaccg tcatcaccga aacgcgcgag gcagcagatc aattcgcgcg  12060
cgaaggcgaa gcggcatgca tttacgttga caccatcgaa tggtgcaaaa cctttcgcgg  12120
tatggcatga tagcgcccgg aagagagtca attcagggtg gtgaatgtga aaccagtaac  12180
gttatacgat gtcgcagagt atgccggtgt ctcttatcag accgtttccc gcgtggtgaa  12240
ccaggccagc cacgtttctg cgaaaacgcg ggaaaaagtg gaagcggcga tggcggagct  12300
gaattacatt cccaaccgcg tggcacaaca actggcgggc aaacagtcgt tgctgattgg  12360
cgttgccacc tccagtctgg ccctgcacgc gccgtcgcaa attgtcgcgg cgattaaatc  12420
tcgcgccgat caactgggtg ccagcgtggt ggtgtcgatg gtagaacgaa gcggcgtcga  12480
agcctgtaaa gcggcggtgc acaatcttct cgcgcaacgc gtcagtgggc tgatcattaa  12540
ctatccgctg gatgaccagg atgccattgc tgtggaagct gcctgcacta atgttccggc  12600
gttatttctt gatgtctctg accagacacc catcaacagt attattttct cccatgaaga  12660
cggtacgcga ctgggcgtgg agcatctggt cgcattgggt caccagcaaa tcgcgctgtt  12720
agcgggccca ttaagttctg tctcggcgcg tctgcgtctg gctggctggc ataaatatct  12780
cactcgcaat caaattcagc cgatagcgga acgggaaggc gactggagtg ccatgtccgg  12840
ttttcaacaa accatgcaaa tgctgaatga gggcatcgtt cccactgcga tgctggttgc  12900
caacgatcag atggcgctgg gcgcaatgcg cgccattacc gagtccgggc tgcgcgttgg  12960
tgcggatatc tcggtagtgg gatacgacga taccgaagac agctcatgtt atatcccgcc  13020
gttaaccacc atcaaacagg attttcgcct gctggggcaa accagcgtgg accgcttgct  13080
gcaactctct cagggccagg cggtgaaggg caatcagctg ttgcccgtct cactggtgaa  13140
aagaaaaacc accctggcgc ccaatacgca aaccgcctct ccccgcgcgt tggccgattc  13200
attaatgcag ctggcacgac aggtttcccg actggaaagc gggcagtgag cgcaacgcaa  13260
ttaatgtgag ttagcgcgaa ttgatctg                                      13288
```

<210> SEQ ID NO 84
<211> LENGTH: 11378
<212> TYPE: DNA
<213> ORGANISM: Artificial Sequence
<220> FEATURE:
<223> OTHER INFORMATION: pT-HBSRYbbO

<400> SEQUENCE: 84

```
gtttgacagc ttatcatcga ctgcacggtg caccaatgct tctggcgtca ggcagccatc     60
ggaagctgtg gtatggctgt gcaggtcgta aatcactgca taattcgtgt cgctcaaggc    120
gcactcccgt tctggataat gtttttgcg ccgacatcat aacggttctg gcaaatattc    180
```

-continued

```
tgaaatgagc tgttgacaat taatcatccg gctcgtataa tgtgtggaat tgtgagcgga    240

taacaatttc acacaggaaa cagaccatgg aattctacgt actagtgaat tcaggaggta    300

ataaatatgg gtctgatgct gattgattgg tgtgcactgg ctctggttgt tttcattggc    360

ctgccgcacg gcgcgctgga tgctgccatt tctttttcta tgatctcttc tgcaaaacgc    420

attgctcgtc tggctggtat tctgctgatc tatctgctgc tggcgaccgc gttcttcctg    480

atctggtatc agctgccagc gtttagcctg ctgatcttcc tgctgatctc cattatccac    540

tttggtatgg cagacttcaa cgcgtcccca agcaaactga aatggccgca tatcatcgcc    600

cacggcggtg ttgttactgt ttggctgccg ctgatccaga aaaacgaagt aactaaactg    660

tttagcatcc tgactaacgg tccgactccg atcctgtggg acatcctgct gattttcttc    720

ctgtgttggt ctattggcgt gtgtctgcac acgtacgaaa ccctgcgctc taaacattac    780

aacatcgcct ttgaactgat cggtctgatt ttcctggcgt ggtatgcgcc gcctctggtt    840

acgtttgcca cttacttctg cttcattcat tcccgtcgcc acttctcctt tgtgtggaag    900

cagctgcaac acatgtcttc caaaaagatg atgattggca gcgcgattat cctgtcctgt    960

acctcttggc tgatcggcgg tggtatctat ttcttcctga actccaaaat gatcgcctct   1020

gaggctgcgc tgcagactgt gttcatcggt ctggcggcac tgaccgtgcc gcacatgatt   1080

ctgatcgact tcatcttccg tccgcactct tcccgtatca aaatcaaaaa ctaattaatt   1140

aaaggaggta ataatatgac tcataaagca acggagatcc tgacaggtaa agttatgcaa   1200

aaatcggtct taattaccgg atgttccagt ggaattggcc tggaaagcgc gctcgaatta   1260

aaacgccagg gttttcatgt gctggcaggt tgccggaaac cggatgatgt tgagcgcatg   1320

aacagcatgg gatttaccgg cgtgttgatc gatctggatt caccagaaag tgttgatcgc   1380

gcagccgacg aggtgatcgc cctgaccgat aattgtctgt atgggatctt taacaatgcc   1440

ggattcggca tgtatggccc cctttccacc atcagccgtg cgcagatgga acagcagttt   1500

tccgccaact tttcggcgc acaccagctc accatgcgcc tgttacccgc gatgttaccg   1560

cacggtgaag ggcgtattgt gatgacatca tcggtgatgg gattaatctc cacgccgggt   1620

cgtggcgctt acgcggccag taaatatgcg ctggaggcgt ggtcagatgc actgcgcatg   1680

gagctgcgcc acagcggaat taaagtcagc ctgatcgaac ccggtcccat tcgtactcgc   1740

ttcaccgaca acgtcaacca gacgcaaagt gataaaccag tcgaaaatcc cggcatcgcc   1800

gcccgcttta cgttgggacc ggaagcggtg gtggacaaag tacgccatgc ttttattagc   1860

gagaagccga agatgcgcta tccggtgacg ctggtgacct gggcggtaat ggtgcttaag   1920

cgcctgctgc cggggcgcgt gatggacaaa atattgcagg ggtaactagt aggaggtaat   1980

aaatatggtg agtggcagta aagcgggcgt ttcgcctcat cgcgaaatag aagtaatgag   2040

acaatccatt gacgatcacc tggctggcct gttacctgaa accgacagcc aggatatcgt   2100

cagccttgcg atgcgtgaag gcgtcatggc acccggtaaa cggatccgtc cgctgctgat   2160

gctgctggcc gcccgcgacc tccgctacca gggcagtatg cctacgctgc tcgatctcgc   2220

ctgcgccgtt gaactgaccc ataccgcgtc gctgatgctc gacgacatgc cctgcatgga   2280

caacgccgag ctgcgccgcg gtcagcccac tacccacaaa aaatttggtg agagcgtggc   2340

gatccttgcc tccgttgggc tgctctctaa agcctttggt ctgatcgccg ccaccggcga   2400

tctgccgggg gagaggcgtg cccaggcggt caacgagctc tctaccgccg tgggcgtgca   2460

gggcctggta ctggggcagt ttcgcgatct taacgatgcc gccctcgacc gtacccctga   2520

cgctatcctc agcaccaacc acctcaagac cggcattctg ttcagcgcga tgctgcagat   2580
```

-continued

```
cgtcgccatt gcttccgcct cgtcgccgag cacgcgagag acgctgcacg ccttcgccct   2640
cgacttcggc caggcgtttc aactgctgga cgatctgcgt gacgatcacc cggaaaccgg   2700
taaagatcgc aataaggacg cgggaaaatc gacgctggtc aaccggctgg gcgcagacgc   2760
ggcccggcaa aagctgcgcg agcatattga ttccgccgac aaacacctca cttttgcctg   2820
tccgcagggc ggcgccatcc gacagtttat gcatctgtgg tttggccatc accttgccga   2880
ctggtcaccg gtcatgaaaa tcgcctgata actcgaggag gtataaagga tgaaaaaaac   2940
cgttgtgatt ggcgcaggct ttggtggcct ggcgctggcg attcgcctgc aggcggcagg   3000
gatcccaacc gtactgctgg agcagcggga caagcccggc ggtcgggcct acgtctggca   3060
tgaccagggc tttacctttg acgccgggcc gacggtgatc accgatccta ccgcgcttga   3120
ggcgctgttc accctggccg gcaggcgcat ggaggattac gtcaggctgc tgccggtaaa   3180
acccttctac cgactctgct gggagtccgg gaagaccctc gactatgcta acgacagcgc   3240
cgagcttgag gcgcagatta cccagttcaa cccccgcgac gtcgagggct accggcgctt   3300
tctggcttac tcccaggcgg tattccagga gggatatttg cgcctcggca gcgtgccgtt   3360
cctctctttt cgcgacatgc tgcgcgccgg gccgcagctg cttaagctcc aggcgtggca   3420
gagcgtctac cagtcggttt cgcgctttat tgaggatgag catctgcggc aggccttctc   3480
gttccactcc ctgctggtag gcggcaaccc cttcaccacc tcgtccatct acaccctgat   3540
ccacgccctt gagcgggagt ggggggtctg gttccctgag ggcggcaccg gggcgctggt   3600
gaacggcatg gtgaagctgt ttaccgatct gggcggggag atcgaactca acgcccgggt   3660
cgaagagctg gtggtggccg ataaccgcgt aagccaggtc cggctggcgg atggtcggat   3720
ctttgacacc gacgccgtag cctcgaacgc tgacgtggtg aacacctata aaaagctgct   3780
cggccaccat ccggtggggc agaagcgggc ggcagcgctg gagcgcaaga gcatgagcaa   3840
ctcgctgttt gtgctctact tcggcctgaa ccagcctcat tcccagctgg cgcaccatac   3900
catctgtttt ggtccccgct accgggagct gatcgacgag atctttaccg gcagcgcgct   3960
ggcggatgac ttctcgctct acctgcactc gccctgcgtg accgatccct cgctcgcgcc   4020
tcccggctgc gccagcttct acgtgctggc ccccggtgccg catcttggca acgcgccgct   4080
ggactgggcg caggaggggc cgaagctgcg cgaccgcatc tttgactacc ttgaagagcg   4140
ctatatgccc ggcctgcgta gccagctggt gacccagcgg atctttaccc cggcagactt   4200
ccacgacacg ctggatgcgc atctgggatc ggccttctcc atcgagccgc tgctgaccca   4260
aagcgcctgg ttccgcccgc acaaccgcga cagcgacatt gccaacctct acctggtggg   4320
cgcaggtact caccctgggg cgggcattcc tggcgtagtg gcctcggcga aagccaccgc   4380
cagcctgatg attgaggatc tgcaatgagc caaccgccgc tgcttgacca cgccacgcag   4440
accatggcca acggctcgaa aagttttgcc accgctgcga agctgttcga cccggccacc   4500
cgccgtagcg tgctgatgct ctacacctgg tgccgccact gcgatgacgt cattgacgac   4560
cagacccacg gcttcgccag cgaggccgcg gcggaggagg aggccaccca gcgcctggcc   4620
cggctgcgca cgctgaccct ggcggcgttt gaaggggccg agatgcagga tccggccttc   4680
gctgcctttc aggaggtggc gctgacccac ggtattacgc cccgcatggc gctcgatcac   4740
ctcgacggct ttgcgatgga cgtggctcag acccgctatg tcacctttga ggatacgctg   4800
cgctactgct atcacgtggc gggcgtggtg ggtctgatga tggccagggt gatgggcgtg   4860
cgggatgagc gggtgctgga tcgcgcctgc gatctggggc tggccttcca gctgacgaat   4920
```

atcgcccggg atattattga cgatgcggct attgaccgct gctatctgcc cgccgagtgg 4980
ctgcaggatg ccgggctgac cccggagaac tatgccgcgc gggagaatcg ggccgcgctg 5040
gcgcgggtgg cggagcggct tattgatgcc gcagagccgt actacatctc ctcccaggcc 5100
gggctacacg atctgccgcc gcgctgcgcc tgggcgatcg ccaccgcccg cagcgtctac 5160
cgggagatcg gtattaaggt aaaagcggcg ggaggcagcg cctgggatcg ccgccagcac 5220
accagcaaag gtgaaaaaat tgccatgctg atggcggcac cggggcaggt tattcgggcg 5280
aagacgacga gggtgacgcc gcgtccggcc ggtctttggc agcgtcccgt ttagtaatct 5340
agaggaggta ataaaatatg cttcgttcgt tgctcagagg cctcacgcat atcccccgcg 5400
tgaactccgc ccagcagccc agctgtgcac acgcgcgact ccagtttaag ctcaggagca 5460
tgcagatgac gctcatgcag cccagcatct cagccaatct gtcgcgcgcc gaggaccgca 5520
cagaccacat gaggggtgca agcacctggg caggcgggca gtcgcaggat gagctgatgc 5580
tgaaggacga gtgcatcttg gtggatgttg aggacaacat cacaggccat gccagcaagc 5640
tggagtgtca caagttccta ccacatcagc ctgcaggcct gctgcaccgg gccttctctg 5700
tgttcctgtt tgacgatcag gggcgactgc tgctgcaaca gcgtgcacgc tcaaaaatca 5760
ccttcccaag tgtgtggacg aacacctgct gcagccaccc tttacatggg cagaccccag 5820
atgaggtgga ccaactaagc caggtggccg acggaacagt acctggcgca aaggctgctg 5880
ccatccgcaa gttggagcac gagctgggga taccagcgca ccagctgccg gcaagcgcgt 5940
ttcgcttcct cacgcgtttg cactactgtg ccgcggacgt gcagccagct gcgacacaat 6000
cagcgctctg gggcgagcac gaaatggact acatcttgtt catccgggcc aacgtcacct 6060
tggcgcccaa ccctgacgag gtggacgaag tcaggtacgt gacgcaagag gagctgcggc 6120
agatgatgca gccggacaac gggctgcaat ggtcgccgtg gtttcgcatc atcgccgcgc 6180
gcttccttga gcgttggtgg gctgacctgg acgcggccct aaacactgac aaacacgagg 6240
attggggaac ggtgcatcac atcaacgaag cgtgataagc ggccgcgtcg acaggaggag 6300
cggctatgca accgcattat gatctgattc tcgtgggggc tggactcgcg aatggcctta 6360
tcgccctgcg tcttcagcag cagcaacctg atatgcgtat tttgcttatc gacgccgcac 6420
cccaggcggg cgggaatcat acgtggtcat ttcaccacga tgatttgact gagagccaac 6480
atcgttggat agctccgctg gtggttcatc actggcccga ctatcaggta cgctttccca 6540
cacgccgtcg taagctgaac agcggctact tttgtattac ttctcagcgt ttcgctgagg 6600
ttttacagcg acagtttggc ccgcacttgt ggatggatac cgcggtcgca gaggttaatg 6660
cggaatctgt tcggttgaaa aagggtcagg ttatcggtgc ccgcgcggtg attgacgggc 6720
ggggttatgc ggcaaattca gcactgagcg tgggcttcca ggcgtttatt ggccaggaat 6780
ggcgattgag ccacccgcat ggtttatcgt ctcccattat catggatgcc acggtcgatc 6840
agcaaaatgg ttatcgcttc gtgtacagcc tgccgctctc gccgaccaga ttgttaattg 6900
aagacacgca ctatattgat aatgcgacat tagatcctga atgcgcgcgg caaaatattt 6960
gcgactatgc cgcgcaacag ggttggcagc ttcagacact gctgcgagaa gaacagggcg 7020
ccttacccat tactctgtcg ggcaatgccg acgcattctg gcagcagcgc cccctggcct 7080
gtagtggatt acgtgccggt ctgttccatc ctaccaccgg ctattcactg ccgctggcgg 7140
ttgccgtggc cgaccgcctg agtgcacttg atgtctttac gtcggcctca attcaccatg 7200
ccattacgca ttttgcccgc gagcgctggc agcagcaggg ctttttccgc atgctgaatc 7260
gcatgctgtt tttagccgga cccgccgatt cacgctggcg ggttatgcag cgtttttatg 7320
gtttacctga agatttaatt gcccgttttt atgcgggaaa actcacgctg accgatcggc 7380
tacgtattct gagcggcaag ccgcctgttc cggtattagc agcattgcaa gccattatga 7440
cgactcatcg ttaactgcag gcatgcaagc tggggatcct acctgacgct tttatcgca 7500
actctctact gtttctccat acccgttttt ttgggctggc ggatgagaga agattttcag 7560
cctgatacag attaaatcag aacgcagaag cggtctgata aaacagaatt tgcctggcgg 7620
cagtagcgcg gtggtcccac ctgaccccat gccgaactca gaagtgaaac gccgtagcgc 7680
cgatggtagt gtggggtctc cccatgcgag agtagggaac tgccaggcat caaataaaac 7740
gaaaggctca gtcgaaagac tgggcctttc gttttatctg ttgtttgtcg gtgaacgctc 7800
tcctgagtag gacaaatccg ccgggagcgg atttgaacgt tgcgaagcaa cggcccggag 7860
ggtggcgggc aggacgcccg ccataaactg ccaggcatca aattaagcag aaggccatcc 7920
tgacggatgg cctttttgcg tttctacaaa ctctttttgt ttatttttct aaatacattc 7980
aaatatgtat ccgctcatga gacaataacc ctgataaatg cttcaataat attgaaaaag 8040
gaagagtatg agtattcaac atttccgtgt cgcccttatt ccctttttttg cggcattttg 8100
ccttcctgtt tttgctcacc cagaaacgct ggtgaaagta aaagatgctg aagatcagtt 8160
gggtgcacga gtgggttaca tcgaactgga tctcaacagc ggtaagatcc ttgagagttt 8220
tcgccccgaa gaacgttttc caatgatgag cacttttaaa gttctgctat gtggcgcggt 8280
attatcccgt gttgacgccg ggcaagagca actcggtcgc cgcatacact attctcagaa 8340
tgacttggtt gagtactcac cagtcacaga aaagcatctt acggatggca tgacagtaag 8400
agaattatgc agtgctgcca taaccatgag tgataacact gcggccaact tacttctgac 8460
aacgatcgga ggaccgaagg agctaaccgc ttttttgcac aacatggggg atcatgtaac 8520
tcgccttgat cgttgggaac cggagctgaa tgaagccata ccaaacgacg agcgtgacac 8580
cacgatgcct acagcaatgg caacaacgtt gcgcaaacta ttaactggcg aactacttac 8640
tctagcttcc cggcaacaat taatagactg gatggaggcg gataaagttg caggaccact 8700
tctgcgctcg gcccttccgg ctggctggtt tattgctgat aaatctggag ccggtgagcg 8760
tgggtctcgc ggtatcattg cagcactggg gccagatggt aagccctccc gtatcgtagt 8820
tatctacacg acggggagtc aggcaactat ggatgaacga aatagacaga tcgctgagat 8880
aggtgcctca ctgattaagc attggtaact gtcagaccaa gtttactcat atatacttta 8940
gattgattta aaacttcatt tttaatttaa aaggatctag gtgaagatcc tttttgataa 9000
tctcatgacc aaaatccctt aacgtgagtt ttcgttccac tgagcgtcag accccgtaga 9060
aaagatcaaa ggatcttctt gagatccttt ttttctgcgc gtaatctgct gcttgcaaac 9120
aaaaaaacca ccgctaccag cggtggtttg tttgccggat caagagctac caactctttt 9180
tccgaaggta actggcttca gcagagcgca gataccaaat actgtccttc tagtgtagcc 9240
gtagttaggc caccacttca agaactctgt agcaccgcct acatacctcg ctctgctaat 9300
cctgttacca gtggctgctg ccagtggcga taagtcgtgt cttaccgggt tggactcaag 9360
acgatagtta ccggataagg cgcagcggtc gggctgaacg gggggttcgt gcacacagcc 9420
cagcttggag cgaacgacct acaccgaact gagataccta cagcgtgagc tatgagaaag 9480
cgccacgctt cccgaaggga gaaaggcgga caggtatccg gtaagcggca gggtcggaac 9540
aggagagcgc acgagggagc ttccaggggg aaacgcctgg tatctttata gtcctgtcgg 9600
gtttcgccac ctctgacttg agcgtcgatt tttgtgatgc tcgtcagggg ggcggagcct 9660

-continued atggaaaaac gccagcaacg cggccttttt acggttcctg gccttttgct ggccttttgc 9720
tcacatgttc tttcctgcgt tatcccctga ttctgtggat aaccgtatta ccgcctttga 9780
gtgagctgat accgctcgcc gcagccgaac gaccgagcgc agcgagtcag tgagcgagga 9840
agcggaagag cgcctgatgc ggtattttct ccttacgcat ctgtgcggta tttcacaccg 9900
catatggtgc actctcagta caatctgctc tgatgccgca tagttaagcc agtatacact 9960
ccgctatcgc tacgtgactg ggtcatggct gcgccccgac acccgccaac acccgctgac 10020
gcgccctgac gggcttgtct gctcccggca tccgcttaca gacaagctgt gaccgtctcc 10080
gggagctgca tgtgtcagag gttttcaccg tcatcaccga aacgcgcgag gcagcagatc 10140
aattcgcgcg cgaaggcgaa gcggcatgca tttacgttga caccatcgaa tggtgcaaaa 10200
cctttcgcgg tatggcatga tagcgcccgg aagagagtca attcagggtg gtgaatgtga 10260
aaccagtaac gttatacgat gtcgcagagt atgccggtgt ctcttatcag accgtttccc 10320
gcgtggtgaa ccaggccagc cacgtttctg cgaaaacgcg ggaaaaagtg gaagcggcga 10380
tggcggagct gaattacatt cccaaccgcg tggcacaaca actggcgggc aaacagtcgt 10440
tgctgattgg cgttgccacc tccagtctgg ccctgcacgc gccgtcgcaa attgtcgcgg 10500
cgattaaatc tcgcgccgat caactgggtg ccagcgtggt ggtgtcgatg gtagaacgaa 10560
gcggcgtcga agcctgtaaa gcggcggtgc acaatcttct cgcgcaacgc gtcagtgggc 10620
tgatcattaa ctatccgctg gatgaccagg atgccattgc tgtggaagct gcctgcacta 10680
atgttccggc gttatttctt gatgtctctg accagacacc catcaacagt attattttct 10740
cccatgaaga cggtacgcga ctgggcgtgg agcatctggt cgcattgggt caccagcaaa 10800
tcgcgctgtt agcgggccca ttaagttctg tctcggcgcg tctgcgtctg gctggctggc 10860
ataaatatct cactcgcaat caaattcagc cgatagcgga acgggaaggc gactggagtg 10920
ccatgtccgg ttttcaacaa accatgcaaa tgctgaatga gggcatcgtt cccactgcga 10980
tgctggttgc caacgatcag atggcgctgg gcgcaatgcg cgccattacc gagtccgggc 11040
tgcgcgttgg tgcggatatc tcggtagtgg gatacgacga taccgaagac agctcatgtt 11100
atatcccgcc gttaaccacc atcaaacagg attttcgcct gctggggcaa accagcgtgg 11160
accgcttgct gcaactctct cagggccagg cggtgaaggg caatcagctg ttgcccgtct 11220
cactggtgaa aagaaaaacc accctggcgc ccaatacgca aaccgcctct ccccgcgcgt 11280
tggccgattc attaatgcag ctggcacgac aggtttcccg actggaaagc gggcagtgag 11340
cgcaacgcaa ttaatgtgag ttagcgcgaa ttgatctg 11378

<210> SEQ ID NO 85
<211> LENGTH: 13938
<212> TYPE: DNA
<213> ORGANISM: Artificial Sequence
<220> FEATURE:
<223> OTHER INFORMATION: pT-HBSREYbbO

<400> SEQUENCE: 85
tcgacaggag gagcggctat gcaaccgcat tatgatctga ttctcgtggg ggctggactc 60
gcgaatggcc ttatcgccct gcgtcttcag cagcagcaac ctgatatgcg tattttgctt 120
atcgacgccg caccccaggc gggcgggaat catacgtggt catttcacca cgatgatttg 180
actgagagcc aacatcgttg gatagctccg ctggtggttc atcactggcc cgactatcag 240
gtacgctttc ccacacgccg tcgtaagctg aacagcggct acttttgtat tacttctcag 300
cgtttcgctg aggttttaca gcgacagttt ggcccgcact tgtggatgga taccgcggtc 360

```
gcagaggtta atgcggaatc tgttcggttg aaaaagggtc aggttatcgg tgcccgcgcg    420
gtgattgacg ggcggggtta tgcggcaaat tcagcactga gcgtgggctt ccaggcgttt    480
attggccagg aatggcgatt gagccacccg catggtttat cgtctcccat tatcatggat    540
gccacggtcg atcagcaaaa tggttatcgc ttcgtgtaca gcctgccgct ctcgccgacc    600
agattgttaa ttgaagacac gcactatatt gataatgcga cattagatcc tgaatgcgcg    660
cggcaaaata tttgcgacta tgccgcgcaa cagggttggc agcttcagac actgctgcga    720
gaagaacagg gcgccttacc cattactctg tcgggcaatg ccgacgcatt ctggcagcag    780
cgcccccctgg cctgtagtgg attacgtgcc ggtctgttcc atcctaccac cggctattca    840
ctgccgctgg cggttgccgt ggccgaccgc ctgagtgcac ttgatgtctt tacgtcggcc    900
tcaattcacc atgccattac gcattttgcc cgcgagcgct ggcagcagca gggctttttc    960
cgcatgctga atcgcatgct gtttttagcc ggacccgccg attcacgctg gcgggttatg   1020
cagcgttttt atggtttacc tgaagattta attgcccgtt tttatgcggg aaaactcacg   1080
ctgaccgatc ggctacgtat tctgagcggc aagccgcctg ttccggtatt agcagcattg   1140
caagccatta tgacgactca tcgttaactg caggcatgca agctggggat cctacctgac   1200
gctttttatc gcaactctct actgtttctc catacccgtt tttttgggct ggcggatgag   1260
agaagatttt cagcctgata cagattaaat cagaacgcag aagcggtctg ataaaacaga   1320
atttgcctgg cggcagtagc gcggtggtcc cacctgaccc catgccgaac tcagaagtga   1380
aacgccgtag cgccgatggt agtgtggggt ctccccatgc gagagtaggg aactgccagg   1440
catcaaataa aacgaaaggc tcagtcgaaa gactgggcct ttcgttttat ctgttgtttg   1500
tcggtgaacg ctctcctgag taggacaaat ccgccgggag cggatttgaa cgttgcgaag   1560
caacggcccg gagggtggcg ggcaggacgc ccgccataaa ctgccaggca tcaaattaag   1620
cagaaggcca tcctgacgga tggccttttt gcgtttctac aaactctttt tgtttatttt   1680
tctaaataca ttcaaatatg tatccgctca tgagacaata accctgataa atgcttcaat   1740
aatattgaaa aaggaagagt atgagtattc aacatttccg tgtcgccctt attccctttt   1800
ttgcggcatt ttgccttcct gtttttgctc acccagaaac gctggtgaaa gtaaaagatg   1860
ctgaagatca gttgggtgca cgagtgggtt acatcgaact ggatctcaac agcggtaaga   1920
tccttgagag ttttcgcccc gaagaacgtt ttccaatgat gagcactttt aaagttctgc   1980
tatgtggcgc ggtattatcc cgtgttgacg ccgggcaaga gcaactcggt cgccgcatac   2040
actattctca gaatgacttg gttgagtact caccagtcac agaaaagcat cttacggatg   2100
gcatgacagt aagagaatta tgcagtgctg ccataaccat gagtgataac actgcggcca   2160
acttacttct gacaacgatc ggaggaccga aggagctaac cgcttttttg cacaacatgg   2220
gggatcatgt aactcgcctt gatcgttggg aaccggagct gaatgaagcc ataccaaacg   2280
acgagcgtga caccacgatg cctacagcaa tggcaacaac gttgcgcaaa ctattaactg   2340
gcgaactact tactctagct tcccggcaac aattaataga ctggatggag gcggataaag   2400
ttgcaggacc acttctgcgc tcggcccttc cggctggctg gtttattgct gataaatctg   2460
gagccggtga gcgtgggtct cgcggtatca ttgcagcact ggggccagat ggtaagccct   2520
cccgtatcgt agttatctac acgacgggga gtcaggcaac tatggatgaa cgaaatagac   2580
agatcgctga gataggtgcc tcactgatta agcattggta actgtcagac caagtttact   2640
catatatact ttagattgat ttaaaacttc atttttaatt taaaaggatc taggtgaaga   2700
```

-continued

```
tcctttttga taatctcatg accaaaatcc cttaacgtga gttttcgttc cactgagcgt   2760
cagaccccgt agaaaagatc aaaggatctt cttgagatcc tttttttctg cgcgtaatct   2820
gctgcttgca aacaaaaaaa ccaccgctac cagcggtggt ttgtttgccg gatcaagagc   2880
taccaactct ttttccgaag gtaactggct tcagcagagc gcagatacca aatactgtcc   2940
ttctagtgta gccgtagtta ggccaccact tcaagaactc tgtagcaccg cctacatacc   3000
tcgctctgct aatcctgtta ccagtggctg ctgccagtgg cgataagtcg tgtcttaccg   3060
ggttggactc aagacgatag ttaccggata aggcgcagcg gtcgggctga acggggggtt   3120
cgtgcacaca gcccagcttg gagcgaacga cctacaccga actgagatac ctacagcgtg   3180
agctatgaga aagcgccacg cttcccgaag ggagaaaggc ggacaggtat ccggtaagcg   3240
gcagggtcgg aacaggagag cgcacgaggg agcttccagg gggaaacgcc tggtatcttt   3300
atagtcctgt cgggtttcgc cacctctgac ttgagcgtcg atttttgtga tgctcgtcag   3360
gggggcggag cctatggaaa aacgccagca acgcggcctt tttacggttc ctggcctttt   3420
gctggccttt tgctcacatg ttctttcctg cgttatcccc tgattctgtg gataaccgta   3480
ttaccgcctt tgagtgagct gataccgctc gccgcagccg aacgaccgag cgcagcgagt   3540
cagtgagcga ggaagcggaa gagcgcctga tgcggtattt tctccttacg catctgtgcg   3600
gtatttcaca ccgcatatgg tgcactctca gtacaatctg ctctgatgcc gcatagttaa   3660
gccagtatac actccgctat cgctacgtga ctgggtcatg gctgcgcccc gacacccgcc   3720
aacacccgct gacgcgccct gacgggcttg tctgctcccg gcatccgctt acagacaagc   3780
tgtgaccgtc tccgggagct gcatgtgtca gaggttttca ccgtcatcac cgaaacgcgc   3840
gaggcagcag atcaattcgc gcgcgaaggc gaagcggcat gcatttacgt tgacaccatc   3900
gaatggtgca aaacctttcg cggtatggca tgatagcgcc cggaagagag tcaattcagg   3960
gtggtgaatg tgaaaccagt aacgttatac gatgtcgcag agtatgccgg tgtctcttat   4020
cagaccgttt cccgcgtggt gaaccaggcc agccacgttt ctgcgaaaac gcgggaaaaa   4080
gtggaagcgg cgatggcgga gctgaattac attcccaacc gcgtggcaca acaactggcg   4140
ggcaaacagt cgttgctgat tggcgttgcc acctccagtc tggccctgca cgcgccgtcg   4200
caaattgtcg cggcgattaa atctcgcgcc gatcaactgg gtgccagcgt ggtggtgtcg   4260
atggtagaac gaagcggcgt cgaagcctgt aaagcggcgg tgcacaatct tctcgcgcaa   4320
cgcgtcagtg ggctgatcat taactatccg ctggatgacc aggatgccat tgctgtggaa   4380
gctgcctgca ctaatgttcc ggcgttattt cttgatgtct ctgaccagac acccatcaac   4440
agtattattt tctcccatga agacggtacg cgactgggcg tggagcatct ggtcgcattg   4500
ggtcaccagc aaatcgcgct gttagcgggc ccattaagtt ctgtctcggc gcgtctgcgt   4560
ctggctggct ggcataaata tctcactcgc aatcaaattc agccgatagc ggaacgggaa   4620
ggcgactgga gtgccatgtc cggttttcaa caaaccatgc aaatgctgaa tgagggcatc   4680
gttcccactg cgatgctggt tgccaacgat cagatggcgc tgggcgcaat gcgcgccatt   4740
accgagtccg ggctgcgcgt tggtgcggat atctcggtag tgggatacga cgataccgaa   4800
gacagctcat gttatatccc gccgttaacc accatcaaac aggattttcg cctgctgggg   4860
caaaccagcg tggaccgctt gctgcaactc tctcagggcc aggcggtgaa gggcaatcag   4920
ctgttgcccg tctcactggt gaaaagaaaa accaccctgg cgcccaatac gcaaaccgcc   4980
tctccccgcg cgttggccga ttcattaatg cagctggcac gacaggtttc ccgactggaa   5040
agcgggcagt gagcgcaacg caattaatgt gagttagcgc gaattgatct ggtttgacag   5100
```

```
cttatcatcg actgcacggt gcaccaatgc ttctggcgtc aggcagccat cggaagctgt   5160
ggtatggctg tgcaggtcgt aaatcactgc ataattcgtg tcgctcaagg cgcactcccg   5220
ttctggataa tgtttttttgc gccgacatca taacggttct ggcaaatatt ctgaaatgag   5280
ctgttgacaa ttaatcatcc ggctcgtata atgtgtggaa ttgtgagcgg ataacaattt   5340
cacacaggaa acagaccatg gaattctacg tactagtgaa ttcaggaggt aataaatatg   5400
ggtctgatgc tgattgattg gtgtgcactg gctctggttg ttttcattgg cctgccgcac   5460
ggcgcgctgg atgctgccat ttctttttct atgatctctt ctgcaaaacg cattgctcgt   5520
ctggctggta ttctgctgat ctatctgctg ctggcgaccg cgttcttcct gatctggtat   5580
cagctgccag cgtttagcct gctgatcttc ctgctgatct ccattatcca ctttggtatg   5640
gcagacttca acgcgtcccc aagcaaactg aaatggccgc atatcatcgc ccacggcggt   5700
gttgttactg tttggctgcc gctgatccag aaaaacgaag taactaaact gtttagcatc   5760
ctgactaacg gtccgactcc gatcctgtgg gacatcctgc tgattttctt cctgtgttgg   5820
tctattggcg tgtgtctgca cacgtacgaa accctgcgct ctaaacatta caacatcgcc   5880
tttgaactga tcggtctgat ttcctggcg tggtatgcgc cgcctctggt tacgtttgcc   5940
acttacttct gcttcattca ttcccgtcgc cacttctcct ttgtgtggaa gcagctgcaa   6000
cacatgtctt ccaaaaagat gatgattggc agcgcgatta tcctgtcctg tacctcttgg   6060
ctgatcggcg gtggtatcta tttcttcctg aactccaaaa tgatcgcctc tgaggctgcg   6120
ctgcagactg tgttcatcgg tctggcggca ctgaccgtgc cgcacatgat tctgatcgac   6180
ttcatcttcc gtccgcactc ttcccgtatc aaaatcaaaa actaattaat taaaggaggt   6240
aataatatga ctcataaagc aacggagatc ctgacaggta aagttatgca aaaatcggtc   6300
ttaattaccg gatgttccag tggaattggc ctggaaagcg cgctcgaatt aaaacgccag   6360
ggttttcatg tgctggcagg ttgccggaaa ccggatgatg ttgagcgcat gaacagcatg   6420
ggatttaccg gcgtgttgat cgatctggat tcaccagaaa gtgttgatcg cgcagccgac   6480
gaggtgatcg ccctgaccga taattgtctg tatgggatct ttaacaatgc cggattcggc   6540
atgtatggcc ccctttccac catcagccgt gcgcagatgg aacagcagtt ttccgccaac   6600
tttttcggcg cacaccagct caccatgcgc ctgttacccg cgatgttacc gcacggtgaa   6660
gggcgtattg tgatgacatc atcggtgatg ggattaatct ccacgccggg tcgtggcgct   6720
tacgcggcca gtaaatatgc gctggaggcg tggtcagatg cactgcgcat ggagctgcgc   6780
cacagcggaa ttaaagtcag cctgatcgaa cccggtccca ttcgtactcg cttcaccgac   6840
aacgtcaacc agacgcaaag tgataaacca gtcgaaaatc ccggcatcgc cgcccgcttt   6900
acgttgggac cggaagcggt ggtggacaaa gtacgccatg cttttattag cgagaagccg   6960
aagatgcgct atccggtgac gctggtgacc tgggcggtaa tggtgcttaa gcgcctgctg   7020
ccggggcgcg tgatggacaa aatattgcag gggtaactag taggaggtaa taaatatggt   7080
gagtggcagt aaagcgggcg tttcgcctca tcgcgaaata gaagtaatga gacaatccat   7140
tgacgatcac ctggctggcc tgttacctga aaccgacagc caggatatcg tcagccttgc   7200
gatgcgtgaa ggcgtcatgg cacccggtaa acggatccgt ccgctgctga tgctgctggc   7260
cgcccgcgac ctccgctacc agggcagtat gcctacgctg ctcgatctcg cctgcgccgt   7320
tgaactgacc cataccgcgt cgctgatgct cgacgacatg ccctgcatgg acaacgccga   7380
gctgcgccgc ggtcagccca ctacccacaa aaaatttggt gagagcgtgg cgatccttgc   7440
```

-continued

```
ctccgttggg ctgctctcta aagcctttgg tctgatcgcc gccaccggcg atctgccggg   7500
ggagaggcgt gcccaggcgg tcaacgagct ctctaccgcc gtgggcgtgc agggcctggt   7560
actggggcag tttcgcgatc ttaacgatgc cgccctcgac cgtaccccctg acgctatcct   7620
cagcaccaac cacctcaaga ccggcattct gttcagcgcg atgctgcaga tcgtcgccat   7680
tgcttccgcc tcgtcgccga gcacgcgaga gacgctgcac gccttcgccc tcgacttcgg   7740
ccaggcgttt caactgctgg acgatctgcg tgacgatcac ccggaaaccg gtaaagatcg   7800
caataaggac gcgggaaaat cgacgctggt caaccggctg ggcgcagacg cggcccggca   7860
aaagctgcgc gagcatattg attccgccga caaacacctc acttttgcct gtccgcaggg   7920
cggcgccatc cgacagttta tgcatctgtg gtttggccat caccttgccg actggtcacc   7980
ggtcatgaaa atcgcctgat aactcgagga ggtataaagg atgaaaaaaa ccgttgtgat   8040
tggcgcaggc tttggtggcc tggcgctggc gattcgcctg caggcggcag ggatcccaac   8100
cgtactgctg gagcagcggg acaagcccgg cggtcgggcc tacgtctggc atgaccaggg   8160
ctttaccttt gacgccgggc cgacggtgat caccgatcct accgcgcttg aggcgctgtt   8220
caccctggcc ggcaggcgca tggaggatta cgtcaggctg ctgccggtaa aacccttcta   8280
ccgactctgc tgggagtccg ggaagaccct cgactatgct aacgacagcg ccgagcttga   8340
ggcgcagatt acccagttca acccccgcga cgtcgagggc taccggcgct ttctggctta   8400
ctcccaggcg gtattccagg agggatattt gcgcctcggc agcgtgccgt tcctctcttt   8460
tcgcgacatg ctgcgcgccg ggccgcagct gcttaagctc caggcgtggc agagcgtcta   8520
ccagtcggtt tcgcgcttta ttgaggatga gcatctgcgg caggccttct cgttccactc   8580
cctgctggta ggcggcaacc ccttcaccac ctcgtccatc tacaccctga tccacgccct   8640
tgagcgggag tggggggtct ggttccctga gggcggcacc ggggcgctgg tgaacggcat   8700
ggtgaagctg tttaccgatc tgggcgggga gatcgaactc aacgcccggg tcgaagagct   8760
ggtggtggcc gataaccgcg taagccaggt ccggctggcg gatggtcgga tctttgacac   8820
cgacgccgta gcctcgaacg ctgacgtggt gaacacctat aaaaagctgc tcggccacca   8880
tccggtgggg cagaagcggg cggcagcgct ggagcgcaag agcatgagca actcgctgtt   8940
tgtgctctac ttcggcctga accagcctca ttcccagctg gcgcaccata ccatctgttt   9000
tggtccccgc taccgggagc tgatcgacga gatctttacc ggcagcgcgc tggcggatga   9060
cttctcgctc tacctgcact cgccctgcgt gaccgatccc tcgctcgcgc ctcccggctg   9120
cgccagcttc tacgtgctgg ccccggtgcc gcatcttggc aacgcgccgc tggactgggc   9180
gcaggagggg ccgaagctgc gcgaccgcat ctttgactac cttgaagagc gctatatgcc   9240
cggcctgcgt agccagctgg tgacccagcg gatctttacc ccggcagact tccacgacac   9300
gctggatgcg catctgggat cggccttctc catcgagccg ctgctgaccc aaagcgcctg   9360
gttccgcccg cacaaccgcg acagcgacat tgccaacctc tacctggtgg gcgcaggtac   9420
tcaccctggg gcgggcattc ctggcgtagt ggcctcggcg aaagccaccg ccagcctgat   9480
gattgaggat ctgcaatgag ccaaccgccg ctgcttgacc acgccacgca gaccatggcc   9540
aacggctcga aaagttttgc caccgctgcg aagctgttcg acccggccac ccgccgtagc   9600
gtgctgatgc tctacacctg gtgccgccac tgcgatgacg tcattgacga ccagacccac   9660
ggcttcgcca gcgaggccgc ggcggaggag gaggccaccc agcgcctggc ccggctgcgc   9720
acgctgaccc tggcggcgtt tgaaggggcc gagatgcagg atccggcctt cgctgccttt   9780
caggaggtgg cgctgaccca cggtattacg ccccgcatgg cgctcgatca cctcgacggc   9840
```

-continued

```
tttgcgatgg acgtggctca gacccgctat gtcacctttg aggatacgct gcgctactgc   9900
tatcacgtgg cgggcgtggt gggtctgatg atggccaggg tgatgggcgt gcgggatgag   9960
cgggtgctgg atcgcgcctg cgatctgggg ctggccttcc agctgacgaa tatcgcccgg  10020
gatattattg acgatgcggc tattgaccgc tgctatctgc ccgccgagtg gctgcaggat  10080
gccgggctga ccccggagaa ctatgccgcg cgggagaatc gggccgcgct ggcgcgggtg  10140
gcggagcggc ttattgatgc cgcagagccg tactacatct cctcccaggc cgggctacac  10200
gatctgccgc cgcgctgcgc ctgggcgatc gccaccgccc gcagcgtcta ccgggagatc  10260
ggtattaagg taaaagcggc gggaggcagc gcctgggatc gccgccagca caccagcaaa  10320
ggtgaaaaaa ttgccatgct gatggcggca ccggggcagg ttattcgggc gaagacgacg  10380
agggtgacgc cgcgtccggc cggtctttgg cagcgtcccg tttagtaatc tagaggaggt  10440
aataaaatat gcttcgttcg ttgctcagag gcctcacgca tatcccccgc gtgaactccg  10500
cccagcagcc cagctgtgca cacgcgcgac tccagtttaa gctcaggagc atgcagatga  10560
cgctcatgca gcccagcatc tcagccaatc tgtcgcgcgc cgaggaccgc acagaccaca  10620
tgaggggtgc aagcacctgg gcaggcgggc agtcgcagga tgagctgatg ctgaaggacg  10680
agtgcatctt ggtggatgtt gaggacaaca tcacaggcca tgccagcaag ctggagtgtc  10740
acaagttcct accacatcag cctgcaggcc tgctgcaccg ggccttctct gtgttcctgt  10800
ttgacgatca ggggcgactg ctgctgcaac agcgtgcacg ctcaaaaatc accttcccaa  10860
gtgtgtggac gaacacctgc tgcagccacc ctttacatgg gcagacccca gatgaggtgg  10920
accaactaag ccaggtggcc gacggaacag tacctggcgc aaaggctgct gccatccgca  10980
agttggagca cgagctgggg ataccagcgc accagctgcc ggcaagcgcg tttcgcttcc  11040
tcacgcgttt gcactactgt gccgcggacg tgcagccagc tgcgacacaa tcagcgctct  11100
ggggcgagca cgaaatggac tacatcttgt tcatccgggc caacgtcacc ttggcgccca  11160
accctgacga ggtggacgaa gtcaggtacg tgacgcaaga ggagctgcgg cagatgatgc  11220
agccggacaa cgggctgcaa tggtcgccgt ggtttcgcat catcgccgcg cgcttccttg  11280
agcgttggtg ggctgacctg gacgcggccc taaacactga caaacacgag gattggggaa  11340
cggtgcatca catcaacgaa gcgtgataag cggccgcgct gttgacaatt aatcatccgg  11400
ctcgtataat gtgtggaatt gtgagcggat aacaatttca cacaggaaac agaccatgga  11460
gttgaaaaca gtagttatta ttgatgcatt acgaacacca attggaaaat ataaaggcag  11520
cttaagtcaa gtaagtgccg tagacttagg aacacatgtt acaacacaac ttttaaaaag  11580
acattccact atttctgaag aaattgatca agtaatcttt ggaaatgttt tacaagctgg  11640
aaatggccaa aatcccgcac gacaaatagc aataaacagc ggtttatctc atgaaattcc  11700
cgcaatgaca gttaatgagg tctgcggatc aggaatgaag gccgttattt tggcgaaaca  11760
attgattcaa ttaggagaag cggaagtttt aattgctggc gggattgaga atatgtccca  11820
agcacctaaa ttacaacgat ttaattacga aacagaaagc tatgatgcgc ctttttctag  11880
tatgatgtac gatgggttaa cggatgcctt tagtggtcaa gcaatgggct taactgctga  11940
aaatgtggcc gaaaagtatc atgtaactag agaagagcaa gatcaatttt ctgtacattc  12000
acaattaaaa gcagctcaag cacaagcaga agggatattc gctgacgaaa tagccccatt  12060
agaagtatca ggaacgcttg tggagaaaga tgaagggatt cgccctaatt cgagcgttga  12120
gaagctagga acgcttaaaa cagtttttaa agaagacggt actgtaacag cagggaatgc  12180
```

-continued

```
atcaaccatt aatgatgggg cttctgcttt gattattgct tcacaagaat atgccgaagc  12240

acacggtctt ccttatttag ctattattcg agacagtgtg gaagtcggta ttgatccagc  12300

ctatatggga atttcgccga ttaaagccat tcaaaaactg ttagcgcgca atcaacttac  12360

tacggaagaa attgatctgt atgaaatcaa cgaagcattt gcagcaactt caatcgtggt  12420

ccaaagagaa ctggctttac cagaggaaaa ggtcaacatt tatggtggcg gtatttcatt  12480

aggtcatgcg attggtgcca caggtgctcg tttattaacg agtttaagtt atcaattaaa  12540

tcaaaaagaa aagaaatatg gagtggcttc tttatgtatc ggcggtggct taggactcgc  12600

tatgctacta gagagacctc agcaaaaaaa aaacagccga ttttatcaaa tgagtcctga  12660

ggaacgcctg gcttctcttc ttaatgaagg ccagatttct gctgatacaa aaaaagaatt  12720

tgaaaatacg gctttatctt cgcagattgc caatcatatg attgaaaatc aaatcagtga  12780

aacagaagtg ccgatgggcg ttggcttaca tttaacagtg gacgaaactg attatttggt  12840

accaatggcg acagaagagc cctcagtgat tgcggctttg agtaatggtg caaaaatagc  12900

acaaggattt aaaacagtga atcaacaacg tttaatgcgt ggacaaatcg tttttacga  12960

tgttgcagac gccgagtcat tgattgatga actacaagta agagaaacgg aaatttttca  13020

acaagcagag ttaagttatc catctatcgt taaacgcggc ggcggcttaa gagatttgca  13080

atatcgtgct tttgatgaat catttgtatc tgtcgacttt ttagtagatg ttaaggatgc  13140

aatgggggca aatatcgtta acgctatgtt ggaaggtgtg gccgagttgt tccgtgaatg  13200

gtttgcggag caaaagattt tattcagtat tttaagtaat tatgccacgg agtcggttgt  13260

tacgatgaaa acggctattc cagtttcacg tttaagtaag gggagcaatg gccgggaaat  13320

tgctgaaaaa attgttttag cttcacgcta tgcttcatta gatccttatc gggcagtcac  13380

gcataacaaa gggatcatga atggcattga agctgtcgtt ttagctacag gaaatgatac  13440

acgcgctgtt agcgcttctt gtcatgcttt tgcggtgaag gaaggtcgct accaaggttt  13500

gactagttgg acgctggatg gcgaacaact aattggtgaa atttcagttc cgcttgcgtt  13560

agccacggtt ggcggtgcca caaaagtctt acctaaatct caagcagctg ctgatttgtt  13620

agcagtgacg gatgcaaaag aactaagtcg agtagtagcg gctgttggtt tggcacaaaa  13680

tttagcggcg ttacgggcct tagtctctga aggaattcaa aaaggacaca tggctctaca  13740

agcacgttct ttagcgatga cggtcggagc tactggtaaa gaagttgagg cagtcgctca  13800

acaattaaaa cgtcaaaaaa cgatgaacca agaccgagcc ttggctattt taaatgattt  13860

aagaaaacaa taaaaaaaca gttcagcaga aattattctg ctgaactgtt ttttttcaca  13920

ttaggtagcc gtttcagc                                                  13938
```

<210> SEQ ID NO 86
<211> LENGTH: 12898
<212> TYPE: DNA
<213> ORGANISM: Artificial Sequence
<220> FEATURE:
<223> OTHER INFORMATION: pT-HBSREYbb0free

<400> SEQUENCE: 86

```
agcttgcgtc agaccccgta gaaaagatca aaggatcttc ttgagatcct tttttctgc     60

gcgtaatctg ctgcttgcaa acaaaaaaac caccgctacc agcggtggtt tgtttgccgg    120

atcaagagct accaactctt tttccgaagg taactggctt cagcagagcg cagataccaa    180

atactgtcct tctagtgtag ccgtagttag gccaccactt caagaactct gtagcaccgc    240

ctacatacct cgctctgcta atcctgttac cagtggctgc tgccagtggc gataagtcgt    300
```

-continued

```
gtcttaccgg gttggactca agacgatagt taccggataa ggcgcagcgg tcgggctgaa    360
cgggggggttc gtgcacacag cccagcttgg agcgaacgac ctacaccgaa ctgagatacc    420
tacagcgtga gctatgagaa agcgccacgc ttcccgaagg gagaaaggcg gacaggtatc    480
cggtaagcgg cagggtcgga acaggagagc gcacgaggga gcttccaggg ggaaacgcct    540
ggtatcttta tagtcctgtc gggtttcgcc acctctgact tgagcgtcga tttttgtgat    600
gctcgtcagg ggggcggagc ctatggaaaa acgccagcaa cgcggccttt ttacggttcc    660
tggccttttg ctggcctttt gctcacatgt tctttcctgc gttatcccct gattctgtgg    720
ataaccgtat taccgccttt gagtgagctg ataccgctcg ccgcagccga acgaccgagc    780
gcagcgagtc agtgagcgag gaagcggaag agcgcctgat gcggtatttt ctccttacgc    840
atctgtgcgg tatttcacac cgcatatggt gcactctcag tacaatctgc tctgatgccg    900
catagttaag ccagtataca ctccgctatc gctacgtgac tgggtcatgg ctgcgccccg    960
acacccgcca acacccgctg acgcgccctg acgggcttgt ctgctcccgg catccgctta   1020
cagacaagct gtgaccgtct ccgggagctg catgtgtcag aggttttcac cgtcatcacc   1080
gaaacgcgcg aggcagcaga tcaattcgcg cgcgaaggcg aagcggcatg catttacgtt   1140
gacaccatcg aatggtgcaa aacctttcgc ggtatggcat gatagcgccc ggaagagagt   1200
caattcaggg tggtgaatgt gaaaccagta acgttatacg atgtcgcaga gtatgccggt   1260
gtctcttatc agaccgtttc ccgcgtggtg aaccaggcca gccacgtttc tgcgaaaacg   1320
cgggaaaaag tggaagcggc gatggcggag ctgaattaca ttcccaaccg cgtggcacaa   1380
caactggcgg gcaaacagtc gttgctgatt ggcgttgcca cctccagtct ggccctgcac   1440
gcgccgtcgc aaattgtcgc ggcgattaaa tctcgcgccg atcaactggg tgccagcgtg   1500
gtggtgtcga tggtagaacg aagcggcgtc gaagcctgta aagcggcggt gcacaatctt   1560
ctcgcgcaac gcgtcagtgg gctgatcatt aactatccgc tggatgacca ggatgccatt   1620
gctgtggaag ctgcctgcac taatgttccg gcgttatttc ttgatgtctc tgaccagaca   1680
cccatcaaca gtattatttt ctcccatgaa gacggtacgc gactgggcgt ggagcatctg   1740
gtcgcattgg gtcaccagca aatcgcgctg ttagcgggcc cattaagttc tgtctcggcg   1800
cgtctgcgtc tggctggctg gcataaatat ctcactcgca atcaaattca gccgatagcg   1860
gaacgggaag gcgactggag tgccatgtcc ggttttcaac aaaccatgca aatgctgaat   1920
gagggcatcg ttcccactgc gatgctggtt gccaacgatc agatggcgct gggcgcaatg   1980
cgcgccatta ccgagtccgg gctgcgcgtt ggtgcggata tctcggtagt gggatacgac   2040
gataccgaag acagctcatg ttatatcccg ccgttaacca ccatcaaaca ggattttcgc   2100
ctgctggggc aaaccagcgt ggaccgcttg ctgcaactct ctcagggcca ggcggtgaag   2160
ggcaatcagc tgttgcccgt ctcactggtg aaaagaaaaa ccaccctggc gcccaatacg   2220
caaaccgcct ctccccgcgc gttggccgat tcattaatgc agctggcacg acaggtttcc   2280
cgactggaaa gcgggcagtg agcgcaacgc aattaatgtg agttagcgcg aattgatctg   2340
gtttgacagc ttatcatcga ctgcacggtg caccaatgct tctggcgtca ggcagccatc   2400
ggaagctgtg gtatggctgt gcaggtcgta aatcactgca taattcgtgt cgctcaaggc   2460
gcactcccgt tctggataat gtttttttgcg ccgacatcat aacggttctg gcaaatattc   2520
tgaaatgagc tgttgacaat taatcatccg gctcgtataa tgtgtggaat tgtgagcgga   2580
taacaatttc acacaggaaa cagaccatgg aattctacgt actagtgaat tcaggaggta   2640
```

```
ataaatatgg gtctgatgct gattgattgg tgtgcactgg ctctggttgt tttcattggc   2700
ctgccgcacg gcgcgctgga tgctgccatt tctttttcta tgatctcttc tgcaaaacgc   2760
attgctcgtc tggctggtat tctgctgatc tatctgctgc tggcgaccgc gttcttcctg   2820
atctggtatc agctgccagc gtttagcctg ctgatcttcc tgctgatctc cattatccac   2880
tttggtatgg cagacttcaa cgcgtcccca agcaaactga aatggccgca tatcatcgcc   2940
cacggcggtg ttgttactgt ttggctgccg ctgatccaga aaaacgaagt aactaaactg   3000
tttagcatcc tgactaacgg tccgactccg atcctgtggg acatcctgct gattttcttc   3060
ctgtgttggt ctattggcgt gtgtctgcac acgtacgaaa ccctgcgctc taaacattac   3120
aacatcgcct ttgaactgat cggtctgatt ttcctggcgt ggtatgcgcc gcctctggtt   3180
acgtttgcca cttacttctg cttcattcat tcccgtcgcc acttctcctt tgtgtggaag   3240
cagctgcaac acatgtcttc caaaaagatg atgattggca gcgcgattat cctgtcctgt   3300
acctcttggc tgatcggcgg tggtatctat ttcttcctga actccaaaat gatcgcctct   3360
gaggctgcgc tgcagactgt gttcatcggt ctggcggcac tgaccgtgcc gcacatgatt   3420
ctgatcgact tcatcttccg tccgcactct tcccgtatca aatcaaaaa ctaattaatt   3480
aaaggaggta ataatatgac tcataaagca acggagatcc tgacaggtaa agttatgcaa   3540
aaatcggtct taattaccgg atgttccagt ggaattggcc tggaaagcgc gctcgaatta   3600
aaacgccagg gttttcatgt gctggcaggt tgccggaaac cggatgatgt tgagcgcatg   3660
aacagcatgg gatttaccgg cgtgttgatc gatctggatt caccagaaag tgttgatcgc   3720
gcagccgacg aggtgatcgc cctgaccgat aattgtctgt atgggatctt taacaatgcc   3780
ggattcggca tgtatggccc cctttccacc atcagccgtg cgcagatgga acagcagttt   3840
tccgccaact tttcggcgc acaccagctc accatgcgcc tgttacccgc gatgttaccg   3900
cacggtgaag ggcgtattgt gatgacatca tcggtgatgg gattaatctc cacgccgggt   3960
cgtggcgctt acgcggccag taaatatgcg ctggaggcgt ggtcagatgc actgcgcatg   4020
gagctgcgcc acagcggaat taaagtcagc ctgatcgaac ccggtcccat tcgtactcgc   4080
ttcaccgaca acgtcaacca gacgcaaagt gataaaccag tcgaaaatcc cggcatcgcc   4140
gcccgcttta cgttgggacc ggaagcggtg gtggacaaag tacgccatgc ttttattagc   4200
gagaagccga agatgcgcta tccggtgacg ctggtgacct gggcggtaat ggtgcttaag   4260
cgcctgctgc cggggcgcgt gatggacaaa atattgcagg ggtaactagt aggaggtaat   4320
aaatatggtg agtggcagta aagcgggcgt ttcgcctcat cgcgaaatag aagtaatgag   4380
acaatccatt gacgatcacc tggctggcct gttacctgaa accgacagcc aggatatcgt   4440
cagccttgcg atgcgtgaag gcgtcatggc acccggtaaa cggatccgtc cgctgctgat   4500
gctgctggcc gcccgcgacc tccgctacca gggcagtatg cctacgctgc tcgatctcgc   4560
ctgcgccgtt gaactgaccc ataccgcgtc gctgatgctc gacgacatgc cctgcatgga   4620
caacgccgag ctgcgccgcg gtcagcccac tacccacaaa aaatttggtg agagcgtggc   4680
gatccttgcc tccgttgggc tgctctctaa agcctttggt ctgatcgccg ccaccggcga   4740
tctgccgggg gagaggcgtg cccaggcggt caacgagctc tctaccgccg tgggcgtgca   4800
gggcctggta ctggggcagt ttcgcgatct taacgatgcc gccctcgacc gtacccctga   4860
cgctatcctc agcaccaacc acctcaagac cggcattctg ttcagcgcga tgctgcagat   4920
cgtcgccatt gcttccgcct cgtcgccgag cacgcgagag acgctgcacg ccttcgccct   4980
cgacttcggc caggcgtttc aactgctgga cgatctgcgt gacgatcacc cggaaaccgg   5040
```

```
taaagatcgc aataaggacg cgggaaaatc gacgctggtc aaccggctgg gcgcagacgc   5100
ggcccggcaa aagctgcgcg agcatattga ttccgccgac aaacacctca cttttgcctg   5160
tccgcagggc ggcgccatcc gacagtttat gcatctgtgg tttggccatc accttgccga   5220
ctggtcaccg gtcatgaaaa tcgcctgata actcgaggag gtataaagga tgaaaaaaac   5280
cgttgtgatt ggcgcaggct ttggtggcct ggcgctggcg attcgcctgc aggcggcagg   5340
gatcccaacc gtactgctgg agcagcggga caagcccggc ggtcgggcct acgtctggca   5400
tgaccagggc tttacctttg acgccgggcc gacggtgatc accgatccta ccgcgcttga   5460
ggcgctgttc accctggccg gcaggcgcat ggaggattac gtcaggctgc tgccggtaaa   5520
acccttctac cgactctgct gggagtccgg gaagaccctc gactatgcta acgacagcgc   5580
cgagcttgag gcgcagatta cccagttcaa cccccgcgac gtcgagggct accggcgctt   5640
tctggcttac tcccaggcgg tattccagga gggatatttg cgcctcggca gcgtgccgtt   5700
cctctctttt cgcgacatgc tgcgcgccgg gccgcagctg cttaagctcc aggcgtggca   5760
gagcgtctac cagtcggttt cgcgctttat tgaggatgag catctgcggc aggccttctc   5820
gttccactcc ctgctggtag gcggcaaccc cttcaccacc tcgtccatct acaccctgat   5880
ccacgccctt gagcgggagt gggggtctg gttccctgag ggcggcaccg gggcgctggt   5940
gaacggcatg gtgaagctgt ttaccgatct gggcggggag atcgaactca acgcccgggt   6000
cgaagagctg gtggtggccg ataaccgcgt aagccaggtc cggctggcgg atggtcggat   6060
ctttgacacc gacgccgtag cctcgaacgc tgacgtggtg aacacctata aaaagctgct   6120
cggccaccat ccggtggggc agaagcgggc ggcagcgctg gagcgcaaga gcatgagcaa   6180
ctcgctgttt gtgctctact tcggcctgaa ccagcctcat tcccagctgg cgcaccatac   6240
catctgtttt ggtccccgct accgggagct gatcgacgag atctttaccg gcagcgcgct   6300
ggcggatgac ttctcgctct acctgcactc gccctgcgtg accgatccct cgctcgcgcc   6360
tcccggctgc gccagcttct acgtgctggc cccggtgccg catcttggca acgcgccgct   6420
ggactgggcg caggaggggc cgaagctgcg cgaccgcatc tttgactacc ttgaagagcg   6480
ctatatgccc ggcctgcgta gccagctggt gacccagcgg atctttaccc cggcagactt   6540
ccacgacacg ctggatgcgc atctgggatc ggccttctcc atcgagccgc tgctgaccca   6600
aagcgcctgg ttccgcccgc acaaccgcga cagcgacatt gccaacctct acctggtggg   6660
cgcaggtact caccctgggg cgggcattcc tggcgtagtg gcctcggcga aagccaccgc   6720
cagcctgatg attgaggatc tgcaatgagc caaccgccgc tgcttgacca cgccacgcag   6780
accatggcca acggctcgaa aagttttgcc accgctgcga agctgttcga cccggccacc   6840
cgccgtagcg tgctgatgct ctacacctgg tgccgccact gcgatgacgt cattgacgac   6900
cagacccacg gcttcgccag cgaggccgcg gcggaggagg aggccaccca gcgcctggcc   6960
cggctgcgca cgctgaccct ggcggcgttt gaaggggccg agatgcagga tccggccttc   7020
gctgcctttc aggaggtggc gctgacccac ggtattacgc cccgcatggc gctcgatcac   7080
ctcgacggct ttgcgatgga cgtggctcag acccgctatg tcacctttga ggatacgctg   7140
cgctactgct atcacgtggc gggcgtggtg ggtctgatga tggccagggt gatgggcgtg   7200
cgggatgagc gggtgctgga tcgcgcctgc gatctggggc tggccttcca gctgacgaat   7260
atcgcccggg atattattga cgatgcggct attgaccgct gctatctgcc cgccgagtgg   7320
ctgcaggatg ccgggctgac cccggagaac tatgccgcgc gggagaatcg ggccgcgctg   7380
```

-continued

```
gcgcgggtgg cggagcggct tattgatgcc gcagagccgt actacatctc ctcccaggcc   7440

gggctacacg atctgccgcc gcgctgcgcc tgggcgatcg ccaccgcccg cagcgtctac   7500

cgggagatcg gtattaaggt aaaagcggcg ggaggcagcg cctgggatcg ccgccagcac   7560

accagcaaag gtgaaaaaat tgccatgctg atggcggcac cggggcaggt tattcgggcg   7620

aagacgacga gggtgacgcc gcgtccggcc ggtctttggc agcgtcccgt ttagtaatct   7680

agaggaggta ataaaatatg cttcgttcgt tgctcagagg cctcacgcat atccccgcg   7740

tgaactccgc ccagcagccc agctgtgcac acgcgcgact ccagtttaag ctcaggagca   7800

tgcagatgac gctcatgcag cccagcatct cagccaatct gtcgcgcgcc gaggaccgca   7860

cagaccacat gaggggtgca agcacctggg caggcgggca gtcgcaggat gagctgatgc   7920

tgaaggacga gtgcatcttg gtggatgttg aggacaacat cacaggccat gccagcaagc   7980

tggagtgtca caagttccta ccacatcagc ctgcaggcct gctgcaccgg gccttctctg   8040

tgttcctgtt tgacgatcag gggcgactgc tgctgcaaca gcgtgcacgc tcaaaaatca   8100

ccttcccaag tgtgtggacg aacacctgct gcagccaccc tttacatggg cagaccccag   8160

atgaggtgga ccaactaagc caggtggccg acggaacagt acctggcgca aaggctgctg   8220

ccatccgcaa gttggagcac gagctgggga taccagcgca ccagctgccg gcaagcgcgt   8280

ttcgcttcct cacgcgtttg cactactgtg ccgcggacgt gcagccagct gcgacacaat   8340

cagcgctctg gggcgagcac gaaatggact acatcttgtt catccgggcc aacgtcacct   8400

tggcgcccaa ccctgacgag gtggacgaag tcaggtacgt gacgcaagag gagctgcggc   8460

agatgatgca gccggacaac gggctgcaat ggtcgccgtg gtttcgcatc atcgccgcgc   8520

gcttccttga gcgttggtgg gctgacctgg acgcggccct aaacactgac aaacacgagg   8580

attggggaac ggtgcatcac atcaacgaag cgtgataagc ggccgcgctg ttgacaatta   8640

atcatccggc tcgtataatg tgtggaattg tgagcggata acaatttcac acaggaaaca   8700

gaccatggag ttgaaaacag tagttattat tgatgcatta cgaacaccaa ttggaaaata   8760

taaaggcagc ttaagtcaag taagtgccgt agacttagga acacatgtta caacacaact   8820

tttaaaaaga cattccacta tttctgaaga aattgatcaa gtaatctttg gaaatgtttt   8880

acaagctgga aatggccaaa atcccgcacg acaaatagca ataaacagcg gtttatctca   8940

tgaaattccc gcaatgacag ttaatgaggt ctgcggatca ggaatgaagg ccgttatttt   9000

ggcgaaacaa ttgattcaat taggagaagc ggaagtttta attgctggcg ggattgagaa   9060

tatgtcccaa gcacctaaat tacaacgatt taattacgaa acagaaagct atgatgcgcc   9120

tttttctagt atgatgtacg atgggttaac ggatgccttt agtggtcaag caatgggctt   9180

aactgctgaa aatgtggccg aaaagtatca tgtaactaga gaagagcaag atcaattttc   9240

tgtacattca caattaaaag cagctcaagc acaagcagaa gggatattcg ctgacgaaat   9300

agccccatta gaagtatcag gaacgcttgt ggagaaagat gaagggattc gccctaattc   9360

gagcgttgag aagctaggaa cgcttaaaac agtttttaaa gaagacggta ctgtaacagc   9420

agggaatgca tcaaccatta atgatggggc ttctgctttg attattgctt cacaagaata   9480

tgccgaagca cacggtcttc cttatttagc tattattcga gacagtgtgg aagtcggtat   9540

tgatccagcc tatatgggaa tttcgccgat taaagccatt caaaaactgt tagcgcgcaa   9600

tcaacttact acggaagaaa ttgatctgta tgaaatcaac gaagcatttg cagcaacttc   9660

aatcgtggtc caaagagaac tggctttacc agaggaaaag gtcaacattt atggtggcgg   9720

tatttcatta ggtcatgcga ttggtgccac aggtgctcgt ttattaacga gtttaagtta   9780
```

-continued

```
tcaattaaat caaaaagaaa agaaatatgg agtggcttct ttatgtatcg gcggtggctt    9840
aggactcgct atgctactag agagacctca gcaaaaaaaa aacagccgat tttatcaaat    9900
gagtcctgag gaacgcctgg cttctcttct taatgaaggc cagatttctg ctgatacaaa    9960
aaaagaattt gaaaatacgg ctttatcttc gcagattgcc aatcatatga ttgaaaatca   10020
aatcagtgaa acagaagtgc cgatgggcgt tggcttacat ttaacagtgg acgaaactga   10080
ttatttggta ccaatggcga cagaagagcc ctcagtgatt gcggctttga gtaatggtgc   10140
aaaaatagca caaggattta aaacagtgaa tcaacaacgt ttaatgcgtg gacaaatcgt   10200
tttttacgat gttgcagacg ccgagtcatt gattgatgaa ctacaagtaa gagaaacgga   10260
aatttttcaa caagcagagt taagttatcc atctatcgtt aaacgcggcg gcggcttaag   10320
agatttgcaa tatcgtgctt ttgatgaatc atttgtatct gtcgactttt tagtagatgt   10380
taaggatgca atgggggcaa atatcgttaa cgctatgttg gaaggtgtgg ccgagttgtt   10440
ccgtgaatgg tttgcggagc aaaagatttt attcagtatt ttaagtaatt atgccacgga   10500
gtcggttgtt acgatgaaaa cggctattcc agtttcacgt ttaagtaagg ggagcaatgg   10560
ccgggaaatt gctgaaaaaa ttgttttagc ttcacgctat gcttcattag atccttatcg   10620
ggcagtcacg cataacaaag ggatcatgaa tggcattgaa gctgtcgttt tagctacagg   10680
aaatgataca cgcgctgtta gcgcttcttg tcatgctttt gcggtgaagg aaggtcgcta   10740
ccaaggtttg actagttgga cgctggatgg cgaacaacta attggtgaaa tttcagttcc   10800
gcttgcgtta gccacggttg gcggtgccac aaaagtctta cctaaatctc aagcagctgc   10860
tgatttgtta gcagtgacgg atgcaaaaga actaagtcga gtagtagcgg ctgttggttt   10920
ggcacaaaat ttagcggcgt tacgggcctt agtctctgaa ggaattcaaa aaggacacat   10980
ggctctacaa gcacgttctt tagcgatgac ggtcggagct actggtaaag aagttgaggc   11040
agtcgctcaa caattaaaac gtcaaaaaac gatgaaccaa gaccgagcct tggctatttt   11100
aaatgattta agaaaacaat aaaaaaacag ttcagcagaa attattctgc tgaactgttt   11160
tttttcacat taggtagccg tttcagctcg acaggaggag cggctatgca accgcattat   11220
gatctgattc tcgtgggggc tggactcgcg aatggcctta tcgccctgcg tcttcagcag   11280
cagcaacctg atatgcgtat tttgcttatc gacgccgcac cccaggcggg cgggaatcat   11340
acgtggtcat ttcaccacga tgatttgact gagagccaac atcgttggat agctccgctg   11400
gtggttcatc actggcccga ctatcaggta cgctttccca cacgccgtcg taagctgaac   11460
agcggctact tttgtattac ttctcagcgt ttcgctgagg ttttacagcg acagtttggc   11520
ccgcacttgt ggatggatac cgcggtcgca gaggttaatg cggaatctgt tcggttgaaa   11580
aagggtcagg ttatcggtgc ccgcgcggtg attgacgggc ggggttatgc ggcaaattca   11640
gcactgagcg tgggcttcca ggcgtttatt ggccaggaat ggcgattgag ccacccgcat   11700
ggtttatcgt ctcccattat catggatgcc acggtcgatc agcaaaatgg ttatcgcttc   11760
gtgtacagcc tgccgctctc gccgaccaga ttgttaattg aagacacgca ctatattgat   11820
aatgcgacat tagatcctga atgcgcgcgg caaaatattt gcgactatgc cgcgcaacag   11880
ggttggcagc ttcagacact gctgcgagaa gaacagggcg ccttacccat tactctgtcg   11940
ggcaatgccg acgcattctg gcagcagcgc cccctggcct gtagtggatt acgtgccggt   12000
ctgttccatc ctaccaccgg ctattcactg ccgctggcgg ttgccgtggc cgaccgcctg   12060
agtgcacttg atgtctttac gtcggcctca attcaccatg ccattacgca ttttgcccgc   12120
```

-continued gagcgctggc agcagcaggg ctttttccgc atgctgaatc gcatgctgtt tttagccgga 12180
cccgccgatt cacgctggcg ggttatgcag cgtttttatg gtttacctga agatttaatt 12240
gcccgttttt atgcgggaaa actcacgctg accgatcggc tacgtattct gagcggcaag 12300
ccgcctgttc cggtattagc agcattgcaa gccattatga cgactcatcg ttaactgcag 12360
gcatgcaagc tggggatcct acctgacgct tttatcgca actctctact gtttctccat 12420
acccgttttt ttgggctggc ggatgagaga agattttcag cctgatacag attaaatcag 12480
aacgcagaag cggtctgata aaacagaatt tgcctggcgg cagtagcgcg gtggtcccac 12540
ctgaccccat gccgaactca gaagtgaaac gccgtagcgc cgatggtagt gtggggtctc 12600
cccatgcgag agtagggaac tgccaggcat caaataaaac gaaaggctca gtcgaaagac 12660
tgggcctttc gttttatctg ttgtttgtcg gtgaacgctc tcctgagtag gacaaatccg 12720
ccgggagcgg atttgaacgt tgcgaagcaa cggcccggag ggtggcgggc aggacgcccg 12780
ccataaactg ccaggcatca aattaagcag aaggccatcc tgacggatgg cctttttgcg 12840
tttctacaaa ctctttttgt ttatttttct aaatacattc aaatatgtat ccgctcaa 12898

<210> SEQ ID NO 87
<211> LENGTH: 5381
<212> TYPE: DNA
<213> ORGANISM: Artificial Sequence
<220> FEATURE:
<223> OTHER INFORMATION: pT-dxr

<400> SEQUENCE: 87
aacaaaccat gcaaatgctg aatgagggca tcgttcccac tgcgatgctg gttgccaacg 60
atcagatggc gctgggcgca atgcgcgcca ttaccgagtc cgggctgcgc gttggtgcgg 120
atatctcggt agtgggatac gacgataccg aagacagctc atgttatatc ccgccgttaa 180
ccaccatcaa acaggatttt cgcctgctgg ggcaaaccag cgtggaccgc ttgctgcaac 240
tctctcaggg ccaggcggtg aagggcaatc agctgttgcc cgtctcactg gtgaaaagaa 300
aaaccaccct ggcgcccaat acgcaaaccg cctctccccg cgcgttggcc gattcattaa 360
tgcagctggc acgacaggtt tcccgactgg aaagcgggca gtgagcgcaa cgcaattaat 420
gtgagttagc gcgaattgat ctggtttgac agcttatcat cgactgcacg gtgcaccaat 480
gcttctggcg tcaggcagcc atcggaagct gtggtatggc tgtgcaggtc gtaaatcact 540
gcataattcg tgtcgctcaa ggcgcactcc cgttctggat aatgtttttt gcgccgacat 600
cataacggtt ctggcaaata ttctgaaatg agctgttgac aattaatcat ccggctcgta 660
taatgtgtgg aattgtgagc ggataacaat ttcacacagg aaacagacca tggaattcga 720
gctcatgaag caactcacca ttctgggctc gaccggctcg attggttgca gcacgctgga 780
cgtggtgcgc cataatcccg aacacttccg cgtagttgcg ctggtggcag gcaaaaatgt 840
cactcgcatg gtagaacagt gcctggaatt ctctccccgc tatgccgtaa tggacgatga 900
agcgagtgcg aaacttctta aaacgatgct acagcaacag ggtagccgca ccgaagtctt 960
aagtgggcaa caagccgctt gcgatatggc agcgcttgag gatgttgatc aggtgatggc 1020
agccattgtt ggcgctgctg ggctgttacc tacgcttgct gcgatccgcg cgggtaaaac 1080
cattttgctg gccaataaag aatcactggt tacctgcgga cgtctgttta tggacgccgt 1140
aaagcagagc aaagcgcaat tgttaccggt cgatagcgaa cataacgcca tttttcagag 1200
tttaccgcaa cctatccagc ataatctggg atacgctgac cttgagcaaa atggcgtggt 1260
gtccatttta cttaccgggt ctggtggccc tttccgtgag acgccattgc gcgatttggc 1320

```
aacaatgacg ccggatcaag cctgccgtca tccgaactgg tcgatggggc gtaaaatttc   1380
tgtcgattcg gctaccatga tgaacaaagg tctggaatac attgaagcgc gttggctgtt   1440
taacgccagc gccagccaga tggaagtgct gattcacccg cagtcagtga ttcactcaat   1500
ggtgcgctat caggacggca gtgttctggc gcagctgggg gaaccggata tgcgtacgcc   1560
aattgcccac accatggcat ggccgaatcg cgtgaactct ggcgtgaagc cgctcgattt   1620
ttgcaaacta agtgcgttga catttgccgc accggattat gatcgttatc catgcctgaa   1680
actggcgatg gaggcgttcg aacaaggcca ggcagcgacg acagcattga atgccgcaaa   1740
cgaaatcacc gttgctgctt ttcttgcgca acaaatccgc tttacggata tcgctgcgtt   1800
gaatttatcc gtactggaaa aaatggatat gcgcgaacca caatgtgtgg acgatgtgtt   1860
atctgttgat gcgaacgcgc gtgaagtcgc cagaaaagag gtgatgcgtc tcgcaagctg   1920
atctagagcg gggatccac tagttctaga gtcgacctgc aggcatgcaa gcttggctgt   1980
tttggcggat gagagaagat tttcagcctg atacagatta aatcagaacg cagaagcggt   2040
ctgataaaac agaatttgcc tggcggcagt agcgcggtgg tcccacctga ccccatgccg   2100
aactcagaag tgaaacgccg tagcgccgat ggtagtgtgg ggtctcccca tgcgagagta   2160
gggaactgcc aggcatcaaa taaaacgaaa ggctcagtcg aaagactggg cctttcgttt   2220
tatctgttgt ttgtcggtga acgctctcct gagtaggaca aatccgccgg gagcggattt   2280
gaacgttgcg aagcaacggc ccggagggtg gcgggcagga cgcccgccat aaactgccag   2340
gcatcaaatt aagcagaagg ccatcctgac ggatggcctt tttgcgtttc tacaaactct   2400
ttttgtttat ttttctaaat acattcaaat atgtatccgc tcatgagaca ataaccctga   2460
taaatgcttc aataatattg aaaaaggaag agtatgagta ttcaacattt ccgtgtcgcc   2520
cttattccct tttttgcggc attttgcctt cctgtttttg ctcacccaga aacgctggtg   2580
aaagtaaaag atgctgaaga tcagttgggt gcacgagtgg gttacatcga actggatctc   2640
aacagcggta agatccttga gagttttcgc cccgaagaac gttttccaat gatgagcact   2700
tttaaagttc tgctatgtgg cgcggtatta tcccgtgttg acgccgggca agagcaactc   2760
ggtcgccgca tacactattc tcagaatgac ttggttgagt actcaccagt cacagaaaag   2820
catcttacgg atggcatgac agtaagagaa ttatgcagtg ctgccataac catgagtgat   2880
aacactgcgg ccaacttact tctgacaacg atcggaggac cgaaggagct aaccgctttt   2940
ttgcacaaca tgggggatca tgtaactcgc cttgatcgtt gggaaccgga gctgaatgaa   3000
gccataccaa acgacgagcg tgacaccacg atgcctacag caatggcaac aacgttgcgc   3060
aaactattaa ctggcgaact acttactcta gcttcccggc aacaattaat agactggatg   3120
gaggcggata aagttgcagg accacttctg cgctcggccc ttccggctgg ctggtttatt   3180
gctgataaat ctggagccgg tgagcgtggg tctcgcggta tcattgcagc actggggcca   3240
gatggtaagc cctcccgtat cgtagttatc tacacgacgg ggagtcaggc aactatggat   3300
gaacgaaata gacagatcgc tgagataggt gcctcactga ttaagcattg gtaactgtca   3360
gaccaagttt actcatatat actttagatt gatttaaaac ttcattttta atttaaaagg   3420
atctaggtga agatcctttt tgataatctc atgaccaaaa tcccttaacg tgagttttcg   3480
ttccactgag cgtcagaccc cgtagaaaag atcaaaggat cttcttgaga tccttttttt   3540
ctgcgcgtaa tctgctgctt gcaaacaaaa aaaccaccgc taccagcggt ggtttgtttg   3600
ccggatcaag agctaccaac tctttttccg aaggtaactg gcttcagcag agcgcagata   3660
```

-continued

```
ccaaatactg tccttctagt gtagccgtag ttaggccacc acttcaagaa ctctgtagca   3720

ccgcctacat acctcgctct gctaatcctg ttaccagtgg ctgctgccag tggcgataag   3780

tcgtgtctta ccgggttgga ctcaagacga tagttaccgg ataaggcgca gcggtcgggc   3840

tgaacggggg gttcgtgcac acagcccagc ttggagcgaa cgacctacac cgaactgaga   3900

tacctacagc gtgagctatg agaaagcgcc acgcttcccg aagggagaaa ggcggacagg   3960

tatccggtaa gcggcagggt cggaacagga gagcgcacga gggagcttcc agggggaaac   4020

gcctggtatc tttatagtcc tgtcgggttt cgccacctct gacttgagcg tcgatttttg   4080

tgatgctcgt caggggggcg gagcctatgg aaaaacgcca gcaacgcggc ctttttacgg   4140

ttcctggcct tttgctggcc ttttgctcac atgttctttc ctgcgttatc ccctgattct   4200

gtggataacc gtattaccgc ctttgagtga gctgataccg ctcgccgcag ccgaacgacc   4260

gagcgcagcg agtcagtgag cgaggaagcg gaagagcgcc tgatgcggta ttttctcctt   4320

acgcatctgt gcggtatttc acaccgcata tggtgcactc tcagtacaat ctgctctgat   4380

gccgcatagt taagccagta tacactccgc tatcgctacg tgactgggtc atggctgcgc   4440

cccgacaccc gccaacaccc gctgacgcgc cctgacgggc ttgtctgctc ccggcatccg   4500

cttacagaca agctgtgacc gtctccggga gctgcatgtg tcagaggttt tcaccgtcat   4560

caccgaaacg cgcgaggcag cagatcaatt cgcgcgcgaa ggcgaagcgg catgcattta   4620

cgttgacacc atcgaatggt gcaaaacctt tcgcggtatg gcatgatagc gcccggaaga   4680

gagtcaattc agggtggtga atgtgaaacc agtaacgtta tacgatgtcg cagagtatgc   4740

cggtgtctct tatcagaccg tttcccgcgt ggtgaaccag gccagccacg tttctgcgaa   4800

aacgcgggaa aaagtggaag cggcgatggc ggagctgaat tacattccca accgcgtggc   4860

acaacaactg gcgggcaaac agtcgttgct gattggcgtt gccacctcca gtctggccct   4920

gcacgcgccg tcgcaaattg tcgcggcgat taaatctcgc gccgatcaac tgggtgccag   4980

cgtggtggtg tcgatggtag aacgaagcgg cgtcgaagcc tgtaaagcgg cggtgcacaa   5040

tcttctcgcg caacgcgtca gtgggctgat cattaactat ccgctggatg accaggatgc   5100

cattgctgtg gaagctgcct gcactaatgt tccggcgtta tttcttgatg tctctgacca   5160

gacacccatc aacagtatta ttttctccca tgaagacggt acgcgactgg gcgtggagca   5220

tctggtcgca ttgggtcacc agcaaatcgc gctgttagcg ggcccattaa gttctgtctc   5280

ggcgcgtctg cgtctggctg gctggcataa atatctcact cgcaatcaaa ttcagccgat   5340

agcggaacgg gaaggcgact ggagtgccat gtccggtttt c                      5381
```

<210> SEQ ID NO 88
<211> LENGTH: 7999
<212> TYPE: DNA
<213> ORGANISM: Artificial Sequence
<220> FEATURE:
<223> OTHER INFORMATION: pTAS-dxr

<400> SEQUENCE: 88

```
tcgacctgca ggcatgcaag cttggctgtt ttggcggatg agagaagatt ttcagcctga     60

tacagattaa atcagaacgc agaagcggtc tgataaaaca gaatttgcct ggcggcagta    120

gcgcggtggt cccacctgac cccatgccga actcagaagt gaaacgccgt agcgccgatg    180

gtagtgtggg gtctccccat gcgagagtag ggaactgcca ggcatcaaat aaaacgaaag    240

gctcagtcga aagactgggc ctttcgtttt atctgttgtt tgtcggtgaa cgctctcctg    300

agtaggacaa atccgccggg agcggatttg aacgttgcga agcaacggcc cggagggtgg    360
```

-continued cgggcaggac gcccgccata aactgccagg catcaaatta agcagaaggc catcctgacg 420
gatggccttt ttgcgtttct acaaactctt tttgtttatt tttctaaata cattcaaata 480
tgtatccgct catgagacaa taaccctgat aaatgcttca ataatattga aaaaggaaga 540
gtatgagtat tcaacatttc cgtgtcgccc ttattccctt ttttgcggca ttttgccttc 600
ctgtttttgc tcacccagaa acgctggtga aagtaaaaga tgctgaagat cagttgggtg 660
cacgagtggg ttacatcgaa ctggatctca acagcggtaa gatccttgag agttttcgcc 720
ccgaagaacg ttttccaatg atgagcactt ttaaagttct gctatgtggc gcggtattat 780
cccgtgttga cgccgggcaa gagcaactcg gtcgccgcat acactattct cagaatgact 840
tggttgagta ctcaccagtc acagaaaagc atcttacgga tggcatgaca gtaagagaat 900
tatgcagtgc tgccataacc atgagtgata acactgcggc caacttactt ctgacaacga 960
tcggaggacc gaaggagcta accgcttttt tgcacaacat gggggatcat gtaactcgcc 1020
ttgatcgttg ggaaccggag ctgaatgaag ccataccaaa cgacgagcgt gacaccacga 1080
tgcctacagc aatggcaaca acgttgcgca aactattaac tggcgaacta cttactctag 1140
cttcccggca acaattaata gactggatgg aggcggataa agttgcagga ccacttctgc 1200
gctcggccct tccggctggc tggtttattg ctgataaatc tggagccggt gagcgtgggt 1260
ctcgcggtat cattgcagca ctggggccag atggtaagcc ctcccgtatc gtagttatct 1320
acacgacggg gagtcaggca actatggatg aacgaaatag acagatcgct gagataggtg 1380
cctcactgat taagcattgg taactgtcag accaagttta ctcatatata ctttagattg 1440
atttaaaact tcatttttaa tttaaaagga tctaggtgaa gatccttttt gataatctca 1500
tgaccaaaat cccttaacgt gagttttcgt tccactgagc gtcagacccc gtagaaaaga 1560
tcaaaggatc ttcttgagat cctttttttc tgcgcgtaat ctgctgcttg caaacaaaaa 1620
aaccaccgct accagcggtg gtttgtttgc cggatcaaga gctaccaact ctttttccga 1680
aggtaactgg cttcagcaga gcgcagatac caaatactgt ccttctagtg tagccgtagt 1740
taggccacca cttcaagaac tctgtagcac cgcctacata cctcgctctg ctaatcctgt 1800
taccagtggc tgctgccagt ggcgataagt cgtgtcttac cgggttggac tcaagacgat 1860
agttaccgga taaggcgcag cggtcgggct gaacgggggg ttcgtgcaca cagcccagct 1920
tggagcgaac gacctacacc gaactgagat acctacagcg tgagctatga gaaagcgcca 1980
cgcttcccga agggagaaag gcggacaggt atccggtaag cggcagggtc ggaacaggag 2040
agcgcacgag ggagcttcca gggggaaacg cctggtatct ttatagtcct gtcgggtttc 2100
gccacctctg acttgagcgt cgatttttgt gatgctcgtc aggggggcgg agcctatgga 2160
aaaacgccag caacgcggcc tttttacggt tcctggcctt ttgctggcct tttgctcaca 2220
tgttctttcc tgcgttatcc cctgattctg tggataaccg tattaccgcc tttgagtgag 2280
ctgataccgc tcgccgcagc cgaacgaccg agcgcagcga gtcagtgagc gaggaagcgg 2340
aagagcgcct gatgcggtat tttctcctta cgcatctgtg cggtatttca caccgcatat 2400
ggtgcactct cagtacaatc tgctctgatg ccgcatagtt aagccagtat acactccgct 2460
atcgctacgt gactgggtca tggctgcgcc ccgacacccg ccaacacccg ctgacgcgcc 2520
ctgacgggct tgtctgctcc cggcatccgc ttacagacaa gctgtgaccg tctccgggag 2580
ctgcatgtgt cagaggtttt caccgtcatc accgaaacgc gcgaggcagc agatcaattc 2640
gcgcgcgaag gcgaagcggc atgcatttac gttgacacca tcgaatggtg caaaaccttt 2700

-continued

```
cgcggtatgg catgatagcg cccggaagag agtcaattca gggtggtgaa tgtgaaacca   2760
gtaacgttat acgatgtcgc agagtatgcc ggtgtctctt atcagaccgt ttcccgcgtg   2820
gtgaaccagg ccagccacgt ttctgcgaaa acgcgggaaa aagtggaagc ggcgatggcg   2880
gagctgaatt acattcccaa ccgcgtggca caacaactgg cgggcaaaca gtcgttgctg   2940
attggcgttg ccacctccag tctggccctg cacgcgccgt cgcaaattgt cgcggcgatt   3000
aaatctcgcg ccgatcaact gggtgccagc gtggtggtgt cgatggtaga acgaagcggc   3060
gtcgaagcct gtaaagcggc ggtgcacaat cttctcgcgc aacgcgtcag tgggctgatc   3120
attaactatc cgctggatga ccaggatgcc attgctgtgg aagctgcctg cactaatgtt   3180
ccggcgttat ttcttgatgt ctctgaccag acacccatca acagtattat tttctcccat   3240
gaagacggta cgcgactggg cgtggagcat ctggtcgcat tgggtcacca gcaaatcgcg   3300
ctgttagcgg gcccattaag ttctgtctcg gcgcgtctgc gtctggctgg ctggcataaa   3360
tatctcactc gcaatcaaat tcagccgata gcggaacggg aaggcgactg gagtgccatg   3420
tccggttttc aacaaaccat gcaaatgctg aatgagggca tcgttcccac tgcgatgctg   3480
gttgccaacg atcagatggc gctgggcgca atgcgcgcca ttaccgagtc cgggctgcgc   3540
gttggtgcgg atatctcggt agtgggatac gacgataccg aagacagctc atgttatatc   3600
ccgccgttaa ccaccatcaa acaggatttt cgcctgctgg ggcaaaccag cgtggaccgc   3660
ttgctgcaac tctctcaggg ccaggcggtg aagggcaatc agctgttgcc cgtctcactg   3720
gtgaaaagaa aaaccaccct ggcgcccaat acgcaaaccg cctctccccg cgcgttggcc   3780
gattcattaa tgcagctggc acgacaggtt tcccgactgg aaagcgggca gtgagcgcaa   3840
cgcaattaat gtgagttagc gcgaattgat ctggtttgac agcttatcat cgactgcacg   3900
gtgcaccaat gcttctggcg tcaggcagcc atcggaagct gtggtatggc tgtgcaggtc   3960
gtaaatcact gcataattcg tgtcgctcaa ggcgcactcc cgttctggat aatgtttttt   4020
gcgccgacat cataacggtt ctggcaaata ttctgaaatg agctgttgac aattaatcat   4080
ccggctcgta taatgtgtgg aattgtgagc ggataacaat ttcacacagg aggtaataaa   4140
tatggaattc atggactttc cgcagcaact cgaagcctgc gttaagcagg ccaaccaggc   4200
gctgagccgt tttatcgccc cactgccctt tcagaacact cccgtggtcg aaaccatgca   4260
gtatggcgca ttattaggtg gtaagcgcct gcgacctttc ctggtttatg ccaccggtca   4320
tatgttcggc gttagcacaa acacgctgga cgcacccgct gccgccgttg agtgtatcca   4380
cgcttactca ttaattcatg atgatttacc ggcaatggat gatgacgatc tgcgtcgcgg   4440
tttgccaacc tgccatgtga agtttggcga agcaaacgcg attctcgctg gcgacgcttt   4500
acaaacgctg gcgttctcga ttttaagcga tgccgatatg ccggaagtgt cggaccgcga   4560
cagaatttcg atgatttctg aactggcgag cgccagtggt attgccggaa tgtgcggtgg   4620
tcaggcatta gatttagacg cggaaggcaa acacgtacct ctggacgcgc ttgagcgtat   4680
tcatcgtcat aaaaccggcg cattgattcg cgccgccgtt cgccttggtg cattaagcgc   4740
cggagataaa ggacgtcgtg ctctgccggt actcgacaag tatgcagaga gcatcggcct   4800
tgccttccag gttcaggatg acatcctgga tgtggtggga gatactgcaa cgttgggaaa   4860
acgccagggt gccgaccagc aacttggtaa aagtacctac cctgcacttc tgggtcttga   4920
gcaagcccgg aagaaagccc gggatctgat cgacgatgcc cgtcagtcgc tgaaacaact   4980
ggctgaacag tcactcgata cctcggcact ggaagcgcta gcggactaca tcatccagcg   5040
taataaataa ggatccaaaa aggaggtaat aaaccatgtc aactcaacaa gtttcatcag   5100
```

-continued

```
agaacattgt tcgtaacgct gcgaatttcc atcctaatat atggggaaac catttcctca   5160
catgtccttc tcagacgatt gatagttgga ctcaacagca ccacaaagaa ctgaaagaag   5220
aggtgaggaa aatgatggtg tctgatgcaa ataaacctgc ccagagattg cgcttgattg   5280
atactgtcca aaggctaggt gtggcttacc actttgaaaa ggagattgat gatgcattgg   5340
agaaaatagg tcatgaccct tttgatgata aagatgatct ctacattgtc tctctttgtt   5400
ttcgattgct gaggcagcat ggaattaaga tatcatgtga tgtgtttgag aagtttaaag   5460
atgacgatgg aaaattcaag gcatcattga tgaatgatgt tcaaggcatg ctaagtttat   5520
atgaggcagc acacctagcc attcacggag aagatatttt agatgaagca attgttttca   5580
cgaccactca ccttaagtca acggtatcta attctcctgt aaactctact tttgctgaac   5640
aaatacgtca ttctctcaga gttcctctcc gtaaagctgt acctaggtta gagtcgaggt   5700
atttcttgga tatctattca agagatgatt tgcacgataa aactttgctc aatttcgcaa   5760
agttagactt taatatacta caagcaatgc accagaagga agcaagtgag atgaccaggt   5820
ggtggagaga ttttgacttc cttaaaaagc tgccttatat aagagacaga gtcgtggagc   5880
tatatttttg gattctggtg ggagtgtctt atcagcccaa attcagcact ggtagaattt   5940
ttttgtccaa aataatatgc cttgagaccc tcgtagatga tacatttgac gcctacggta   6000
cttttgacga gctcgcaatc tttactgaag cagttacaag atgggacctt ggccacagag   6060
atgcactacc agaatacatg aaattcattt tcaagacact cattgatgtc tacagtgaag   6120
ctgagcaaga actggcaaag gaagggagat catacagcat acactatgca atacgatcgt   6180
tccaagaact agttatgaag tacttctgcg aagccaagtg gttaaataaa ggttatgttc   6240
cgagcctgga cgattataaa tcagtttcat taagaagtat cggtttttta ccgatagcgg   6300
tagcttcctt cgttttcatg ggtgatattg caactaagga ggtctttgaa tgggaaatga   6360
ataaccctaa gatcataata gccgcagaaa cgattttcag attcctggat gacatagcag   6420
gccataggtt tgagcaaaag agagaacata gtccatcagc tattgaatgc tacaagaatc   6480
aacatggagt gtctgaggaa gaggcagtta aagcgttgtc gttagaagtt gctaatagtt   6540
ggaaagatat aaatgaggag ctgcttctca acccaatggc tattccttta cctctgcttc   6600
aggtgattct tgatctctca cgttcggccg attttatgta cggtaatgct caagatcgct   6660
tcacgcattc aacgatgatg aaagaccaag ttgatttggt gctgaaggac cccgttaagc   6720
ttgacgatta aagatctgtg tggaattgtg agcggataac aatttcacac aggaaacaga   6780
ccatggaatt cgagctcatg aagcaactca ccattctggg ctcgaccggc tcgattggtt   6840
gcagcacgct ggacgtggtg cgccataatc ccgaacactt ccgcgtagtt gcgctggtgg   6900
caggcaaaaa tgtcactcgc atggtagaac agtgcctgga attctctccc cgctatgccg   6960
taatggacga tgaagcgagt gcgaaacttc ttaaaacgat gctacagcaa cagggtagcc   7020
gcaccgaagt cttaagtggg caacaagccg cttgcgatat ggcagcgctt gaggatgttg   7080
atcaggtgat ggcagccatt gttggcgctg ctgggctgtt acctacgctt gctgcgatcc   7140
gcgcgggtaa aaccattttg ctggccaata aagaatcact ggttacctgc ggacgtctgt   7200
ttatggacgc cgtaaagcag agcaaagcgc aattgttacc ggtcgatagc gaacataacg   7260
ccatttttca gagtttaccg caacctatcc agcataatct gggatacgct gaccttgagc   7320
aaaatggcgt ggtgtccatt ttacttaccg ggtctggtgg ccctttccgt gagacgccat   7380
tgcgcgattt ggcaacaatg acgccggatc aagcctgccg tcatccgaac tggtcgatgg   7440
```

```
ggcgtaaaat ttctgtcgat tcggctacca tgatgaacaa aggtctggaa tacattgaag   7500

cgcgttggct gtttaacgcc agcgccagcc agatggaagt gctgattcac ccgcagtcag   7560

tgattcactc aatggtgcgc tatcaggacg gcagtgttct ggcgcagctg gggaaccgg   7620

atatgcgtac gccaattgcc cacaccatgg catggccgaa tcgcgtgaac tctggcgtga   7680

agccgctcga tttttgcaaa ctaagtgcgt tgacatttgc cgcaccggat tatgatcgtt   7740

atccatgcct gaaactggcg atggaggcgt tcgaacaagg ccaggcagcg acgacagcat   7800

tgaatgccgc aaacgaaatc accgttgctg cttttcttgc gcaacaaatc cgctttacgg   7860

atatcgctgc gttgaattta tccgtactgg aaaaaatgga tatgcgcgaa ccacaatgtg   7920

tggacgatgt gttatctgtt gatgcgaacg cgcgtgaagt cgccagaaaa gaggtgatgc   7980

gtctcgcaag ctgatctac                                                7999
```

```
<210> SEQ ID NO 89
<211> LENGTH: 7275
<212> TYPE: DNA
<213> ORGANISM: Artificial Sequence
<220> FEATURE:
<223> OTHER INFORMATION: pT-dxr/s

<400> SEQUENCE: 89

gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gtttttgcg ccgacatcat aacggttctg gcaaatattc    180

tgaaatgagc tgttgacaat taatcatccg gctcgtataa tgtgtggaat tgtgagcgga    240

taacaatttc acacaggaaa cagaccatgg aattcatgag ttttgatatt gccaaatacc    300

cgaccctggc actggtcgac tccacccagg agttacgact gttgccgaaa gagagtttac    360

cgaaactctg cgacgaactg cgccgctatt tactcgacag cgtgagccgt tccagcgggc    420

acttcgcctc cgggctgggc acggtcgaac tgaccgtggc gctgcactat gtctacaaca    480

ccccgtttga ccaattgatt tgggatgtgg ggcatcaggc ttatccgcat aaaattttga    540

ccggacgccg cgacaaaatc ggcaccatcc gtcagaaagg cggtctgcac ccgttcccgt    600

ggcgcggcga aagcgaatat gacgtattaa gcgtcgggca ttcatcaacc tccatcagtg    660

ccggaattgg tattgcggtt gctgccgaaa aagaaggcaa aaatcgccgc accgtctgtg    720

tcattggcga tggcgcgatt accgcaggca tggcgtttga agcgatgaat cacgcgggcg    780

atatccgtcc tgatatgctg gtgattctca acgacaatga aatgtcgatt tccgaaaatg    840

tcggcgcgct caacaaccat ctggcacagc tgctttccgg taagctttac tcttcactgc    900

gcgaaggcgg gaaaaaagtt ttctctggcg tgccgccaat taaagagctg ctcaaacgca    960

ccgaagaaca tattaaaggc atggtagtgc ctggcacgtt gtttgaagag ctgggcttta   1020

actacatcgg cccggtggac ggtcacgatg tgctggggct tatcaccacg ctaaagaaca   1080

tgcgcgacct gaaaggcccg cagttcctgc atatcatgac caaaaaaggt cgtggttatg   1140

aaccggcaga aaaagacccg atcactttcc acgccgtgcc taaatttgat ccctccagcg   1200

gttgtttgcc gaaaagtagc ggcggtttgc cgagctattc aaaaatcttt ggcgactggt   1260

tgtgcgaaac ggcagcgaaa gacaacaagc tgatggcgat tactccggcg atgcgtgaag   1320

gttccggcat ggtcgagttt tcacgtaaat tcccggatcg ctacttcgac gtggcaattg   1380

ccgagcaaca cgcggtgacc tttgctgcgg gtctggcgat tggtgggtac aaacccattg   1440

tcgcgattta ctccactttc ctgcaacgcg cctatgatca ggtgctgcat gacgtggcga   1500
```

-continued

```
ttcaaaagct tccggtcctg ttcgccatcg accgcgcggg cattgttggt gctgacggtc   1560
aaacccatca gggtgctttt gatctctctt acctgcgctg cataccggaa atggtcatta   1620
tgaccccgag cgatgaaaac gaatgtcgcc agatgctcta taccggctat cactataacg   1680
atggcccgtc agcggtgcgc tacccgcgtg gcaacgcggt cggcgtggaa ctgacgccgc   1740
tggaaaaact accaattggc aaaggcattg tgaagcgtcg tggcgagaaa ctggcgatcc   1800
ttaactttgg tacgctgatg ccagaagcgg cgaaagtcgc cgaatcgctg aacgccacgc   1860
tggtcgatat gcgttttgtg aaaccgcttg atgaagcgtt aattctggaa atggccgcca   1920
gccatgaagc gctggtcacc gtagaagaaa acgccattat gggcggcgca ggcagcggcg   1980
tgaacgaagt gctgatggcc catcgtaaac cagtacccgt gctgaacatt ggcctgccgg   2040
acttctttat tccgcaagga actcaggaag aaatgcgcgc cgaactcggc ctcgatgccg   2100
ctggtatgga agccaaaatc aaggcctggc tggcataagg taccacacag gaaacagacc   2160
atggaattcg agctcatgaa gcaactcacc attctgggct cgaccggctc gattggttgc   2220
agcacgctgg acgtggtgcg ccataatccc gaacacttcc gcgtagttgc gctggtggca   2280
ggcaaaaatg tcactcgcat ggtagaacag tgcctggaat tctctccccg ctatgccgta   2340
atggacgatg aagcgagtgc gaaacttctt aaaacgatgc tacagcaaca gggtagccgc   2400
accgaagtct taagtgggca acaagccgct tgcgatatgg cagcgcttga ggatgttgat   2460
caggtgatgg cagccattgt tggcgctgct gggctgttac ctacgcttgc tgcgatccgc   2520
gcgggtaaaa ccattttgct ggccaataaa gaatcactgg ttacctgcgg acgtctgttt   2580
atggacgccg taaagcagag caaagcgcaa ttgttaccgg tcgatagcga acataacgcc   2640
atttttcaga gtttaccgca acctatccag cataatctgg gatacgctga ccttgagcaa   2700
aatggcgtgg tgtccatttt acttaccggg tctggtggcc ctttccgtga gacgccattg   2760
cgcgatttgg caacaatgac gccggatcaa gcctgccgtc atccgaactg gtcgatgggg   2820
cgtaaaattt ctgtcgattc ggctaccatg atgaacaaag gtctggaata cattgaagcg   2880
cgttggctgt ttaacgccag cgccagccag atggaagtgc tgattcaccc gcagtcagtg   2940
attcactcaa tggtgcgcta tcaggacggc agtgttctgg cgcagctggg ggaaccggat   3000
atgcgtacgc caattgccca caccatggca tggccgaatc gcgtgaactc tggcgtgaag   3060
ccgctcgatt tttgcaaact aagtgcgttg acatttgccg caccggatta tgatcgttat   3120
ccatgcctga aactggcgat ggaggcgttc gaacaaggcc aggcagcgac gacagcattg   3180
aatgccgcaa acgaaatcac cgttgctgct tttcttgcgc aacaaatccg ctttacggat   3240
atcgctgcgt tgaatttatc cgtactggaa aaaatggata tgcgcgaacc acaatgtgtg   3300
gacgatgtgt tatctgttga tgcgaacgcg cgtgaagtcg ccagaaaaga ggtgatgcgt   3360
ctcgcaagct gatctagagc gggggatcca ctagttctag agtcgacctg caggcatgca   3420
agcttggctg ttttggcgga tgagagaaga ttttcagcct gatacagatt aaatcagaac   3480
gcagaagcgg tctgataaaa cagaatttgc ctggcggcag tagcgcggtg gtcccacctg   3540
accccatgcc gaactcagaa gtgaaacgcc gtagcgccga tggtagtgtg gggtctcccc   3600
atgcgagagt agggaactgc caggcatcaa ataaaacgaa aggctcagtc gaaagactgg   3660
gcctttcgtt ttatctgttg tttgtcggtg aacgctctcc tgagtaggac aaatccgccg   3720
ggagcggatt tgaacgttgc gaagcaacgg cccggagggt ggcgggcagg acgcccgcca   3780
taaactgcca ggcatcaaat taagcagaag gccatcctga cggatggcct ttttgcgttt   3840
```

-continued

```
ctacaaactc tttttgttta tttttctaaa tacattcaaa tatgtatccg ctcatgagac   3900
aataaccctg ataaatgctt caataatatt gaaaaaggaa gagtatgagt attcaacatt   3960
tccgtgtcgc ccttattccc ttttttgcgg cattttgcct tcctgttttt gctcacccag   4020
aaacgctggt gaaagtaaaa gatgctgaag atcagttggg tgcacgagtg ggttacatcg   4080
aactggatct caacagcggt aagatccttg agagttttcg ccccgaagaa cgttttccaa   4140
tgatgagcac ttttaaagtt ctgctatgtg gcgcggtatt atcccgtgtt gacgccgggc   4200
aagagcaact cggtcgccgc atacactatt ctcagaatga cttggttgag tactcaccag   4260
tcacagaaaa gcatcttacg gatggcatga cagtaagaga attatgcagt gctgccataa   4320
ccatgagtga taacactgcg gccaacttac ttctgacaac gatcggagga ccgaaggagc   4380
taaccgcttt tttgcacaac atgggggatc atgtaactcg ccttgatcgt tgggaaccgg   4440
agctgaatga agccatacca aacgacgagc gtgacaccac gatgcctaca gcaatggcaa   4500
caacgttgcg caaactatta actggcgaac tacttactct agcttcccgg caacaattaa   4560
tagactggat ggaggcggat aaagttgcag gaccacttct gcgctcggcc cttccggctg   4620
gctggtttat tgctgataaa tctggagccg gtgagcgtgg gtctcgcggt atcattgcag   4680
cactggggcc agatggtaag ccctcccgta tcgtagttat ctacacgacg gggagtcagg   4740
caactatgga tgaacgaaat agacagatcg ctgagatagg tgcctcactg attaagcatt   4800
ggtaactgtc agaccaagtt tactcatata tactttagat tgatttaaaa cttcattttt   4860
aatttaaaag gatctaggtg aagatccttt ttgataatct catgaccaaa atcccttaac   4920
gtgagttttc gttccactga gcgtcagacc ccgtagaaaa gatcaaagga tcttcttgag   4980
atcctttttt tctgcgcgta atctgctgct tgcaaacaaa aaaaccaccg ctaccagcgg   5040
tggtttgttt gccggatcaa gagctaccaa ctctttttcc gaaggtaact ggcttcagca   5100
gagcgcagat accaaatact gtccttctag tgtagccgta gttaggccac cacttcaaga   5160
actctgtagc accgcctaca tacctcgctc tgctaatcct gttaccagtg gctgctgcca   5220
gtggcgataa gtcgtgtctt accgggttgg actcaagacg atagttaccg gataaggcgc   5280
agcggtcggg ctgaacgggg ggttcgtgca cacagcccag cttggagcga acgacctaca   5340
ccgaactgag atacctacag cgtgagctat gagaaagcgc cacgcttccc gaagggagaa   5400
aggcggacag gtatccggta agcggcaggg tcggaacagg agagcgcacg agggagcttc   5460
caggggggaaa cgcctggtat ctttatagtc ctgtcgggtt tcgccacctc tgacttgagc   5520
gtcgattttt gtgatgctcg tcaggggggc ggagcctatg gaaaaacgcc agcaacgcgg   5580
cctttttacg gttcctggcc ttttgctggc cttttgctca catgttcttt cctgcgttat   5640
cccctgattc tgtggataac cgtattaccg cctttgagtg agctgatacc gctcgccgca   5700
gccgaacgac cgagcgcagc gagtcagtga gcgaggaagc ggaagagcgc ctgatgcggt   5760
attttctcct tacgcatctg tgcggtattt cacaccgcat atggtgcact ctcagtacaa   5820
tctgctctga tgccgcatag ttaagccagt atacactccg ctatcgctac gtgactgggt   5880
catggctgcg ccccgacacc cgccaacacc cgctgacgcg ccctgacggg cttgtctgct   5940
cccggcatcc gcttacagac aagctgtgac cgtctccggg agctgcatgt gtcagaggtt   6000
ttcaccgtca tcaccgaaac gcgcgaggca gcagatcaat tcgcgcgcga aggcgaagcg   6060
gcatgcattt acgttgacac catcgaatgg tgcaaaacct ttcgcggtat ggcatgatag   6120
cgcccggaag agagtcaatt cagggtggtg aatgtgaaac cagtaacgtt atacgatgtc   6180
gcagagtatg ccggtgtctc ttatcagacc gtttcccgcg tggtgaacca ggccagccac   6240
```

gtttctgcga aaacgcggga aaaagtggaa gcggcgatgg cggagctgaa ttacattccc 6300
aaccgcgtgg cacaacaact ggcgggcaaa cagtcgttgc tgattggcgt tgccacctcc 6360
agtctggccc tgcacgcgcc gtcgcaaatt gtcgcggcga ttaaatctcg cgccgatcaa 6420
ctgggtgcca gcgtggtggt gtcgatggta gaacgaagcg gcgtcgaagc ctgtaaagcg 6480
gcggtgcaca atcttctcgc gcaacgcgtc agtgggctga tcattaacta tccgctggat 6540
gaccaggatg ccattgctgt ggaagctgcc tgcactaatg ttccggcgtt atttcttgat 6600
gtctctgacc agacacccat caacagtatt attttctccc atgaagacgg tacgcgactg 6660
ggcgtggagc atctggtcgc attgggtcac cagcaaatcg cgctgttagc gggcccatta 6720
agttctgtct cggcgcgtct gcgtctggct ggctggcata aatatctcac tcgcaatcaa 6780
attcagccga tagcggaacg ggaaggcgac tggagtgcca tgtccggttt tcaacaaacc 6840
atgcaaatgc tgaatgaggg catcgttccc actgcgatgc tggttgccaa cgatcagatg 6900
gcgctgggcg caatgcgcgc cattaccgag tccgggctgc gcgttggtgc ggatatctcg 6960
gtagtgggat acgacgatac cgaagacagc tcatgttata tcccgccgtt aaccaccatc 7020
aaacaggatt ttcgcctgct ggggcaaacc agcgtggacc gcttgctgca actctctcag 7080
ggccaggcgg tgaagggcaa tcagctgttg cccgtctcac tggtgaaaag aaaaaccacc 7140
ctggcgccca atacgcaaac cgcctctccc cgcgcgttgg ccgattcatt aatgcagctg 7200
gcacgacagg tttcccgact ggaaagcggg cagtgagcgc aacgcaatta atgtgagtta 7260
gcgcgaattg atctg 7275

<210> SEQ ID NO 90
<211> LENGTH: 6798
<212> TYPE: DNA
<213> ORGANISM: Artificial Sequence
<220> FEATURE:
<223> OTHER INFORMATION: pT-ispA-MrBBS

<400> SEQUENCE: 90
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagaccatgg aattcatgga ctttccgcag caactcgaag 300
cctgcgttaa gcaggccaac caggcgctga gccgttttat cgccccactg ccctttcaga 360
acactcccgt ggtcgaaacc atgcagtatg gcgcattatt aggtggtaag cgcctgcgac 420
ctttcctggt ttatgccacc ggtcatatgt tcggcgttag cacaaacacg ctggacgcac 480
ccgctgccgc cgttgagtgt atccacgctt actcattaat tcatgatgat ttaccggcaa 540
tggatgatga cgatctgcgt cgcggtttgc caacctgcca tgtgaagttt ggcgaagcaa 600
acgcgattct cgctggcgac gctttacaaa cgctggcgtt ctcgatttta agcgatgccg 660
atatgccgga agtgtcggac cgcgacagaa tttcgatgat ttctgaactg gcgagcgcca 720
gtggtattgc cggaatgtgc ggtggtcagg cattagattt agacgcggaa ggcaaacacg 780
tacctctgga cgcgcttgag cgtattcatc gtcataaaac cggcgcattg attcgcgccg 840
ccgttcgcct tggtgcatta agcgccggag ataaaggacg tcgtgctctg ccggtactcg 900
acaagtatgc agagagcatc ggccttgcct tccaggttca ggatgacatc ctggatgtgg 960

-continued

```
tgggagatac tgcaacgttg ggaaaacgcc agggtgccga ccagcaactt ggtaaaagta   1020
cctaccctgc acttctgggt cttgagcaag cccggaagaa agcccgggat ctgatcgacg   1080
atgcccgtca gtcgctgaaa caactggctg aacagtcact cgatacctcg gcactggaag   1140
cgctagcgga ctacatcatc cagcgtaata aataaggatc caaggagata tatcaaatgt   1200
caaccctgtc agtctccacg ccgtccttct catcgtcgcc gctgtcctca gtgaacaaaa   1260
atagcacgaa acaacacgtt acgcgcaata gtgtgatctt tcatgattcc atttggggcg   1320
accagttcct ggaatacaaa gaaaaattca acgttgcaac cgaaaaacaa ctgattgaag   1380
aactgaaaga agaagtccgc aatgaactga tgatccgtgc gtgcaacgaa gccagtcgct   1440
atattaaact gatccagctg attgatgtgg ttgaacgtct gggcctggcc taccactttg   1500
aaaaagaaat cgaagaatcc ctgcaacata tttatgttac ctacggtcac aaatggacga   1560
actacaacaa catcgaaagc ctgtctctgt ggtttcgcct gctgcgtcag aacggtttta   1620
atgtcagctc tgatatcttc gaaaaccata ttgacgaaaa aggcaatttc caagaaagtc   1680
tgtgcaacga tccgcaaggc atgctggcac tgtatgaagc ggcctacatg cgcgtggaag   1740
gcgaaattat cctggacaaa gctctggaat ttaccaaact gcacctgggt attatcagca   1800
acgatccgtc ttgtgacagt tccctgcgta cggaaattaa acaggcgctg aaacagccgc   1860
tgcgtcgccg tctgccgcgt ctggaagcag ttcgttatat tgctatctac cagcaaaaag   1920
cgagtcattc cgaagtcctg ctgaaactgg ccaaactgga tttcaatgtg ctgcaggaaa   1980
tgcacaaaga cgaactgtca caaatttgta aatggtggaa agacctggac atccgtaaca   2040
aactgccgta tgttcgcgat cgtctgattg aaggctattt ttggattctg ggtatttact   2100
tcgaaccgca gcattcgcgc acccgtatgt ttctgatgaa aacgtgcatg tggctgatcg   2160
tcctggatga cacctttgat aattatggca cgtacgaaga actggaaatt ttcacccagg   2220
cggtggaacg ctggagcatc acgtgtctgg atgaactgcc ggaatacatg aaactgatct   2280
accatgaaca gttccgtgtg caccaagaaa tggaagaatc tctggaaaaa gaaggtaaag   2340
cataccagat ccattacatc aaagaaatgg ctaaagaagg cacccgctct ctgctgctgg   2400
aagcgaaatg gctgaaagaa ggttatatgc cgacgctgga tgaatacctg tcaaactcgc   2460
tggttacctg cggctatgca ctgatgacgg ctcgctcata cgttgcccgt gatgacggta   2520
ttgtcaccga agatgcgttt aaatgggtgg ccacgcaccc gccgatcgtt aaagcagctt   2580
gtaaaattct gcgtctgatg gatgacatcg cgacccataa agaagaacag gaacgcggcc   2640
acatcgcctc atcgattgaa tgctatcgta aagaaaccgg tgcatctgaa gaagaagcgt   2700
gtatggattt tctgaaacag gtcgaagacg gctggaaagt gatcaatcaa gaatcactga   2760
tgccgaccga tgtgccgttc ccgctgctga tcccggcgat taacctggcc cgcgtttcgg   2820
acacgctgta taaagataac gacggttaca atcatgctga taaagaagtg attggttaca   2880
ttaaaagtct gtttgtccac ccgatgattg tgtgaagatc ttaggtcgac ctgcaggcat   2940
gcaagcttgg ctgttttggc ggatgagaga agattttcag cctgatacag attaaatcag   3000
aacgcagaag cggtctgata aaacagaatt tgcctggcgg cagtagcgcg gtggtcccac   3060
ctgaccccat gccgaactca gaagtgaaac gccgtagcgc cgatggtagt gtggggtctc   3120
cccatgcgag agtagggaac tgccaggcat caaataaaac gaaaggctca gtcgaaagac   3180
tgggcctttc gttttatctg ttgtttgtcg gtgaacgctc tcctgagtag gacaaatccg   3240
ccgggagcgg atttgaacgt tgcgaagcaa cggcccggag ggtggcgggc aggacgcccg   3300
ccataaactg ccaggcatca aattaagcag aaggccatcc tgacggatgg cctttttgcg   3360
```

-continued

```
tttctacaaa ctctttttgt ttatttttct aaatacattc aaatatgtat ccgctcatga   3420
gacaataacc ctgataaatg cttcaataat attgaaaaag gaagagtatg agtattcaac   3480
atttccgtgt cgcccttatt cccttttttg cggcattttg ccttcctgtt tttgctcacc   3540
cagaaacgct ggtgaaagta aaagatgctg aagatcagtt gggtgcacga gtgggttaca   3600
tcgaactgga tctcaacagc ggtaagatcc ttgagagttt tcgccccgaa gaacgttttc   3660
caatgatgag cacttttaaa gttctgctat gtggcgcggt attatcccgt gttgacgccg   3720
ggcaagagca actcggtcgc cgcatacact attctcagaa tgacttggtt gagtactcac   3780
cagtcacaga aaagcatctt acggatggca tgacagtaag agaattatgc agtgctgcca   3840
taaccatgag tgataacact gcggccaact tacttctgac aacgatcgga ggaccgaagg   3900
agctaaccgc ttttttgcac aacatggggg atcatgtaac tcgccttgat cgttgggaac   3960
cggagctgaa tgaagccata ccaaacgacg agcgtgacac cacgatgcct acagcaatgg   4020
caacaacgtt gcgcaaacta ttaactggcg aactacttac tctagcttcc cggcaacaat   4080
taatagactg gatggaggcg gataaagttg caggaccact tctgcgctcg gcccttccgg   4140
ctggctggtt tattgctgat aaatctggag ccggtgagcg tgggtctcgc ggtatcattg   4200
cagcactggg gccagatggt aagccctccc gtatcgtagt tatctacacg acggggagtc   4260
aggcaactat ggatgaacga aatagacaga tcgctgagat aggtgcctca ctgattaagc   4320
attggtaact gtcagaccaa gtttactcat atatacttta gattgattta aaacttcatt   4380
tttaatttaa aaggatctag gtgaagatcc tttttgataa tctcatgacc aaaatccctt   4440
aacgtgagtt ttcgttccac tgagcgtcag accccgtaga aaagatcaaa ggatcttctt   4500
gagatccttt ttttctgcgc gtaatctgct gcttgcaaac aaaaaaacca ccgctaccag   4560
cggtggtttg tttgccggat caagagctac caactctttt tccgaaggta actggcttca   4620
gcagagcgca gataccaaat actgtccttc tagtgtagcc gtagttaggc caccacttca   4680
agaactctgt agcaccgcct acatacctcg ctctgctaat cctgttacca gtggctgctg   4740
ccagtggcga taagtcgtgt cttaccgggt tggactcaag acgatagtta ccggataagg   4800
cgcagcggtc gggctgaacg gggggttcgt gcacacagcc cagcttggag cgaacgacct   4860
acaccgaact gagataccta cagcgtgagc tatgagaaag cgccacgctt cccgaaggga   4920
gaaaggcgga caggtatccg gtaagcggca gggtcggaac aggagagcgc acgagggagc   4980
ttccaggggg aaacgcctgg tatctttata gtcctgtcgg gtttcgccac ctctgacttg   5040
agcgtcgatt tttgtgatgc tcgtcagggg ggcggagcct atggaaaaac gccagcaacg   5100
cggccttttt acggttcctg gccttttgct ggccttttgc tcacatgttc tttcctgcgt   5160
tatcccctga ttctgtggat aaccgtatta ccgcctttga gtgagctgat accgctcgcc   5220
gcagccgaac gaccgagcgc agcgagtcag tgagcgagga agcggaagag cgcctgatgc   5280
ggtattttct ccttacgcat ctgtgcggta tttcacaccg catatggtgc actctcagta   5340
caatctgctc tgatgccgca tagttaagcc agtatacact ccgctatcgc tacgtgactg   5400
ggtcatggct gcgccccgac acccgccaac acccgctgac gcgccctgac gggcttgtct   5460
gctcccggca tccgcttaca gacaagctgt gaccgtctcc gggagctgca tgtgtcagag   5520
gttttcaccg tcatcaccga aacgcgcgag gcagcagatc aattcgcgcg cgaaggcgaa   5580
gcggcatgca tttacgttga caccatcgaa tggtgcaaaa cctttcgcgg tatggcatga   5640
tagcgcccgg aagagagtca attcagggtg gtgaatgtga aaccagtaac gttatacgat   5700
```

gtcgcagagt atgccggtgt ctcttatcag accgtttccc gcgtggtgaa ccaggccagc 5760
cacgtttctg cgaaaacgcg ggaaaaagtg gaagcggcga tggcggagct gaattacatt 5820
cccaaccgcg tggcacaaca actggcgggc aaacagtcgt tgctgattgg cgttgccacc 5880
tccagtctgg ccctgcacgc gccgtcgcaa attgtcgcgg cgattaaatc tcgcgccgat 5940
caactgggtg ccagcgtggt ggtgtcgatg gtagaacgaa gcggcgtcga agcctgtaaa 6000
gcggcggtgc acaatcttct cgcgcaacgc gtcagtgggc tgatcattaa ctatccgctg 6060
gatgaccagg atgccattgc tgtggaagct gcctgcacta atgttccggc gttatttctt 6120
gatgtctctg accagacacc catcaacagt attattttct cccatgaaga cggtacgcga 6180
ctgggcgtgg agcatctggt cgcattgggt caccagcaaa tcgcgctgtt agcgggccca 6240
ttaagttctg tctcggcgcg tctgcgtctg gctggctggc ataaatatct cactcgcaat 6300
caaattcagc cgatagcgga acgggaaggc gactggagtg ccatgtccgg ttttcaacaa 6360
accatgcaaa tgctgaatga gggcatcgtt cccactgcga tgctggttgc caacgatcag 6420
atggcgctgg gcgcaatgcg cgccattacc gagtccgggc tgcgcgttgg tgcggatatc 6480
tcggtagtgg gatacgacga taccgaagac agctcatgtt atatcccgcc gttaaccacc 6540
atcaaacagg attttcgcct gctggggcaa accagcgtgg accgcttgct gcaactctct 6600
cagggccagg cggtgaaggg caatcagctg ttgcccgtct cactggtgaa aagaaaaacc 6660
accctggcgc ccaatacgca aaccgcctct ccccgcgcgt tggccgattc attaatgcag 6720
ctggcacgac aggtttcccg actggaaagc gggcagtgag cgcaacgcaa ttaatgtgag 6780
ttagcgcgaa ttgatctg 6798

<210> SEQ ID NO 91
<211> LENGTH: 8655
<212> TYPE: DNA
<213> ORGANISM: Artificial Sequence
<220> FEATURE:
<223> OTHER INFORMATION: pTAS-dxs

<400> SEQUENCE: 91
tcgacctgca ggcatgcaag cttggctgtt ttggcggatg agagaagatt ttcagcctga 60
tacagattaa atcagaacgc agaagcggtc tgataaaaca gaatttgcct ggcggcagta 120
gcgcggtggt cccacctgac cccatgccga actcagaagt gaaacgccgt agcgccgatg 180
gtagtgtggg gtctccccat gcgagagtag ggaactgcca ggcatcaaat aaaacgaaag 240
gctcagtcga aagactgggc ctttcgtttt atctgttgtt tgtcggtgaa cgctctcctg 300
agtaggacaa atccgccggg agcggatttg aacgttgcga agcaacggcc cggagggtgg 360
cgggcaggac gcccgccata aactgccagg catcaaatta agcagaaggc catcctgacg 420
gatggccttt ttgcgtttct acaaactctt tttgtttatt tttctaaata cattcaaata 480
tgtatccgct catgagacaa taaccctgat aaatgcttca ataatattga aaaaggaaga 540
gtatgagtat tcaacatttc cgtgtcgccc ttattccctt ttttgcggca ttttgccttc 600
ctgtttttgc tcacccagaa acgctggtga aagtaaaaga tgctgaagat cagttgggtg 660
cacgagtggg ttacatcgaa ctggatctca acagcggtaa gatccttgag agttttcgcc 720
ccgaagaacg ttttccaatg atgagcactt ttaaagttct gctatgtggc gcggtattat 780
cccgtgttga cgccgggcaa gagcaactcg gtcgccgcat acactattct cagaatgact 840
tggttgagta ctcaccagtc acagaaaagc atcttacgga tggcatgaca gtaagagaat 900
tatgcagtgc tgccataacc atgagtgata acactgcggc caacttactt ctgacaacga 960
tcggaggacc gaaggagcta accgcttttt tgcacaacat gggggatcat gtaactcgcc 1020
ttgatcgttg ggaaccggag ctgaatgaag ccataccaaa cgacgagcgt gacaccacga 1080
tgcctacagc aatggcaaca acgttgcgca aactattaac tggcgaacta cttactctag 1140
cttcccggca acaattaata gactggatgg aggcggataa agttgcagga ccacttctgc 1200
gctcggccct tccggctggc tggtttattg ctgataaatc tggagccggt gagcgtgggt 1260
ctcgcggtat cattgcagca ctggggccag atggtaagcc ctcccgtatc gtagttatct 1320
acacgacggg gagtcaggca actatggatg aacgaaatag acagatcgct gagataggtg 1380
cctcactgat taagcattgg taactgtcag accaagttta ctcatatata ctttagattg 1440
atttaaaact tcatttttaa tttaaaagga tctaggtgaa gatccttttt gataatctca 1500
tgaccaaaat cccttaacgt gagttttcgt tccactgagc gtcagacccc gtagaaaaga 1560
tcaaaggatc ttcttgagat cctttttttc tgcgcgtaat ctgctgcttg caaacaaaaa 1620
aaccaccgct accagcggtg gtttgtttgc cggatcaaga gctaccaact ctttttccga 1680
aggtaactgg cttcagcaga gcgcagatac caaatactgt ccttctagtg tagccgtagt 1740
taggccacca cttcaagaac tctgtagcac cgcctacata cctcgctctg ctaatcctgt 1800
taccagtggc tgctgccagt ggcgataagt cgtgtcttac cgggttggac tcaagacgat 1860
agttaccgga taaggcgcag cggtcgggct gaacgggggg ttcgtgcaca cagcccagct 1920
tggagcgaac gacctacacc gaactgagat acctacagcg tgagctatga gaaagcgcca 1980
cgcttcccga agggagaaag gcggacaggt atccggtaag cggcagggtc ggaacaggag 2040
agcgcacgag ggagcttcca gggggaaacg cctggtatct ttatagtcct gtcgggtttc 2100
gccacctctg acttgagcgt cgatttttgt gatgctcgtc aggggggcgg agcctatgga 2160
aaaacgccag caacgcggcc tttttacggt tcctggcctt ttgctggcct tttgctcaca 2220
tgttctttcc tgcgttatcc cctgattctg tggataaccg tattaccgcc tttgagtgag 2280
ctgataccgc tcgccgcagc cgaacgaccg agcgcagcga gtcagtgagc gaggaagcgg 2340
aagagcgcct gatgcggtat tttctcctta cgcatctgtg cggtatttca caccgcatat 2400
ggtgcactct cagtacaatc tgctctgatg ccgcatagtt aagccagtat acactccgct 2460
atcgctacgt gactgggtca tggctgcgcc ccgacacccg ccaacacccg ctgacgcgcc 2520
ctgacgggct tgtctgctcc cggcatccgc ttacagacaa gctgtgaccg tctccgggag 2580
ctgcatgtgt cagaggtttt caccgtcatc accgaaacgc gcgaggcagc agatcaattc 2640
gcgcgcgaag gcgaagcggc atgcatttac gttgacacca tcgaatggtg caaaaccttt 2700
cgcggtatgg catgatagcg cccggaagag agtcaattca gggtggtgaa tgtgaaacca 2760
gtaacgttat acgatgtcgc agagtatgcc ggtgtctctt atcagaccgt ttcccgcgtg 2820
gtgaaccagg ccagccacgt ttctgcgaaa acgcgggaaa aagtggaagc ggcgatggcg 2880
gagctgaatt acattcccaa ccgcgtggca caacaactgg cgggcaaaca gtcgttgctg 2940
attggcgttg ccacctccag tctggccctg cacgcgccgt cgcaaattgt cgcggcgatt 3000
aaatctcgcg ccgatcaact gggtgccagc gtggtggtgt cgatggtaga acgaagcggc 3060
gtcgaagcct gtaaagcggc ggtgcacaat cttctcgcgc aacgcgtcag tgggctgatc 3120
attaactatc cgctggatga ccaggatgcc attgctgtgg aagctgcctg cactaatgtt 3180
ccggcgttat ttcttgatgt ctctgaccag acacccatca acagtattat tttctcccat 3240
gaagacggta cgcgactggg cgtggagcat ctggtcgcat tgggtcacca gcaaatcgcg 3300

-continued

```
ctgttagcgg gcccattaag ttctgtctcg gcgcgtctgc gtctggctgg ctggcataaa   3360

tatctcactc gcaatcaaat tcagccgata gcggaacggg aaggcgactg gagtgccatg   3420

tccggttttc aacaaaccat gcaaatgctg aatgagggca tcgttcccac tgcgatgctg   3480

gttgccaacg atcagatggc gctgggcgca atgcgcgcca ttaccgagtc cgggctgcgc   3540

gttggtgcgg atatctcggt agtgggatac gacgataccg aagacagctc atgttatatc   3600

ccgccgttaa ccaccatcaa acaggatttt cgcctgctgg ggcaaaccag cgtggaccgc   3660

ttgctgcaac tctctcaggg ccaggcggtg aagggcaatc agctgttgcc cgtctcactg   3720

gtgaaaagaa aaaccaccct ggcgcccaat acgcaaaccg cctctccccg cgcgttggcc   3780

gattcattaa tgcagctggc acgacaggtt tcccgactgg aaagcgggca gtgagcgcaa   3840

cgcaattaat gtgagttagc gcgaattgat ctggtttgac agcttatcat cgactgcacg   3900

gtgcaccaat gcttctggcg tcaggcagcc atcggaagct gtggtatggc tgtgcaggtc   3960

gtaaatcact gcataattcg tgtcgctcaa ggcgcactcc cgttctggat aatgtttttt   4020

gcgccgacat cataacggtt ctggcaaata ttctgaaatg agctgttgac aattaatcat   4080

ccggctcgta taatgtgtgg aattgtgagc ggataacaat ttcacacagg aggtaataaa   4140

tatggaattc atggactttc cgcagcaact cgaagcctgc gttaagcagg ccaaccaggc   4200

gctgagccgt tttatcgccc cactgccctt tcagaacact cccgtggtcg aaaccatgca   4260

gtatggcgca ttattaggtg gtaagcgcct gcgacctttc ctggtttatg ccaccggtca   4320

tatgttcggc gttagcacaa acacgctgga cgcacccgct gccgccgttg agtgtatcca   4380

cgcttactca ttaattcatg atgatttacc ggcaatggat gatgacgatc tgcgtcgcgg   4440

tttgccaacc tgccatgtga agtttggcga agcaaacgcg attctcgctg gcgacgcttt   4500

acaaacgctg gcgttctcga ttttaagcga tgccgatatg ccggaagtgt cggaccgcga   4560

cagaatttcg atgatttctg aactggcgag cgccagtggt attgccggaa tgtgcggtgg   4620

tcaggcatta gatttagacg cggaaggcaa acacgtacct ctggacgcgc ttgagcgtat   4680

tcatcgtcat aaaaccggcg cattgattcg cgccgccgtt cgccttggtg cattaagcgc   4740

cggagataaa ggacgtcgtg ctctgccggt actcgacaag tatgcagaga gcatcggcct   4800

tgccttccag gttcaggatg acatcctgga tgtggtggga gatactgcaa cgttgggaaa   4860

acgccagggt gccgaccagc aacttggtaa aagtacctac cctgcacttc tgggtcttga   4920

gcaagcccgg aagaaagccc gggatctgat cgacgatgcc cgtcagtcgc tgaaacaact   4980

ggctgaacag tcactcgata cctcggcact ggaagcgcta gcggactaca tcatccagcg   5040

taataaataa ggatccaaaa aggaggtaat aaaccatgtc aactcaacaa gtttcatcag   5100

agaacattgt tcgtaacgct gcgaatttcc atcctaatat atggggaaac catttcctca   5160

catgtccttc tcagacgatt gatagttgga ctcaacagca ccacaaagaa ctgaaagaag   5220

aggtgaggaa aatgatggtg tctgatgcaa ataaacctgc ccagagattg cgcttgattg   5280

atactgtcca aaggctaggt gtggcttacc actttgaaaa ggagattgat gatgcattgg   5340

agaaaatagg tcatgaccct tttgatgata aagatgatct ctacattgtc tctctttgtt   5400

ttcgattgct gaggcagcat ggaattaaga tatcatgtga tgtgtttgag aagtttaaag   5460

atgacgatgg aaaattcaag gcatcattga tgaatgatgt tcaaggcatg ctaagtttat   5520

atgaggcagc acacctagcc attcacggag aagatatttt agatgaagca attgttttca   5580

cgaccactca ccttaagtca acggtatcta attctcctgt aaactctact tttgctgaac   5640

aaatacgtca ttctctcaga gttcctctcc gtaaagctgt acctaggtta gagtcgaggt   5700
```

atttcttgga tatctattca agagatgatt tgcacgataa aactttgctc aatttcgcaa 5760
agttagactt taatatacta caagcaatgc accagaagga agcaagtgag atgaccaggt 5820
ggtggagaga ttttgacttc cttaaaaagc tgccttatat aagagacaga gtcgtggagc 5880
tatatttttg gattctggtg ggagtgtctt atcagcccaa attcagcact ggtagaattt 5940
ttttgtccaa aataatatgc cttgagaccc tcgtagatga tacatttgac gcctacggta 6000
cttttgacga gctcgcaatc tttactgaag cagttacaag atgggacctt ggccacagag 6060
atgcactacc agaatacatg aaattcattt tcaagacact cattgatgtc tacagtgaag 6120
ctgagcaaga actggcaaag gaagggagat catacagcat acactatgca atacgatcgt 6180
tccaagaact agttatgaag tacttctgcg aagccaagtg gttaaataaa ggttatgttc 6240
cgagcctgga cgattataaa tcagtttcat taagaagtat cggtttttta ccgatagcgg 6300
tagcttcctt cgttttcatg ggtgatattg caactaagga ggtctttgaa tgggaaatga 6360
ataaccctaa gatcataata gccgcagaaa cgattttcag attcctggat gacatagcag 6420
gccataggtt tgagcaaaag agagaacata gtccatcagc tattgaatgc tacaagaatc 6480
aacatggagt gtctgaggaa gaggcagtta aagcgttgtc gttagaagtt gctaatagtt 6540
ggaaagatat aaatgaggag ctgcttctca acccaatggc tattccttta cctctgcttc 6600
aggtgattct tgatctctca cgttcggccg attttatgta cggtaatgct caagatcgct 6660
tcacgcattc aacgatgatg aaagaccaag ttgatttggt gctgaaggac cccgttaagc 6720
ttgacgatta aagatctgtg tggaattgtg agcggataac aatttcacac aggaaacaga 6780
ccatggaatt catgagtttt gatattgcca aatacccgac cctggcactg gtcgactcca 6840
cccaggagtt acgactgttg ccgaaagaga gtttaccgaa actctgcgac gaactgcgcc 6900
gctatttact cgacagcgtg agccgttcca gcgggcactt cgcctccggg ctgggcacgg 6960
tcgaactgac cgtggcgctg cactatgtct acaacacccc gtttgaccaa ttgatttggg 7020
atgtggggca tcaggcttat ccgcataaaa ttttgaccgg acgccgcgac aaaatcggca 7080
ccatccgtca gaaaggcggt ctgcacccgt tcccgtggcg cggcgaaagc gaatatgacg 7140
tattaagcgt cgggcattca tcaacctcca tcagtgccgg aattggtatt gcggttgctg 7200
ccgaaaaaga aggcaaaaat cgccgcaccg tctgtgtcat tggcgatggc gcgattaccg 7260
caggcatggc gtttgaagcg atgaatcacg cgggcgatat ccgtcctgat atgctggtga 7320
ttctcaacga caatgaaatg tcgatttccg aaaatgtcgg cgcgctcaac aaccatctgg 7380
cacagctgct ttccggtaag ctttactctt cactgcgcga aggcgggaaa aaagttttct 7440
ctggcgtgcc gccaattaaa gagctgctca aacgcaccga agaacatatt aaaggcatgg 7500
tagtgcctgg cacgttgttt gaagagctgg gctttaacta catcggcccg gtggacggtc 7560
acgatgtgct ggggcttatc accacgctaa agaacatgcg cgacctgaaa ggcccgcagt 7620
tcctgcatat catgaccaaa aaaggtcgtg gttatgaacc ggcagaaaaa gacccgatca 7680
ctttccacgc cgtgcctaaa tttgatccct ccagcggttg tttgccgaaa agtagcggcg 7740
gtttgccgag ctattcaaaa atctttggcg actggttgtg cgaaacggca gcgaaagaca 7800
acaagctgat ggcgattact ccggcgatgc gtgaaggttc cggcatggtc gagttttcac 7860
gtaaattccc ggatcgctac ttcgacgtgg caattgccga gcaacacgcg gtgacctttg 7920
ctgcgggtct ggcgattggt gggtacaaac ccattgtcgc gatttactcc actttcctgc 7980
aacgcgccta tgatcaggtg ctgcatgacg tggcgattca aaagcttccg gtcctgttcg 8040

-continued

```
ccatcgaccg cgcgggcatt gttggtgctg acggtcaaac ccatcagggt gcttttgatc   8100

tctcttacct gcgctgcata ccggaaatgg tcattatgac cccgagcgat gaaaacgaat   8160

gtcgccagat gctctatacc ggctatcact ataacgatgg cccgtcagcg gtgcgctacc   8220

cgcgtggcaa cgcggtcggc gtggaactga cgccgctgga aaaactacca attggcaaag   8280

gcattgtgaa gcgtcgtggc gagaaactgg cgatccttaa ctttggtacg ctgatgccag   8340

aagcggcgaa agtcgccgaa tcgctgaacg ccacgctggt cgatatgcgt tttgtgaaac   8400

cgcttgatga agcgttaatt ctggaaatgg ccgccagcca tgaagcgctg gtcaccgtag   8460

aagaaaacgc cattatgggc ggcgcaggca gcggcgtgaa cgaagtgctg atggcccatc   8520

gtaaaccagt acccgtgctg aacattggcc tgccggactt ctttattccg caaggaactc   8580

aggaagaaat gcgcgccgaa ctcggcctcg atgccgctgg tatggaagcc aaaatcaagg   8640

cctggctggc ataac                                                    8655
```

<210> SEQ ID NO 92
<211> LENGTH: 8656
<212> TYPE: DNA
<213> ORGANISM: Artificial Sequence
<220> FEATURE:
<223> OTHER INFORMATION: pTAB-idi-dxr

<400> SEQUENCE: 92

```
gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gtttttttgcg ccgacatcat aacggttctg gcaaatattc    180

tgaaatgagc tgttgacaat taatcatccg gctcgtataa tgtgtggaat tgtgagcgga    240

taacaatttc acacaggaaa cagaccatgg aattcgagct cggtacccgg ggatccgatc    300

cgggaggttt tcagtaatgg actttccgca gcaactcgaa gcctgcgtta agcaggccaa    360

ccaggcgctg agccgtttta tcgccccact gccctttcag aacactcccg tggtcgaaac    420

catgcagtat ggcgcattat taggtggtaa gcgcctgcga cctttcctgg tttatgccac    480

cggtcatatg ttcggcgtta gcacaaacac gctggacgca cccgctgccg ccgttgagtg    540

tatccacgct tactcattaa ttcatgatga tttaccggca atggatgatg acgatctgcg    600

tcgcggtttg ccaacctgcc atgtgaagtt tggcgaagca aacgcgattc tcgctggcga    660

cgctttacaa acgctggcgt tctcgatttt aagcgatgcc gatatgccgg aagtgtcgga    720

ccgcgacaga atttcgatga tttctgaact ggcgagcgcc agtggtattg ccggaatgtg    780

cggtggtcag gcattagatt tagacgcgga aggcaaacac gtacctctgg acgcgcttga    840

gcgtattcat cgtcataaaa ccggcgcatt gattcgcgcc gccgttcgcc ttggtgcatt    900

aagcgccgga gataaaggac gtcgtgctct gccggtactc gacaagtatg cagagagcat    960

cggccttgcc ttccaggttc aggatgacat cctggatgtg gtgggagata ctgcaacgtt   1020

gggaaaacgc cagggtgccg accagcaact tggtaaaagt acctaccctg cacttctggg   1080

tcttgagcaa gcccggaaga aagcccggga tctgatcgac gatgcccgtc agtcgctgaa   1140

acaactggct gaacagtcac tcgatacctc ggcactggaa gcgctagcgg actacatcat   1200

ccagcgtaat aaataagatc cataaaggag gtaagaatgt caaccctgtc agtctccacg   1260

ccgtccttct catcgtcgcc gctgtcctca gtgaacaaaa atagcacgaa acaacacgtt   1320

acgcgcaata gtgtgatctt tcatgattcc atttggggcg accagttcct ggaatacaaa   1380

gaaaaattca acgttgcaac cgaaaaacaa ctgattgaag aactgaaaga agaagtccgc   1440
```

aatgaactga tgatccgtgc gtgcaacgaa gccagtcgct atattaaact gatccagctg 1500
attgatgtgg ttgaacgtct gggcctggcc taccactttg aaaaagaaat cgaagaatcc 1560
ctgcaacata tttatgttac ctacggtcac aaatggacga actacaacaa catcgaaagc 1620
ctgtctctgt ggtttcgcct gctgcgtcag aacggtttta atgtcagctc tgatatcttc 1680
gaaaaccata ttgacgaaaa aggcaatttc caagaaagtc tgtgcaacga tccgcaaggc 1740
atgctggcac tgtatgaagc ggcctacatg cgcgtggaag gcgaaattat cctggacaaa 1800
gctctggaat ttaccaaact gcacctgggt attatcagca acgatccgtc ttgtgacagt 1860
tccctgcgta cggaaattaa acaggcgctg aaacagccgc tgcgtcgccg tctgccgcgt 1920
ctggaagcag ttcgttatat tgctatctac cagcaaaaag cgagtcattc cgaagtcctg 1980
ctgaaactgg ccaaactgga tttcaatgtg ctgcaggaaa tgcacaaaga cgaactgtca 2040
caaatttgta aatggtggaa agacctggac atccgtaaca aactgccgta tgttcgcgat 2100
cgtctgattg aaggctattt ttggattctg ggtatttact tcgaaccgca gcattcgcgc 2160
acccgtatgt ttctgatgaa aacgtgcatg tggctgatcg tcctggatga cacctttgat 2220
aattatggca cgtacgaaga actggaaatt ttcacccagg cggtggaacg ctggagcatc 2280
acgtgtctgg atgaactgcc ggaatacatg aaactgatct accatgaaca gttccgtgtg 2340
caccaagaaa tggaagaatc tctggaaaaa gaaggtaaag cataccagat ccattacatc 2400
aaagaaatgg ctaaagaagg cacccgctct ctgctgctgg aagcgaaatg gctgaaagaa 2460
ggttatatgc cgacgctgga tgaatacctg tcaaactcgc tggttacctg cggctatgca 2520
ctgatgacgg ctcgctcata cgttgcccgt gatgacggta ttgtcaccga agatgcgttt 2580
aaatgggtgg ccacgcaccc gccgatcgtt aaagcagctt gtaaaattct gcgtctgatg 2640
gatgacatcg cgacccataa agaagaacag gaacgcggcc acatcgcctc atcgattgaa 2700
tgctatcgta aagaaaccgg tgcatctgaa gaagaagcgt gtatggattt tctgaaacag 2760
gtcgaagacg gctggaaagt gatcaatcaa gaatcactga tgccgaccga tgtgccgttc 2820
ccgctgctga tcccggcgat taacctggcc cgcgtttcgg acacgctgta taaagataac 2880
gacggttaca atcatgctga taaagaagtg attggttaca ttaaaagtct gtttgtccac 2940
ccgatgattg tgtgaagatc ctgaggaggt aacgtatgca aacggaacac gtcattttat 3000
tgaatgcaca gggagttccc acgggtacgc tggaaaagta tgccgcacac acggcagaca 3060
cccgcttaca tctcgcgttc tccagttggc tgtttaatgc caaaggacaa ttattagtta 3120
cccgccgcgc actgagcaaa aaagcatggc ctggcgtgtg gactaactcg gtttgtgggc 3180
acccacaact gggagaaagc aacgaagacg cagtgatccg ccgttgccgt tatgagcttg 3240
gcgtggaaat tacgcctcct gaatctatct atcctgactt tcgctaccgc gccaccgatc 3300
cgagtggcat tgtggaaaat gaagtgtgtc cggtatttgc cgcacgcacc actagtgcgt 3360
tacagatcaa tgatgatgaa gtgatggatt atcaatggtg tgatttagca gatgtattac 3420
acggtattga tgccacgccg tgggcgttca gtccgtggat ggtgatgcag gcgacaaatc 3480
gcgaagccag aaaacgatta tctgcattta cccagcttaa ataagatctt agagtcgacg 3540
tgtggaattg tgagcggata acaatttcac acaggaaaca gaccatggaa ttcgagctca 3600
tgaagcaact caccattctg ggctcgaccg gctcgattgg ttgcagcacg ctggacgtgg 3660
tgcgccataa tcccgaacac ttccgcgtag ttgcgctggt ggcaggcaaa aatgtcactc 3720
gcatggtaga acagtgcctg gaattctctc cccgctatgc cgtaatggac gatgaagcga 3780

-continued

```
gtgcgaaact tcttaaaacg atgctacagc aacagggtag ccgcaccgaa gtcttaagtg   3840
ggcaacaagc cgcttgcgat atggcagcgc ttgaggatgt tgatcaggtg atggcagcca   3900
ttgttggcgc tgctgggctg ttacctacgc ttgctgcgat ccgcgcgggt aaaaccattt   3960
tgctggccaa taaagaatca ctggttacct gcggacgtct gtttatggac gccgtaaagc   4020
agagcaaagc gcaattgtta ccggtcgata gcgaacataa cgccattttt cagagtttac   4080
cgcaacctat ccagcataat ctgggatacg ctgaccttga gcaaaatggc gtggtgtcca   4140
ttttacttac cgggtctggt ggccctttcc gtgagacgcc attgcgcgat ttggcaacaa   4200
tgacgccgga tcaagcctgc cgtcatccga actggtcgat ggggcgtaaa atttctgtcg   4260
attcggctac catgatgaac aaaggtctgg aatacattga agcgcgttgg ctgtttaacg   4320
ccagcgccag ccagatggaa gtgctgattc acccgcagtc agtgattcac tcaatggtgc   4380
gctatcagga cggcagtgtt ctggcgcagc tgggggaacc ggatatgcgt acgccaattg   4440
cccacaccat ggcatggccg aatcgcgtga actctggcgt gaagccgctc gatttttgca   4500
aactaagtgc gttgacattt gccgcaccgg attatgatcg ttatccatgc ctgaaactgg   4560
cgatggaggc gttcgaacaa ggccaggcag cgacgacagc attgaatgcc gcaaacgaaa   4620
tcaccgttgc tgcttttctt gcgcaacaaa tccgctttac ggatatcgct gcgttgaatt   4680
tatccgtact ggaaaaaatg gatatgcgcg aaccacaatg tgtggacgat gtgttatctg   4740
ttgatgcgaa cgcgcgtgaa gtcgccagaa aagaggtgat gcgtctcgca agctgatcta   4800
aagcttggct gttttggcgg atgagagaag attttcagcc tgatacagat taaatcagaa   4860
cgcagaagcg gtctgataaa acagaatttg cctggcggca gtagcgcggt ggtcccacct   4920
gaccccatgc cgaactcaga agtgaaacgc cgtagcgccg atggtagtgt ggggtctccc   4980
catgcgagag tagggaactg ccaggcatca aataaaacga aaggctcagt cgaaagactg   5040
ggcctttcgt tttatctgtt gtttgtcggt gaacgctctc ctgagtagga caaatccgcc   5100
gggagcggat ttgaacgttg cgaagcaacg gcccggaggg tggcgggcag gacgcccgcc   5160
ataaactgcc aggcatcaaa ttaagcagaa ggccatcctg acggatggcc tttttgcgtt   5220
tctacaaact ctttttgttt atttttctaa atacattcaa atatgtatcc gctcatgaga   5280
caataaccct gataaatgct tcaataatat tgaaaaagga agagtatgag tattcaacat   5340
ttccgtgtcg cccttattcc cttttttgcg gcattttgcc ttcctgtttt tgctcaccca   5400
gaaacgctgg tgaaagtaaa agatgctgaa gatcagttgg gtgcacgagt gggttacatc   5460
gaactggatc tcaacagcgg taagatcctt gagagttttc gccccgaaga acgttttcca   5520
atgatgagca cttttaaagt tctgctatgt ggcgcggtat tatcccgtgt tgacgccggg   5580
caagagcaac tcggtcgccg catacactat tctcagaatg acttggttga gtactcacca   5640
gtcacagaaa agcatcttac ggatggcatg acagtaagag aattatgcag tgctgccata   5700
accatgagtg ataacactgc ggccaactta cttctgacaa cgatcggagg accgaaggag   5760
ctaaccgctt ttttgcacaa catgggggat catgtaactc gccttgatcg ttgggaaccg   5820
gagctgaatg aagccatacc aaacgacgag cgtgacacca cgatgcctac agcaatggca   5880
acaacgttgc gcaaactatt aactggcgaa ctacttactc tagcttcccg gcaacaatta   5940
atagactgga tggaggcgga taaagttgca ggaccacttc tgcgctcggc ccttccggct   6000
ggctggttta ttgctgataa atctggagcc ggtgagcgtg ggtctcgcgg tatcattgca   6060
gcactggggc cagatggtaa gccctcccgt atcgtagtta tctacacgac ggggagtcag   6120
gcaactatgg atgaacgaaa tagacagatc gctgagatag gtgcctcact gattaagcat   6180
```

-continued

```
tggtaactgt cagaccaagt ttactcatat atactttaga ttgatttaaa acttcatttt   6240
taatttaaaa ggatctaggt gaagatcctt tttgataatc tcatgaccaa aatcccttaa   6300
cgtgagtttt cgttccactg agcgtcagac cccgtagaaa agatcaaagg atcttcttga   6360
gatccttttt ttctgcgcgt aatctgctgc ttgcaaacaa aaaaaccacc gctaccagcg   6420
gtggtttgtt tgccggatca agagctacca actctttttc cgaaggtaac tggcttcagc   6480
agagcgcaga taccaaatac tgtccttcta gtgtagccgt agttaggcca ccacttcaag   6540
aactctgtag caccgcctac atacctcgct ctgctaatcc tgttaccagt ggctgctgcc   6600
agtggcgata agtcgtgtct taccgggttg gactcaagac gatagttacc ggataaggcg   6660
cagcggtcgg gctgaacggg gggttcgtgc acacagccca gcttggagcg aacgacctac   6720
accgaactga gatacctaca gcgtgagcta tgagaaagcg ccacgcttcc cgaagggaga   6780
aaggcggaca ggtatccggt aagcggcagg gtcggaacag gagagcgcac gagggagctt   6840
ccagggggaa acgcctggta tctttatagt cctgtcgggt ttcgccacct ctgacttgag   6900
cgtcgatttt tgtgatgctc gtcagggggg cggagcctat ggaaaaacgc cagcaacgcg   6960
gcctttttac ggttcctggc cttttgctgg ccttttgctc acatgttctt tcctgcgtta   7020
tcccctgatt ctgtggataa ccgtattacc gcctttgagt gagctgatac cgctcgccgc   7080
agccgaacga ccgagcgcag cgagtcagtg agcgaggaag cggaagagcg cctgatgcgg   7140
tattttctcc ttacgcatct gtgcggtatt tcacaccgca tatggtgcac tctcagtaca   7200
atctgctctg atgccgcata gttaagccag tatacactcc gctatcgcta cgtgactggg   7260
tcatggctgc gccccgacac ccgccaacac ccgctgacgc gccctgacgg gcttgtctgc   7320
tcccggcatc cgcttacaga caagctgtga ccgtctccgg gagctgcatg tgtcagaggt   7380
tttcaccgtc atcaccgaaa cgcgcgaggc agcagatcaa ttcgcgcgcg aaggcgaagc   7440
ggcatgcatt tacgttgaca ccatcgaatg gtgcaaaacc tttcgcggta tggcatgata   7500
gcgcccggaa gagagtcaat tcagggtggt gaatgtgaaa ccagtaacgt tatacgatgt   7560
cgcagagtat gccggtgtct cttatcagac cgtttcccgc gtggtgaacc aggccagcca   7620
cgtttctgcg aaaacgcggg aaaaagtgga agcggcgatg gcggagctga attacattcc   7680
caaccgcgtg gcacaacaac tggcgggcaa acagtcgttg ctgattggcg ttgccacctc   7740
cagtctggcc ctgcacgcgc cgtcgcaaat tgtcgcggcg attaaatctc gcgccgatca   7800
actgggtgcc agcgtggtgg tgtcgatggt agaacgaagc ggcgtcgaag cctgtaaagc   7860
ggcggtgcac aatcttctcg cgcaacgcgt cagtgggctg atcattaact atccgctgga   7920
tgaccaggat gccattgctg tggaagctgc ctgcactaat gttccggcgt tatttcttga   7980
tgtctctgac cagacaccca tcaacagtat tattttctcc catgaagacg gtacgcgact   8040
gggcgtggag catctggtcg cattgggtca ccagcaaatc gcgctgttag cgggcccatt   8100
aagttctgtc tcggcgcgtc tgcgtctggc tggctggcat aaatatctca ctcgcaatca   8160
aattcagccg atagcggaac gggaaggcga ctggagtgcc atgtccggtt ttcaacaaac   8220
catgcaaatg ctgaatgagg gcatcgttcc cactgcgatg ctggttgcca acgatcagat   8280
ggcgctgggc gcaatgcgcg ccattaccga gtccgggctg cgcgttggtg cggatatctc   8340
ggtagtggga tacgacgata ccgaagacag ctcatgttat atcccgccgt taaccaccat   8400
caaacaggat tttcgcctgc tggggcaaac cagcgtggac cgcttgctgc aactctctca   8460
gggccaggcg gtgaagggca atcagctgtt gcccgtctca ctggtgaaaa gaaaaaccac   8520
```

cctggcgccc aatacgcaaa ccgcctctcc ccgcgcgttg gccgattcat taatgcagct 8580
ggcacgacag gtttcccgac tggaaagcgg gcagtgagcg caacgcaatt aatgtgagtt 8640
agcgcgaatt gatctg 8656

<210> SEQ ID NO 93
<211> LENGTH: 9789
<212> TYPE: DNA
<213> ORGANISM: Artificial Sequence
<220> FEATURE:
<223> OTHER INFORMATION: pSNAK(-E)-dxs

<400> SEQUENCE: 93
gatctcatta ggtagccgtt tcaggcacaa ttgggattga taaaattagt ttttttgtgc 60
ccccttatta tattgatatg acggcactgg ctgaagccag aaatgtagac cctggaaaat 120
ttcatattgg tattgggcaa gaccaaatgg cggtgaaccc aatcagccaa gatattgtga 180
catttgcagc caatgccgca gaagcgatct tgaccaaaga agataaagag gccattgata 240
tggtgattgt cgggactgag tccagtatcg atgagtcaaa agcggccgca gttgtcttac 300
atcgtttaat ggggattcaa cctttcgctc gctctttcga aatcaaggaa gcttgttacg 360
gagcaacagc aggcttacag ttagctaaga atcacgtagc cttacatcca gataaaaaag 420
tcttggttgt agcagcagat attgcaaaat atggattaaa ttctggcggt gagcctacac 480
aaggagctgg ggcggttgca atgttagttg ctagtgaacc gcgcatcttg gctttaaaag 540
aggataatgt gatgctgacg caagatatct atgacttttg gcgtccaaca ggccatccgt 600
atcctatggt cgatggtcct ttgtcaaacg aaacctacat ccaatctttt gcccaagtct 660
gggatgaaca taaaaaaaga accggtcttg attttgcaga ttatgatgct ttagcgttcc 720
atattcctta cacaaaaatg ggcaaaaaag ccttattagc aaaaatctcc gaccaaactg 780
aagcagaaca ggaacgaatt ttagcccgtt atgaagaaag catcatctat agtcgtcgcg 840
taggaaactt gtatacgggt tcactttatc tgggactcat ttccctttta gaaaatgcaa 900
cgactttaac cgcaggcaat caaattgggt tattcagtta tggttctggt gctgtcgctg 960
aatttttcac tggtgaatta gtagctggtt atcaaaatca tttacaaaaa gaaactcatt 1020
tagcactgct agataatcgg acagaacttt ctatcgctga atatgaagcc atgtttgcag 1080
aaactttaga cacagatatt gatcaaacgt tagaagatga attaaaatat agtatttctg 1140
ctattaataa taccgttcgc tcttatcgaa actaactgca gcctcgacct gcaggcatgc 1200
aagcttggca ctggccgtcg ttttacaacg tcgtgactgg gaaaaccctg gcgttaccca 1260
acttaatcgc cttgcagcac atcccccttt cgccagctgg cgtaatagcg aagaggcccg 1320
caccgatcgc ccttcccaac agttgcgcag cctgaatggc gaatgagctt atcgatgata 1380
agctgtcaaa catgagaatt acaacttata tcgtatgggg ctgacttcag gtgctacatt 1440
tgaagagata aattgcactg aaatctagaa atattttatc tgattaataa gatgatcttc 1500
ttgagatcgt tttggtctgc gcgtaatctc ttgctctgaa aacgaaaaaa ccgccttgca 1560
gggcggtttt tcgaaggttc tctgagctac caactctttg aaccgaggta actggcttgg 1620
aggagcgcag tcaccaaaac ttgtcctttc agtttagcct taaccggcgc atgacttcaa 1680
gactaactcc tctaaatcaa ttaccagtgg ctgctgccag tggtgctttt gcatgtcttt 1740
ccgggttgga ctcaagacga tagttaccgg ataaggcgca gcggtcggac tgaacggggg 1800
gttcgtgcat acagtccagc ttggagcgaa ctgcctaccc ggaactgagt gtcaggcgtg 1860
gaatgagaca aacgcggcca taacagcgga atgacaccgg taaaccgaaa ggcaggaaca 1920

```
ggagagcgca cgagggagcc gccaggggaa acgcctggta tctttatagt cctgtcgggt   1980
ttcgccacca ctgatttgag cgtcagattt cgtgatgctt gtcagggggg cggagcctat   2040
ggaaaaacgg ctttgccgcg gccctctcac ttccctgtta agtatcttcc tggcatcttc   2100
caggaaatct ccgccccgtt cgtaagccat ttccgctcgc cgcagtcgaa cgaccgagcg   2160
tagcgagtca gtgagcgagg aagcggaata tatcctgtat cacatattct gctgacgcac   2220
cggtgcagcc tttttctcc tgccacatga agcacttcac tgacaccctc atcagtgcca    2280
acatagtaag ccagtataca ctccgctagc gctgatgtcc ggcggtgctt ttgccgttac   2340
gcaccacccc gtcagtagct gaacaggagg gacagctgat agaaacagaa gccactggag   2400
cacctcaaaa acaccatcat acactaaatc agtaagttgg cagcatcacc cgacgcactt   2460
tgcgccgaat aaatacctgt gacggaagat cacttcgcag aataaataaa tcctggtgtc   2520
cctgttgata ccgggaagcc ctgggccaac ttttggcgaa aatgagacgt tgatcggcac   2580
gtaagaggtt ccaactttca ccataatgaa ataagatcac taccgggcgt atttttgag    2640
ttatcgagat tttcaggagc taaggaagct aaaatgagcc atattcaacg ggaaacgtct   2700
tgctctaggc cgcgattaaa ttccaacatg gatgctgatt tatatgggta taaatgggct   2760
cgcgataatg tcgggcaatc aggtgcgaca atctatcgat tgtatgggaa gcccgatgcg   2820
ccagagttgt ttctgaaaca tggcaaaggt agcgttgcca atgatgttac agatgagatg   2880
gtcagactaa actggctgac ggaatttatg cctcttccga ccatcaagca ttttatccgt   2940
actcctgatg atgcatggtt actcaccact gcgatccccg ggaaaacagc attccaggta   3000
ttagaagaat atcctgattc aggtgaaaat attgttgatg cgctggcagt gttcctgcgc   3060
cggttgcatt cgattcctgt ttgtaattgt ccttttaaca gcgatcgcgt atttcgtctc   3120
gctcaggcgc aatcacgaat gaataacggt ttggttgatg cgagtgattt tgatgacgag   3180
cgtaatggct ggcctgttga acaagtctgg aaagaaatgc ataaactttt gccattctca   3240
ccggattcag tcgtcactca tggtgatttc tcacttgata accttatttt tgacgagggg   3300
aaattaatag gttgtattga tgttggacga gtcggaatcg cagaccgata ccaggatctt   3360
gccatcctat ggaactgcct cggtgagttt tctccttcat tacagaaacg gctttttcaa   3420
aaatatggta ttgataatcc tgatatgaat aaattgcagt ttcatttgat gctcgatgag   3480
tttttctaaa gtactgcgat gagtggcagg gcggggcgta atttttttaa ggcagttatt   3540
ggtgccctta aacgcctggt gctacgcctg aataagtgat aataagcgga tgaatggcag   3600
aaattcgaaa gcaaattcga cccggtcgtc ggttcagggc agggtcgtta aatagccgct   3660
tatgtctatt gctggtttac cggtttattg actaccggaa gcagtgtgac cgtgtgcttc   3720
tcaaatgcct gaggccagtt tgctcaggct ctccccgtgg aggtaataat tgacgatatg   3780
atcatttatt ctgcctccca gagcctgata aaaacggtta gcgcttcgtt aatacagatg   3840
taggtgttcc acagggtagc cagcagcatc ctgcgatgca gatccggaac ataatggtgc   3900
agggcgcttg tttcggcgtg ggtatggtgg caggccccgt ggccggggga ctgttgggcg   3960
ctgccggcac ctgtcctacg agttgcatga taaagaagac agtcataagt gcggcgacga   4020
tagtcatgcc ccgcgcccac cggaaggagc taccggacag cggtgcggac tgttgtaact   4080
cagaataaga aatgaggccg ctcatggcgt tccaatacgc aaaccgcctc tccccgcgcg   4140
ttggccgatt cattaatgca gctggcacga caggtttccc gactggaaag cgggcagtga   4200
gcgcaacgca attaatgtga gttagctcac tcattaggca ccccaggctt tacactttat   4260
```

-continued

```
gcttccggct cgtatgttgt gtggaattgt gagcggataa caatttcaca caggaaacag   4320
ctatgaccat gattacgaat tcgagctcgg tacccgggga tcctacctga cgctttttat   4380
cgcaactctc tactgtttct ccatacccgt ttttttgggc tagcaggagg aattcaccat   4440
ggtaccaatg acaaaaaaag ttggtgtcgg tcaggcacat agtaagataa ttttaatagg   4500
ggaacatgcg gtcgtttacg gttatcctgc catttccctg cctcttttgg aggtggaggt   4560
gacctgtaag gtagttcctg cagagagtcc ttggcgcctt tatgaggagg ataccttgtc   4620
catggcggtt tatgcctcac tggagtattt gaatatcaca gaagcctgca ttcgttgtga   4680
gattgactcg gctatccctg agaaacgggg gatgggttcg tcagcggcta tcagcatagc   4740
ggccattcgt gcagtatttg actactatca ggctgatctg cctcatgatg tactagaaat   4800
cttggtcaat cgagctgaaa tgattgccca tatgaatcct agtggtttgg atgctaagac   4860
ctgtcttagt gaccaaccta ttcgctttat caagaacgta ggatttacag aacttgagat   4920
ggatttatcc gcctatttgg tgattgccga tacgggtgtt tatggtcata ctcgtgaagc   4980
catccaagtg gttcaaaata agggcaagga tgccctaccg tttttgcatg ccttgggaga   5040
attaacccag caagcagaag ttgcgatttc acaaaaagat gctgaaggac tgggacaaat   5100
cctcagtcaa gcgcatttac atttaaaaga aattggagtc agtagccctg aggcagactt   5160
tttggttgaa acgactctta gccatggtgc tctgggtgcc aagatgagcg gtggtgggct   5220
aggaggttgt atcatagcct tggtaaccaa tttgacacac gcacaagaac tagcagaaag   5280
attagaagag aaaggagctg ttcagacatg gatagagagc ctgtaacagt acgttcctac   5340
gcaaatattg ctattatcaa atattgggga aagaaaaaag aaaaagagat ggtgcctgct   5400
actagcagta tttctctaac tttggaaaat atgtatacag agacgacctt gtcgccttta   5460
ccagccaatg taacagctga cgaattttac atcaatggtc agctacaaaa tgaggtcgag   5520
catgccaaga tgagtaagat tattgaccgt tatcgtccag ctggtgaggg ctttgtccgt   5580
atcgatactc aaaacaatat gcctacggca gcgggcctgt cctcaagttc tagtggtttg   5640
tccgccctgg tcaaggcttg taatgcttat ttcaagcttg gattggatag aagtcagttg   5700
gcacaggaag ccaaatttgc ctcaggctct tcttctcgga gtttttatgg accactagga   5760
gcctgggata aggatagtgg agaaatttac cctgtagaga cagacttgaa actagctatg   5820
attatgttgg tgctagagga caagaaaaaa ccaatctcta gccgtgacgg gatgaaactt   5880
tgtgtggaaa cctcgacgac ttttgacgac tgggttcgtc agtctgagaa ggactatcag   5940
gatatgctga tttatctcaa ggaaaatgat tttgccaaga ttggagaatt aacggagaaa   6000
aatgctctgg ctatgcatgc tacgacaaag actgctagtc cagccttttc ttatctgacg   6060
gatgcctctt atgaggctat ggcctttgtt cgccagcttc gtgagaaagg agaggcctgc   6120
tactttacca tggatgctgg tcccaatgtt aaggtcttct gtcaggagaa agacttggag   6180
catttgtcag aaattttcgg tcagcgttat cgcttgattg tgtcaaaaac aaaggatttg   6240
agtcaagatg attgctgtta aaacttgcgg aaaactctat tgggcaggtg aatatgctat   6300
tttagagcca gggcagttag ctttgataaa ggatattccc atctatatga gggctgagat   6360
tgctttttct gacagctacc gtatctattc agatatgttt gatttcgcag tggacttaag   6420
gcccaatcct gactacagct tgattcaaga aacgattgct ttgatgggag acttcctcgc   6480
tgttcgcggt cagaatttaa gacctttttc cctaaaaatc tgtggcaaaa tggaacgaga   6540
agggaaaaag tttggtctag gttctagtgg cagcgtcgtt gtcttggttg tcaaggcttt   6600
actggctctc tataatcttt cggttgatca gaatctcttg ttcaagctga ctagcgctgt   6660
```

```
cttgctcaag cgaggagaca atggttccat gggcgacctt gcctgtattg tggcagagga   6720
tttggttctt taccagtcat ttgatcgcca gaaggcggct gcttggttag aagaagaaaa   6780
cttggcgaca gttctggagc gtgattgggg attttttatc tcacaagtga aaccaacttt   6840
agaatgtgat ttcttagtgg gatggaccaa ggaagtggct gtatcgagtc acatggtcca   6900
gcaaatcaag caaaatatca atcaaaattt tttaagttcc tcaaaagaaa cggtggtttc   6960
tttggtcgaa gccttggagc aggggaaagc cgaaaaagtt atcgagcaag tagaagtagc   7020
cagcaagctt ttagaaggct tgagtacaga tatttacacg cctttgctta gacagttgaa   7080
agaagccagt caagatttgc aggccgttgc caagagtagt ggtgctggtg gtggtgactg   7140
tggcatcgcc ctgagttttg atgcgcaatc ttctcgaaac actttaaaaa atcgttgggc   7200
cgatctgggg attgagctct tatatcaaga aaggatagga catgacgaca aatcgtaatc   7260
tagccccggg aggagagaaa ttatgcaaac ggaacacgtc attttattga atgcacaggg   7320
agttcccacg ggtacgctgg aaaagtatgc cgcacacacg gcagacaccc gcttacatct   7380
cgcgttctcc agttggctgt ttaatgccaa aggacaatta ttagttaccc gccgcgcact   7440
gagcaaaaaa gcatggcctg gcgtgtggac taactcggtt tgtgggcacc cacaactggg   7500
agaaagcaac gaagacgcag tgatccgccg ttgccgttat gagcttggcg tggaaattac   7560
gcctcctgaa tctatctatc ctgactttcg ctaccgcgcc accgatccga gtggcattgt   7620
ggaaaatgaa gtgtgtccgg tatttgccgc acgcaccact agtgcgttac agatcaatga   7680
tgatgaagtg atggattatc aatggtgtga tttagcagat gtattacacg gtattgatgc   7740
cacgccgtgg gcgttcagtc cgtggatggt gatgcaggcg acaaatcgcg aagccagaaa   7800
acgattatct gcatttaccc agcttaaata agcatgcact agagtcgagg aaacagacca   7860
tggagtctcg agtgtggaat tgtgagcgga taacaatttc acacaggaaa cagaccatgg   7920
aattcatgag ttttgatatt gccaaatacc cgaccctggc actggtcgac tccacccagg   7980
agttacgact gttgccgaaa gagagtttac cgaaactctg cgacgaactg cgccgctatt   8040
tactcgacag cgtgagccgt tccagcgggc acttcgcctc cgggctgggc acggtcgaac   8100
tgaccgtggc gctgcactat gtctacaaca ccccgtttga ccaattgatt tgggatgtgg   8160
ggcatcaggc ttatccgcat aaaattttga ccggacgccg cgacaaaatc ggcaccatcc   8220
gtcagaaagg cggtctgcac ccgttcccgt ggcgcggcga aagcgaatat gacgtattaa   8280
gcgtcgggca ttcatcaacc tccatcagtg ccggaattgg tattgcggtt gctgccgaaa   8340
aagaaggcaa aaatcgccgc accgtctgtg tcattggcga tggcgcgatt accgcaggca   8400
tggcgtttga agcgatgaat cacgcgggcg atatccgtcc tgatatgctg gtgattctca   8460
acgacaatga aatgtcgatt tccgaaaatg tcggcgcgct caacaaccat ctggcacagc   8520
tgctttccgg taagctttac tcttcactgc gcgaaggcgg gaaaaaagtt ttctctggcg   8580
tgccgccaat taaagagctg ctcaaacgca ccgaagaaca tattaaaggc atggtagtgc   8640
ctggcacgtt gtttgaagag ctgggcttta actacatcgg cccggtggac ggtcacgatg   8700
tgctggggct tatcaccacg ctaaagaaca tgcgcgacct gaaaggcccg cagttcctgc   8760
atatcatgac caaaaaaggt cgtggttatg aaccggcaga aaaagacccg atcactttcc   8820
acgccgtgcc taaatttgat ccctccagcg gttgtttgcc gaaaagtagc ggcggtttgc   8880
cgagctattc aaaaatcttt ggcgactggt tgtgcgaaac ggcagcgaaa gacaacaagc   8940
tgatggcgat tactccggcg atgcgtgaag gttccggcat ggtcgagttt tcacgtaaat   9000
```

tcccggatcg ctacttcgac gtggcaattg ccgagcaaca cgcggtgacc tttgctgcgg 9060
gtctggcgat tggtgggtac aaacccattg tcgcgattta ctccactttc ctgcaacgcg 9120
cctatgatca ggtgctgcat gacgtggcga ttcaaaagct tccggtcctg ttcgccatcg 9180
accgcgcggg cattgttggt gctgacggtc aaacccatca gggtgctttt gatctctctt 9240
acctgcgctg cataccggaa atggtcatta tgaccccgag cgatgaaaac gaatgtcgcc 9300
agatgctcta taccggctat cactataacg atggcccgtc agcggtgcgc tacccgcgtg 9360
gcaacgcggt cggcgtggaa ctgacgccgc tggaaaaact accaattggc aaaggcattg 9420
tgaagcgtcg tggcgagaaa ctggcgatcc ttaactttgg tacgctgatg ccagaagcgg 9480
cgaaagtcgc cgaatcgctg aacgccacgc tggtcgatat gcgttttgtg aaaccgcttg 9540
atgaagcgtt aattctggaa atggccgcca gccatgaagc gctggtcacc gtagaagaaa 9600
acgccattat gggcggcgca ggcagcggcg tgaacgaagt gctgatggcc catcgtaaac 9660
cagtacccgt gctgaacatt ggcctgccgg acttctttat tccgcaagga actcaggaag 9720
aaatgcgcgc cgaactcggc ctcgatgccg ctggtatgga agccaaaatc aaggcctggc 9780
tggcataaa 9789

<210> SEQ ID NO 94
<211> LENGTH: 8938
<212> TYPE: DNA
<213> ORGANISM: Artificial Sequence
<220> FEATURE:
<223> OTHER INFORMATION: pSNA(-E)-dxsfree

<400> SEQUENCE: 94
gatctcatta ggtagccgtt tcaggcacaa ttgggattga taaaattagt ttttttgtgc 60
ccccttatta tattgatatg acggcactgg ctgaagccag aaatgtagac cctggaaaat 120
ttcatattgg tattgggcaa gaccaaatgg cggtgaaccc aatcagccaa gatattgtga 180
catttgcagc caatgccgca gaagcgatct tgaccaaaga agataaagag gccattgata 240
tggtgattgt cgggactgag tccagtatcg atgagtcaaa agcggccgca gttgtcttac 300
atcgtttaat ggggattcaa cctttcgctc gctctttcga aatcaaggaa gcttgttacg 360
gagcaacagc aggcttacag ttagctaaga atcacgtagc cttacatcca gataaaaaag 420
tcttggttgt agcagcagat attgcaaaat atggattaaa ttctggcggt gagcctacac 480
aaggagctgg ggcggttgca atgttagttg ctagtgaacc gcgcatcttg gctttaaaag 540
aggataatgt gatgctgacg caagatatct atgacttttg gcgtccaaca ggccatccgt 600
atcctatggt cgatggtcct ttgtcaaacg aaacctacat ccaatctttt gcccaagtct 660
gggatgaaca taaaaaaaga accggtcttg attttgcaga ttatgatgct ttagcgttcc 720
atattcctta cacaaaaatg ggcaaaaaag ccttattagc aaaaatctcc gaccaaactg 780
aagcagaaca ggaacgaatt ttagcccgtt atgaagaaag catcatctat agtcgtcgcg 840
taggaaactt gtatacgggt tcactttatc tgggactcat ttccctttta gaaaatgcaa 900
cgactttaac cgcaggcaat caaattgggt tattcagtta tggttctggt gctgtcgctg 960
aatttttcac tggtgaatta gtagctggtt atcaaaatca tttacaaaaa gaaactcatt 1020
tagcactgct agataatcgg acagaacttt ctatcgctga atatgaagcc atgtttgcag 1080
aaactttaga cacagatatt gatcaaacgt tagaagatga attaaaatat agtatttctg 1140
ctattaataa taccgttcgc tcttatcgaa actaactgca gcctcgacct gcaggcatgc 1200
aagcttggca ctggccgtcg ttttacaacg tcgtgactgg gaaaaccctg gcgttaccca 1260

```
acttaatcgc cttgcagcac atcccccttt cgccagctgg cgtaatagcg aagaggcccg   1320
caccgatcgc ccttcccaac agttgcgcag cctgaatggc gaatgagctt atcgatgata   1380
agctgtcaaa catgagaatt acaacttata tcgtatgggg ctgacttcag gtgctacatt   1440
tgaagagata aattgcactg aaatctagaa atattttatc tgattaataa gatgatcttc   1500
ttgagatcgt tttggtctgc gcgtaatctc ttgctctgaa aacgaaaaaa ccgccttgca   1560
gggcggtttt tcgaaggttc tctgagctac caactctttg aaccgaggta actggcttgg   1620
aggagcgcag tcaccaaaac ttgtcctttc agtttagcct taaccggcgc atgacttcaa   1680
gactaactcc tctaaatcaa ttaccagtgg ctgctgccag tggtgctttt gcatgtcttt   1740
ccgggttgga ctcaagacga tagttaccgg ataaggcgca gcggtcggac tgaacggggg   1800
gttcgtgcat acagtccagc ttggagcgaa ctgcctaccc ggaactgagt gtcaggcgtg   1860
gaatgagaca aacgcggcca taacagcgga atgacaccgg taaaccgaaa ggcaggaaca   1920
ggagagcgca cgagggagcc gccaggggaa acgcctggta tctttatagt cctgtcgggt   1980
ttcgccacca ctgatttgag cgtcagattt cgtgatgctt gtcagggggg cggagcctat   2040
ggaaaaacgg ctttgccgcg gccctctcac ttccctgtta agtatcttcc tggcatcttc   2100
caggaaatct ccgccccgtt cgtaagccat ttccgctcgc cgcagtcgaa cgaccgagcg   2160
tagcgagtca gtgagcgagg aagcggaata tatcctgtat cacatattct gctgacgcac   2220
cggtgcagcc tttttctcc tgccacatga agcacttcac tgacaccctc atcagtgcca   2280
acatagtaag ccagtataca ctccgctagc gctgatgtcc ggcggtgctt ttgccgttac   2340
gcaccacccc gtcagtagct gaacaggagg gacagctgat agaaacagaa gccactggag   2400
cacctcaaaa acaccatcat acactaaatc agtaagttgg cagcatcacc cgacgcactt   2460
tgcgccgaat aaatacctgt gacggaagat cacttcgcag aataaataaa tcctggtgtc   2520
cctgttgata ccgggaagcc ctgggccaac ttttggcgaa aatgagacgt tgatcggcac   2580
gtaagaggtt ccaactttca ccataatgaa ataagatcac taccgggcgt atttttgag    2640
ttatcgagat tttcaggagc taaggaagct tttttttaag gcagttattg gtgcccttaa   2700
acgcctggtg ctacgcctga ataagtgata ataagcggat gaatggcaga aattcgaaag   2760
caaattcgac ccggtcgtcg gttcagggca gggtcgttaa atagccgctt atgtctattg   2820
ctggtttacc ggtttattga ctaccggaag cagtgtgacc gtgtgcttct caaatgcctg   2880
aggccagttt gctcaggctc tccccgtgga ggtaataatt gacgatatga tcatttattc   2940
tgcctcccag agcctgataa aaacggttag cgcttcgtta atacagatgt aggtgttcca   3000
cagggtagcc agcagcatcc tgcgatgcag atccggaaca taatggtgca gggcgcttgt   3060
ttcggcgtgg gtatggtggc aggccccgtg gccgggggac tgttgggcgc tgccggcacc   3120
tgtcctacga gttgcatgat aaagaagaca gtcataagtg cggcgacgat agtcatgccc   3180
cgcgcccacc ggaaggagct accggacagc ggtgcggact gttgtaactc agaataagaa   3240
atgaggccgc tcatggcgtt ccaatacgca aaccgcctct ccccgcgcgt tggccgattc   3300
attaatgcag ctggcacgac aggtttcccg actggaaagc gggcagtgag cgcaacgcaa   3360
ttaatgtgag ttagctcact cattaggcac cccaggcttt acactttatg cttccggctc   3420
gtatgttgtg tggaattgtg agcggataac aatttcacac aggaaacagc tatgaccatg   3480
attacgaatt cgagctcggt acccggggat cctacctgac gctttttatc gcaactctct   3540
actgtttctc catacccgtt tttttgggct agcaggagga attcaccatg gtaccaatga   3600
```

-continued caaaaaaagt tggtgtcggt caggcacata gtaagataat tttaataggg gaacatgcgg 3660
tcgtttacgg ttatcctgcc atttccctgc ctcttttgga ggtggaggtg acctgtaagg 3720
tagttcctgc agagagtcct tggcgccttt atgaggagga taccttgtcc atggcggttt 3780
atgcctcact ggagtatttg aatatcacag aagcctgcat tcgttgtgag attgactcgg 3840
ctatccctga gaaacggggg atgggttcgt cagcggctat cagcatagcg gccattcgtg 3900
cagtatttga ctactatcag gctgatctgc ctcatgatgt actagaaatc ttggtcaatc 3960
gagctgaaat gattgcccat atgaatccta gtggtttgga tgctaagacc tgtcttagtg 4020
accaacctat tcgctttatc aagaacgtag gatttacaga acttgagatg gatttatccg 4080
cctatttggt gattgccgat acgggtgttt atggtcatac tcgtgaagcc atccaagtgg 4140
ttcaaaataa gggcaaggat gccctaccgt tttgcatgc cttgggagaa ttaacccagc 4200
aagcagaagt tgcgatttca caaaaagatg ctgaaggact gggacaaatc ctcagtcaag 4260
cgcatttaca tttaaaagaa attggagtca gtagccctga ggcagacttt ttggttgaaa 4320
cgactcttag ccatggtgct ctgggtgcca agatgagcgg tggtgggcta ggaggttgta 4380
tcatagcctt ggtaaccaat ttgacacacg cacaagaact agcagaaaga ttagaagaga 4440
aaggagctgt tcagacatgg atagagagcc tgtaacagta cgttcctacg caaatattgc 4500
tattatcaaa tattggggaa agaaaaaaga aaaagagatg gtgcctgcta ctagcagtat 4560
ttctctaact ttggaaaata tgtatacaga gacgaccttg tcgcctttac cagccaatgt 4620
aacagctgac gaattttaca tcaatggtca gctacaaaat gaggtcgagc atgccaagat 4680
gagtaagatt attgaccgtt atcgtccagc tggtgagggc tttgtccgta tcgatactca 4740
aaacaatatg cctacggcag cgggcctgtc ctcaagttct agtggtttgt ccgccctggt 4800
caaggcttgt aatgcttatt tcaagcttgg attggataga agtcagttgg cacaggaagc 4860
caaatttgcc tcaggctctt cttctcggag tttttatgga ccactaggag cctgggataa 4920
ggatagtgga gaaatttacc ctgtagagac agacttgaaa ctagctatga ttatgttggt 4980
gctagaggac aagaaaaaac caatctctag ccgtgacggg atgaaacttt gtgtggaaac 5040
ctcgacgact tttgacgact gggttcgtca gtctgagaag gactatcagg atatgctgat 5100
ttatctcaag gaaaatgatt ttgccaagat tggagaatta acggagaaaa atgctctggc 5160
tatgcatgct acgacaaaga ctgctagtcc agccttttct tatctgacgg atgcctctta 5220
tgaggctatg gcctttgttc gccagcttcg tgagaaagga gaggcctgct actttaccat 5280
ggatgctggt cccaatgtta aggtcttctg tcaggagaaa gacttggagc atttgtcaga 5340
aattttcggt cagcgttatc gcttgattgt gtcaaaaaca aaggatttga gtcaagatga 5400
ttgctgttaa aacttgcgga aaactctatt gggcaggtga atatgctatt ttagagccag 5460
ggcagttagc tttgataaag gatattccca tctatatgag ggctgagatt gctttttctg 5520
acagctaccg tatctattca gatatgtttg atttcgcagt ggacttaagg cccaatcctg 5580
actacagctt gattcaagaa acgattgctt tgatgggaga cttcctcgct gttcgcggtc 5640
agaatttaag acctttttcc ctaaaaatct gtggcaaaat ggaacgagaa gggaaaaagt 5700
ttggtctagg ttctagtggc agcgtcgttg tcttggttgt caaggcttta ctggctctct 5760
ataatctttc ggttgatcag aatctcttgt tcaagctgac tagcgctgtc ttgctcaagc 5820
gaggagacaa tggttccatg ggcgaccttg cctgtattgt ggcagaggat ttggttcttt 5880
accagtcatt tgatcgccag aaggcggctg cttggttaga agaagaaaac ttggcgacag 5940
ttctggagcg tgattgggga tttttatct cacaagtgaa accaacttta gaatgtgatt 6000

```
tcttagtggg atggaccaag gaagtggctg tatcgagtca catggtccag caaatcaagc   6060
aaaatatcaa tcaaaatttt ttaagttcct caaaagaaac ggtggtttct ttggtcgaag   6120
ccttggagca ggggaaagcc gaaaaagtta tcgagcaagt agaagtagcc agcaagcttt   6180
tagaaggctt gagtacagat atttacacgc ctttgcttag acagttgaaa gaagccagtc   6240
aagatttgca ggccgttgcc aagagtagtg gtgctggtgg tggtgactgt ggcatcgccc   6300
tgagttttga tgcgcaatct tctcgaaaca ctttaaaaaa tcgttgggcc gatctgggga   6360
ttgagctctt atatcaagaa aggataggac atgacgacaa atcgtaatct agccccggga   6420
ggagagaaat tatgcaaacg gaacacgtca ttttattgaa tgcacaggga gttcccacgg   6480
gtacgctgga aaagtatgcc gcacacacgg cagacacccg cttacatctc gcgttctcca   6540
gttggctgtt taatgccaaa ggacaattat tagttacccg ccgcgcactg agcaaaaaag   6600
catggcctgg cgtgtggact aactcggttt gtgggcaccc acaactggga gaaagcaacg   6660
aagacgcagt gatccgccgt tgccgttatg agcttggcgt ggaaattacg cctcctgaat   6720
ctatctatcc tgactttcgc taccgcgcca ccgatccgag tggcattgtg gaaaatgaag   6780
tgtgtccggt atttgccgca cgcaccacta gtgcgttaca gatcaatgat gatgaagtga   6840
tggattatca atggtgtgat ttagcagatg tattacacgg tattgatgcc acgccgtggg   6900
cgttcagtcc gtggatggtg atgcaggcga caaatcgcga agccagaaaa cgattatctg   6960
catttaccca gcttaaataa gcatgcacta gagtcgagga aacagaccat ggagtctcga   7020
gtgtggaatt gtgagcggat aacaatttca cacaggaaac agaccatgga attcatgagt   7080
tttgatattg ccaaataccc gaccctggca ctggtcgact ccacccagga gttacgactg   7140
ttgccgaaag agagtttacc gaaactctgc gacgaactgc gccgctattt actcgacagc   7200
gtgagccgtt ccagcgggca cttcgcctcc gggctgggca cggtcgaact gaccgtggcg   7260
ctgcactatg tctacaacac cccgtttgac caattgattt gggatgtggg gcatcaggct   7320
tatccgcata aaattttgac cggacgccgc gacaaaatcg gcaccatccg tcagaaaggc   7380
ggtctgcacc cgttcccgtg gcgcggcgaa agcgaatatg acgtattaag cgtcgggcat   7440
tcatcaacct ccatcagtgc cggaattggt attgcggttg ctgccgaaaa agaaggcaaa   7500
aatcgccgca ccgtctgtgt cattggcgat ggcgcgatta ccgcaggcat ggcgtttgaa   7560
gcgatgaatc acgcgggcga tatccgtcct gatatgctgg tgattctcaa cgacaatgaa   7620
atgtcgattt ccgaaaatgt cggcgcgctc aacaaccatc tggcacagct gctttccggt   7680
aagctttact cttcactgcg cgaaggcggg aaaaaagttt tctctggcgt gccgccaatt   7740
aaagagctgc tcaaacgcac cgaagaacat attaaaggca tggtagtgcc tggcacgttg   7800
tttgaagagc tgggctttaa ctacatcggc ccggtggacg gtcacgatgt gctggggctt   7860
atcaccacgc taaagaacat gcgcgacctg aaaggcccgc agttcctgca tatcatgacc   7920
aaaaaaggtc gtggttatga accggcagaa aaagacccga tcactttcca cgccgtgcct   7980
aaatttgatc cctccagcgg ttgtttgccg aaaagtagcg gcggtttgcc gagctattca   8040
aaaatctttg gcgactggtt gtgcgaaacg gcagcgaaag acaacaagct gatggcgatt   8100
actccggcga tgcgtgaagg ttccggcatg gtcgagtttt cacgtaaatt cccggatcgc   8160
tacttcgacg tggcaattgc cgagcaacac gcggtgacct ttgctgcggg tctggcgatt   8220
ggtgggtaca aacccattgt cgcgatttac tccactttcc tgcaacgcgc ctatgatcag   8280
gtgctgcatg acgtggcgat tcaaaagctt ccggtcctgt tcgccatcga ccgcgcgggc   8340
```

attgttggtg ctgacggtca aacccatcag ggtgcttttg atctctctta cctgcgctgc 8400
ataccggaaa tggtcattat gaccccgagc gatgaaaacg aatgtcgcca gatgctctat 8460
accggctatc actataacga tggcccgtca gcggtgcgct acccgcgtgg caacgcggtc 8520
ggcgtggaac tgacgccgct ggaaaaacta ccaattggca aaggcattgt gaagcgtcgt 8580
ggcgagaaac tggcgatcct taactttggt acgctgatgc cagaagcggc gaaagtcgcc 8640
gaatcgctga acgccacgct ggtcgatatg cgttttgtga aaccgcttga tgaagcgtta 8700
attctggaaa tggccgccag ccatgaagcg ctggtcaccg tagaagaaaa cgccattatg 8760
ggcggcgcag gcagcggcgt gaacgaagtg ctgatggccc atcgtaaacc agtacccgtg 8820
ctgaacattg gcctgccgga cttctttatt ccgcaaggaa ctcaggaaga aatgcgcgcc 8880
gaactcggcc tcgatgccgc tggtatggaa gccaaaatca aggcctggct ggcataaa 8938

<210> SEQ ID NO 95
<211> LENGTH: 14034
<212> TYPE: DNA
<213> ORGANISM: Artificial Sequence
<220> FEATURE:
<223> OTHER INFORMATION: pT-HBSREYbbOdxrfree

<400> SEQUENCE: 95
ctagcacaga atttgcctgg cggcagtagc gcggtggtcc cacctgaccc catgccgaac 60
tcagaagtga aacgccgtag cgccgatggt agtgtggggt ctccccatgc gagagtaggg 120
aactgccagg catcaaataa aacgaaaggc tcagtcgaaa gactgggcct ttcgttttat 180
ctgttgtttg tcggtgaacg ctctcctgag taggacaaat ccgccgggag cggatttgaa 240
cgttgcgaag caacggcccg gagggtggcg ggcaggacgc ccgccataaa ctgccaggca 300
tcaaattaag cagaaggcca tcctgacgga tggccttttt gcgtttctac aaactctttt 360
tgtttatttt tctaaataca ttcaaatatg tatccgctca aagcttgcgt cagaccccgt 420
agaaaagatc aaaggatctt cttgagatcc tttttttctg cgcgtaatct gctgcttgca 480
aacaaaaaaa ccaccgctac cagcggtggt ttgtttgccg gatcaagagc taccaactct 540
ttttccgaag gtaactggct tcagcagagc gcagatacca aatactgtcc ttctagtgta 600
gccgtagtta ggccaccact tcaagaactc tgtagcaccg cctacatacc tcgctctgct 660
aatcctgtta ccagtggctg ctgccagtgg cgataagtcg tgtcttaccg ggttggactc 720
aagacgatag ttaccggata aggcgcagcg gtcgggctga acggggggtt cgtgcacaca 780
gcccagcttg gagcgaacga cctacaccga actgagatac ctacagcgtg agctatgaga 840
aagcgccacg cttcccgaag ggagaaaggc ggacaggtat ccggtaagcg gcagggtcgg 900
aacaggagag cgcacgaggg agcttccagg gggaaacgcc tggtatcttt atagtcctgt 960
cgggtttcgc cacctctgac ttgagcgtcg atttttgtga tgctcgtcag gggggcggag 1020
cctatggaaa aacgccagca acgcggcctt tttacggttc ctggcctttt gctggccttt 1080
tgctcacatg ttctttcctg cgttatcccc tgattctgtg gataaccgta ttaccgcctt 1140
tgagtgagct gataccgctc gccgcagccg aacgaccgag cgcagcgagt cagtgagcga 1200
ggaagcggaa gagcgcctga tgcggtattt tctccttacg catctgtgcg gtatttcaca 1260
ccgcatatgg tgcactctca gtacaatctg ctctgatgcc gcatagttaa gccagtatac 1320
actccgctat cgctacgtga ctgggtcatg gctgcgcccc gacacccgcc aacacccgct 1380
gacgcgccct gacgggcttg tctgctcccg gcatccgctt acagacaagc tgtgaccgtc 1440
tccgggagct gcatgtgtca gaggttttca ccgtcatcac cgaaacgcgc gaggcagcag 1500

-continued

```
atcaattcgc gcgcgaaggc gaagcggcat gcatttacgt tgacaccatc gaatggtgca   1560
aaacctttcg cggtatggca tgatagcgcc cggaagagag tcaattcagg gtggtgaatg   1620
tgaaaccagt aacgttatac gatgtcgcag agtatgccgg tgtctcttat cagaccgttt   1680
cccgcgtggt gaaccaggcc agccacgttt ctgcgaaaac gcgggaaaaa gtggaagcgg   1740
cgatggcgga gctgaattac attcccaacc gcgtggcaca acaactggcg ggcaaacagt   1800
cgttgctgat tggcgttgcc acctccagtc tggccctgca cgcgccgtcg caaattgtcg   1860
cggcgattaa atctcgcgcc gatcaactgg gtgccagcgt ggtggtgtcg atggtagaac   1920
gaagcggcgt cgaagcctgt aaagcggcgg tgcacaatct tctcgcgcaa cgcgtcagtg   1980
ggctgatcat taactatccg ctggatgacc aggatgccat tgctgtggaa gctgcctgca   2040
ctaatgttcc ggcgttattt cttgatgtct ctgaccagac acccatcaac agtattattt   2100
tctcccatga agacggtacg cgactgggcg tggagcatct ggtcgcattg ggtcaccagc   2160
aaatcgcgct gttagcgggc ccattaagtt ctgtctcggc gcgtctgcgt ctggctggct   2220
ggcataaata tctcactcgc aatcaaattc agccgatagc ggaacgggaa ggcgactgga   2280
gtgccatgtc cggttttcaa caaaccatgc aaatgctgaa tgagggcatc gttcccactg   2340
cgatgctggt tgccaacgat cagatggcgc tgggcgcaat gcgcgccatt accgagtccg   2400
ggctgcgcgt tggtgcggat atctcggtag tgggatacga cgataccgaa gacagctcat   2460
gttatatccc gccgttaacc accatcaaac aggattttcg cctgctgggg caaaccagcg   2520
tggaccgctt gctgcaactc tctcagggcc aggcggtgaa gggcaatcag ctgttgcccg   2580
tctcactggt gaaaagaaaa accaccctgg cgcccaatac gcaaaccgcc tctccccgcg   2640
cgttggccga ttcattaatg cagctggcac gacaggtttc ccgactggaa agcgggcagt   2700
gagcgcaacg caattaatgt gagttagcgc gaattgatct ggtttgacag cttatcatcg   2760
actgcacggt gcaccaatgc ttctggcgtc aggcagccat cggaagctgt ggtatggctg   2820
tgcaggtcgt aaatcactgc ataattcgtg tcgctcaagg cgcactcccg ttctggataa   2880
tgttttttgc gccgacatca taacggttct ggcaaatatt ctgaaatgag ctgttgacaa   2940
ttaatcatcc ggctcgtata atgtgtggaa ttgtgagcgg ataacaattt cacacaggaa   3000
acagaccatg gaattctacg tactagtgaa ttcaggaggt aataaatatg ggtctgatgc   3060
tgattgattg gtgtgcactg gctctggttg ttttcattgg cctgccgcac ggcgcgctgg   3120
atgctgccat ttctttttct atgatctctt ctgcaaaacg cattgctcgt ctggctggta   3180
ttctgctgat ctatctgctg ctggcgaccg cgttcttcct gatctggtat cagctgccag   3240
cgtttagcct gctgatcttc ctgctgatct ccattatcca ctttggtatg gcagacttca   3300
acgcgtcccc aagcaaactg aaatggccgc atatcatcgc ccacggcggt gttgttactg   3360
tttggctgcc gctgatccag aaaaacgaag taactaaact gtttagcatc ctgactaacg   3420
gtccgactcc gatcctgtgg gacatcctgc tgattttctt cctgtgttgg tctattggcg   3480
tgtgtctgca cacgtacgaa accctgcgct ctaaacatta caacatcgcc tttgaactga   3540
tcggtctgat tttcctggcg tggtatgcgc cgcctctggt tacgtttgcc acttacttct   3600
gcttcattca ttcccgtcgc cacttctcct ttgtgtggaa gcagctgcaa cacatgtctt   3660
ccaaaaagat gatgattggc agcgcgatta tcctgtcctg tacctcttgg ctgatcggcg   3720
gtggtatcta tttcttcctg aactccaaaa tgatcgcctc tgaggctgcg ctgcagactg   3780
tgttcatcgg tctggcggca ctgaccgtgc cgcacatgat tctgatcgac ttcatcttcc   3840
```

-continued

```
gtccgcactc ttcccgtatc aaaatcaaaa actaattaat taaaggaggt aataatatga   3900
ctcataaagc aacggagatc ctgacaggta aagttatgca aaaatcggtc ttaattaccg   3960
gatgttccag tggaattggc ctggaaagcg cgctcgaatt aaaacgccag ggttttcatg   4020
tgctggcagg ttgccggaaa ccggatgatg ttgagcgcat gaacagcatg ggatttaccg   4080
gcgtgttgat cgatctggat tcaccagaaa gtgttgatcg cgcagccgac gaggtgatcg   4140
ccctgaccga taattgtctg tatgggatct ttaacaatgc cggattcggc atgtatggcc   4200
ccctttccac catcagccgt gcgcagatgg aacagcagtt ttccgccaac tttttcggcg   4260
cacaccagct caccatgcgc ctgttacccg cgatgttacc gcacggtgaa gggcgtattg   4320
tgatgacatc atcggtgatg ggattaatct ccacgccggg tcgtggcgct tacgcggcca   4380
gtaaatatgc gctggaggcg tggtcagatg cactgcgcat ggagctgcgc cacagcggaa   4440
ttaaagtcag cctgatcgaa cccggtccca ttcgtactcg cttcaccgac aacgtcaacc   4500
agacgcaaag tgataaacca gtcgaaaatc ccggcatcgc cgcccgcttt acgttgggac   4560
cggaagcggt ggtggacaaa gtacgccatg cttttattag cgagaagccg aagatgcgct   4620
atccggtgac gctggtgacc tgggcggtaa tggtgcttaa gcgcctgctg ccggggcgcg   4680
tgatggacaa aatattgcag ggtaactag taggaggtaa taaatatggt gagtggcagt   4740
aaagcgggcg tttcgcctca tcgcgaaata gaagtaatga gacaatccat tgacgatcac   4800
ctggctggcc tgttacctga aaccgacagc caggatatcg tcagccttgc gatgcgtgaa   4860
ggcgtcatgg cacccggtaa acggatccgt ccgctgctga tgctgctggc cgcccgcgac   4920
ctccgctacc agggcagtat gcctacgctg ctcgatctcg cctgcgccgt tgaactgacc   4980
cataccgcgt cgctgatgct cgacgacatg ccctgcatgg acaacgccga gctgcgccgc   5040
ggtcagccca ctacccacaa aaaatttggt gagagcgtgg cgatccttgc ctccgttggg   5100
ctgctctcta aagcctttgg tctgatcgcc gccaccggcg atctgccggg ggagaggcgt   5160
gcccaggcgg tcaacgagct ctctaccgcc gtgggcgtgc agggcctggt actggggcag   5220
tttcgcgatc ttaacgatgc cgccctcgac cgtacccctg acgctatcct cagcaccaac   5280
cacctcaaga ccggcattct gttcagcgcg atgctgcaga tcgtcgccat tgcttccgcc   5340
tcgtcgccga gcacgcgaga gacgctgcac gccttcgccc tcgacttcgg ccaggcgttt   5400
caactgctgg acgatctgcg tgacgatcac ccggaaaccg gtaaagatcg caataaggac   5460
gcgggaaaat cgacgctggt caaccggctg ggcgcagacg cggcccggca aaagctgcgc   5520
gagcatattg attccgccga caaacacctc actttgcct gtccgcaggg cggcgccatc   5580
cgacagttta tgcatctgtg gtttggccat caccttgccg actggtcacc ggtcatgaaa   5640
atcgcctgat aactcgagga ggtataaagg atgaaaaaaa ccgttgtgat tggcgcaggc   5700
tttggtggcc tggcgctggc gattcgcctg caggcggcag ggatcccaac cgtactgctg   5760
gagcagcggg acaagcccgg cggtcgggcc tacgtctggc atgaccaggg ctttaccttt   5820
gacgccgggc cgacggtgat caccgatcct accgcgcttg aggcgctgtt caccctggcc   5880
ggcaggcgca tggaggatta cgtcaggctg ctgccggtaa aacccttcta ccgactctgc   5940
tgggagtccg ggaagaccct cgactatgct aacgacagcg ccgagcttga ggcgcagatt   6000
acccagttca acccccgcga cgtcgagggc taccggcgct ttctggctta ctcccaggcg   6060
gtattccagg agggatattt gcgcctcggc agcgtgccgt tcctctcttt tcgcgacatg   6120
ctgcgcgccg ggccgcagct gcttaagctc caggcgtggc agagcgtcta ccagtcggtt   6180
tcgcgcttta ttgaggatga gcatctgcgg caggccttct cgttccactc cctgctggta   6240
```

ggcggcaacc ccttcaccac ctcgtccatc tacaccctga tccacgccct tgagcgggag 6300
tggggggtct ggttccctga gggcggcacc ggggcgctgg tgaacggcat ggtgaagctg 6360
tttaccgatc tgggcgggga gatcgaactc aacgcccggg tcgaagagct ggtggtggcc 6420
gataaccgcg taagccaggt ccggctggcg gatggtcgga tctttgacac cgacgccgta 6480
gcctcgaacg ctgacgtggt gaacacctat aaaaagctgc tcggccacca tccggtgggg 6540
cagaagcggg cggcagcgct ggagcgcaag agcatgagca actcgctgtt tgtgctctac 6600
ttcggcctga accagcctca ttcccagctg gcgcaccata ccatctgttt tggtccccgc 6660
taccgggagc tgatcgacga gatctttacc ggcagcgcgc tggcggatga cttctcgctc 6720
tacctgcact cgccctgcgt gaccgatccc tcgctcgcgc ctcccggctg cgccagcttc 6780
tacgtgctgg ccccggtgcc gcatcttggc aacgcgccgc tggactgggc gcaggagggg 6840
ccgaagctgc gcgaccgcat ctttgactac cttgaagagc gctatatgcc cggcctgcgt 6900
agccagctgg tgacccagcg gatctttacc ccggcagact tccacgacac gctggatgcg 6960
catctgggat cggccttctc catcgagccg ctgctgaccc aaagcgcctg gttccgcccg 7020
cacaaccgcg acagcgacat tgccaacctc tacctggtgg gcgcaggtac tcaccctggg 7080
gcgggcattc ctggcgtagt ggcctcggcg aaagccaccg ccagcctgat gattgaggat 7140
ctgcaatgag ccaaccgccg ctgcttgacc acgccacgca gaccatggcc aacggctcga 7200
aaagttttgc caccgctgcg aagctgttcg acccggccac ccgccgtagc gtgctgatgc 7260
tctacacctg gtgccgccac tgcgatgacg tcattgacga ccagacccac ggcttcgcca 7320
gcgaggccgc ggcggaggag gaggccaccc agcgcctggc ccggctgcgc acgctgaccc 7380
tggcggcgtt tgaaggggcc gagatgcagg atccggcctt cgctgccttt caggaggtgg 7440
cgctgaccca cggtattacg ccccgcatgg cgctcgatca cctcgacggc tttgcgatgg 7500
acgtggctca gacccgctat gtcacctttg aggatacgct gcgctactgc tatcacgtgg 7560
cgggcgtggt gggtctgatg atggccaggg tgatgggcgt gcgggatgag cgggtgctgg 7620
atcgcgcctg cgatctgggg ctggccttcc agctgacgaa tatcgcccgg gatattattg 7680
acgatgcggc tattgaccgc tgctatctgc ccgccgagtg gctgcaggat gccgggctga 7740
ccccggagaa ctatgccgcg cgggagaatc gggccgcgct ggcgcgggtg gcggagcggc 7800
ttattgatgc cgcagagccg tactacatct cctcccaggc cgggctacac gatctgccgc 7860
cgcgctgcgc ctgggcgatc gccaccgccc gcagcgtcta ccgggagatc ggtattaagg 7920
taaaagcggc gggaggcagc gcctgggatc gccgccagca caccagcaaa ggtgaaaaaa 7980
ttgccatgct gatggcggca ccggggcagg ttattcgggc gaagacgacg agggtgacgc 8040
cgcgtccggc cggtctttgg cagcgtcccg tttagtaatc tagaggaggt aataaaatat 8100
gcttcgttcg ttgctcagag gcctcacgca tatccccccgc gtgaactccg cccagcagcc 8160
cagctgtgca cacgcgcgac tccagtttaa gctcaggagc atgcagatga cgctcatgca 8220
gcccagcatc tcagccaatc tgtcgcgcgc cgaggaccgc acagaccaca tgaggggtgc 8280
aagcacctgg gcaggcgggc agtcgcagga tgagctgatg ctgaaggacg agtgcatctt 8340
ggtggatgtt gaggacaaca tcacaggcca tgccagcaag ctggagtgtc acaagttcct 8400
accacatcag cctgcaggcc tgctgcaccg ggccttctct gtgttcctgt ttgacgatca 8460
ggggcgactg ctgctgcaac agcgtgcacg ctcaaaaatc accttcccaa gtgtgtggac 8520
gaacacctgc tgcagccacc ctttacatgg gcagacccca gatgaggtgg accaactaag 8580

```
ccaggtggcc gacggaacag tacctggcgc aaaggctgct gccatccgca agttggagca   8640
cgagctgggg ataccagcgc accagctgcc ggcaagcgcg tttcgcttcc tcacgcgttt   8700
gcactactgt gccgcggacg tgcagccagc tgcgacacaa tcagcgctct ggggcgagca   8760
cgaaatggac tacatcttgt tcatccgggc caacgtcacc ttggcgccca accctgacga   8820
ggtggacgaa gtcaggtacg tgacgcaaga ggagctgcgg cagatgatgc agccggacaa   8880
cgggctgcaa tggtcgccgt ggtttcgcat catcgccgcg cgcttccttg agcgttggtg   8940
ggctgacctg gacgcggccc taaacactga caaacacgag gattggggaa cggtgcatca   9000
catcaacgaa gcgtgataag cggccgcgct gttgacaatt aatcatccgg ctcgtataat   9060
gtgtggaatt gtgagcggat aacaatttca cacaggaaac agaccatgga gttgaaaaca   9120
gtagttatta ttgatgcatt acgaacacca attggaaaat ataaaggcag cttaagtcaa   9180
gtaagtgccg tagacttagg aacacatgtt acaacacaac ttttaaaaag acattccact   9240
atttctgaag aaattgatca agtaatcttt ggaaatgttt tacaagctgg aaatggccaa   9300
aatcccgcac gacaaatagc aataaacagc ggtttatctc atgaaattcc cgcaatgaca   9360
gttaatgagg tctgcggatc aggaatgaag gccgttattt tggcgaaaca attgattcaa   9420
ttaggagaag cggaagtttt aattgctggc gggattgaga atatgtccca agcacctaaa   9480
ttacaacgat ttaattacga aacagaaagc tatgatgcgc ctttttctag tatgatgtac   9540
gatgggttaa cggatgcctt tagtggtcaa gcaatgggct taactgctga aaatgtggcc   9600
gaaaagtatc atgtaactag agaagagcaa gatcaatttt ctgtacattc acaattaaaa   9660
gcagctcaag cacaagcaga agggatattc gctgacgaaa tagccccatt agaagtatca   9720
ggaacgcttg tggagaaaga tgaagggatt cgccctaatt cgagcgttga gaagctagga   9780
acgcttaaaa cagtttttaa agaagacggt actgtaacag cagggaatgc atcaaccatt   9840
aatgatgggg cttctgcttt gattattgct tcacaagaat atgccgaagc acacggtctt   9900
ccttatttag ctattattcg agacagtgtg gaagtcggta ttgatccagc ctatatggga   9960
atttcgccga ttaaagccat tcaaaaactg ttagcgcgca atcaacttac tacggaagaa  10020
attgatctgt atgaaatcaa cgaagcattt gcagcaactt caatcgtggt ccaaagagaa  10080
ctggctttac cagaggaaaa ggtcaacatt tatggtggcg gtatttcatt aggtcatgcg  10140
attggtgcca caggtgctcg tttattaacg agtttaagtt atcaattaaa tcaaaaagaa  10200
aagaaatatg gagtggcttc tttatgtatc ggcggtggct taggactcgc tatgctacta  10260
gagagacctc agcaaaaaaa aaacagccga ttttatcaaa tgagtcctga ggaacgcctg  10320
gcttctcttc ttaatgaagg ccagatttct gctgatacaa aaaaagaatt tgaaaatacg  10380
gctttatctt cgcagattgc caatcatatg attgaaaatc aaatcagtga aacagaagtg  10440
ccgatgggcg ttggcttaca tttaacagtg gacgaaactg attatttggt accaatggcg  10500
acagaagagc cctcagtgat tgcggctttg agtaatggtg caaaaatagc acaaggattt  10560
aaaacagtga atcaacaacg tttaatgcgt ggacaaatcg ttttttacga tgttgcagac  10620
gccgagtcat tgattgatga actacaagta agagaaacgg aaatttttca acaagcagag  10680
ttaagttatc catctatcgt taaacgcggc ggcggcttaa gagatttgca atatcgtgct  10740
tttgatgaat catttgtatc tgtcgacttt ttagtagatg ttaaggatgc aatgggggca  10800
aatatcgtta acgctatgtt ggaaggtgtg gccgagttgt tccgtgaatg gtttgcggag  10860
caaaagattt tattcagtat tttaagtaat tatgccacgg agtcggttgt tacgatgaaa  10920
acggctattc cagtttcacg tttaagtaag ggagcaatg gccgggaaat tgctgaaaaa  10980
```

-continued

```
attgttttag cttcacgcta tgcttcatta gatccttatc gggcagtcac gcataacaaa  11040
gggatcatga atggcattga agctgtcgtt ttagctacag gaaatgatac acgcgctgtt  11100
agcgcttctt gtcatgcttt tgcggtgaag gaaggtcgct accaaggttt gactagttgg  11160
acgctggatg gcgaacaact aattggtgaa atttcagttc cgcttgcgtt agccacggtt  11220
ggcggtgcca caaaagtctt acctaaatct caagcagctg ctgatttgtt agcagtgacg  11280
gatgcaaaag aactaagtcg agtagtagcg gctgttggtt tggcacaaaa tttagcggcg  11340
ttacgggcct tagtctctga aggaattcaa aaaggacaca tggctctaca agcacgttct  11400
ttagcgatga cggtcggagc tactggtaaa gaagttgagg cagtcgctca acaattaaaa  11460
cgtcaaaaaa cgatgaacca agaccgagcc ttggctattt taaatgattt aagaaaacaa  11520
taaaaaaaca gttcagcaga aattattctg ctgaactgtt ttttttcaca ttaggtagcc  11580
gtttcagctc gacaggagga gcggctatgc aaccgcatta tgatctgatt ctcgtggggg  11640
ctggactcgc gaatggcctt atcgccctgc gtcttcagca gcagcaacct gatatgcgta  11700
ttttgcttat cgacgccgca ccccaggcgg gcgggaatca tacgtggtca tttcaccacg  11760
atgatttgac tgagagccaa catcgttgga tagctccgct ggtggttcat cactggcccg  11820
actatcaggt acgctttccc acacgccgtc gtaagctgaa cagcggctac ttttgtatta  11880
cttctcagcg tttcgctgag gttttacagc gacagtttgg cccgcacttg tggatggata  11940
ccgcggtcgc agaggttaat gcggaatctg ttcggttgaa aaagggtcag gttatcggtg  12000
cccgcgcggt gattgacggg cggggttatg cggcaaattc agcactgagc gtgggcttcc  12060
aggcgtttat tggccaggaa tggcgattga gccacccgca tggtttatcg tctcccatta  12120
tcatggatgc cacggtcgat cagcaaaatg gttatcgctt cgtgtacagc ctgccgctct  12180
cgccgaccag attgttaatt gaagacacgc actatattga taatgcgaca ttagatcctg  12240
aatgcgcgcg gcaaaatatt tgcgactatg ccgcgcaaca gggttggcag cttcagacac  12300
tgctgcgaga agaacagggc gccttaccca ttactctgtc gggcaatgcc gacgcattct  12360
ggcagcagcg ccccctggcc tgtagtggat tacgtgccgg tctgttccat cctaccaccg  12420
gctattcact gccgctggcg gttgccgtgg ccgaccgcct gagtgcactt gatgtcttta  12480
cgtcggcctc aattcaccat gccattacgc attttgcccg cgagcgctgg cagcagcagg  12540
gctttttccg catgctgaat cgcatgctgt tttagccgg acccgccgat tcacgctggc  12600
gggttatgca gcgtttttat ggtttacctg aagatttaat tgcccgtttt tatgcgggaa  12660
aactcacgct gaccgatcgg ctacgtattc tgagcggcaa gccgcctgtt ccggtattag  12720
cagcattgca agccattatg acgactcatc gttaactgca ggcatgagta ctgtgtggaa  12780
ttgtgagcgg ataacaattt cacacaggaa acagaccatg gaattcgagc tcatgaagca  12840
actcaccatt ctgggctcga ccggctcgat tggttgcagc acgctggacg tggtgcgcca  12900
taatcccgaa cacttccgcg tagttgcgct ggtggcaggc aaaaatgtca ctcgcatggt  12960
agaacagtgc ctggaattct ctccccgcta tgccgtaatg gacgatgaag cgagtgcgaa  13020
acttcttaaa acgatgctac agcaacaggg tagccgcacc gaagtcttaa gtgggcaaca  13080
agccgcttgc gatatggcag cgcttgagga tgttgatcag gtgatggcag ccattgttgg  13140
cgctgctggg ctgttaccta cgcttgctgc gatccgcgcg ggtaaaacca ttttgctggc  13200
caataaagaa tcactggtta cctgcggacg tctgtttatg gacgccgtaa agcagagcaa  13260
agcgcaattg ttaccggtcg atagcgaaca taacgccatt tttcagagtt taccgcaacc  13320
```

```
tatccagcat aatctgggat acgctgacct tgagcaaaat ggcgtggtgt ccattttact  13380

taccgggtct ggtggccctt tccgtgagac gccattgcgc gatttggcaa caatgacgcc  13440

ggatcaagcc tgccgtcatc cgaactggtc gatggggcgt aaaatttctg tcgattcggc  13500

taccatgatg aacaaaggtc tggaatacat tgaagcgcgt tggctgttta acgccagcgc  13560

cagccagatg gaagtgctga ttcacccgca gtcagtgatt cactcaatgg tgcgctatca  13620

ggacggcagt gttctggcgc agctggggga accggatatg cgtacgccaa ttgcccacac  13680

catggcatgg ccgaatcgcg tgaactctgg cgtgaagccg ctcgattttt gcaaactaag  13740

tgcgttgaca tttgccgcac cggattatga tcgttatcca tgcctgaaac tggcgatgga  13800

ggcgttcgaa caaggccagg cagcgacgac agcattgaat gccgcaaacg aaatcaccgt  13860

tgctgctttt cttgcgcaac aaatccgctt tacggatatc gctgcgttga atttatccgt  13920

actggaaaaa atggatatgc gcgaaccaca atgtgtggac gatgtgttat ctgttgatgc  13980

gaacgcgcgt gaagtcgcca gaaaagaggt gatgcgtctc gcaagctgat ctag        14034
```

<210> SEQ ID NO 96
<211> LENGTH: 3355
<212> TYPE: DNA
<213> ORGANISM: Artificial Sequence
<220> FEATURE:
<223> OTHER INFORMATION: pEGFP

<400> SEQUENCE: 96

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagcttg    240

catgcctgca ggtcgactct agaggatccc cgggtaccgg tcgccaccat ggtgagcaag    300

ggcgaggagc tgttcaccgg ggtggtgccc atcctggtcg agctggacgg cgacgtaaac    360

ggccacaagt tcagcgtgtc cggcgagggc gagggcgatg ccacctacgg caagctgacc    420

ctgaagttca tctgcaccac cggcaagctg cccgtgccct ggcccaccct cgtgaccacc    480

ctgacctacg gcgtgcagtg cttcagccgc taccccgacc acatgaagca gcacgacttc    540

ttcaagtccg ccatgcccga aggctacgtc caggagcgca ccatcttctt caaggacgac    600

ggcaactaca agacccgcgc cgaggtgaag ttcgagggcg acaccctggt gaaccgcatc    660

gagctgaagg gcatcgactt caaggaggac ggcaacatcc tggggcacaa gctggagtac    720

aactacaaca gccacaacgt ctatatcatg gccgacaagc agaagaacgg catcaaggtg    780

aacttcaaga tccgccacaa catcgaggac ggcagcgtgc agctcgccga ccactaccag    840

cagaacaccc ccatcggcga cggccccgtg ctgctgcccg acaaccacta cctgagcacc    900

cagtccgccc tgagcaaaga ccccaacgag aagcgcgatc acatggtcct gctggagttc    960

gtgaccgccg ccgggatcac tctcggcatg gacgagctgt acaagtaaag cggccgcgac   1020

tctagaattc caactgagcg ccggtcgcta ccattaccaa cttgtctggt gtcaaaaata   1080

ataggcctac tagtcggccg tacgggccct ttcgtctcgc gcgtttcggt gatgacggtg   1140

aaaacctctg acacatgcag ctcccggaga cggtcacagc ttgtctgtaa gcggatgccg   1200

ggagcagaca agcccgtcag ggcgcgtcag cgggtgttgg cgggtgtcgg ggctggctta   1260

actatgcggc atcagagcag attgtactga gagtgcacca tatgcggtgt gaaataccgc   1320

acagatgcgt aaggagaaaa taccgcatca ggcggcctta agggcctcgt gatacgccta   1380
```

```
tttttatagg ttaatgtcat gataataatg gtttcttaga cgtcaggtgg cacttttcgg   1440

ggaaatgtgc gcggaacccc tatttgttta tttttctaaa tacattcaaa tatgtatccg   1500

ctcatgagac aataaccctg ataaatgctt caataatatt gaaaaaggaa gagtatgagt   1560

attcaacatt tccgtgtcgc ccttattccc ttttttgcgg cattttgcct tcctgttttt   1620

gctcacccag aaacgctggt gaaagtaaaa gatgctgaag atcagttggg tgcacgagtg   1680

ggttacatcg aactggatct caacagcggt aagatccttg agagttttcg ccccgaagaa   1740

cgttttccaa tgatgagcac ttttaaagtt ctgctatgtg gcgcggtatt atcccgtatt   1800

gacgccgggc aagagcaact cggtcgccgc atacactatt ctcagaatga cttggttgag   1860

tactcaccag tcacagaaaa gcatcttacg gatggcatga cagtaagaga attatgcagt   1920

gctgccataa ccatgagtga taacactgcg gccaacttac ttctgacaac gatcggagga   1980

ccgaaggagc taaccgcttt tttgcacaac atgggggatc atgtaactcg ccttgatcgt   2040

tgggaaccgg agctgaatga agccatacca aacgacgagc gtgacaccac gatgcctgta   2100

gcaatggcaa caacgttgcg caaactatta actggcgaac tacttactct agcttcccgg   2160

caacaattaa tagactggat ggaggcggat aaagttgcag gaccacttct gcgctcggcc   2220

cttccggctg gctggtttat tgctgataaa tctggagccg gtgagcgtgg gtctcgcggt   2280

atcattgcag cactggggcc agatggtaag ccctcccgta tcgtagttat ctacacgacg   2340

gggagtcagg caactatgga tgaacgaaat agacagatcg ctgagatagg tgcctcactg   2400

attaagcatt ggtaactgtc agaccaagtt tactcatata tactttagat tgatttaaaa   2460

cttcattttt aatttaaaag gatctaggtg aagatccttt ttgataatct catgaccaaa   2520

atcccttaac gtgagttttc gttccactga gcgtcagacc ccgtagaaaa gatcaaagga   2580

tcttcttgag atcctttttt tctgcgcgta atctgctgct tgcaaacaaa aaaaccaccg   2640

ctaccagcgg tggtttgttt gccggatcaa gagctaccaa ctctttttcc gaaggtaact   2700

ggcttcagca gagcgcagat accaaatact gtccttctag tgtagccgta gttaggccac   2760

cacttcaaga actctgtagc accgcctaca tacctcgctc tgctaatcct gttaccagtg   2820

gctgctgcca gtggcgataa gtcgtgtctt accgggttgg actcaagacg atagttaccg   2880

gataaggcgc agcggtcggg ctgaacgggg ggttcgtgca cacagcccag cttggagcga   2940

acgacctaca ccgaactgag atacctacag cgtgagctat gagaaagcgc cacgcttccc   3000

gaagggagaa aggcggacag gtatccggta agcggcaggg tcggaacagg agagcgcacg   3060

agggagcttc cagggggaaa cgcctggtat ctttatagtc ctgtcgggtt tcgccacctc   3120

tgacttgagc gtcgattttt gtgatgctcg tcaggggggc ggagcctatg gaaaaacgcc   3180

agcaacgcgg cctttttacg gttcctggcc ttttgctggc cttttgctca catgttcttt   3240

cctgcgttat cccctgattc tgtggataac cgtattaccg cctttgagtg agctgatacc   3300

gctcgccgca gccgaacgac cgagcgcagc gagtcagtga gcgaggaagc ggaag        3355
```

<210> SEQ ID NO 97
<211> LENGTH: 4616
<212> TYPE: DNA
<213> ORGANISM: Artificial Sequence
<220> FEATURE:
<223> OTHER INFORMATION: pEGFP-dxr

<400> SEQUENCE: 97

```
ctagtcggcc gtacgggccc tttcgtctcg cgcgtttcgg tgatgacggt gaaaacctct     60
```

-continued

```
gacacatgca gctcccggag acggtcacag cttgtctgta agcggatgcc gggagcagac    120
aagcccgtca gggcgcgtca gcgggtgttg gcgggtgtcg gggctggctt aactatgcgg    180
catcagagca gattgtactg agagtgcacc atatgcggtg tgaaataccg cacagatgcg    240
taaggagaaa ataccgcatc aggcggcctt aagggcctcg tgatacgcct atttttatag    300
gttaatgtca tgataataat ggtttcttag acgtcaggtg gcacttttcg gggaaatgtg    360
cgcggaaccc ctatttgttt atttttctaa atacattcaa atatgtatcc gctcatgaga    420
caataaccct gataaatgct tcaataatat tgaaaaagga agagtatgag tattcaacat    480
ttccgtgtcg cccttattcc cttttttgcg gcattttgcc ttcctgtttt tgctcaccca    540
gaaacgctgg tgaaagtaaa agatgctgaa gatcagttgg gtgcacgagt gggttacatc    600
gaactggatc tcaacagcgg taagatcctt gagagttttc gccccgaaga acgttttcca    660
atgatgagca cttttaaagt tctgctatgt ggcgcggtat tatcccgtat tgacgccggg    720
caagagcaac tcggtcgccg catacactat tctcagaatg acttggttga gtactcacca    780
gtcacagaaa agcatcttac ggatggcatg acagtaagag aattatgcag tgctgccata    840
accatgagtg ataacactgc ggccaactta cttctgacaa cgatcggagg accgaaggag    900
ctaaccgctt ttttgcacaa catgggggat catgtaactc gccttgatcg ttgggaaccg    960
gagctgaatg aagccatacc aaacgacgag cgtgacacca cgatgcctgt agcaatggca   1020
acaacgttgc gcaaactatt aactggcgaa ctacttactc tagcttcccg gcaacaatta   1080
atagactgga tggaggcgga taaagttgca ggaccacttc tgcgctcggc ccttccggct   1140
ggctggttta ttgctgataa atctggagcc ggtgagcgtg ggtctcgcgg tatcattgca   1200
gcactggggc cagatggtaa gccctcccgt atcgtagtta tctacacgac ggggagtcag   1260
gcaactatgg atgaacgaaa tagacagatc gctgagatag gtgcctcact gattaagcat   1320
tggtaactgt cagaccaagt ttactcatat atactttaga ttgatttaaa acttcatttt   1380
taatttaaaa ggatctaggt gaagatcctt tttgataatc tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cccaatacgc   2280
aaaccgcctc tccccgcgcg ttggccgatt cattaatgca gctggcacga caggtttccc   2340
gactggaaag cgggcagtga gcgcaacgca attaatgtga gttagctcac tcattaggca   2400
ccccaggctt tacactttat gcttccggct cgtatgttgt gtggaattgt gagcggataa   2460
```

caatttcaca caggaaacag ctatgaccat gattacgcca agcttgcatg cctgcaggtc 2520
gactctagag gatccccggg taccggtcgc caccatggtg agcaagggcg aggagctgtt 2580
caccggggtg gtgcccatcc tggtcgagct ggacggcgac gtaaacggcc acaagttcag 2640
cgtgtccggc gagggcgagg gcgatgccac ctacggcaag ctgaccctga agttcatctg 2700
caccaccggc aagctgcccg tgccctggcc caccctcgtg accaccctga cctacggcgt 2760
gcagtgcttc agccgctacc ccgaccacat gaagcagcac gacttcttca agtccgccat 2820
gcccgaaggc tacgtccagg agcgcaccat cttcttcaag gacgacggca actacaagac 2880
ccgcgccgag gtgaagttcg agggcgacac cctggtgaac cgcatcgagc tgaagggcat 2940
cgacttcaag gaggacggca acatcctggg gcacaagctg gagtacaact acaacagcca 3000
caacgtctat atcatggccg acaagcagaa gaacggcatc aaggtgaact tcaagatccg 3060
ccacaacatc gaggacggca gcgtgcagct cgccgaccac taccagcaga acacccccat 3120
cggcgacggc cccgtgctgc tgcccgacaa ccactacctg agcacccagt ccgccctgag 3180
caaagacccc aacgagaagc gcgatcacat ggtcctgctg gagttcgtga ccgccgccgg 3240
gatcactctc ggcatggacg agctgtacaa gtaaagcggc cgcgactcta gaattccaac 3300
tgagcgccgg tcgctaccat taccaacttg tctggtgtca aaaataatag gactgtgtgg 3360
aattgtgagc ggataacaat ttcacacagg aaacagacca tggaattcga gctcatgaag 3420
caactcacca ttctgggctc gaccggctcg attggttgca gcacgctgga cgtggtgcgc 3480
cataatcccg aacacttccg cgtagttgcg ctggtggcag gcaaaaatgt cactcgcatg 3540
gtagaacagt gcctggaatt ctctccccgc tatgccgtaa tggacgatga agcgagtgcg 3600
aaacttctta aaacgatgct acagcaacag ggtagccgca ccgaagtctt aagtgggcaa 3660
caagccgctt gcgatatggc agcgcttgag gatgttgatc aggtgatggc agccattgtt 3720
ggcgctgctg ggctgttacc tacgcttgct gcgatccgcg cgggtaaaac cattttgctg 3780
gccaataaag aatcactggt tacctgcgga cgtctgttta tggacgccgt aaagcagagc 3840
aaagcgcaat tgttaccggt cgatagcgaa cataacgcca tttttcagag tttaccgcaa 3900
cctatccagc ataatctggg atacgctgac cttgagcaaa atggcgtggt gtccatttta 3960
cttaccgggt ctggtggccc tttccgtgag acgccattgc gcgatttggc aacaatgacg 4020
ccggatcaag cctgccgtca tccgaactgg tcgatggggc gtaaaatttc tgtcgattcg 4080
gctaccatga tgaacaaagg tctggaatac attgaagcgc gttggctgtt taacgccagc 4140
gccagccaga tggaagtgct gattcacccg cagtcagtga ttcactcaat ggtgcgctat 4200
caggacggca gtgttctggc gcagctgggg gaaccggata tgcgtacgcc aattgcccac 4260
accatggcat ggccgaatcg cgtgaactct ggcgtgaagc cgctcgattt ttgcaaacta 4320
agtgcgttga catttgccgc accggattat gatcgttatc catgcctgaa actggcgatg 4380
gaggcgttcg aacaaggcca ggcagcgacg acagcattga atgccgcaaa cgaaatcacc 4440
gttgctgctt ttcttgcgca acaaatccgc tttacggata tcgctgcgtt gaatttatcc 4500
gtactggaaa aaatggatat gcgcgaacca caatgtgtgg acgatgtgtt atctgttgat 4560
gcgaacgcgc gtgaagtcgc cagaaaagag gtgatgcgtc tcgcaagctg atctag 4616

<210> SEQ ID NO 98
<211> LENGTH: 2230
<212> TYPE: DNA
<213> ORGANISM: Artificial Sequence
<220> FEATURE:

<223> OTHER INFORMATION: pORI19

<400> SEQUENCE: 98

```
ggaggctcaa gggagtatga gggaatgaaa ttccctcatg ggtttgattt taaaaattgc     60
ttgcaatttt gccgagcggt agcgctggaa aatttttgaa aaaaatttgg aatttggaaa    120
aaaatggggg gaaaggaagc gaattttgct tccgtactac gaccccccat taagtgccga    180
gtgccaattt ttgtgccaaa aacgctctat cccaactggc tcaagggttt aaggggtttt    240
tcaatcgcca acgaatcgcc aacgttttcg ccaacgtttt ttataaatct atatttaagt    300
agctttattg ttgtttttat gattacaaag tgatacacta actttataaa attatttgat    360
tggagttttt taaatggtga tttcagaatc gctagttcta gtgcaccata tgcggtgtga    420
aataccgcac agatgcgtaa ggagaaaata ccgcatcagg cgccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattcgagct cggtacccgg ggatcctcta gagtcgacct    660
gcaggcatgc aagcttggcg taatcatggt catagctgtt tcctgtgtga aattgttatc    720
cgctcacaat tccacacaac atacgagccg gaagcataaa gtgtaaagcc tggggtgcct    780
aatgagtgag ctaactcaca ttaattgcgt tgcgctcact gcccgctttc cagtcgggaa    840
acctgtcgtg ccagctgcat taatgaatcg gccaacgcgc ggggagaggc ggtttgcgta    900
ttgggcgctc ttccgcttcc tcgctcactg actcgctgcg ctcggtcgtt cggctgcggc    960
gagcggtatc agctcactca aaggcggtaa tacggttatc cacagaatca ggggataacg   1020
caggaaagaa catggatctc gacccgtgct ataattatac taattttata aggaggaaaa   1080
aatatgggca tttttagtat ttttgtaatc agcacagttc attatcaacc aaacaaaaaa   1140
taagtggtta taatgaatcg ttaataagca aaattcatat aaccaaatta aagagggtta   1200
taatgaacga gaaaaatata aaacacagtc aaaactttat tacttcaaaa cataatatag   1260
ataaaataat gacaaatata agattaaatg aacatgataa tatctttgaa atcggctcag   1320
gaaaaggcca ttttaccctt gaattagtaa agaggtgtaa tttcgtaact gccattgaaa   1380
tagaccataa attatgcaaa actacagaaa ataaacttgt tgatcacgat aatttccaag   1440
ttttaaacaa ggatatattg cagtttaaat ttcctaaaaa ccaatcctat aaaatatatg   1500
gtaatatacc ttataacata agtacggata taatacgcaa aattgttttt gatagtatag   1560
ctaatgagat ttatttaatc gtggaatacg ggtttgctaa aagattatta aatacaaaac   1620
gctcattggc attactttta atggcagaag ttgatatttc tatattaagt atggttccaa   1680
gagaatattt tcatcctaaa cctaaagtga atagctcact tatcagatta agtagaaaaa   1740
aatcaagaat atcacacaaa gataaacaaa agtataatta tttcgttatg aaatgggtta   1800
acaaagaata caagaaaata tttacaaaaa atcaatttaa caattcctta aaacatgcag   1860
gaattgacga tttaaacaat attagctttg aacaattctt atctcttttc aatagctata   1920
aattatttaa taagtaagtt aagggatgca taaactgcat cccttaactt gtttttcgtg   1980
tgcctatttt ttgtgaatcg ggtcgaggcc tcggactagc gatttttat taaaacgtct    2040
caaaatcgtt tctgagacgt tttagcgttt atttcgttta gttatcggca taatcgttaa   2100
aacaggcgtt atcgtagcgt aaaagccctt gagcgtagcg tggctttgca gcgaagatgt   2160
tgtctgttag attatgaaag ccgatgactg aatgaaataa taagcgcagc gcccttctat   2220
ttcggttgga                                                          2230
```

<210> SEQ ID NO 99
<211> LENGTH: 4215
<212> TYPE: DNA
<213> ORGANISM: Artificial Sequence
<220> FEATURE:
<223> OTHER INFORMATION: pORI19-mvaA

<400> SEQUENCE: 99
ggaggctcaa gggagtatga gggaatgaaa ttccctcatg ggtttgattt taaaaattgc 60
ttgcaatttt gccgagcggt agcgctggaa aatttttgaa aaaaatttgg aatttggaaa 120
aaaatggggg gaaaggaagc gaattttgct tccgtactac gaccccccat taagtgccga 180
gtgccaattt ttgtgccaaa aacgctctat cccaactggc tcaagggttt aaggggtttt 240
tcaatcgcca acgaatcgcc aacgttttcg ccaacgtttt ttataaatct atatttaagt 300
agctttattg ttgtttttat gattacaaag tgatacacta actttataaa attatttgat 360
tggagttttt taaatggtga tttcagaatc gctagttcta gtgcaccata tgcggtgtga 420
aataccgcac agatgcgtaa ggagaaaata ccgcatcagg cgccattcgc cattcaggct 480
gcgcaactgt tgggaagggc gatcggtgcg ggcctcttcg ctattacgcc agctggcgaa 540
agggggatgt gctgcaaggc gattaagttg ggtaacgcca gggttttccc agtcacgacg 600
ttgtaaaacg acggccagtg aattcgagct cggtaccagc ttcaaccatt aatgaagttt 660
gtggttcagg gatgaaggca gtaattctag ctaagcaact tttacagttg ggcgaagcag 720
aagttgttat tgctggtgga acggaatcaa tgtctaatgc gcctattctt aaaaatcgta 780
aaactgaaga agaaacatta agcatgttaa gtgacggctt aattgatgct ttttctggca 840
tttcaatggg aattattgga gaaacaattg cggagcagtt tgatgttagt cgtgctgacc 900
aagacctatt cgcacaaaat tctcaagaga aggcagtagc agccagtcaa gcaggaattt 960
ttaatgacga gatcgtagct cttgggaaac ttactgttga tgaaactcct cgaccttcat 1020
ctagcctaga aaaattggct acattacgga cagcctttaa ggaaaatgga acagttacag 1080
ctgggaattc ttcaccagtt aatgacggag cttctgcttt aattttggcc actaaagagt 1140
atgctgaaaa acatggaatt tcttatttag ctgaattagt tgagagtgcg gaagttggta 1200
ttgaccctgc aattatggga gtatcaccga ttgatgcaat tcaaaaatta gttcaacgct 1260
caggcgttca gctttcagaa atagatcttt ttgaaattaa tgaggccttt gctgcatcaa 1320
gtattgctgt taatcgtgaa ttgggcttaa aagattctca agttaatatt tatggaggag 1380
cgattgctct tggacatgct attgggtcaa gtggtgccaa aatcctgaca actttgggat 1440
atgctttgaa acgagaacaa aagcgttatg gaattgctag tctttgtatt ggcggtggtc 1500
tagggcttgc tattttattg aaaaatcctg acttttaaaa attgatggag gaattgccca 1560
gtatttctgg gcatttttgg gaaatatgag aaaaaaattt taactaaaaa atttgagaaa 1620
ataatagcct gtcaagattt tttcttgaca gcatgaaatt agtctgctat aatattaaat 1680
ataataaaaa agaaatagga aatataaaat gtctgtaaaa attcgtttga ctcgtatggg 1740
ttctaagaaa aaacctttct accgtattaa tgttgctgat tcacgtgcac cacgtgatgg 1800
taaattcatc gaaacagttg gaacttacaa tccacttgta actgaaaacc aagtaactct 1860
taaagaagaa cgcgtattgg aatggttgag caacggagca caaccttcag atacagttcg 1920
taacctcctt tcaaaagcgg gcgttatgaa aaaattccac gaatcaaaac tttctaaata 1980
atttttgaga taagctgctt tttagcagct tttcgtgaat ataaaaatca cataaaatgg 2040

-continued

```
acttgaataa ctttcaagtt agagtagagg taagaaatgc aaaaagatgt gaaagaactc   2100
gttttaacta ttgtaaaacc tttggtgact cagcctgatg aagtttcttt ggaaattatt   2160
gaaggtgagg agtttatgga ataccatctc aaagttgctg acggagatat tggaagaata   2220
attggacgtc aaggtcgaat tattcaagcc attcgtacag ttgtatactt tgttcctgtt   2280
gaagggaaaa aagttcgact cctcgtggac caataataag taaaaataaa agaactcatc   2340
attgatgagt tcttttattt ttggaaaacg gaacgttctt ttgagaaata aaatagttat   2400
ttagaatttc cttttattgt ccccaaaaat atgctagaat gaaaaaatat tgattaataa   2460
ttgtagaaat aatcagtgat aaatataaat taactgattt ttatataggt ggataatgga   2520
taagaaaaaa ggaatcttat tagtagcttt agggacgcct cgttcttgtg agacagagga   2580
tgtaagggaa tatttaaaag aatttttggg tgatccactc gtcattcatc ctctagagtc   2640
gacctgcagg catgcaagct tggcgtaatc atggtcatag ctgtttcctg tgtgaaattg   2700
ttatccgctc acaattccac acaacatacg agccggaagc ataaagtgta aagcctgggg   2760
tgcctaatga gtgagctaac tcacattaat tgcgttgcgc tcactgcccg ctttccagtc   2820
gggaaacctg tcgtgccagc tgcattaatg aatcggccaa cgcgcgggga gaggcggttt   2880
gcgtattggg cgctcttccg cttcctcgct cactgactcg ctgcgctcgg tcgttcggct   2940
gcggcgagcg gtatcagctc actcaaaggc ggtaatacgg ttatccacag aatcagggga   3000
taacgcagga aagaacatgg atctcgaccc gtgctataat tatactaatt ttataaggag   3060
gaaaaaatat gggcattttt agtatttttg taatcagcac agttcattat caaccaaaca   3120
aaaaataagt ggttataatg aatcgttaat aagcaaaatt catataacca aattaaagag   3180
ggttataatg aacgagaaaa atataaaaca cagtcaaaac tttattactt caaaacataa   3240
tatagataaa ataatgacaa atataagatt aaatgaacat gataatatct ttgaaatcgg   3300
ctcaggaaaa ggccatttta cccttgaatt agtaaagagg tgtaatttcg taactgccat   3360
tgaaatagac cataaattat gcaaaactac agaaaataaa cttgttgatc acgataattt   3420
ccaagtttta aacaaggata tattgcagtt taaatttcct aaaaaccaat cctataaaat   3480
atatggtaat ataccttata acataagtac ggatataata cgcaaaattg tttttgatag   3540
tatagctaat gagatttatt taatcgtgga atacgggttt gctaaaagat tattaaatac   3600
aaaacgctca ttggcattac ttttaatggc agaagttgat atttctatat taagtatggt   3660
tccaagagaa tattttcatc ctaaacctaa agtgaatagc tcacttatca gattaagtag   3720
aaaaaaatca agaatatcac acaaagataa acaaaagtat aattatttcg ttatgaaatg   3780
ggttaacaaa gaatacaaga aaatatttac aaaaaatcaa tttaacaatt ccttaaaaca   3840
tgcaggaatt gacgatttaa acaatattag ctttgaacaa ttcttatctc ttttcaatag   3900
ctataaatta tttaataagt aagttaaggg atgcataaac tgcatccctt aacttgtttt   3960
tcgtgtgcct attttttgtg aatcgggtcg aggcctcgga ctagcgattt tttattaaaa   4020
cgtctcaaaa tcgtttctga gacgttttag cgtttatttc gtttagttat cggcataatc   4080
gttaaaacag gcgttatcgt agcgtaaaag cccttgagcg tagcgtggct ttgcagcgaa   4140
gatgttgtct gttagattat gaaagccgat gactgaatga aataataagc gcagcgccct   4200
tctatttcgg ttgga                                                    4215
```

<210> SEQ ID NO 100
<211> LENGTH: 5790
<212> TYPE: DNA
<213> ORGANISM: Artificial Sequence
<220> FEATURE:
<223> OTHER INFORMATION: pCI372

<400> SEQUENCE: 100

```
gtaaatcgct ccttttagg tggcacaaat gtgaggcatt ttcgctcttt ccggcgaggc     60
tagttaccct taagttattg gtatgactgg ttttaagcgc aaaaaaagtt gctttttcgt    120
acctattaat gtatcgttag aaaaccgact gtaaaaagta cagtcggcat tatctcatat    180
tataaaagcc agtcattagg cctatctgac aattcctgaa tagagttcat aaacaatcct    240
gcatgataac catcacaaac agaatgatgt acctgtaaag atagcggtaa atatattgaa    300
ttacctttat taatgaattt tcctgctgta ataatgggta gaaggtaatt actattatta    360
ttgatattta agttaaaccc agtaaatgaa gtccatggaa taatagaaag agaaaaagca    420
ttttcaggta taggtgtttt gggaaacaat ttccccgaac cattatattt ctctacatca    480
gaaaggtata aatcataaaa ctctttgaag tcattcttta caggagtcca aataccagag    540
aatgttttag atacaccatc aaaaattgta taaagtggct ctaacttatc ccaataacct    600
aactctccgt cgctattgta accagttcta aaagctgtat ttgagtttat caccccttgtc   660
actaagaaaa taaatgcagg gtaaaattta tatccttctt gttttatgtt tcggtataaa    720
acactaatat caatttctgt ggttatacta aaagtcgttt gttggttcaa ataatgatta    780
aatatctctt ttctcttcca attgtctaaa tcaattttat taaagttcat ttgatatgcc    840
tcctaaattt ttatcttgct cttttgtcag agaaatcata actctttttt tcgattctga    900
aatcaccatt taaaaaactc caatcaaata attttataaa attagtgtat cactttgtaa    960
tcataaaaac aacaataaag ctacttaaat atagatttat aaaaaacgtt ggcgaaaacg   1020
ttggcgattc gttggcgatt gaaaaacccc tcaaaccctt gagccagttg ggatagagcg   1080
tttttggcac aaaaattggc actcggcact taatgggggg tcgtagtacg gaagcaaaat   1140
tcgcttcctt tccccccatt tttttccaaa ttccaaattt ttttcaaaaa ttttccagcg   1200
ctaccgctcg gcaaaattgc aagcaatttt taaaatcaaa cccatgaggg aatttcattc   1260
cctcaaactc ccttgagcct cctccaaccg aaatagaagg acgctgcgct tattatttca   1320
ttcagtcatc ggctttcata atctaacaga caacatcttc gctgcaaagc cacgctacgc   1380
tcaagggctt ttacgctacg ataacgcctg ttttaacgat tatgccgata actaaacgaa   1440
ataaacgcta aaacgtctca gaaacgattt tgagacgttt taataaaaaa tcgacttcgt   1500
tctttttta cctctcggtt atgagttagt tcaaattcgt tctttttagg ttctaaatcg    1560
tgtttttctt ggaattgtgc tgttttatcc tttaccttgt ctacaaaccc cttaaaaacg   1620
tttttaaagg cttttaagcc gtctgtacgt tccttaagga attcgagctc ggtacccggg   1680
gatcctctag agtcgacctg cagcaatggc aacaacgttg cgcaaactat taactggcga   1740
actacttact ctagcttccc ggcaacaatt aatagactgg atggaggcgg ataaagttgc   1800
aggaccactt ctgcgctcgg cccttccggc tggctggttt attgctgata aatctggagc   1860
cggtgagcgt gggtctcgcg gtatcattgc agcactgggg ccagatggta agccctcccg   1920
tatcgtagtt atctacacga cggggagtca ggcaactatg gatgaacgaa atagacagat   1980
cgctgagata ggtgcctcac tgattaagca ttggtaactg tcagaccaag tttactcata   2040
tatactttag attgatttaa aacttcattt ttaatttaaa aggatctagg tgaagatcct   2100
ttttgataat ctcatgacca aaatccctta acgtgagttt tcgttccact gagcgtcaga   2160
ccccgtagaa aagatcaaag gatcttcttg agatcctttt tttctgcgcg taatctgctg   2220
```

-continued

```
cttgcaaaca aaaaaaccac cgctaccagc ggtggtttgt ttgccggatc aagagctacc   2280
aactcttttt ccgaaggtaa ctggcttcag cagagcgcag ataccaaata ctgtccttct   2340
agtgtagccg tagttaggcc accacttcaa gaactctgta gcaccgccta catacctcgc   2400
tctgctaatc ctgttaccag tggctgctgc cagtggcgat aagtcgtgtc ttaccgggtt   2460
ggactcaaga cgatagttac cggataaggc gcagcggtcg ggctgaacgg ggggttcgtg   2520
cacacagccc agcttggagc gaacgaccta caccgaactg agatacctac agcgtgagct   2580
atgagaaagc gccacgcttc ccgaagggag aaaggcggac aggtatccgg taagcggcag   2640
ggtcggaaca ggagagcgca cgagggagct tccaggggga aacgcctggt atctttatag   2700
tcctgtcggg tttcgccacc tctgacttga gcgtcgattt ttgtgatgct cgtcaggggg   2760
gcggagccta tggaaaaacg ccagcaacgc ggccttttta cggttcctgg ccttttgctg   2820
gccttttgct cacatgttct ttcctgcgtt atcccctgat tctgtggata accgtattac   2880
cgcctttgag tgagctgata ccgctcgccg cagccgaacg accgagcgca gcgagtcagt   2940
gagcgaggaa gcggaagagc gcctgatgcg gtattttctc cttacgcatc tgtgcggtat   3000
ttcacaccgc atatggtgca ctctcagtac aatctgctct gatgccgcat agttaagcca   3060
gtatacactc cgctatcgct acgtgactgg gtcatggctg cgccccgaca cccgccaaca   3120
cccgctgacg cgccctgacg ggcttgtctg ctcccggcat ccgcttacag acaagctgtg   3180
accgtctccg ggagctgcat gtgtcagagg ttttcaccgt catcaccgaa acgcgcgagg   3240
cagatctttt gcccatttta tttttataaa atgggcaggt ggcgtttgtg taaagcaaat   3300
cgacacaatc caaaggggat aaaaggggaa agtgaaactt ccccctttc aagccacatt   3360
gtaatacaag aacgaagtgt tttgtattac aatgtgatag cttgcagtat ttatggtttt   3420
atatggtcta ttttgttgtg aggattgtaa ccgaataggg cgcaatgctt attacaaaat   3480
caatgacaaa gggcgattga ggaatgagcg ctgaggcatt ttatctttga gtaagttatt   3540
gatggatcag aaaaatgtat cacaaattga aacaaagact cactcattta agagaagcta   3600
ctatcatgaa attttgttgt tgtgataagc aacttctaat acacgatttt tagccattac   3660
atcactcgtt tttagagtga tgtgtaagtg cgcattgcac tcttttttta cgaaacaagc   3720
cgaccagcgt ttgaaacttt ttagtttttc atcattctat tttaaaacgt tctaaaactc   3780
gatttaagcg actttaattc gaaactgtct atttgttcaa agggagcatt aagaatgctt   3840
aaacgagctt ttaagggggt ttaaattgat tttgaattga atagcttgtt gtaagttgta   3900
aaaaaaacaa gttaaacaaa gtatcagttt tccatttaag ggttgttagg gcttgccctg   3960
accgtctgta agacgcttga ttgcatgata tgagtattta gctagtcaaa cagttaaaac   4020
agcttatatg agcaattaga gggaatccaa taaattccta aaagcggttt tgatcttttc   4080
ttttagcgag tgaacgctgc aagtaaaatg tgagcgttca ctcgctcact cctttttttg   4140
atgactttga cctttggttt taaatttttg aaaaaaataa aaaataggcg aagcctatta   4200
tatatttatc ttatatattt taatctttta ttcttttgcg tcaaaaaaaa tcaatatttt   4260
caaggcttta tagaattata taccaacaaa aaactgtgta tataccaaca aaaaactgtg   4320
catacaccaa caaaaaactg tgcatatacc aacttctttg tttgtttcgt tggtatataa   4380
tgatataata aaagcatgaa gaatctctct acgaaaagtg tttcttcatg cttatctaaa   4440
ctcactcaca aaggagcagt tttctatgtc tagtatatca aaaaatgaac ctaatcaaaa   4500
gcaggtgcaa accttgaacg aattgtcaaa acgaaaagta gtggaacata attctttaat   4560
taccagtatt gcgaaaatgg ataaaacgcc actgaaaatg tttgaattag ccgtgtcttg   4620
```

-continued tattaatacc gaagaaccac ccaaagatca tacggtttat ctctcaaaag aagaattgtt 4680
tgcctttttt aaggtatctg ataatgacaa acatagtcgt tttaaacaag cagtagagaa 4740
tatgcaaaaa caagcctttt ttcaaattaa agaagaagta ggtaaaggat ttaaatttag 4800
gagtattgtt cccattccat atgtcgagtg gacagattat catgatgacg taaaaattga 4860
atttcatcgt gaaatcatgc cctacttaat taatctaaaa caaaatttca cgcaacatgc 4920
tttgtctgat attgcagagc tgaatagcaa atactctatt atcttgtacc gttggttatc 4980
catgaattat aaccaatacg agcattatag ttataagggc ggacggagag aagaacaagt 5040
ggaagcctac cgcaatccta ccatttcaat gcgagaatta cgagaaatga cggatacagt 5100
tgatgaatac ccccgctttg atagattaga acatagagtt ttaaaagaac caatagaaga 5160
aattaacgaa aacacctctt ttaacgtgac gtatgacaag ataaaaaaag gacgaagcat 5220
tgattctatt gtctttcata tcacgaaaaa acgtcgagca gatgataaca gctacaagtt 5280
agaagataaa gattatcaat ccgacaaaga ggaaaaatca agaaatgaag ctgacttatt 5340
aaaacaggca atggaaagca agtacacacg attattgatt gaaaactttc tcttatcccc 5400
tcttgaaatg acggacacgg cacttatggc aggtttgcaa aagaacgtct atccgttgta 5460
tgacgagtta aaggaattaa gaggattgaa tggggtcaaa gaccacttgt cttatatatc 5520
tagcaaaaaa gaagcctatt ctaaacgcaa tgtagcgaag tatctgaaaa aagcaatcga 5580
gcaatatcta cctacggtta aaaggcagga cttaaaccat gagtgagaac ttaaaaacga 5640
ttaaagagtt ggctgatgag ttgggcgtat caaaaaagaa aattcattat caagtatcta 5700
aattagatag tgatttgata caaaaattag acggcactat atatctagct gatttcactt 5760
tttgcattct acaaactgca taactcatat 5790

<210> SEQ ID NO 101
<211> LENGTH: 6350
<212> TYPE: DNA
<213> ORGANISM: Artificial Sequence
<220> FEATURE:
<223> OTHER INFORMATION: pCIN

<400> SEQUENCE: 101
gtaaatcgct cctttttagg tggcacaaat gtgaggcatt ttcgctcttt ccggcgaggc 60
tagttaccct taagttattg gtatgactgg ttttaagcgc aaaaaaagtt gctttttcgt 120
acctattaat gtatcgttag aaaaccgact gtaaaaagta cagtcggcat tatctcatat 180
tataaaagcc agtcattagg cctatctgac aattcctgaa tagagttcat aaacaatcct 240
gcatgataac catcacaaac agaatgatgt acctgtaaag atagcggtaa atatattgaa 300
ttacctttat taatgaattt tcctgctgta ataatgggta gaaggtaatt actattatta 360
ttgatattta agttaaaccc agtaaatgaa gtccatggaa taatagaaag agaaaaagca 420
ttttcaggta taggtgtttt gggaaacaat ttccccgaac cattatattt ctctacatca 480
gaaaggtata aatcataaaa ctctttgaag tcattcttta caggagtcca aataccagag 540
aatgttttag atacaccatc aaaaattgta taaagtggct ctaacttatc ccaataacct 600
aactctccgt cgctattgta accagttcta aaagctgtat ttgagtttat cacccttgtc 660
actaagaaaa taaatgcagg gtaaaattta tatccttctt gttttatgtt tcggtataaa 720
acactaatat caatttctgt ggttatacta aaagtcgttt gttggttcaa ataatgatta 780
aatatctctt ttctcttcca attgtctaaa tcaattttat taaagttcat ttgatatgcc 840

-continued

```
tcctaaattt ttatcttgct cttttgtcag agaaatcata actctttttt tcgattctga    900
aatcaccatt taaaaaactc caatcaaata attttataaa attagtgtat cactttgtaa    960
tcataaaaac aacaataaag ctacttaaat atagatttat aaaaaacgtt ggcgaaaacg   1020
ttggcgattc gttggcgatt gaaaaacccc tcaaaccctt gagccagttg ggatagagcg   1080
tttttggcac aaaaattggc actcggcact taatgggggg tcgtagtacg gaagcaaaat   1140
tcgcttcctt tccccccatt tttttccaaa ttccaaattt ttttcaaaaa ttttccagcg   1200
ctaccgctcg gcaaaattgc aagcaatttt taaaatcaaa cccatgaggg aatttcattc   1260
cctcaaactc ccttgagcct cctccaaccg aaatagaagg acgctgcgct tattatttca   1320
ttcagtcatc ggctttcata atctaacaga caacatcttc gctgcaaagc cacgctacgc   1380
tcaagggctt ttacgctacg ataacgcctg ttttaacgat tatgccgata actaaacgaa   1440
ataaacgcta aaacgtctca gaaacgattt tgagacgttt taataaaaaa tcgacttcgt   1500
tctttttta cctctcggtt atgagttagt tcaaattcgt tctttttagg ttctaaatcg   1560
tgtttttctt ggaattgtgc tgttttatcc tttaccttgt ctacaaaccc cttaaaaacg   1620
tttttaaagg cttttaagcc gtctgtacgt tccttaaggg ctagcataga ttagtttatt   1680
cttgacacta caagctaaat gtggtataat cccatagagt gtggaattgt gagcggataa   1740
caatttcaca caggaaacag accatggaat tcgagctcgg tacccgggga tcctctagag   1800
tcgacctgca ggcatgcaag cttggctgtt ttggcggatg agagaagatt ttcagcctga   1860
tacagattaa atcagaacgc agaagcggtc tgataaaaca gaatttgcct ggcggcagta   1920
gcgcggtggt cccacctgac cccatgccga actcagaagt gaaacgccgt agcgccgatg   1980
gtagtgtggg gtctccccat gcgagagtag ggaactgcca ggcatcaaat aaaacgaaag   2040
gctcagtcga aagactgggc ctttcgtttt atctgttgtt tgtcggtgaa cgctctcctg   2100
agtaggacaa atccgccggg agcggatttg aacgttgcga agcaacggcc cggagggtgg   2160
cgggcaggac gcccgccata aactgccagg catcaaatta agcagaaggc catcctgacg   2220
gatggccttt ttgcgtttct acaaactctt accggtcctg cagcaatggc aacaacgttg   2280
cgcaaactat taactggcga actacttact ctagcttccc ggcaacaatt aatagactgg   2340
atggaggcgg ataaagttgc aggaccactt ctgcgctcgg cccttccggc tggctggttt   2400
attgctgata aatctggagc cggtgagcgt gggtctcgcg gtatcattgc agcactgggg   2460
ccagatggta agccctcccg tatcgtagtt atctacacga cggggagtca ggcaactatg   2520
gatgaacgaa atagacagat cgctgagata ggtgcctcac tgattaagca ttggtaactg   2580
tcagaccaag tttactcata tatactttag attgatttaa aacttcattt ttaatttaaa   2640
aggatctagg tgaagatcct ttttgataat ctcatgacca aaatccctta acgtgagttt   2700
tcgttccact gagcgtcaga ccccgtagaa aagatcaaag gatcttcttg agatcctttt   2760
tttctgcgcg taatctgctg cttgcaaaca aaaaaaccac cgctaccagc ggtggtttgt   2820
ttgccggatc aagagctacc aactcttttt ccgaaggtaa ctggcttcag cagagcgcag   2880
ataccaaata ctgtccttct agtgtagccg tagttaggcc accacttcaa gaactctgta   2940
gcaccgccta catacctcgc tctgctaatc ctgttaccag tggctgctgc cagtggcgat   3000
aagtcgtgtc ttaccgggtt ggactcaaga cgatagttac cggataaggc gcagcggtcg   3060
ggctgaacgg ggggttcgtg cacacagccc agcttggagc gaacgaccta caccgaactg   3120
agatacctac agcgtgagct atgagaaagc gccacgcttc ccgaagggag aaaggcggac   3180
aggtatccgg taagcggcag ggtcggaaca ggagagcgca cgagggagct tccaggggga   3240
```

-continued

```
aacgcctggt atctttatag tcctgtcggg tttcgccacc tctgacttga gcgtcgattt   3300
ttgtgatgct cgtcaggggg gcggagccta tggaaaaacg ccagcaacgc ggccttttta   3360
cggttcctgg ccttttgctg gccttttgct cacatgttct ttcctgcgtt atcccctgat   3420
tctgtggata accgtattac cgcctttgag tgagctgata ccgctcgccg cagccgaacg   3480
accgagcgca gcgagtcagt gagcgaggaa gcggaagagc gcctgatgcg gtattttctc   3540
cttacgcatc tgtgcggtat ttcacaccgc atatggtgca ctctcagtac aatctgctct   3600
gatgccgcat agttaagcca gtatacactc cgctatcgct acgtgactgg gtcatggctg   3660
cgccccgaca cccgccaaca cccgctgacg cgccctgacg ggcttgtctg ctcccggcat   3720
ccgcttacag acaagctgtg accgtctccg ggagctgcat gtgtcagagg ttttcaccgt   3780
catcaccgaa acgcgcgagg cagatctttt gcccatttta tttttataaa atgggcaggt   3840
ggcgtttgtg taaagcaaat cgacacaatc caaaggggat aaaaggggaa agtgaaactt   3900
ccccctttc aagccacatt gtaatacaag aacgaagtgt tttgtattac aatgtgatag   3960
cttgcagtat ttatggtttt atatggtcta ttttgttgtg aggattgtaa ccgaataggg   4020
cgcaatgctt attacaaaat caatgacaaa gggcgattga ggaatgagcg ctgaggcatt   4080
ttatctttga gtaagttatt gatggatcag aaaaatgtat cacaaattga aacaaagact   4140
cactcattta agagaagcta ctatcatgaa attttgttgt tgtgataagc aacttctaat   4200
acacgatttt tagccattac atcactcgtt tttagagtga tgtgtaagtg cgcattgcac   4260
tcttttttta cgaaacaagc cgaccagcgt ttgaaacttt ttagtttttc atcattctat   4320
tttaaaacgt tctaaaactc gatttaagcg actttaattc gaaactgtct atttgttcaa   4380
agggagcatt aagaatgctt aaacgagctt ttaagggggt ttaaattgat tttgaattga   4440
atagcttgtt gtaagttgta aaaaaaacaa gttaaacaaa gtatcagttt tccatttaag   4500
ggttgttagg gcttgccctg accgtctgta agacgcttga ttgcatgata tgagtattta   4560
gctagtcaaa cagttaaaac agcttatatg agcaattaga gggaatccaa taaattccta   4620
aaagcggttt tgatcttttc ttttagcgag tgaacgctgc aagtaaaatg tgagcgttca   4680
ctcgctcact cctttttttg atgactttga cctttggttt taaatttttg aaaaaaataa   4740
aaaataggcg aagcctatta tatatttatc ttatatattt taatctttta ttcttttgcg   4800
tcaaaaaaaa tcaatatttt caaggcttta tagaattata taccaacaaa aaactgtgta   4860
tataccaaca aaaaactgtg catacaccaa caaaaaactg tgcatatacc aacttctttg   4920
tttgtttcgt tggtatataa tgatataata aaagcatgaa gaatctctct acgaaaagtg   4980
tttcttcatg cttatctaaa ctcactcaca aaggagcagt tttctatgtc tagtatatca   5040
aaaaatgaac ctaatcaaaa gcaggtgcaa accttgaacg aattgtcaaa acgaaaagta   5100
gtggaacata attctttaat taccagtatt gcgaaaatgg ataaaacgcc actgaaaatg   5160
tttgaattag ccgtgtcttg tattaatacc gaagaaccac ccaaagatca tacggtttat   5220
ctctcaaaag aagaattgtt tgcctttttt aaggtatctg ataatgacaa acatagtcgt   5280
tttaaacaag cagtagagaa tatgcaaaaa caagcctttt ttcaaattaa agaagaagta   5340
ggtaaaggat ttaaatttag gagtattgtt cccattccat atgtcgagtg gacagattat   5400
catgatgacg taaaaattga atttcatcgt gaaatcatgc cctacttaat taatctaaaa   5460
caaaatttca cgcaacatgc tttgtctgat attgcagagc tgaatagcaa atactctatt   5520
atcttgtacc gttggttatc catgaattat aaccaatacg agcattatag ttataagggc   5580
```

ggacggagag aagaacaagt ggaagcctac cgcaatccta ccatttcaat gcgagaatta 5640
cgagaaatga cggatacagt tgatgaatac ccccgctttg atagattaga acatagagtt 5700
ttaaaagaac caatagaaga aattaacgaa aacacctctt ttaacgtgac gtatgacaag 5760
ataaaaaaag gacgaagcat tgattctatt gtctttcata tcacgaaaaa acgtcgagca 5820
gatgataaca gctacaagtt agaagataaa gattatcaat ccgacaaaga ggaaaaatca 5880
agaaatgaag ctgacttatt aaaacaggca atggaaagca agtacacacg attattgatt 5940
gaaaactttc tcttatcccc tcttgaaatg acggacacgg cacttatggc aggtttgcaa 6000
aagaacgtct atccgttgta tgacgagtta aaggaattaa gaggattgaa tggggtcaaa 6060
gaccacttgt cttatatatc tagcaaaaaa gaagcctatt ctaaacgcaa tgtagcgaag 6120
tatctgaaaa aagcaatcga gcaatatcta cctacggtta aaaggcagga cttaaaccat 6180
gagtgagaac ttaaaaacga ttaaagagtt ggctgatgag ttgggcgtat caaaaaagaa 6240
aattcattat caagtatcta aattagatag tgatttgata caaaaattag acggcactat 6300
atatctagct gatttcactt tttgcattct acaaactgca taactcatat 6350

<210> SEQ ID NO 102
<211> LENGTH: 7597
<212> TYPE: DNA
<213> ORGANISM: Artificial Sequence
<220> FEATURE:
<223> OTHER INFORMATION: pCIN-mvaA

<400> SEQUENCE: 102
gtaaatcgct cctttttagg tggcacaaat gtgaggcatt ttcgctcttt ccggcgaggc 60
tagttaccct taagttattg gtatgactgg ttttaagcgc aaaaaaagtt gctttttcgt 120
acctattaat gtatcgttag aaaaccgact gtaaaaagta cagtcggcat tatctcatat 180
tataaaagcc agtcattagg cctatctgac aattcctgaa tagagttcat aaacaatcct 240
gcatgataac catcacaaac agaatgatgt acctgtaaag atagcggtaa atatattgaa 300
ttacctttat taatgaattt tcctgctgta ataatgggta gaaggtaatt actattatta 360
ttgatattta agttaaaccc agtaaatgaa gtccatggaa taatagaaag agaaaaagca 420
ttttcaggta taggtgtttt gggaaacaat ttccccgaac cattatattt ctctacatca 480
gaaaggtata aatcataaaa ctctttgaag tcattcttta caggagtcca aataccagag 540
aatgttttag atacaccatc aaaaattgta taaagtggct ctaacttatc ccaataacct 600
aactctccgt cgctattgta accagttcta aaagctgtat ttgagtttat cacccttgtc 660
actaagaaaa taaatgcagg gtaaaattta tatccttctt gttttatgtt tcggtataaa 720
acactaatat caatttctgt ggttatacta aaagtcgttt gttggttcaa ataatgatta 780
aatatctctt ttctcttcca attgtctaaa tcaattttat taaagttcat ttgatatgcc 840
tcctaaattt ttatcttgct cttttgtcag agaaatcata actctttttt tcgattctga 900
aatcaccatt taaaaaactc caatcaaata attttataaa attagtgtat cactttgtaa 960
tcataaaaac aacaataaag ctacttaaat atagatttat aaaaaacgtt ggcgaaaacg 1020
ttggcgattc gttggcgatt gaaaaacccc tcaaaccctt gagccagttg ggatagagcg 1080
tttttggcac aaaaattggc actcggcact taatgggggg tcgtagtacg gaagcaaaat 1140
tcgcttcctt tccccccatt tttttccaaa ttccaaattt ttttcaaaaa ttttccagcg 1200
ctaccgctcg gcaaaattgc aagcaatttt taaaatcaaa cccatgaggg aatttcattc 1260
cctcaaactc ccttgagcct cctccaaccg aaatagaagg acgctgcgct tattatttca 1320

-continued ttcagtcatc ggctttcata atctaacaga caacatcttc gctgcaaagc cacgctacgc 1380
tcaagggctt ttacgctacg ataacgcctg ttttaacgat tatgccgata actaaacgaa 1440
ataaacgcta aaacgtctca gaaacgattt tgagacgttt taataaaaaa tcgacttcgt 1500
tctttttttta cctctcggtt atgagttagt tcaaattcgt tctttttagg ttctaaatcg 1560
tgtttttctt ggaattgtgc tgttttatcc tttaccttgt ctacaaaccc cttaaaaacg 1620
tttttaaagg cttttaagcc gtctgtacgt tccttaaggg ctagcataga ttagtttatt 1680
cttgacacta caagctaaat gtggtataat cccatagagt gtggaattgt gagcggataa 1740
caatttcaca caggaaacag accatggaat tcgagctcgg tacccgggga tccaggaggt 1800
aataaatatg agaaaaaaat tttatcaaat gtcgccacaa gagcgattga attcgttaaa 1860
cttatccgaa aagagtcaag aaattttaag tgagatggcc ctagatacaa ctattttgga 1920
caatctcata gaaaatcaaa tttctgaatt tgaattgcca atgggaattg cccaaaattt 1980
tgttattaat ggacaaagtt ttctaatacc aatggttaca gaggaaccgt cagtaattgc 2040
cgcagcaagt aatggagcaa aaatagctgg aaattttgta gctgaaatta aagaacgttt 2100
aatgcgtggt caaattgtat tttatgatgt taaaaattca gataagattg caaatgaaat 2160
acttgaaaag caagaaaaaa tctttgaaca agccgaactt tcttaccctt caatcgttaa 2220
acgaggtggc ggtttgagag aggtttctag tcggattttc tctagtcaaa agtttttatc 2280
tgttgatgtc aaggttgatg ttaaagacgc catgggtgca aatattatta attcaatctt 2340
agagggaatt gctgaactct ttcggaggtg gtttcctgat gaaaaaattc tgtttagtat 2400
tttatcaaat tatgctactg aatcactagt gaaagtgacc tgtgaaattc cggttgaacg 2460
cctttcaaaa aaagcagatg gatatgaaat tggtcaaaaa attatggctg cttcccaata 2520
ttcaaaaatt gatccttatc gtgctagcac ccataacaaa gggattatga acggtatcaa 2580
tgcggtcatt ttagctacag gaaatgatac tcgggccatc tcagctgcta ttcatgctta 2640
tgcggcaaaa gatggagcct accaagggtt agccaactgg gaacttcaag agaaaatgtt 2700
agttggcgaa ctcgaatttc ctttaccagt ggcaactgtc ggaggggggag tcaaggtttt 2760
gccaaaagca caagcggcca tggagattct gggtatcagt gatgctaagg agctcgcaaa 2820
agttattgct gcagtgggac tagctcaaaa cttagccgct ttacgtgccc tagtttcaga 2880
aggaattcaa cagggacaca tgagtctaca agctcgttct ttggctttga gtgtaggagc 2940
acaagcggat gaaatcgcga tattaagtca acaattgcgc aaagaaaaag tgatgaatca 3000
agaagtagcc caaaatttac taaaaaattt gagaaaataa tctagagtcg acctgcaggc 3060
atgcaagctt ggctgttttg gcggatgaga gaagattttc agcctgatac agattaaatc 3120
agaacgcaga agcggtctga taaaacagaa tttgcctggc ggcagtagcg cggtggtccc 3180
acctgacccc atgccgaact cagaagtgaa acgccgtagc gccgatggta gtgtggggtc 3240
tccccatgcg agagtaggga actgccaggc atcaaataaa acgaaaggct cagtcgaaag 3300
actgggcctt tcgttttatc tgttgtttgt cggtgaacgc tctcctgagt aggacaaatc 3360
cgccgggagc ggatttgaac gttgcgaagc aacggcccgg agggtggcgg gcaggacgcc 3420
cgccataaac tgccaggcat caaattaagc agaaggccat cctgacggat ggcctttttg 3480
cgtttctaca aactcttacc ggtcctgcag caatggcaac aacgttgcgc aaactattaa 3540
ctggcgaact acttactcta gcttcccggc aacaattaat agactggatg gaggcggata 3600
aagttgcagg accacttctg cgctcggccc ttccggctgg ctggtttatt gctgataaat 3660
ctggagccgg tgagcgtggg tctcgcggta tcattgcagc actggggcca gatggtaagc 3720
cctcccgtat cgtagttatc tacacgacgg ggagtcaggc aactatggat gaacgaaata 3780
gacagatcgc tgagataggt gcctcactga ttaagcattg gtaactgtca gaccaagttt 3840
actcatatat actttagatt gatttaaaac ttcattttta atttaaaagg atctaggtga 3900
agatcctttt tgataatctc atgaccaaaa tcccttaacg tgagttttcg ttccactgag 3960
cgtcagaccc cgtagaaaag atcaaaggat cttcttgaga tccttttttt ctgcgcgtaa 4020
tctgctgctt gcaaacaaaa aaaccaccgc taccagcggt ggtttgtttg ccggatcaag 4080
agctaccaac tctttttccg aaggtaactg gcttcagcag agcgcagata ccaaatactg 4140
tccttctagt gtagccgtag ttaggccacc acttcaagaa ctctgtagca ccgcctacat 4200
acctcgctct gctaatcctg ttaccagtgg ctgctgccag tggcgataag tcgtgtctta 4260
ccgggttgga ctcaagacga tagttaccgg ataaggcgca gcggtcgggc tgaacggggg 4320
gttcgtgcac acagcccagc ttggagcgaa cgacctacac cgaactgaga tacctacagc 4380
gtgagctatg agaaagcgcc acgcttcccg aagggagaaa ggcggacagg tatccggtaa 4440
gcggcagggt cggaacagga gagcgcacga gggagcttcc agggggaaac gcctggtatc 4500
tttatagtcc tgtcgggttt cgccacctct gacttgagcg tcgatttttg tgatgctcgt 4560
caggggggcg gagcctatgg aaaaacgcca gcaacgcggc ctttttacgg ttcctggcct 4620
tttgctggcc ttttgctcac atgttctttc ctgcgttatc ccctgattct gtggataacc 4680
gtattaccgc ctttgagtga gctgataccg ctcgccgcag ccgaacgacc gagcgcagcg 4740
agtcagtgag cgaggaagcg gaagagcgcc tgatgcggta ttttctcctt acgcatctgt 4800
gcggtatttc acaccgcata tggtgcactc tcagtacaat ctgctctgat gccgcatagt 4860
taagccagta tacactccgc tatcgctacg tgactgggtc atggctgcgc cccgacaccc 4920
gccaacaccc gctgacgcgc cctgacgggc ttgtctgctc ccggcatccg cttacagaca 4980
agctgtgacc gtctccggga gctgcatgtg tcagaggttt tcaccgtcat caccgaaacg 5040
cgcgaggcag atcttttgcc cattttattt ttataaaatg ggcaggtggc gtttgtgtaa 5100
agcaaatcga cacaatccaa aggggataaa aggggaaagt gaaacttccc cctttttcaag 5160
ccacattgta atacaagaac gaagtgtttt gtattacaat gtgatagctt gcagtattta 5220
tggttttata tggtctattt tgttgtgagg attgtaaccg aatagggcgc aatgcttatt 5280
acaaaatcaa tgacaaaggg cgattgagga atgagcgctg aggcatttta tctttgagta 5340
agttattgat ggatcagaaa aatgtatcac aaattgaaac aaagactcac tcatttaaga 5400
gaagctacta tcatgaaatt ttgttgttgt gataagcaac ttctaataca cgatttttag 5460
ccattacatc actcgttttt agagtgatgt gtaagtgcgc attgcactct ttttttacga 5520
aacaagccga ccagcgtttg aaacttttta gtttttcatc attctatttt aaaacgttct 5580
aaaactcgat ttaagcgact ttaattcgaa actgtctatt tgttcaaagg gagcattaag 5640
aatgcttaaa cgagctttta agggggttta aattgatttt gaattgaata gcttgttgta 5700
agttgtaaaa aaaacaagtt aaacaaagta tcagttttcc atttaagggt tgttagggct 5760
tgccctgacc gtctgtaaga cgcttgattg catgatatga gtatttagct agtcaaacag 5820
ttaaaacagc ttatatgagc aattagaggg aatccaataa attcctaaaa gcggttttga 5880
tcttttcttt tagcgagtga acgctgcaag taaaatgtga gcgttcactc gctcactcct 5940
ttttttgatg actttgacct ttggttttaa atttttgaaa aaaataaaaa ataggcgaag 6000
cctattatat atttatctta tatattttaa tcttttattc ttttgcgtca aaaaaaatca 6060
atattttcaa ggctttatag aattatatac caacaaaaaa ctgtgtatat accaacaaaa 6120
aactgtgcat acaccaacaa aaaactgtgc atataccaac ttctttgttt gtttcgttgg 6180
tatataatga tataataaaa gcatgaagaa tctctctacg aaaagtgttt cttcatgctt 6240
atctaaactc actcacaaag gagcagtttt ctatgtctag tatatcaaaa aatgaaccta 6300
atcaaaagca ggtgcaaacc ttgaacgaat tgtcaaaacg aaaagtagtg gaacataatt 6360
ctttaattac cagtattgcg aaaatggata aaacgccact gaaaatgttt gaattagccg 6420
tgtcttgtat taataccgaa gaaccaccca aagatcatac ggtttatctc tcaaaagaag 6480
aattgtttgc ctttttttaag gtatctgata atgacaaaca tagtcgtttt aaacaagcag 6540
tagagaatat gcaaaaacaa gcctttttttc aaattaaaga agaagtaggt aaaggattta 6600
aatttaggag tattgttccc attccatatg tcgagtggac agattatcat gatgacgtaa 6660
aaattgaatt tcatcgtgaa atcatgccct acttaattaa tctaaaacaa aatttcacgc 6720
aacatgcttt gtctgatatt gcagagctga atagcaaata ctctattatc ttgtaccgtt 6780
ggttatccat gaattataac caatacgagc attatagtta taagggcgga cggagagaag 6840
aacaagtgga agcctaccgc aatcctacca tttcaatgcg agaattacga gaaatgacgg 6900
atacagttga tgaatacccc cgctttgata gattagaaca tagagtttta aaagaaccaa 6960
tagaagaaat taacgaaaac acctctttta acgtgacgta tgacaagata aaaaaaggac 7020
gaagcattga ttctattgtc tttcatatca cgaaaaaacg tcgagcagat gataacagct 7080
acaagttaga agataaagat tatcaatccg acaaagagga aaaatcaaga aatgaagctg 7140
acttattaaa acaggcaatg gaaagcaagt acacacgatt attgattgaa aactttctct 7200
tatcccctct tgaaatgacg gacacggcac ttatggcagg tttgcaaaag aacgtctatc 7260
cgttgtatga cgagttaaag gaattaagag gattgaatgg ggtcaaagac cacttgtctt 7320
atatatctag caaaaaagaa gcctattcta aacgcaatgt agcgaagtat ctgaaaaaag 7380
caatcgagca atatctacct acggttaaaa ggcaggactt aaaccatgag tgagaactta 7440
aaaacgatta aagagttggc tgatgagttg ggcgtatcaa aaaagaaaat tcattatcaa 7500
gtatctaaat tagatagtga tttgatacaa aaattagacg gcactatata tctagctgat 7560
ttcacttttt gcattctaca aactgcataa ctcatat 7597

<210> SEQ ID NO 103
<211> LENGTH: 8327
<212> TYPE: DNA
<213> ORGANISM: Artificial Sequence
<220> FEATURE:
<223> OTHER INFORMATION: pCIN-mvaA-EGFP

<400> SEQUENCE: 103
gtaaatcgct cctttttagg tggcacaaat gtgaggcatt ttcgctcttt ccggcgaggc 60
tagttaccct taagttattg gtatgactgg ttttaagcgc aaaaaaagtt gctttttcgt 120
acctattaat gtatcgttag aaaaccgact gtaaaaagta cagtcggcat tatctcatat 180
tataaaagcc agtcattagg cctatctgac aattcctgaa tagagttcat aaacaatcct 240
gcatgataac catcacaaac agaatgatgt acctgtaaag atagcggtaa atatattgaa 300
ttacctttat taatgaattt tcctgctgta ataatgggta gaaggtaatt actattatta 360
ttgatattta agttaaaccc agtaaatgaa gtccatggaa taatagaaag agaaaaagca 420
ttttcaggta taggtgtttt gggaaacaat ttccccgaac cattatattt ctctacatca 480

-continued

```
gaaaggtata aatcataaaa ctctttgaag tcattcttta caggagtcca aataccagag    540
aatgttttag atacaccatc aaaaattgta taaagtggct ctaacttatc ccaataacct    600
aactctccgt cgctattgta accagttcta aaagctgtat ttgagtttat cacccttgtc    660
actaagaaaa taaatgcagg gtaaaattta tatccttctt gttttatgtt tcggtataaa    720
acactaatat caatttctgt ggttatacta aaagtcgttt gttggttcaa ataatgatta    780
aatatctctt ttctcttcca attgtctaaa tcaattttat taaagttcat ttgatatgcc    840
tcctaaattt ttatcttgct cttttgtcag agaaatcata actctttttt tcgattctga    900
aatcaccatt taaaaaactc caatcaaata attttataaa attagtgtat cactttgtaa    960
tcataaaaac aacaataaag ctacttaaat atagatttat aaaaaacgtt ggcgaaaacg   1020
ttggcgattc gttggcgatt gaaaaacccc tcaaaccctt gagccagttg ggatagagcg   1080
tttttggcac aaaaattggc actcggcact taatgggggg tcgtagtacg gaagcaaaat   1140
tcgcttcctt tccccccatt tttttccaaa ttccaaattt ttttcaaaaa ttttccagcg   1200
ctaccgctcg gcaaaattgc aagcaatttt taaaatcaaa cccatgaggg aatttcattc   1260
cctcaaactc ccttgagcct cctccaaccg aaatagaagg acgctgcgct tattatttca   1320
ttcagtcatc ggctttcata atctaacaga caacatcttc gctgcaaagc cacgctacgc   1380
tcaagggctt ttacgctacg ataacgcctg ttttaacgat tatgccgata actaaacgaa   1440
ataaacgcta aaacgtctca gaaacgattt tgagacgttt taataaaaaa tcgacttcgt   1500
tctttttta cctctcggtt atgagttagt tcaaattcgt tctttttagg ttctaaatcg    1560
tgtttttctt ggaattgtgc tgttttatcc tttaccttgt ctacaaaccc cttaaaaacg   1620
tttttaaagg cttttaagcc gtctgtacgt tccttaaggg ctagcataga ttagtttatt   1680
cttgacacta caagctaaat gtggtataat cccatagagt gtggaattgt gagcggataa   1740
caatttcaca caggaaacag accatggaat tcgagctcgg tacccgggga tccaggaggt   1800
aataaatatg agaaaaaaat tttatcaaat gtcgccacaa gagcgattga attcgttaaa   1860
cttatccgaa aagagtcaag aaattttaag tgagatggcc ctagatacaa ctattttgga   1920
caatctcata gaaaatcaaa tttctgaatt tgaattgcca atgggaattg cccaaaattt   1980
tgttattaat ggacaaagtt ttctaatacc aatggttaca gaggaaccgt cagtaattgc   2040
cgcagcaagt aatggagcaa aaatagctgg aaattttgta gctgaaatta aagaacgttt   2100
aatgcgtggt caaattgtat tttatgatgt taaaaattca gataagattg caaatgaaat   2160
acttgaaaag caagaaaaaa tctttgaaca agccgaactt tcttaccctt caatcgttaa   2220
acgaggtggc ggtttgagag aggtttctag tcggattttc tctagtcaaa agtttttatc   2280
tgttgatgtc aaggttgatg ttaaagacgc catgggtgca aatattatta attcaatctt   2340
agagggaatt gctgaactct ttcggaggtg gtttcctgat gaaaaaattc tgtttagtat   2400
tttatcaaat tatgctactg aatcactagt gaaagtgacc tgtgaaattc cggttgaacg   2460
cctttcaaaa aaagcagatg gatatgaaat tggtcaaaaa attatggctg cttcccaata   2520
ttcaaaaatt gatccttatc gtgctagcac ccataacaaa gggattatga acggtatcaa   2580
tgcggtcatt ttagctacag gaaatgatac tcgggccatc tcagctgcta ttcatgctta   2640
tgcggcaaaa gatggagcct accaagggtt agccaactgg gaacttcaag agaaaatgtt   2700
agttggcgaa ctcgaatttc ctttaccagt ggcaactgtc ggagggggag tcaaggtttt   2760
gccaaaagca caagcggcca tggagattct gggtatcagt gatgctaagg agctcgcaaa   2820
agttattgct gcagtgggac tagctcaaaa cttagccgct ttacgtgccc tagtttcaga   2880
```

-continued

```
aggaattcaa cagggacaca tgagtctaca agctcgttct ttggctttga gtgtaggagc   2940
acaagcggat gaaatcgcga tattaagtca acaattgcgc aaagaaaaag tgatgaatca   3000
agaagtagcc caaaatttac taaaaaattt gagaaaataa tctagagtcg acaggaggta   3060
ataaatatgg tgagcaaggg cgaggagctg ttcaccgggg tggtgcccat cctggtcgag   3120
ctggacggcg acgtaaacgg ccacaagttc agcgtgtccg gcgagggcga gggcgatgcc   3180
acctacggca agctgaccct gaagttcatc tgcaccaccg gcaagctgcc cgtgccctgg   3240
cccaccctcg tgaccaccct gacctggggc gtgcagtgct tcagccgcta ccccgaccac   3300
atgaagcagc acgacttctt caagtccgcc atgcccgaag gctacgtcca ggagcgcacc   3360
atcttcttca aggacgacgg caactacaag acccgcgccg aggtgaagtt cgagggcgac   3420
accctggtga accgcatcga gctgaagggc atcgacttca aggaggacgg caacatcctg   3480
gggcacaagc tggagtacaa ctacatcagc cacaacgtct atatcaccgc cgacaagcag   3540
aagaacggca tcaaggccaa cttcaagatc cgccacaaca tcgaggacgg cagcgtgcag   3600
ctcgccgacc actaccagca gaacaccccc atcggcgacg gccccgtgct gctgcccgac   3660
aaccactacc tgagcaccca gtccgccctg agcaaagacc ccaacgagaa gcgcgatcac   3720
atggtcctgc tggagttcgt gaccgccgcc gggatcactc tcggcatgga cgagctgtac   3780
aagtaagcat gcaagcttgg ctgttttggc ggatgagaga agattttcgg cctgatacag   3840
attaaatcag aacgcagaag cggtctgata aaacagaatt tgcctggcgg cagtagcgcg   3900
gtggtcccac ctgaccccat gccgaactca gaagtgaaac gccgtagcgc cgatggtagt   3960
gtggggtctc cccatgcgga gagtagggaa ctgccaggca tcaaataaaa cgaaaggctc   4020
agtcgaaaga ctgggccctt tcgttttatc tgttgtttgt cggtgaacgc tctcctgagt   4080
aggacaaatc cgccgggagc ggatttgaac gttgcgaagc aacggcccgg agggtggcgg   4140
gcaggacgcc cgccataaac tgccaggcat caaattaagc agaaggccat cctgacggat   4200
ggcctttttg cgtttctaca aactcttacc ggtcctgcag caatggcaac aacgttgcgc   4260
aaactattaa ctggcgaact acttactcta gcttcccggc aacaattaat agactggatg   4320
gaggcggata aagttgcagg accacttctg cgctcggccc ttccggctgg ctggtttatt   4380
gctgataaat ctggagccgg tgagcgtggg tctcgcggta tcattgcagc actggggcca   4440
gatggtaagc cctcccgtat cgtagttatc tacacgacgg ggagtcaggc aactatggat   4500
gaacgaaata gacagatcgc tgagataggt gcctcactga ttaagcattg gtaactgtca   4560
gaccaagttt actcatatat actttagatt gatttaaaac ttcattttta atttaaaagg   4620
atctaggtga agatcctttt tgataatctc atgaccaaaa tcccttaacg tgagttttcg   4680
ttccactgag cgtcagaccc cgtagaaaag atcaaaggat cttcttgaga tccttttttt   4740
ctgcgcgtaa tctgctgctt gcaaacaaaa aaaccaccgc taccagcggt ggtttgtttg   4800
ccggatcaag agctaccaac tctttttccg aaggtaactg gcttcagcag agcgcagata   4860
ccaaatactg tccttctagt gtagccgtag ttaggccacc acttcaagaa ctctgtagca   4920
ccgcctacat acctcgctct gctaatcctg ttaccagtgg ctgctgccag tggcgataag   4980
tcgtgtctta ccgggttgga ctcaagacga tagttaccgg ataaggcgca gcggtcgggc   5040
tgaacggggg gttcgtgcac acagcccagc ttggagcgaa cgacctacac cgaactgaga   5100
tacctacagc gtgagctatg agaaagcgcc acgcttcccg aagggagaaa ggcggacagg   5160
tatccggtaa gcggcagggt cggaacagga gagcgcacga gggagcttcc agggggaaac   5220
```

gcctggtatc tttatagtcc tgtcgggttt cgccacctct gacttgagcg tcgatttttg 5280
tgatgctcgt caggggggcg gagcctatgg aaaaacgcca gcaacgcggc ctttttacgg 5340
ttcctggcct tttgctggcc ttttgctcac atgttctttc ctgcgttatc ccctgattct 5400
gtggataacc gtattaccgc ctttgagtga gctgataccg ctcgccgcag ccgaacgacc 5460
gagcgcagcg agtcagtgag cgaggaagcg gaagagcgcc tgatgcggta ttttctcctt 5520
acgcatctgt gcggtatttc acaccgcata tggtgcactc tcagtacaat ctgctctgat 5580
gccgcatagt taagccagta tacactccgc tatcgctacg tgactgggtc atggctgcgc 5640
cccgacaccc gccaacaccc gctgacgcgc cctgacgggc ttgtctgctc ccggcatccg 5700
cttacagaca agctgtgacc gtctccggga gctgcatgtg tcagaggttt tcaccgtcat 5760
caccgaaacg cgcgaggcag atcttttgcc cattttattt ttataaaatg ggcaggtggc 5820
gtttgtgtaa agcaaatcga cacaatccaa aggggataaa aggggaaagt gaaacttccc 5880
ccttttcaag ccacattgta atacaagaac gaagtgtttt gtattacaat gtgatagctt 5940
gcagtattta tggttttata tggtctattt tgttgtgagg attgtaaccg aatagggcgc 6000
aatgcttatt acaaaatcaa tgacaaaggg cgattgagga atgagcgctg aggcatttta 6060
tctttgagta agttattgat ggatcagaaa aatgtatcac aaattgaaac aaagactcac 6120
tcatttaaga gaagctacta tcatgaaatt ttgttgttgt gataagcaac ttctaataca 6180
cgatttttag ccattacatc actcgttttt agagtgatgt gtaagtgcgc attgcactct 6240
ttttttacga aacaagccga ccagcgtttg aaacttttta gtttttcatc attctatttt 6300
aaaacgttct aaaactcgat ttaagcgact ttaattcgaa actgtctatt tgttcaaagg 6360
gagcattaag aatgcttaaa cgagctttta aggggggtta aattgatttt gaattgaata 6420
gcttgttgta agttgtaaaa aaaacaagtt aaacaaagta tcagttttcc atttaagggt 6480
tgttagggct tgccctgacc gtctgtaaga cgcttgattg catgatatga gtatttagct 6540
agtcaaacag ttaaaacagc ttatatgagc aattagaggg aatccaataa attcctaaaa 6600
gcggttttga tcttttcttt tagcgagtga acgctgcaag taaaatgtga gcgttcactc 6660
gctcactcct ttttttgatg actttgacct ttggttttaa atttttgaaa aaaataaaaa 6720
ataggcgaag cctattatat atttatctta tatattttaa tcttttattc ttttgcgtca 6780
aaaaaaatca atattttcaa ggctttatag aattatatac caacaaaaaa ctgtgtatat 6840
accaacaaaa aactgtgcat acaccaacaa aaaactgtgc atataccaac ttctttgttt 6900
gtttcgttgg tatataatga tataataaaa gcatgaagaa tctctctacg aaaagtgttt 6960
cttcatgctt atctaaactc actcacaaag gagcagtttt ctatgtctag tatatcaaaa 7020
aatgaaccta atcaaaagca ggtgcaaacc ttgaacgaat tgtcaaaacg aaaagtagtg 7080
gaacataatt ctttaattac cagtattgcg aaaatggata aaacgccact gaaaatgttt 7140
gaattagccg tgtcttgtat taataccgaa gaaccaccca aagatcatac ggtttatctc 7200
tcaaaagaag aattgtttgc ctttttttaag gtatctgata atgacaaaca tagtcgtttt 7260
aaacaagcag tagagaatat gcaaaaacaa gccttttttc aaattaaaga agaagtaggt 7320
aaaggattta aatttaggag tattgttccc attccatatg tcgagtggac agattatcat 7380
gatgacgtaa aaattgaatt tcatcgtgaa atcatgccct acttaattaa tctaaaacaa 7440
aatttcacgc aacatgcttt gtctgatatt gcagagctga atagcaaata ctctattatc 7500
ttgtaccgtt ggttatccat gaattataac caatacgagc attatagtta taagggcgga 7560
cggagagaag aacaagtgga agcctaccgc aatcctacca tttcaatgcg agaattacga 7620

```
gaaatgacgg atacagttga tgaataccccc cgctttgata gattagaaca tagagtttta   7680

aaagaaccaa tagaagaaat taacgaaaac acctctttta acgtgacgta tgacaagata   7740

aaaaaaggac gaagcattga ttctattgtc tttcatatca cgaaaaaacg tcgagcagat   7800

gataacagct acaagttaga agataaagat tatcaatccg acaaagagga aaaatcaaga   7860

aatgaagctg acttattaaa acaggcaatg gaaagcaagt acacacgatt attgattgaa   7920

aactttctct tatcccctct tgaaatgacg gacacggcac ttatggcagg tttgcaaaag   7980

aacgtctatc cgttgtatga cgagttaaag gaattaagag gattgaatgg ggtcaaagac   8040

cacttgtctt atatatctag caaaaaagaa gcctattcta aacgcaatgt agcgaagtat   8100

ctgaaaaaag caatcgagca atatctacct acggttaaaa ggcaggactt aaaccatgag   8160

tgagaactta aaaacgatta aagagttggc tgatgagttg ggcgtatcaa aaaagaaaat   8220

tcattatcaa gtatctaaat tagatagtga tttgatacaa aaattagacg gcactatata   8280

tctagctgat ttcacttttt gcattctaca aactgcataa ctcatat                 8327
```

<210> SEQ ID NO 104
<211> LENGTH: 2412
<212> TYPE: DNA
<213> ORGANISM: Enterococcus faecalis mvaE

<400> SEQUENCE: 104

```
ttgaaaacag tagttattat tgatgcatta cgaacaccaa ttggaaaata taaaggcagc     60

ttaagtcaag taagtgccgt agacttagga acacatgtta caacacaact tttaaaaaga    120

cattccacta tttctgaaga aattgatcaa gtaatctttg gaaatgtttt acaagctgga    180

aatggccaaa atcccgcacg acaaatagca ataaacagcg gtttatctca tgaaattccc    240

gcaatgacag ttaatgaggt ctgcggatca ggaatgaagg ccgttatttt ggcgaaacaa    300

ttgattcaat taggagaagc ggaagtttta attgctggcg ggattgagaa tatgtcccaa    360

gcacctaaat tacaacgatt taattacgaa acagaaagct atgatgcgcc tttttctagt    420

atgatgtacg atgggttaac ggatgccttt agtggtcaag caatgggctt aactgctgaa    480

aatgtggccg aaaagtatca tgtaactaga gaagagcaag atcaattttc tgtacattca    540

caattaaaag cagctcaagc acaagcagaa gggatattcg ctgacgaaat agccccatta    600

gaagtatcag gaacgcttgt ggagaaagat gaagggattc gccctaattc gagcgttgag    660

aagctaggaa cgcttaaaac agtttttaaa gaagacggta ctgtaacagc agggaatgca    720

tcaaccatta atgatggggc ttctgctttg attattgctt cacaagaata tgccgaagca    780

cacggtcttc cttatttagc tattattcga gacagtgtgg aagtcggtat tgatccagcc    840

tatatgggaa tttcgccgat taaagccatt caaaaactgt tagcgcgcaa tcaacttact    900

acggaagaaa ttgatctgta tgaaatcaac gaagcatttg cagcaacttc aatcgtggtc    960

caaagagaac tggctttacc agaggaaaag gtcaacattt atggtggcgg tatttcatta   1020

ggtcatgcga ttggtgccac aggtgctcgt ttattaacga gtttaagtta tcaattaaat   1080

caaaaagaaa agaaatatgg agtggcttct ttatgtatcg gcggtggctt aggactcgct   1140

atgctactag agagacctca gcaaaaaaaa aacagccgat tttatcaaat gagtcctgag   1200

gaacgcctgg cttctcttct taatgaaggc cagatttctg ctgatacaaa aaaagaattt   1260

gaaaatacgg ctttatcttc gcagattgcc aatcatatga ttgaaaatca aatcagtgaa   1320

acagaagtgc cgatgggcgt tggcttacat ttaacagtgg acgaaactga ttatttggta   1380
```

```
ccaatggcga cagaagagcc ctcagtgatt gcggctttga gtaatggtgc aaaaatagca   1440
caaggattta aaacagtgaa tcaacaacgt ttaatgcgtg gacaaatcgt tttttacgat   1500
gttgcagacg ccgagtcatt gattgatgaa ctacaagtaa gagaaacgga aatttttcaa   1560
caagcagagt taagttatcc atctatcgtt aaacgcggcg gcggcttaag agatttgcaa   1620
tatcgtgctt ttgatgaatc atttgtatct gtcgactttt tagtagatgt taaggatgca   1680
atgggggcaa atatcgttaa cgctatgttg gaaggtgtgg ccgagttgtt ccgtgaatgg   1740
tttgcggagc aaaagatttt attcagtatt ttaagtaatt atgccacgga gtcggttgtt   1800
acgatgaaaa cggctattcc agtttcacgt ttaagtaagg ggagcaatgg ccgggaaatt   1860
gctgaaaaaa ttgttttagc ttcacgctat gcttcattag atccttatcg ggcagtcacg   1920
cataacaaag ggatcatgaa tggcattgaa gctgtcgttt tagctacagg aaatgataca   1980
cgcgctgtta gcgcttcttg tcatgctttt gcggtgaagg aaggtcgcta ccaaggtttg   2040
actagttgga cgctggatgg cgaacaacta attggtgaaa tttcagttcc gcttgcgtta   2100
gccacggttg gcggtgccac aaaagtctta cctaaatctc aagcagctgc tgatttgtta   2160
gcagtgacgg atgcaaaaga actaagtcga gtagtagcgg ctgttggttt ggcacaaaat   2220
ttagcggcgt tacgggcctt agtctctgaa ggaattcaaa aaggacacat ggctctacaa   2280
gcacgttctt tagcgatgac ggtcggagct actggtaaag aagttgaggc agtcgctcaa   2340
caattaaaac gtcaaaaaac gatgaaccaa gaccgagcct tggctatttt aaatgattta   2400
agaaaacaat aa                                                       2412
```

<210> SEQ ID NO 105
<211> LENGTH: 1149
<212> TYPE: DNA
<213> ORGANISM: Enterococcus faecalis mvaS

<400> SEQUENCE: 105

```
atgacaattg ggattgataa aattagtttt tttgtgcccc cttattatat tgatatgacg     60
gcactggctg aagccagaaa tgtagaccct ggaaaatttc atattggtat tgggcaagac    120
caaatggcgg tgaacccaat cagccaagat attgtgacat ttgcagccaa tgccgcagaa    180
gcgatcttga ccaaagaaga taaagaggcc attgatatgg tgattgtcgg gactgagtcc    240
agtatcgatg agtcaaaagc ggccgcagtt gtcttacatc gtttaatggg gattcaacct    300
ttcgctcgct ctttcgaaat caaggaagct tgttacggag caacagcagg cttacagtta    360
gctaagaatc acgtagcctt acatccagat aaaaaagtct tggttgtagc agcagatatt    420
gcaaaatatg gattaaattc tggcggtgag cctacacaag gagctggggc ggttgcaatg    480
ttagttgcta gtgaaccgcg catcttggct ttaaaagagg ataatgtgat gctgacgcaa    540
gatatctatg acttttggcg tccaacaggc catccgtatc ctatggtcga tggtcctttg    600
tcaaacgaaa cctacatcca atcttttgcc caagtctggg atgaacataa aaaaagaacc    660
ggtcttgatt ttgcagatta tgatgcttta gcgttccata ttccttacac aaaaatgggc    720
aaaaaagcct tattagcaaa aatctccgac caaactgaag cagaacagga acgaatttta    780
gcccgttatg aagaaagcat catctatagt cgtcgcgtag gaaacttgta tacgggttca    840
ctttatctgg gactcatttc ccttttagaa aatgcaacga ctttaaccgc aggcaatcaa    900
attgggttat tcagttatgg ttctggtgct gtcgctgaat tttcactggg tgaattagta    960
gctggttatc aaaatcattt acaaaaagaa actcatttag cactgctaga taatcggaca   1020
gaactttcta tcgctgaata tgaagccatg tttgcagaaa ctttagacac agatattgat   1080
```

caaacgttag aagatgaatt aaaatatagt atttctgcta ttaataatac cgttcgctct 1140
tatcgaaac 1149

<210> SEQ ID NO 106
<211> LENGTH: 879
<212> TYPE: DNA
<213> ORGANISM: Streptococcus pneumoniae mvaK1

<400> SEQUENCE: 106
atgacaaaaa aagttggtgt cggtcaggca catagtaaga taattttaat aggggaacat 60
gcggtcgttt acggttatcc tgccatttcc ctgcctcttt tggaggtgga ggtgacctgt 120
aaggtagttc ctgcagagag tccttggcgc ctttatgagg aggatacctt gtccatggcg 180
gtttatgcct cactggagta tttgaatatc acagaagcct gcattcgttg tgagattgac 240
tcggctatcc ctgagaaacg gggatgggt tcgtcagcgg ctatcagcat agcggccatt 300
cgtgcagtat ttgactacta tcaggctgat ctgcctcatg atgtactaga aatcttggtc 360
aatcgagctg aaatgattgc ccatatgaat cctagtggtt tggatgctaa gacctgtctt 420
agtgaccaac ctattcgctt tatcaagaac gtaggattta cagaacttga gatggattta 480
tccgcctatt tggtgattgc cgatacgggt gtttatggtc atactcgtga agccatccaa 540
gtggttcaaa ataagggcaa ggatgcccta ccgtttttgc atgccttggg agaattaacc 600
cagcaagcag aagttgcgat ttcacaaaaa gatgctgaag gactgggaca aatcctcagt 660
caagcgcatt tacatttaaa agaaattgga gtcagtagcc ctgaggcaga ctttttggtt 720
gaaacgactc ttagccatgg tgctctgggt gccaagatga gcggtggtgg gctaggaggt 780
tgtatcatag ccttggtaac caatttgaca cacgcacaag aactagcaga aagattagaa 840
gagaaaggag ctgttcagac atggatagag agcctgtaa 879

<210> SEQ ID NO 107
<211> LENGTH: 1011
<212> TYPE: DNA
<213> ORGANISM: Streptococcus pneumoniae mvaK2

<400> SEQUENCE: 107
atgattgctg ttaaaacttg cggaaaactc tattgggcag gtgaatatgc tattttagag 60
ccagggcagt tagctttgat aaaggatatt cccatctata tgagggctga gattgctttt 120
tctgacagct accgtatcta ttcagatatg tttgatttcg cagtggactt aaggcccaat 180
cctgactaca gcttgattca agaaacgatt gctttgatgg gagacttcct cgctgttcgc 240
ggtcagaatt taagaccttt ttccctaaaa atctgtggca aaatggaacg agaagggaaa 300
aagtttggtc taggttctag tggcagcgtc gttgtcttgg ttgtcaaggc tttactggct 360
ctctataatc tttcggttga tcagaatctc ttgttcaagc tgactagcgc tgtcttgctc 420
aagcgaggag acaatggttc catgggcgac cttgcctgta ttgtggcaga ggatttggtt 480
ctttaccagt catttgatcg ccagaaggcg gctgcttggt tagaagaaga aaacttggcg 540
acagttctgg agcgtgattg gggatttttt atctcacaag tgaaaccaac tttagaatgt 600
gatttcttag tgggatggac caaggaagtg gctgtatcga gtcacatggt ccagcaaatc 660
aagcaaaata tcaatcaaaa ttttttaagt tcctcaaaag aaacggtggt ttctttggtc 720
gaagccttgg agcaggggaa agccgaaaaa gttatcgagc aagtagaagt agccagcaag 780
cttttagaag gcttgagtac agatatttac acgcctttgc ttagacagtt gaaagaagcc 840
agtcaagatt tgcaggccgt tgccaagagt agtggtgctg gtggtggtga ctgtggcatc 900
gccctgagtt ttgatgcgca atcttctcga aacactttaa aaaatcgttg ggccgatctg 960
gggattgagc tcttatatca agaaaggata ggacatgacg acaaatcgta a 1011

<210> SEQ ID NO 108
<211> LENGTH: 954
<212> TYPE: DNA
<213> ORGANISM: Streptococcus pneumoniae mvaD

<400> SEQUENCE: 108
atggatagag agcctgtaac agtacgttcc tacgcaaata ttgctattat caaatattgg 60
ggaaagaaaa aagaaaaaga gatggtgcct gctactagca gtatttctct aactttggaa 120
aatatgtata cagagacgac cttgtcgcct ttaccagcca atgtaacagc tgacgaattt 180
tacatcaatg gtcagctaca aaatgaggtc gagcatgcca agatgagtaa gattattgac 240
cgttatcgtc cagctggtga gggctttgtc cgtatcgata ctcaaaacaa tatgcctacg 300
gcagcgggcc tgtcctcaag ttctagtggt ttgtccgccc tggtcaaggc ttgtaatgct 360
tatttcaagc ttggattgga tagaagtcag ttggcacagg aagccaaatt tgcctcaggc 420
tcttcttctc ggagttttta tggaccacta ggagcctggg ataaggatag tggagaaatt 480
taccctgtag agacagactt gaaactagct atgattatgt tggtgctaga ggacaagaaa 540
aaaccaatct ctagccgtga cgggatgaaa ctttgtgtgg aaacctcgac gacttttgac 600
gactgggttc gtcagtctga gaaggactat caggatatgc tgatttatct caaggaaaat 660
gattttgcca agattggaga attaacggag aaaaatgctc tggctatgca tgctacgaca 720
aagactgcta gtccagcctt ttcttatctg acggatgcct cttatgaggc tatggccttt 780
gttcgccagc ttcgtgagaa aggagaggcc tgctacttta ccatggatgc tggtcccaat 840
gttaaggtct tctgtcagga gaaagacttg gagcatttgt cagaaatttt cggtcagcgt 900
tatcgcttga ttgtgtcaaa aacaaaggat ttgagtcaag atgattgctg ttaa 954

<210> SEQ ID NO 109
<211> LENGTH: 549
<212> TYPE: DNA
<213> ORGANISM: Escherichia coli idi

<400> SEQUENCE: 109
atgcaaacgg aacacgtcat tttattgaat gcacagggag ttcccacggg tacgctggaa 60
aagtatgccg cacacacggc agacacccgc ttacatctcg cgttctccag ttggctgttt 120
aatgccaaag gacaattatt agttacccgc cgcgcactga gcaaaaaagc atggcctggc 180
gtgtggacta actcggtttg tgggcaccca caactgggag aaagcaacga agacgcagtg 240
atccgccgtt gccgttatga gcttggcgtg gaaattacgc ctcctgaatc tatctatcct 300
gactttcgct accgcgccac cgatccgagt ggcattgtgg aaaatgaagt gtgtccggta 360
tttgccgcac gcaccactag tgcgttacag atcaatgatg atgaagtgat ggattatcaa 420
tggtgtgatt tagcagatgt attacacggt attgatgcca cgccgtgggc gttcagtccg 480
tggatggtga tgcaggcgac aaatcgcgaa gccagaaaac gattatctgc atttacccag 540
cttaaataa 549

<210> SEQ ID NO 110
<211> LENGTH: 915
<212> TYPE: DNA
<213> ORGANISM: Haematococcus pluvialis ipiHp1

<400> SEQUENCE: 110
atgcttcgtt cgttgctcag aggcctcacg catatccccc gcgtgaactc cgcccagcag 60
cccagctgtg cacacgcgcg actccagttt aagctcagga gcatgcagat gacgctcatg 120
cagcccagca tctcagccaa tctgtcgcgc gccgaggacc gcacagacca catgaggggt 180
gcaagcacct gggcaggcgg gcagtcgcag gatgagctga tgctgaagga cgagtgcatc 240
ttggtggatg ttgaggacaa catcacaggc catgccagca agctggagtg tcacaagttc 300
ctaccacatc agcctgcagg cctgctgcac cgggccttct ctgtgttcct gtttgacgat 360
caggggcgac tgctgctgca acagcgtgca cgctcaaaaa tcaccttccc aagtgtgtgg 420
acgaacacct gctgcagcca ccctttacat gggcagaccc cagatgaggt ggaccaacta 480
agccaggtgg ccgacggaac agtacctggc gcaaaggctg ctgccatccg caagttggag 540
cacgagctgg ggataccagc gcaccagctg ccggcaagcg cgtttcgctt cctcacgcgt 600
ttgcactact gtgccgcgga cgtgcagcca gctgcgacac aatcagcgct ctggggcgag 660
cacgaaatgg actacatctt gttcatccgg gccaacgtca ccttggcgcc caaccctgac 720
gaggtggacg aagtcaggta cgtgacgcaa gaggagctgc ggcagatgat gcagccggac 780
aacgggctgc aatggtcgcc gtggtttcgc atcatcgccg cgcgcttcct tgagcgttgg 840
tgggctgacc tggacgcggc cctaaacact gacaaacacg aggattgggg aacggtgcat 900
cacatcaacg aagcg 915

<210> SEQ ID NO 111
<211> LENGTH: 924
<212> TYPE: DNA
<213> ORGANISM: pantoea agglomerans crtE

<400> SEQUENCE: 111
atggtgagtg gcagtaaagc gggcgtttcg cctcatcgcg aaatagaagt aatgagacaa 60
tccattgacg atcacctggc tggcctgtta cctgaaaccg acagccagga tatcgtcagc 120
cttgcgatgc gtgaaggcgt catggcaccc ggtaaacgga tccgtccgct gctgatgctg 180
ctggccgccc gcgacctccg ctaccagggc agtatgccta cgctgctcga tctcgcctgc 240
gccgttgaac tgacccatac cgcgtcgctg atgctcgacg acatgccctg catggacaac 300
gccgagctgc gccgcggtca gcccactacc cacaaaaaat ttggtgagag cgtggcgatc 360
cttgcctccg ttgggctgct ctctaaagcc tttggtctga tcgccgccac cggcgatctg 420
ccgggggaga ggcgtgccca ggcggtcaac gagctctcta ccgccgtggg cgtgcagggc 480
ctggtactgg ggcagtttcg cgatcttaac gatgccgccc tcgaccgtac ccctgacgct 540
atcctcagca ccaaccacct caagaccggc attctgttca gcgcgatgct gcagatcgtc 600
gccattgctt ccgcctcgtc gccgagcacg cgagagacgc tgcacgcctt cgccctcgac 660
ttcggccagg cgtttcaact gctggacgat ctgcgtgacg atcacccgga aaccggtaaa 720
gatcgcaata aggacgcggg aaaatcgacg ctggtcaacc ggctgggcgc agacgcggcc 780
cggcaaaagc tgcgcgagca tattgattcc gccgacaaac acctcacttt tgcctgtccg 840
cagggcggcg ccatccgaca gtttatgcat ctgtggtttg gccatcacct tgccgactgg 900
tcaccggtca tgaaaatcgc ctga 924

<210> SEQ ID NO 112
<211> LENGTH: 930
<212> TYPE: DNA

<213> ORGANISM: pantoea agglomerans crtB

<400> SEQUENCE: 112

```
atgagccaac cgccgctgct tgaccacgcc acgcagacca tggccaacgg ctcgaaaagt     60
tttgccaccg ctgcgaagct gttcgacccg gccacccgcc gtagcgtgct gatgctctac    120
acctggtgcc gccactgcga tgacgtcatt gacgaccaga cccacggctt cgccagcgag    180
gccgcggcgg aggaggaggc cacccagcgc ctggcccggc tgcgcacgct gaccctggcg    240
gcgtttgaag ggccgagat gcaggatccg gccttcgctg cctttcagga ggtggcgctg    300
acccacggta ttacgccccg catggcgctc gatcacctcg acggctttgc gatggacgtg    360
gctcagaccc gctatgtcac ctttgaggat acgctgcgct actgctatca cgtggcgggc    420
gtggtgggtc tgatgatggc cagggtgatg ggcgtgcggg atgagcgggt gctggatcgc    480
gcctgcgatc tggggctggc cttccagctg acgaatatcg cccgggatat tattgacgat    540
gcggctattg accgctgcta tctgcccgcc gagtggctgc aggatgccgg gctgaccccg    600
gagaactatg ccgcgcggga gaatcgggcc gcgctggcgc gggtggcgga gcggcttatt    660
gatgccgcag agccgtacta catctcctcc caggccgggc tacacgatct gccgccgcgc    720
tgcgcctggg cgatcgccac cgcccgcagc gtctaccggg agatcggtat taaggtaaaa    780
gcggcgggag gcagcgcctg ggatcgccgc cagcacacca gcaaaggtga aaaaattgcc    840
atgctgatgg cggcaccggg gcaggttatt cgggcgaaga cgacgagggt gacgccgcgt    900
ccggccggtc tttggcagcg tcccgtttag                                     930
```

<210> SEQ ID NO 113
<211> LENGTH: 1479
<212> TYPE: DNA
<213> ORGANISM: pantoea agglomerans crtI

<400> SEQUENCE: 113

```
atgaaaaaaa ccgttgtgat tggcgcaggc tttggtggcc tggcgctggc gattcgcctg     60
caggcggcag ggatcccaac cgtactgctg gagcagcggg acaagcccgg cggtcgggcc    120
tacgtctggc atgaccaggg ctttaccttt gacgccgggc cgacggtgat caccgatcct    180
accgcgcttg aggcgctgtt caccctggcc ggcaggcgca tggaggatta cgtcaggctg    240
ctgccggtaa aacccttcta ccgactctgc tgggagtccg ggaagaccct cgactatgct    300
aacgacagcg ccgagcttga ggcgcagatt acccagttca acccccgcga cgtcgagggc    360
taccggcgct ttctggctta ctcccaggcg gtattccagg agggatattt gcgcctcggc    420
agcgtgccgt tcctctcttt tcgcgacatg ctgcgcgccg ggccgcagct gcttaagctc    480
caggcgtggc agagcgtcta ccagtcggtt tcgcgcttta ttgaggatga gcatctgcgg    540
caggccttct cgttccactc cctgctggta ggcggcaacc ccttcaccac ctcgtccatc    600
tacaccctga tccacgccct tgagcgggag tggggggtct ggttccctga gggcggcacc    660
ggggcgctgg tgaacggcat ggtgaagctg tttaccgatc tgggcgggga gatcgaactc    720
aacgcccggg tcgaagagct ggtggtggcc gataaccgcg taagccaggt ccggctggcg    780
gatggtcgga tctttgacac cgacgccgta gcctcgaacg ctgacgtggt gaacacctat    840
aaaaagctgc tcggccacca tccggtgggg cagaagcggg cggcagcgct ggagcgcaag    900
agcatgagca actcgctgtt tgtgctctac ttcggcctga accagcctca ttcccagctg    960
gcgcaccata ccatctgttt tggtccccgc taccgggagc tgatcgacga gatctttacc   1020
ggcagcgcgc tggcggatga cttctcgctc tacctgcact cgccctgcgt gaccgatccc   1080
```

```
tcgctcgcgc ctcccggctg cgccagcttc tacgtgctgg ccccggtgcc gcatcttggc   1140

aacgcgccgc tggactgggc gcaggagggg ccgaagctgc gcgaccgcat ctttgactac   1200

cttgaagagc gctatatgcc cggcctgcgt agccagctgg tgacccagcg gatctttacc   1260

ccggcagact tccacgacac gctggatgcg catctgggat cggccttctc catcgagccg   1320

ctgctgaccc aaagcgcctg gttccgcccg cacaaccgcg acagcgacat tgccaacctc   1380

tacctggtgg gcgcaggtac tcaccctggg gcgggcattc ctggcgtagt ggcctcggcg   1440

aaagccaccg ccagcctgat gattgaggat ctgcaatga                          1479
```

<210> SEQ ID NO 114
<211> LENGTH: 1146
<212> TYPE: DNA
<213> ORGANISM: pantoea ananatis crtY

<400> SEQUENCE: 114

```
atgcaaccgc attatgatct gattctcgtg ggggctggac tcgcgaatgg ccttatcgcc     60

ctgcgtcttc agcagcagca acctgatatg cgtattttgc ttatcgacgc cgcaccccag    120

gcgggcggga atcatacgtg gtcatttcac cacgatgatt tgactgagag ccaacatcgt    180

tggatagctc cgctggtggt tcatcactgg cccgactatc aggtacgctt tcccacacgc    240

cgtcgtaagc tgaacagcgg ctacttttgt attacttctc agcgtttcgc tgaggtttta    300

cagcgacagt ttggcccgca cttgtggatg gataccgcgg tcgcagaggt taatgcggaa    360

tctgttcggt tgaaaaaggg tcaggttatc ggtgcccgcg cggtgattga cgggcggggt    420

tatgcggcaa attcagcact gagcgtgggc ttccaggcgt ttattggcca ggaatggcga    480

ttgagccacc cgcatggttt atcgtctccc attatcatgg atgccacggt cgatcagcaa    540

aatggttatc gcttcgtgta cagcctgccg ctctcgccga ccagattgtt aattgaagac    600

acgcactata ttgataatgc gacattagat cctgaatgcg cgcggcaaaa tatttgcgac    660

tatgccgcgc aacagggttg gcagcttcag acactgctgc gagaagaaca gggcgcctta    720

cccattactc tgtcgggcaa tgccgacgca ttctggcagc agcgccccct ggcctgtagt    780

ggattacgtg ccggtctgtt ccatcctacc accggctatt cactgccgct ggcggttgcc    840

gtggccgacc gcctgagtgc acttgatgtc tttacgtcgg cctcaattca ccatgccatt    900

acgcattttg cccgcgagcg ctggcagcag cagggctttt tccgcatgct gaatcgcatg    960

ctgtttttag ccggacccgc cgattcacgc tggcgggtta tgcagcgttt ttatggttta   1020

cctgaagatt taattgcccg tttttatgcg ggaaaactca cgctgaccga tcggctacgt   1080

attctgagcg gcaagccgcc tgttccggta ttagcagcat tgcaagccat tatgacgact   1140

catcgt                                                              1146
```

<210> SEQ ID NO 115
<211> LENGTH: 828
<212> TYPE: DNA
<213> ORGANISM: uncultured marine bacterium 66A03 SR

<400> SEQUENCE: 115

```
atgggtctga tgctgattga ttggtgtgca ctggctctgg ttgttttcat tggcctgccg     60

cacggcgcgc tggatgctgc catttctttt tctatgatct cttctgcaaa acgcattgct    120

cgtctggctg gtattctgct gatctatctg ctgctggcga ccgcgttctt cctgatctgg    180

tatcagctgc cagcgtttag cctgctgatc ttcctgctga tctccattat ccactttggt    240
```

```
atggcagact tcaacgcgtc cccaagcaaa ctgaaatggc cgcatatcat cgcccacggc    300
ggtgttgtta ctgtttggct gccgctgatc cagaaaaacg aagtaactaa actgtttagc    360
atcctgacta acggtccgac tccgatcctg tgggacatcc tgctgatttt cttcctgtgt    420
tggtctattg gcgtgtgtct gcacacgtac gaaaccctgc gctctaaaca ttacaacatc    480
gcctttgaac tgatcggtct gattttcctg gcgtggtatg cgccgcctct ggttacgttt    540
gccacttact tctgcttcat tcattcccgt cgccacttct cctttgtgtg gaagcagctg    600
caacacatgt cttccaaaaa gatgatgatt ggcagcgcga ttatcctgtc ctgtacctct    660
tggctgatcg gcggtggtat ctatttcttc ctgaactcca aaatgatcgc ctctgaggct    720
gcgctgcaga ctgtgttcat cggtctggcg gcactgaccg tgccgcacat gattctgatc    780
gacttcatct tccgtccgca ctcttcccgt atcaaaatca aaaactaa                828
```

<210> SEQ ID NO 116
<211> LENGTH: 810
<212> TYPE: DNA
<213> ORGANISM: Escherichia coli MG1655 YbbO

<400> SEQUENCE: 116

```
atgactcata aagcaacgga gatcctgaca ggtaaagtta tgcaaaaatc ggtcttaatt     60
accggatgtt ccagtggaat tggcctggaa agcgcgctcg aattaaaacg ccagggtttt    120
catgtgctgg caggttgccg gaaaccggat gatgttgagc gcatgaacag catgggattt    180
accggcgtgt tgatcgatct ggattcacca gaaagtgttg atcgcgcagc cgacgaggtg    240
atcgccctga ccgataattg tctgtatggg atctttaaca atgccggatt cggcatgtat    300
ggcccccttt ccaccatcag ccgtgcgcag atggaacagc agttttccgc caactttttc    360
ggcgcacacc agctcaccat gcgcctgtta cccgcgatgt taccgcacgg tgaagggcgt    420
attgtgatga catcatcggt gatgggatta atctccacgc cgggtcgtgg cgcttacgcg    480
gccagtaaat atgcgctgga ggcgtggtca gatgcactgc gcatggagct gcgccacagc    540
ggaattaaag tcagcctgat cgaacccggt cccattcgta ctcgcttcac cgacaacgtc    600
aaccagacgc aaagtgataa accagtcgaa aatcccggca tcgccgcccg ctttacgttg    660
ggaccggaag cggtggtgga caaagtacgc catgctttta ttagcgagaa gccgaagatg    720
cgctatccgg tgacgctggt gacctgggcg gtaatggtgc ttaagcgcct gctgccgggg    780
cgcgtgatgg acaaaatatt gcaggggtaa                                    810
```

<210> SEQ ID NO 117
<211> LENGTH: 1863
<212> TYPE: DNA
<213> ORGANISM: Escherichia coli dxs

<400> SEQUENCE: 117

```
atgagttttg atattgccaa atacccgacc ctggcactgg tcgactccac ccaggagtta     60
cgactgttgc cgaaagagag tttaccgaaa ctctgcgacg aactgcgccg ctatttactc    120
gacagcgtga gccgttccag cgggcacttc gcctccgggc tgggcacggt cgaactgacc    180
gtggcgctgc actatgtcta caacaccccg tttgaccaat tgatttggga tgtggggcat    240
caggcttatc cgcataaaat tttgaccgga cgccgcgaca aaatcggcac catccgtcag    300
aaaggcggtc tgcacccgtt cccgtggcgc ggcgaaagcg aatatgacgt attaagcgtc    360
gggcattcat caacctccat cagtgccgga attggtattg cggttgctgc cgaaaaagaa    420
ggcaaaaatc gccgcaccgt ctgtgtcatt ggcgatggcg cgattaccgc aggcatggcg    480
```

```
tttgaagcga tgaatcacgc gggcgatatc cgtcctgata tgctggtgat tctcaacgac    540
aatgaaatgt cgatttccga aaatgtcggc gcgctcaaca accatctggc acagctgctt    600
tccggtaagc tttactcttc actgcgcgaa ggcgggaaaa aagttttctc tggcgtgccg    660
ccaattaaag agctgctcaa acgcaccgaa gaacatatta aaggcatggt agtgcctggc    720
acgttgtttg aagagctggg ctttaactac atcggcccgg tggacggtca cgatgtgctg    780
gggcttatca ccacgctaaa gaacatgcgc gacctgaaag gcccgcagtt cctgcatatc    840
atgaccaaaa aaggtcgtgg ttatgaaccg gcagaaaaag acccgatcac tttccacgcc    900
gtgcctaaat ttgatccctc cagcggttgt ttgccgaaaa gtagcggcgg tttgccgagc    960
tattcaaaaa tctttggcga ctggttgtgc gaaacggcag cgaaagacaa caagctgatg   1020
gcgattactc cggcgatgcg tgaaggttcc ggcatggtcg agttttcacg taaattcccg   1080
gatcgctact tcgacgtggc aattgccgag caacacgcgg tgacctttgc tgcgggtctg   1140
gcgattggtg ggtacaaacc cattgtcgcg atttactcca ctttcctgca acgcgcctat   1200
gatcaggtgc tgcatgacgt ggcgattcaa aagcttccgg tcctgttcgc catcgaccgc   1260
gcgggcattg ttggtgctga cggtcaaacc catcagggtg cttttgatct ctcttacctg   1320
cgctgcatac cggaaatggt cattatgacc ccgagcgatg aaaacgaatg tcgccagatg   1380
ctctataccg gctatcacta taacgatggc ccgtcagcgg tgcgctaccc gcgtggcaac   1440
gcggtcggcg tggaactgac gccgctggaa aaactaccaa ttggcaaagg cattgtgaag   1500
cgtcgtggcg agaaactggc gatccttaac tttggtacgc tgatgccaga agcggcgaaa   1560
gtcgccgaat cgctgaacgc cacgctggtc gatatgcgtt ttgtgaaacc gcttgatgaa   1620
gcgttaattc tggaaatggc cgccagccat gaagcgctgg tcaccgtaga agaaaacgcc   1680
attatgggcg gcgcaggcag cggcgtgaac gaagtgctga tggcccatcg taaaccagta   1740
cccgtgctga acattggcct gccggacttc tttattccgc aaggaactca ggaagaaatg   1800
cgcgccgaac tcggcctcga tgccgctggt atggaagcca aaatcaaggc ctggctggca   1860
taa                                                                 1863
```

<210> SEQ ID NO 118
<211> LENGTH: 1197
<212> TYPE: DNA
<213> ORGANISM: Escherichia coli dxr

<400> SEQUENCE: 118

```
atgaagcaac tcaccattct gggctcgacc ggctcgattg gttgcagcac gctggacgtg     60
gtgcgccata atcccgaaca cttccgcgta gttgcgctgg tggcaggcaa aaatgtcact    120
cgcatggtag aacagtgcct ggaattctct ccccgctatg ccgtaatgga cgatgaagcg    180
agtgcgaaac ttcttaaaac gatgctacag caacagggta gccgcaccga agtcttaagt    240
gggcaacaag ccgcttgcga tatggcagcg cttgaggatg ttgatcaggt gatggcagcc    300
attgttggcg ctgctgggct gttacctacg cttgctgcga tccgcgcggg taaaaccatt    360
ttgctggcca ataaagaatc actggttacc tgcggacgtc tgtttatgga cgccgtaaag    420
cagagcaaag cgcaattgtt accggtcgat agcgaacata acgccatttt tcagagttta    480
ccgcaaccta tccagcataa tctgggatac gctgaccttg agcaaaatgg cgtggtgtcc    540
attttactta ccgggtctgg tggccctttc cgtgagacgc cattgcgcga tttggcaaca    600
atgacgccgg atcaagcctg ccgtcatccg aactggtcga tggggcgtaa aatttctgtc    660
```

```
gattcggcta ccatgatgaa caaaggtctg gaatacattg aagcgcgttg gctgtttaac    720

gccagcgcca gccagatgga agtgctgatt cacccgcagt cagtgattca ctcaatggtg    780

cgctatcagg acggcagtgt tctggcgcag ctgggggaac cggatatgcg tacgccaatt    840

gcccacacca tggcatggcc gaatcgcgtg aactctggcg tgaagccgct cgatttttgc    900

aaactaagtg cgttgacatt tgccgcaccg gattatgatc gttatccatg cctgaaactg    960

gcgatggagg cgttcgaaca aggccaggca gcgacgacag cattgaatgc cgcaaacgaa   1020

atcaccgttg ctgcttttct tgcgcaacaa atccgcttta cggatatcgc tgcgttgaat   1080

ttatccgtac tggaaaaaat ggatatgcgc gaaccacaat gtgtggacga tgtgttatct   1140

gttgatgcga acgcgcgtga agtcgccaga aaagaggtga tgcgtctcgc aagctga      1197
```

<210> SEQ ID NO 119
<211> LENGTH: 900
<212> TYPE: DNA
<213> ORGANISM: Escherichia coli ispA

<400> SEQUENCE: 119

```
atggactttc cgcagcaact cgaagcctgc gttaagcagg ccaaccaggc gctgagccgt     60

tttatcgccc cactgccctt tcagaacact cccgtggtcg aaaccatgca gtatggcgca    120

ttattaggtg gtaagcgcct gcgacctttc ctggtttatg ccaccggtca tatgttcggc    180

gttagcacaa acacgctgga cgcacccgct gccgccgttg agtgtatcca cgcttactca    240

ttaattcatg atgatttacc ggcaatggat gatgacgatc tgcgtcgcgg tttgccaacc    300

tgccatgtga agtttggcga agcaaacgcg attctcgctg gcgacgcttt acaaacgctg    360

gcgttctcga ttttaagcga tgccgatatg ccggaagtgt cggaccgcga cagaatttcg    420

atgatttctg aactggcgag cgccagtggt attgccggaa tgtgcggtgg tcaggcatta    480

gatttagacg cggaaggcaa acacgtacct ctggacgcgc ttgagcgtat tcatcgtcat    540

aaaaccggcg cattgattcg cgccgccgtt cgccttggtg cattaagcgc cggagataaa    600

ggacgtcgtg ctctgccggt actcgacaag tatgcagaga gcatcggcct tgccttccag    660

gttcaggatg acatcctgga tgtggtggga gatactgcaa cgttgggaaa acgccagggt    720

gccgaccagc aacttggtaa aagtacctac cctgcacttc tgggtcttga gcaagcccgg    780

aagaaagccc gggatctgat cgacgatgcc cgtcagtcgc tgaaacaact ggctgaacag    840

tcactcgata cctcggcact ggaagcgcta gcggactaca tcatccagcg taataaataa    900
```

<210> SEQ ID NO 120
<211> LENGTH: 1656
<212> TYPE: DNA
<213> ORGANISM: Clausena lansium STS

<400> SEQUENCE: 120

```
atgtcaactc aacaagtttc atcagagaac attgttcgta acgctgcgaa tttccatcct     60

aatatatggg gaaaccattt cctcacatgt ccttctcaga cgattgatag ttggactcaa    120

cagcaccaca aagaactgaa agaagaggtg aggaaaatga tggtgtctga tgcaaataaa    180

cctgcccaga gattgcgctt gattgatact gtccaaaggc taggtgtggc ttaccacttt    240

gaaaaggaga ttgatgatgc attggagaaa ataggtcatg acccttttga tgataaagat    300

gatctctaca ttgtctctct ttgttttcga ttgctgaggc agcatggaat taagatatca    360

tgtgatgtgt ttgagaagtt taaagatgac gatggaaaat tcaaggcatc attgatgaat    420

gatgttcaag gcatgctaag tttatatgag gcagcacacc tagccattca cggagaagat    480
```

attttagatg aagcaattgt tttcacgacc actcacctta agtcaacggt atctaattct 540
cctgtaaact ctacttttgc tgaacaaata cgtcattctc tcagagttcc tctccgtaaa 600
gctgtaccta ggttagagtc gaggtatttc ttggatatct attcaagaga tgatttgcac 660
gataaaactt tgctcaattt cgcaaagtta gactttaata tactacaagc aatgcaccag 720
aaggaagcaa gtgagatgac caggtggtgg agagattttg acttccttaa aaagctgcct 780
tatataagag acagagtcgt ggagctatat ttttggattc tggtgggagt gtcttatcag 840
cccaaattca gcactggtag aatttttttg tccaaaataa tatgccttga gaccctcgta 900
gatgatacat ttgacgccta cggtactttt gacgagctcg caatctttac tgaagcagtt 960
acaagatggg accttggcca cagagatgca ctaccagaat acatgaaatt cattttcaag 1020
acactcattg atgtctacag tgaagctgag caagaactgg caaaggaagg gagatcatac 1080
agcatacact atgcaatacg atcgttccaa gaactagtta tgaagtactt ctgcgaagcc 1140
aagtggttaa ataaaggtta tgttccgagc ctggacgatt ataaatcagt ttcattaaga 1200
agtatcggtt ttttaccgat agcggtagct tccttcgttt tcatgggtga tattgcaact 1260
aaggaggtct ttgaatggga aatgaataac cctaagatca taatagccgc agaaacgatt 1320
ttcagattcc tggatgacat agcaggccat aggtttgagc aaaagagaga acatagtcca 1380
tcagctattg aatgctacaa gaatcaacat ggagtgtctg aggaagaggc agttaaagcg 1440
ttgtcgttag aagttgctaa tagttggaaa gatataaatg aggagctgct tctcaaccca 1500
atggctattc ctttacctct gcttcaggtg attcttgatc tctcacgttc ggccgatttt 1560
atgtacggta atgctcaaga tcgcttcacg cattcaacga tgatgaaaga ccaagttgat 1620
ttggtgctga aggaccccgt taagcttgac gattaa 1656

<210> SEQ ID NO 121
<211> LENGTH: 1719
<212> TYPE: DNA
<213> ORGANISM: Artificial Sequence
<220> FEATURE:
<223> OTHER INFORMATION: Matricaria recutita MrBBS

<400> SEQUENCE: 121
atgtcaaccc tgtcagtctc cacgccgtcc ttctcatcgt cgccgctgtc ctcagtgaac 60
aaaaatagca cgaaacaaca cgttacgcgc aatagtgtga tctttcatga ttccatttgg 120
ggcgaccagt tcctggaata caaagaaaaa ttcaacgttg caaccgaaaa acaactgatt 180
gaagaactga aagaagaagt ccgcaatgaa ctgatgatcc gtgcgtgcaa cgaagccagt 240
cgctatatta aactgatcca gctgattgat gtggttgaac gtctgggcct ggcctaccac 300
tttgaaaaag aaatcgaaga atccctgcaa catatttatg ttacctacgg tcacaaatgg 360
acgaactaca acaacatcga aagcctgtct ctgtggtttc gcctgctgcg tcagaacggt 420
tttaatgtca gctctgatat cttcgaaaac catattgacg aaaaaggcaa tttccaagaa 480
agtctgtgca acgatccgca aggcatgctg gcactgtatg aagcggccta catgcgcgtg 540
gaaggcgaaa ttatcctgga caaagctctg gaatttacca aactgcacct gggtattatc 600
agcaacgatc cgtcttgtga cagttccctg cgtacggaaa ttaaacaggc gctgaaacag 660
ccgctgcgtc gccgtctgcc gcgtctggaa gcagttcgtt atattgctat ctaccagcaa 720
aaagcgagtc attccgaagt cctgctgaaa ctggccaaac tggatttcaa tgtgctgcag 780
gaaatgcaca aagacgaact gtcacaaatt tgtaaatggt ggaaagacct ggacatccgt 840

-continued

```
aacaaactgc cgtatgttcg cgatcgtctg attgaaggct atttttggat tctgggtatt    900

tacttcgaac cgcagcattc gcgcacccgt atgtttctga tgaaaacgtg catgtggctg    960

atcgtcctgg atgacacctt tgataattat ggcacgtacg aagaactgga aattttcacc   1020

caggcggtgg aacgctggag catcacgtgt ctggatgaac tgccggaata catgaaactg   1080

atctaccatg aacagttccg tgtgcaccaa gaaatggaag aatctctgga aaaagaaggt   1140

aaagcatacc agatccatta catcaaagaa atggctaaag aaggcacccg ctctctgctg   1200

ctggaagcga aatggctgaa agaaggttat atgccgacgc tggatgaata cctgtcaaac   1260

tcgctggtta cctgcggcta tgcactgatg acggctcgct catacgttgc ccgtgatgac   1320

ggtattgtca ccgaagatgc gtttaaatgg gtggccacgc acccgccgat cgttaaagca   1380

gcttgtaaaa ttctgcgtct gatggatgac atcgcgaccc ataaagaaga acaggaacgc   1440

ggccacatcg cctcatcgat tgaatgctat cgtaaagaaa ccggtgcatc tgaagaagaa   1500

gcgtgtatgg attttctgaa acaggtcgaa gacggctgga aagtgatcaa tcaagaatca   1560

ctgatgccga ccgatgtgcc gttcccgctg ctgatcccgg cgattaacct ggcccgcgtt   1620

tcggacacgc tgtataaaga taacgacggt tacaatcatg ctgataaaga agtgattggt   1680

tacattaaaa gtctgtttgt ccacccgatg attgtgtga                           1719
```

<210> SEQ ID NO 122
<211> LENGTH: 717
<212> TYPE: DNA
<213> ORGANISM: Artificial Sequence
<220> FEATURE:
<223> OTHER INFORMATION: EGFP

<400> SEQUENCE: 122

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaag       717
```

<210> SEQ ID NO 123
<211> LENGTH: 1233
<212> TYPE: DNA
<213> ORGANISM: Artificial Sequence
<220> FEATURE:
<223> OTHER INFORMATION: MG1363 (Hydroxymethylglutaryl-CoA reductase)

<400> SEQUENCE: 123

```
atgagaaaaa aattttatca aatgtcgcca caagagcgat tgaattcgtt aaacttatcc     60

gaaaagagtc aagaaatttt aagtgagatg gccctagata caactatttt ggacaatctc    120

atagaaaatc aaatttctga atttgaattg ccaatgggaa ttgcccaaaa ttttgttatt    180
```

```
aatggacaaa gttttctaat accaatggtt acagaggaac cgtcagtaat tgccgcagca    240

agtaatggag caaaaatagc tggaaatttt gtagctgaaa ttaaagaacg tttaatgcgt    300

ggtcaaattg tattttatga tgttaaaaat tcagataaga ttgcaaatga aatacttgaa    360

aagcaagaaa aaatctttga acaagccgaa ctttcttacc cttcaatcgt taaacgaggt    420

ggcggtttga gagaggtttc tagtcggatt ttctctagtc aaaagttttt atctgttgat    480

gtcaaggttg atgttaaaga cgccatgggt gcaaatatta ttaattcaat cttagaggga    540

attgctgaac tctttcggag gtggtttcct gatgaaaaaa ttctgtttag tattttatca    600

aattatgcta ctgaatcact agtgaaagtg acctgtgaaa ttccggttga acgcctttca    660

aaaaaagcag atggatatga aattggtcaa aaaattatgg ctgcttccca atattcaaaa    720

attgatcctt atcgtgctag cacccataac aaagggatta tgaacggtat caatgcggtc    780

attttagcta caggaaatga tactcgggcc atctcagctg ctattcatgc ttatgcggca    840

aaagatggag cctaccaagg gttagccaac tgggaacttc aagagaaaat gttagttggc    900

gaactcgaat ttcctttacc agtggcaact gtcggagggg gagtcaaggt tttgccaaaa    960

gcacaagcgg ccatggagat tctgggtatc agtgatgcta aggagctcgc aaaagttatt   1020

gctgcagtgg gactagctca aaacttagcc gctttacgtg ccctagtttc agaaggaatt   1080

caacagggac acatgagtct acaagctcgt tctttggctt tgagtgtagg agcacaagcg   1140

gatgaaatcg cgatattaag tcaacaattg cgcaaagaaa aagtgatgaa tcaagaagta   1200

gcccaaaatt tactaaaaaa tttgagaaaa taa                                1233
```

```
<210> SEQ ID NO 124
<211> LENGTH: 803
<212> TYPE: PRT
<213> ORGANISM: Enterococcus faecalis mvaE

<400> SEQUENCE: 124

Leu Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
                85                  90                  95

Leu Ala Lys Gln Leu Ile Gln Leu Gly Glu Ala Glu Val Leu Ile Ala
            100                 105                 110

Gly Gly Ile Glu Asn Met Ser Gln Ala Pro Lys Leu Gln Arg Phe Asn
        115                 120                 125

Tyr Glu Thr Glu Ser Tyr Asp Ala Pro Phe Ser Ser Met Met Tyr Asp
    130                 135                 140

Gly Leu Thr Asp Ala Phe Ser Gly Gln Ala Met Gly Leu Thr Ala Glu
145                 150                 155                 160

Asn Val Ala Glu Lys Tyr His Val Thr Arg Glu Glu Gln Asp Gln Phe
                165                 170                 175

Ser Val His Ser Gln Leu Lys Ala Ala Gln Ala Gln Ala Glu Gly Ile
```

```
            180                 185                 190

Phe Ala Asp Glu Ile Ala Pro Leu Glu Val Ser Gly Thr Leu Val Glu
        195                 200                 205

Lys Asp Glu Gly Ile Arg Pro Asn Ser Ser Val Glu Lys Leu Gly Thr
    210                 215                 220

Leu Lys Thr Val Phe Lys Glu Asp Gly Thr Val Thr Ala Gly Asn Ala
225                 230                 235                 240

Ser Thr Ile Asn Asp Gly Ala Ser Ala Leu Ile Ile Ala Ser Gln Glu
                245                 250                 255

Tyr Ala Glu Ala His Gly Leu Pro Tyr Leu Ala Ile Ile Arg Asp Ser
            260                 265                 270

Val Glu Val Gly Ile Asp Pro Ala Tyr Met Gly Ile Ser Pro Ile Lys
        275                 280                 285

Ala Ile Gln Lys Leu Leu Ala Arg Asn Gln Leu Thr Thr Glu Glu Ile
    290                 295                 300

Asp Leu Tyr Glu Ile Asn Glu Ala Phe Ala Ala Thr Ser Ile Val Val
305                 310                 315                 320

Gln Arg Glu Leu Ala Leu Pro Glu Glu Lys Val Asn Ile Tyr Gly Gly
                325                 330                 335

Gly Ile Ser Leu Gly His Ala Ile Gly Ala Thr Gly Ala Arg Leu Leu
            340                 345                 350

Thr Ser Leu Ser Tyr Gln Leu Asn Gln Lys Glu Lys Lys Tyr Gly Val
        355                 360                 365

Ala Ser Leu Cys Ile Gly Gly Gly Leu Gly Leu Ala Met Leu Leu Glu
    370                 375                 380

Arg Pro Gln Gln Lys Lys Asn Ser Arg Phe Tyr Gln Met Ser Pro Glu
385                 390                 395                 400

Glu Arg Leu Ala Ser Leu Leu Asn Glu Gly Gln Ile Ser Ala Asp Thr
                405                 410                 415

Lys Lys Glu Phe Glu Asn Thr Ala Leu Ser Ser Gln Ile Ala Asn His
            420                 425                 430

Met Ile Glu Asn Gln Ile Ser Glu Thr Glu Val Pro Met Gly Val Gly
        435                 440                 445

Leu His Leu Thr Val Asp Glu Thr Asp Tyr Leu Val Pro Met Ala Thr
    450                 455                 460

Glu Glu Pro Ser Val Ile Ala Ala Leu Ser Asn Gly Ala Lys Ile Ala
465                 470                 475                 480

Gln Gly Phe Lys Thr Val Asn Gln Gln Arg Leu Met Arg Gly Gln Ile
                485                 490                 495

Val Phe Tyr Asp Val Ala Asp Ala Glu Ser Leu Ile Asp Glu Leu Gln
            500                 505                 510

Val Arg Glu Thr Glu Ile Phe Gln Gln Ala Glu Leu Ser Tyr Pro Ser
        515                 520                 525

Ile Val Lys Arg Gly Gly Gly Leu Arg Asp Leu Gln Tyr Arg Ala Phe
    530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
                565                 570                 575

Phe Arg Glu Trp Phe Ala Glu Gln Lys Ile Leu Phe Ser Ile Leu Ser
            580                 585                 590

Asn Tyr Ala Thr Glu Ser Val Val Thr Met Lys Thr Ala Ile Pro Val
        595                 600                 605
```

```
Ser Arg Leu Ser Lys Gly Ser Asn Gly Arg Glu Ile Ala Glu Lys Ile
    610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Val Leu Ala Thr
                645                 650                 655

Gly Asn Asp Thr Arg Ala Val Ser Ala Ser Cys His Ala Phe Ala Val
            660                 665                 670

Lys Glu Gly Arg Tyr Gln Gly Leu Thr Ser Trp Thr Leu Asp Gly Glu
        675                 680                 685

Gln Leu Ile Gly Glu Ile Ser Val Pro Leu Ala Leu Ala Thr Val Gly
    690                 695                 700

Gly Ala Thr Lys Val Leu Pro Lys Ser Gln Ala Ala Ala Asp Leu Leu
705                 710                 715                 720

Ala Val Thr Asp Ala Lys Glu Leu Ser Arg Val Val Ala Ala Val Gly
                725                 730                 735

Leu Ala Gln Asn Leu Ala Ala Leu Arg Ala Leu Val Ser Glu Gly Ile
            740                 745                 750

Gln Lys Gly His Met Ala Leu Gln Ala Arg Ser Leu Ala Met Thr Val
        755                 760                 765

Gly Ala Thr Gly Lys Glu Val Glu Ala Val Ala Gln Gln Leu Lys Arg
    770                 775                 780

Gln Lys Thr Met Asn Gln Asp Arg Ala Leu Ala Ile Leu Asn Asp Leu
785                 790                 795                 800

Arg Lys Gln


<210> SEQ ID NO 125
<211> LENGTH: 383
<212> TYPE: PRT
<213> ORGANISM: Enterococcus faecalis mvaS

<400> SEQUENCE: 125

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175
```

```
Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
                325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
        355                 360                 365

Tyr Ser Ile Ser Ala Ile Asn Asn Thr Val Arg Ser Tyr Arg Asn
    370                 375                 380


<210> SEQ ID NO 126
<211> LENGTH: 292
<212> TYPE: PRT
<213> ORGANISM: Streptococcus pneumoniae mvaK1

<400> SEQUENCE: 126

Met Thr Lys Lys Val Gly Val Gly Gln Ala His Ser Lys Ile Ile Leu
1               5                   10                  15

Ile Gly Glu His Ala Val Val Tyr Gly Tyr Pro Ala Ile Ser Leu Pro
            20                  25                  30

Leu Leu Glu Val Glu Val Thr Cys Lys Val Val Pro Ala Glu Ser Pro
        35                  40                  45

Trp Arg Leu Tyr Glu Glu Asp Thr Leu Ser Met Ala Val Tyr Ala Ser
    50                  55                  60

Leu Glu Tyr Leu Asn Ile Thr Glu Ala Cys Ile Arg Cys Glu Ile Asp
65                  70                  75                  80

Ser Ala Ile Pro Glu Lys Arg Gly Met Gly Ser Ser Ala Ala Ile Ser
                85                  90                  95

Ile Ala Ala Ile Arg Ala Val Phe Asp Tyr Tyr Gln Ala Asp Leu Pro
            100                 105                 110

His Asp Val Leu Glu Ile Leu Val Asn Arg Ala Glu Met Ile Ala His
        115                 120                 125

Met Asn Pro Ser Gly Leu Asp Ala Lys Thr Cys Leu Ser Asp Gln Pro
    130                 135                 140

Ile Arg Phe Ile Lys Asn Val Gly Phe Thr Glu Leu Glu Met Asp Leu
145                 150                 155                 160

Ser Ala Tyr Leu Val Ile Ala Asp Thr Gly Val Tyr Gly His Thr Arg
```

```
                165                 170                 175

Glu Ala Ile Gln Val Val Gln Asn Lys Gly Lys Asp Ala Leu Pro Phe
            180                 185                 190

Leu His Ala Leu Gly Glu Leu Thr Gln Gln Ala Glu Val Ala Ile Ser
        195                 200                 205

Gln Lys Asp Ala Glu Gly Leu Gly Gln Ile Leu Ser Gln Ala His Leu
    210                 215                 220

His Leu Lys Glu Ile Gly Val Ser Ser Pro Glu Ala Asp Phe Leu Val
225                 230                 235                 240

Glu Thr Thr Leu Ser His Gly Ala Leu Gly Ala Lys Met Ser Gly Gly
                245                 250                 255

Gly Leu Gly Gly Cys Ile Ile Ala Leu Val Thr Asn Leu Thr His Ala
            260                 265                 270

Gln Glu Leu Ala Glu Arg Leu Glu Glu Lys Gly Ala Val Gln Thr Trp
        275                 280                 285

Ile Glu Ser Leu
    290


<210> SEQ ID NO 127
<211> LENGTH: 336
<212> TYPE: PRT
<213> ORGANISM: Streptococcus pneumoniae mvaK2

<400> SEQUENCE: 127

Met Ile Ala Val Lys Thr Cys Gly Lys Leu Tyr Trp Ala Gly Glu Tyr
1               5                   10                  15

Ala Ile Leu Glu Pro Gly Gln Leu Ala Leu Ile Lys Asp Ile Pro Ile
            20                  25                  30

Tyr Met Arg Ala Glu Ile Ala Phe Ser Asp Ser Tyr Arg Ile Tyr Ser
        35                  40                  45

Asp Met Phe Asp Phe Ala Val Asp Leu Arg Pro Asn Pro Asp Tyr Ser
    50                  55                  60

Leu Ile Gln Glu Thr Ile Ala Leu Met Gly Asp Phe Leu Ala Val Arg
65                  70                  75                  80

Gly Gln Asn Leu Arg Pro Phe Ser Leu Lys Ile Cys Gly Lys Met Glu
                85                  90                  95

Arg Glu Gly Lys Lys Phe Gly Leu Gly Ser Ser Gly Ser Val Val Val
            100                 105                 110

Leu Val Val Lys Ala Leu Leu Ala Leu Tyr Asn Leu Ser Val Asp Gln
        115                 120                 125

Asn Leu Leu Phe Lys Leu Thr Ser Ala Val Leu Leu Lys Arg Gly Asp
    130                 135                 140

Asn Gly Ser Met Gly Asp Leu Ala Cys Ile Val Ala Glu Asp Leu Val
145                 150                 155                 160

Leu Tyr Gln Ser Phe Asp Arg Gln Lys Ala Ala Ala Trp Leu Glu Glu
                165                 170                 175

Glu Asn Leu Ala Thr Val Leu Glu Arg Asp Trp Gly Phe Phe Ile Ser
            180                 185                 190

Gln Val Lys Pro Thr Leu Glu Cys Asp Phe Leu Val Gly Trp Thr Lys
        195                 200                 205

Glu Val Ala Val Ser Ser His Met Val Gln Gln Ile Lys Gln Asn Ile
    210                 215                 220

Asn Gln Asn Phe Leu Ser Ser Ser Lys Glu Thr Val Val Ser Leu Val
225                 230                 235                 240
```

```
Glu Ala Leu Glu Gln Gly Lys Ala Glu Lys Val Ile Glu Gln Val Glu
                245                 250                 255

Val Ala Ser Lys Leu Leu Glu Gly Leu Ser Thr Asp Ile Tyr Thr Pro
            260                 265                 270

Leu Leu Arg Gln Leu Lys Glu Ala Ser Gln Asp Leu Gln Ala Val Ala
        275                 280                 285

Lys Ser Ser Gly Ala Gly Gly Gly Asp Cys Gly Ile Ala Leu Ser Phe
    290                 295                 300

Asp Ala Gln Ser Ser Arg Asn Thr Leu Lys Asn Arg Trp Ala Asp Leu
305                 310                 315                 320

Gly Ile Glu Leu Leu Tyr Gln Glu Arg Ile Gly His Asp Asp Lys Ser
                325                 330                 335


<210> SEQ ID NO 128
<211> LENGTH: 317
<212> TYPE: PRT
<213> ORGANISM: Streptococcus pneumoniae mvaD

<400> SEQUENCE: 128

Met Asp Arg Glu Pro Val Thr Val Arg Ser Tyr Ala Asn Ile Ala Ile
1               5                   10                  15

Ile Lys Tyr Trp Gly Lys Lys Lys Glu Lys Glu Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Ala Asn Val Thr Ala Asp Glu Phe Tyr Ile Asn Gly
    50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Ser Gly Leu Ser
            100                 105                 110

Ala Leu Val Lys Ala Cys Asn Ala Tyr Phe Lys Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285
```

```
Asp Leu Glu His Leu Ser Glu Ile Phe Gly Gln Arg Tyr Arg Leu Ile
    290                 295                 300

Val Ser Lys Thr Lys Asp Leu Ser Gln Asp Asp Cys Cys
305                 310                 315


<210> SEQ ID NO 129
<211> LENGTH: 182
<212> TYPE: PRT
<213> ORGANISM: Escherichia coli idi

<400> SEQUENCE: 129

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

Thr Arg Arg Ala Leu Ser Lys Lys Ala Trp Pro Gly Val Trp Thr Asn
    50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
    130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180


<210> SEQ ID NO 130
<211> LENGTH: 305
<212> TYPE: PRT
<213> ORGANISM: Haematococcus pluvialis ipiHp1

<400> SEQUENCE: 130

Met Leu Arg Ser Leu Leu Arg Gly Leu Thr His Ile Pro Arg Val Asn
1               5                   10                  15

Ser Ala Gln Gln Pro Ser Cys Ala His Ala Arg Leu Gln Phe Lys Leu
            20                  25                  30

Arg Ser Met Gln Met Thr Leu Met Gln Pro Ser Ile Ser Ala Asn Leu
        35                  40                  45

Ser Arg Ala Glu Asp Arg Thr Asp His Met Arg Gly Ala Ser Thr Trp
    50                  55                  60

Ala Gly Gly Gln Ser Gln Asp Glu Leu Met Leu Lys Asp Glu Cys Ile
65                  70                  75                  80

Leu Val Asp Val Glu Asp Asn Ile Thr Gly His Ala Ser Lys Leu Glu
                85                  90                  95

Cys His Lys Phe Leu Pro His Gln Pro Ala Gly Leu Leu His Arg Ala
            100                 105                 110
```

Phe Ser Val Phe Leu Phe Asp Asp Gln Gly Arg Leu Leu Leu Gln Gln
115 120 125

Arg Ala Arg Ser Lys Ile Thr Phe Pro Ser Val Trp Thr Asn Thr Cys
130 135 140

Cys Ser His Pro Leu His Gly Gln Thr Pro Asp Glu Val Asp Gln Leu
145 150 155 160

Ser Gln Val Ala Asp Gly Thr Val Pro Gly Ala Lys Ala Ala Ala Ile
165 170 175

Arg Lys Leu Glu His Glu Leu Gly Ile Pro Ala His Gln Leu Pro Ala
180 185 190

Ser Ala Phe Arg Phe Leu Thr Arg Leu His Tyr Cys Ala Ala Asp Val
195 200 205

Gln Pro Ala Ala Thr Gln Ser Ala Leu Trp Gly Glu His Glu Met Asp
210 215 220

Tyr Ile Leu Phe Ile Arg Ala Asn Val Thr Leu Ala Pro Asn Pro Asp
225 230 235 240

Glu Val Asp Glu Val Arg Tyr Val Thr Gln Glu Glu Leu Arg Gln Met
245 250 255

Met Gln Pro Asp Asn Gly Leu Gln Trp Ser Pro Trp Phe Arg Ile Ile
260 265 270

Ala Ala Arg Phe Leu Glu Arg Trp Trp Ala Asp Leu Asp Ala Ala Leu
275 280 285

Asn Thr Asp Lys His Glu Asp Trp Gly Thr Val His His Ile Asn Glu
290 295 300

Ala
305

<210> SEQ ID NO 131
<211> LENGTH: 309
<212> TYPE: PRT
<213> ORGANISM: pantoea agglomerans crtB

<400> SEQUENCE: 131

Met Ser Gln Pro Pro Leu Leu Asp His Ala Thr Gln Thr Met Ala Asn
1 5 10 15

Gly Ser Lys Ser Phe Ala Thr Ala Ala Lys Leu Phe Asp Pro Ala Thr
20 25 30

Arg Arg Ser Val Leu Met Leu Tyr Thr Trp Cys Arg His Cys Asp Asp
35 40 45

Val Ile Asp Asp Gln Thr His Gly Phe Ala Ser Glu Ala Ala Ala Glu
50 55 60

Glu Glu Ala Thr Gln Arg Leu Ala Arg Leu Arg Thr Leu Thr Leu Ala
65 70 75 80

Ala Phe Glu Gly Ala Glu Met Gln Asp Pro Ala Phe Ala Ala Phe Gln
85 90 95

Glu Val Ala Leu Thr His Gly Ile Thr Pro Arg Met Ala Leu Asp His
100 105 110

Leu Asp Gly Phe Ala Met Asp Val Ala Gln Thr Arg Tyr Val Thr Phe
115 120 125

Glu Asp Thr Leu Arg Tyr Cys Tyr His Val Ala Gly Val Val Gly Leu
130 135 140

Met Met Ala Arg Val Met Gly Val Arg Asp Glu Arg Val Leu Asp Arg
145 150 155 160

Ala Cys Asp Leu Gly Leu Ala Phe Gln Leu Thr Asn Ile Ala Arg Asp

```
                165                 170                 175

Ile Ile Asp Asp Ala Ala Ile Asp Arg Cys Tyr Leu Pro Ala Glu Trp
            180                 185                 190

Leu Gln Asp Ala Gly Leu Thr Pro Glu Asn Tyr Ala Ala Arg Glu Asn
        195                 200                 205

Arg Ala Ala Leu Ala Arg Val Ala Glu Arg Leu Ile Asp Ala Ala Glu
    210                 215                 220

Pro Tyr Tyr Ile Ser Ser Gln Ala Gly Leu His Asp Leu Pro Pro Arg
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
            260                 265                 270

Thr Ser Lys Gly Glu Lys Ile Ala Met Leu Met Ala Ala Pro Gly Gln
        275                 280                 285

Val Ile Arg Ala Lys Thr Thr Arg Val Thr Pro Arg Pro Ala Gly Leu
    290                 295                 300

Trp Gln Arg Pro Val
305


<210> SEQ ID NO 132
<211> LENGTH: 492
<212> TYPE: PRT
<213> ORGANISM: pantoea agglomerans crtI

<400> SEQUENCE: 132

Met Lys Lys Thr Val Val Ile Gly Ala Gly Phe Gly Gly Leu Ala Leu
1               5                   10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Ala Glu Leu Glu Ala Gln Ile Thr Gln
            100                 105                 110

Phe Asn Pro Arg Asp Val Glu Gly Tyr Arg Arg Phe Leu Ala Tyr Ser
        115                 120                 125

Gln Ala Val Phe Gln Glu Gly Tyr Leu Arg Leu Gly Ser Val Pro Phe
    130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
                165                 170                 175

Glu His Leu Arg Gln Ala Phe Ser Phe His Ser Leu Leu Val Gly Gly
            180                 185                 190

Asn Pro Phe Thr Thr Ser Ser Ile Tyr Thr Leu Ile His Ala Leu Glu
        195                 200                 205

Arg Glu Trp Gly Val Trp Phe Pro Glu Gly Gly Thr Gly Ala Leu Val
    210                 215                 220
```

```
Asn Gly Met Val Lys Leu Phe Thr Asp Leu Gly Gly Glu Ile Glu Leu
225                 230                 235                 240

Asn Ala Arg Val Glu Glu Leu Val Val Ala Asp Asn Arg Val Ser Gln
                245                 250                 255

Val Arg Leu Ala Asp Gly Arg Ile Phe Asp Thr Asp Ala Val Ala Ser
            260                 265                 270

Asn Ala Asp Val Val Asn Thr Tyr Lys Lys Leu Leu Gly His His Pro
        275                 280                 285

Val Gly Gln Lys Arg Ala Ala Ala Leu Glu Arg Lys Ser Met Ser Asn
    290                 295                 300

Ser Leu Phe Val Leu Tyr Phe Gly Leu Asn Gln Pro His Ser Gln Leu
305                 310                 315                 320

Ala His His Thr Ile Cys Phe Gly Pro Arg Tyr Arg Glu Leu Ile Asp
                325                 330                 335

Glu Ile Phe Thr Gly Ser Ala Leu Ala Asp Asp Phe Ser Leu Tyr Leu
            340                 345                 350

His Ser Pro Cys Val Thr Asp Pro Ser Leu Ala Pro Pro Gly Cys Ala
        355                 360                 365

Ser Phe Tyr Val Leu Ala Pro Val Pro His Leu Gly Asn Ala Pro Leu
    370                 375                 380

Asp Trp Ala Gln Glu Gly Pro Lys Leu Arg Asp Arg Ile Phe Asp Tyr
385                 390                 395                 400

Leu Glu Glu Arg Tyr Met Pro Gly Leu Arg Ser Gln Leu Val Thr Gln
                405                 410                 415

Arg Ile Phe Thr Pro Ala Asp Phe His Asp Thr Leu Asp Ala His Leu
            420                 425                 430

Gly Ser Ala Phe Ser Ile Glu Pro Leu Leu Thr Gln Ser Ala Trp Phe
        435                 440                 445

Arg Pro His Asn Arg Asp Ser Asp Ile Ala Asn Leu Tyr Leu Val Gly
    450                 455                 460

Ala Gly Thr His Pro Gly Ala Gly Ile Pro Gly Val Val Ala Ser Ala
465                 470                 475                 480

Lys Ala Thr Ala Ser Leu Met Ile Glu Asp Leu Gln
                485                 490


<210> SEQ ID NO 133
<211> LENGTH: 382
<212> TYPE: PRT
<213> ORGANISM: pantoea ananatis crtY

<400> SEQUENCE: 133

Met Gln Pro His Tyr Asp Leu Ile Leu Val Gly Ala Gly Leu Ala Asn
1               5                   10                  15

Gly Leu Ile Ala Leu Arg Leu Gln Gln Gln Pro Asp Met Arg Ile
            20                  25                  30

Leu Leu Ile Asp Ala Ala Pro Gln Ala Gly Gly Asn His Thr Trp Ser
        35                  40                  45

Phe His His Asp Asp Leu Thr Glu Ser Gln His Arg Trp Ile Ala Pro
    50                  55                  60

Leu Val Val His His Trp Pro Asp Tyr Gln Val Arg Phe Pro Thr Arg
65                  70                  75                  80

Arg Arg Lys Leu Asn Ser Gly Tyr Phe Cys Ile Thr Ser Gln Arg Phe
                85                  90                  95

Ala Glu Val Leu Gln Arg Gln Phe Gly Pro His Leu Trp Met Asp Thr
            100                 105                 110
```

```
Ala Val Ala Glu Val Asn Ala Glu Ser Val Arg Leu Lys Lys Gly Gln
        115                 120                 125

Val Ile Gly Ala Arg Ala Val Ile Asp Gly Arg Gly Tyr Ala Ala Asn
    130                 135                 140

Ser Ala Leu Ser Val Gly Phe Gln Ala Phe Ile Gly Gln Glu Trp Arg
145                 150                 155                 160

Leu Ser His Pro His Gly Leu Ser Ser Pro Ile Ile Met Asp Ala Thr
                165                 170                 175

Val Asp Gln Gln Asn Gly Tyr Arg Phe Val Tyr Ser Leu Pro Leu Ser
            180                 185                 190

Pro Thr Arg Leu Leu Ile Glu Asp Thr His Tyr Ile Asp Asn Ala Thr
        195                 200                 205

Leu Asp Pro Glu Cys Ala Arg Gln Asn Ile Cys Asp Tyr Ala Ala Gln
    210                 215                 220

Gln Gly Trp Gln Leu Gln Thr Leu Leu Arg Glu Glu Gln Gly Ala Leu
225                 230                 235                 240

Pro Ile Thr Leu Ser Gly Asn Ala Asp Ala Phe Trp Gln Gln Arg Pro
                245                 250                 255

Leu Ala Cys Ser Gly Leu Arg Ala Gly Leu Phe His Pro Thr Thr Gly
            260                 265                 270

Tyr Ser Leu Pro Leu Ala Val Ala Val Ala Asp Arg Leu Ser Ala Leu
        275                 280                 285

Asp Val Phe Thr Ser Ala Ser Ile His His Ala Ile Thr His Phe Ala
    290                 295                 300

Arg Glu Arg Trp Gln Gln Gln Gly Phe Phe Arg Met Leu Asn Arg Met
305                 310                 315                 320

Leu Phe Leu Ala Gly Pro Ala Asp Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Leu Thr Asp Arg Leu Arg Ile Leu Ser Gly Lys Pro Pro Val
        355                 360                 365

Pro Val Leu Ala Ala Leu Gln Ala Ile Met Thr Thr His Arg
    370                 375                 380


<210> SEQ ID NO 134
<211> LENGTH: 275
<212> TYPE: PRT
<213> ORGANISM: uncultured marine bacterium 66A03 SR

<400> SEQUENCE: 134

Met Gly Leu Met Leu Ile Asp Trp Cys Ala Leu Ala Leu Val Val Phe
1               5                   10                  15

Ile Gly Leu Pro His Gly Ala Leu Asp Ala Ala Ile Ser Phe Ser Met
            20                  25                  30

Ile Ser Ser Ala Lys Arg Ile Ala Arg Leu Ala Gly Ile Leu Leu Ile
        35                  40                  45

Tyr Leu Leu Leu Ala Thr Ala Phe Phe Leu Ile Trp Tyr Gln Leu Pro
    50                  55                  60

Ala Phe Ser Leu Leu Ile Phe Leu Leu Ile Ser Ile Ile His Phe Gly
65                  70                  75                  80

Met Ala Asp Phe Asn Ala Ser Pro Ser Lys Leu Lys Trp Pro His Ile
                85                  90                  95

Ile Ala His Gly Gly Val Val Thr Val Trp Leu Pro Leu Ile Gln Lys
```

```
            100                 105                 110

Asn Glu Val Thr Lys Leu Phe Ser Ile Leu Thr Asn Gly Pro Thr Pro
        115                 120                 125

Ile Leu Trp Asp Ile Leu Leu Ile Phe Phe Leu Cys Trp Ser Ile Gly
    130                 135                 140

Val Cys Leu His Thr Tyr Glu Thr Leu Arg Ser Lys His Tyr Asn Ile
145                 150                 155                 160

Ala Phe Glu Leu Ile Gly Leu Ile Phe Leu Ala Trp Tyr Ala Pro Pro
                165                 170                 175

Leu Val Thr Phe Ala Thr Tyr Phe Cys Phe Ile His Ser Arg Arg His
            180                 185                 190

Phe Ser Phe Val Trp Lys Gln Leu Gln His Met Ser Ser Lys Lys Met
        195                 200                 205

Met Ile Gly Ser Ala Ile Ile Leu Ser Cys Thr Ser Trp Leu Ile Gly
    210                 215                 220

Gly Gly Ile Tyr Phe Phe Leu Asn Ser Lys Met Ile Ala Ser Glu Ala
225                 230                 235                 240

Ala Leu Gln Thr Val Phe Ile Gly Leu Ala Ala Leu Thr Val Pro His
                245                 250                 255

Met Ile Leu Ile Asp Phe Ile Phe Arg Pro His Ser Ser Arg Ile Lys
            260                 265                 270

Ile Lys Asn
        275


<210> SEQ ID NO 135
<211> LENGTH: 269
<212> TYPE: PRT
<213> ORGANISM: Escherichia coli MG1655 YbbO

<400> SEQUENCE: 135

Met Thr His Lys Ala Thr Glu Ile Leu Thr Gly Lys Val Met Gln Lys
1               5                   10                  15

Ser Val Leu Ile Thr Gly Cys Ser Ser Gly Ile Gly Leu Glu Ser Ala
            20                  25                  30

Leu Glu Leu Lys Arg Gln Gly Phe His Val Leu Ala Gly Cys Arg Lys
        35                  40                  45

Pro Asp Asp Val Glu Arg Met Asn Ser Met Gly Phe Thr Gly Val Leu
    50                  55                  60

Ile Asp Leu Asp Ser Pro Glu Ser Val Asp Arg Ala Ala Asp Glu Val
65                  70                  75                  80

Ile Ala Leu Thr Asp Asn Cys Leu Tyr Gly Ile Phe Asn Asn Ala Gly
                85                  90                  95

Phe Gly Met Tyr Gly Pro Leu Ser Thr Ile Ser Arg Ala Gln Met Glu
            100                 105                 110

Gln Gln Phe Ser Ala Asn Phe Phe Gly Ala His Gln Leu Thr Met Arg
        115                 120                 125

Leu Leu Pro Ala Met Leu Pro His Gly Glu Gly Arg Ile Val Met Thr
    130                 135                 140

Ser Ser Val Met Gly Leu Ile Ser Thr Pro Gly Arg Gly Ala Tyr Ala
145                 150                 155                 160

Ala Ser Lys Tyr Ala Leu Glu Ala Trp Ser Asp Ala Leu Arg Met Glu
                165                 170                 175

Leu Arg His Ser Gly Ile Lys Val Ser Leu Ile Glu Pro Gly Pro Ile
            180                 185                 190
```

Arg Thr Arg Phe Thr Asp Asn Val Asn Gln Thr Gln Ser Asp Lys Pro
195 200 205

Val Glu Asn Pro Gly Ile Ala Ala Arg Phe Thr Leu Gly Pro Glu Ala
210 215 220

Val Val Asp Lys Val Arg His Ala Phe Ile Ser Glu Lys Pro Lys Met
225 230 235 240

Arg Tyr Pro Val Thr Leu Val Thr Trp Ala Val Met Val Leu Lys Arg
245 250 255

Leu Leu Pro Gly Arg Val Met Asp Lys Ile Leu Gln Gly
260 265

<210> SEQ ID NO 136
<211> LENGTH: 620
<212> TYPE: PRT
<213> ORGANISM: Escherichia coli dxs

<400> SEQUENCE: 136

Met Ser Phe Asp Ile Ala Lys Tyr Pro Thr Leu Ala Leu Val Asp Ser
1 5 10 15

Thr Gln Glu Leu Arg Leu Leu Pro Lys Glu Ser Leu Pro Lys Leu Cys
20 25 30

Asp Glu Leu Arg Arg Tyr Leu Leu Asp Ser Val Ser Arg Ser Ser Gly
35 40 45

His Phe Ala Ser Gly Leu Gly Thr Val Glu Leu Thr Val Ala Leu His
50 55 60

Tyr Val Tyr Asn Thr Pro Phe Asp Gln Leu Ile Trp Asp Val Gly His
65 70 75 80

Gln Ala Tyr Pro His Lys Ile Leu Thr Gly Arg Arg Asp Lys Ile Gly
85 90 95

Thr Ile Arg Gln Lys Gly Gly Leu His Pro Phe Pro Trp Arg Gly Glu
100 105 110

Ser Glu Tyr Asp Val Leu Ser Val Gly His Ser Ser Thr Ser Ile Ser
115 120 125

Ala Gly Ile Gly Ile Ala Val Ala Ala Glu Lys Glu Gly Lys Asn Arg
130 135 140

Arg Thr Val Cys Val Ile Gly Asp Gly Ala Ile Thr Ala Gly Met Ala
145 150 155 160

Phe Glu Ala Met Asn His Ala Gly Asp Ile Arg Pro Asp Met Leu Val
165 170 175

Ile Leu Asn Asp Asn Glu Met Ser Ile Ser Glu Asn Val Gly Ala Leu
180 185 190

Asn Asn His Leu Ala Gln Leu Leu Ser Gly Lys Leu Tyr Ser Ser Leu
195 200 205

Arg Glu Gly Gly Lys Lys Val Phe Ser Gly Val Pro Pro Ile Lys Glu
210 215 220

Leu Leu Lys Arg Thr Glu Glu His Ile Lys Gly Met Val Val Pro Gly
225 230 235 240

Thr Leu Phe Glu Glu Leu Gly Phe Asn Tyr Ile Gly Pro Val Asp Gly
245 250 255

His Asp Val Leu Gly Leu Ile Thr Thr Leu Lys Asn Met Arg Asp Leu
260 265 270

Lys Gly Pro Gln Phe Leu His Ile Met Thr Lys Lys Gly Arg Gly Tyr
275 280 285

Glu Pro Ala Glu Lys Asp Pro Ile Thr Phe His Ala Val Pro Lys Phe
290 295 300

```
Asp Pro Ser Ser Gly Cys Leu Pro Lys Ser Ser Gly Gly Leu Pro Ser
305                 310                 315                 320

Tyr Ser Lys Ile Phe Gly Asp Trp Leu Cys Glu Thr Ala Ala Lys Asp
                325                 330                 335

Asn Lys Leu Met Ala Ile Thr Pro Ala Met Arg Glu Gly Ser Gly Met
            340                 345                 350

Val Glu Phe Ser Arg Lys Phe Pro Asp Arg Tyr Phe Asp Val Ala Ile
        355                 360                 365

Ala Glu Gln His Ala Val Thr Phe Ala Ala Gly Leu Ala Ile Gly Gly
    370                 375                 380

Tyr Lys Pro Ile Val Ala Ile Tyr Ser Thr Phe Leu Gln Arg Ala Tyr
385                 390                 395                 400

Asp Gln Val Leu His Asp Val Ala Ile Gln Lys Leu Pro Val Leu Phe
                405                 410                 415

Ala Ile Asp Arg Ala Gly Ile Val Gly Ala Asp Gly Gln Thr His Gln
            420                 425                 430

Gly Ala Phe Asp Leu Ser Tyr Leu Arg Cys Ile Pro Glu Met Val Ile
        435                 440                 445

Met Thr Pro Ser Asp Glu Asn Glu Cys Arg Gln Met Leu Tyr Thr Gly
    450                 455                 460

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
                485                 490                 495

Gly Ile Val Lys Arg Arg Gly Glu Lys Leu Ala Ile Leu Asn Phe Gly
            500                 505                 510

Thr Leu Met Pro Glu Ala Ala Lys Val Ala Glu Ser Leu Asn Ala Thr
        515                 520                 525

Leu Val Asp Met Arg Phe Val Lys Pro Leu Asp Glu Ala Leu Ile Leu
    530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
            580                 585                 590

Pro Gln Gly Thr Gln Glu Glu Met Arg Ala Glu Leu Gly Leu Asp Ala
        595                 600                 605

Ala Gly Met Glu Ala Lys Ile Lys Ala Trp Leu Ala
    610                 615                 620


<210> SEQ ID NO 137
<211> LENGTH: 398
<212> TYPE: PRT
<213> ORGANISM: Escherichia coli dxr

<400> SEQUENCE: 137

Met Lys Gln Leu Thr Ile Leu Gly Ser Thr Gly Ser Ile Gly Cys Ser
1               5                   10                  15

Thr Leu Asp Val Val Arg His Asn Pro Glu His Phe Arg Val Val Ala
            20                  25                  30

Leu Val Ala Gly Lys Asn Val Thr Arg Met Val Glu Gln Cys Leu Glu
        35                  40                  45

Phe Ser Pro Arg Tyr Ala Val Met Asp Asp Glu Ala Ser Ala Lys Leu
```

```
    50                  55                  60

Leu Lys Thr Met Leu Gln Gln Gln Gly Ser Arg Thr Glu Val Leu Ser
65                  70                  75                  80

Gly Gln Gln Ala Ala Cys Asp Met Ala Ala Leu Glu Asp Val Asp Gln
                85                  90                  95

Val Met Ala Ala Ile Val Gly Ala Ala Gly Leu Leu Pro Thr Leu Ala
            100                 105                 110

Ala Ile Arg Ala Gly Lys Thr Ile Leu Leu Ala Asn Lys Glu Ser Leu
        115                 120                 125

Val Thr Cys Gly Arg Leu Phe Met Asp Ala Val Lys Gln Ser Lys Ala
    130                 135                 140

Gln Leu Leu Pro Val Asp Ser Glu His Asn Ala Ile Phe Gln Ser Leu
145                 150                 155                 160

Pro Gln Pro Ile Gln His Asn Leu Gly Tyr Ala Asp Leu Glu Gln Asn
                165                 170                 175

Gly Val Val Ser Ile Leu Leu Thr Gly Ser Gly Gly Pro Phe Arg Glu
            180                 185                 190

Thr Pro Leu Arg Asp Leu Ala Thr Met Thr Pro Asp Gln Ala Cys Arg
        195                 200                 205

His Pro Asn Trp Ser Met Gly Arg Lys Ile Ser Val Asp Ser Ala Thr
    210                 215                 220

Met Met Asn Lys Gly Leu Glu Tyr Ile Glu Ala Arg Trp Leu Phe Asn
225                 230                 235                 240

Ala Ser Ala Ser Gln Met Glu Val Leu Ile His Pro Gln Ser Val Ile
                245                 250                 255

His Ser Met Val Arg Tyr Gln Asp Gly Ser Val Leu Ala Gln Leu Gly
            260                 265                 270

Glu Pro Asp Met Arg Thr Pro Ile Ala His Thr Met Ala Trp Pro Asn
        275                 280                 285

Arg Val Asn Ser Gly Val Lys Pro Leu Asp Phe Cys Lys Leu Ser Ala
    290                 295                 300

Leu Thr Phe Ala Ala Pro Asp Tyr Asp Arg Tyr Pro Cys Leu Lys Leu
305                 310                 315                 320

Ala Met Glu Ala Phe Glu Gln Gly Gln Ala Ala Thr Thr Ala Leu Asn
                325                 330                 335

Ala Ala Asn Glu Ile Thr Val Ala Ala Phe Leu Ala Gln Gln Ile Arg
            340                 345                 350

Phe Thr Asp Ile Ala Ala Leu Asn Leu Ser Val Leu Glu Lys Met Asp
        355                 360                 365

Met Arg Glu Pro Gln Cys Val Asp Asp Val Leu Ser Val Asp Ala Asn
    370                 375                 380

Ala Arg Glu Val Ala Arg Lys Glu Val Met Arg Leu Ala Ser
385                 390                 395
```

<210> SEQ ID NO 138
<211> LENGTH: 299
<212> TYPE: PRT
<213> ORGANISM: Escherichia coli ispA

<400> SEQUENCE: 138

```
Met Asp Phe Pro Gln Gln Leu Glu Ala Cys Val Lys Gln Ala Asn Gln
1               5                   10                  15

Ala Leu Ser Arg Phe Ile Ala Pro Leu Pro Phe Gln Asn Thr Pro Val
            20                  25                  30
```

```
Val Glu Thr Met Gln Tyr Gly Ala Leu Leu Gly Gly Lys Arg Leu Arg
        35                  40                  45

Pro Phe Leu Val Tyr Ala Thr Gly His Met Phe Gly Val Ser Thr Asn
    50                  55                  60

Thr Leu Asp Ala Pro Ala Ala Ala Val Glu Cys Ile His Ala Tyr Ser
65                  70                  75                  80

Leu Ile His Asp Asp Leu Pro Ala Met Asp Asp Asp Asp Leu Arg Arg
                85                  90                  95

Gly Leu Pro Thr Cys His Val Lys Phe Gly Glu Ala Asn Ala Ile Leu
            100                 105                 110

Ala Gly Asp Ala Leu Gln Thr Leu Ala Phe Ser Ile Leu Ser Asp Ala
        115                 120                 125

Asp Met Pro Glu Val Ser Asp Arg Asp Arg Ile Ser Met Ile Ser Glu
    130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
            180                 185                 190

Gly Ala Leu Ser Ala Gly Asp Lys Gly Arg Arg Ala Leu Pro Val Leu
        195                 200                 205

Asp Lys Tyr Ala Glu Ser Ile Gly Leu Ala Phe Gln Val Gln Asp Asp
    210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
            260                 265                 270

Ser Leu Lys Gln Leu Ala Glu Gln Ser Leu Asp Thr Ser Ala Leu Glu
        275                 280                 285

Ala Leu Ala Asp Tyr Ile Ile Gln Arg Asn Lys
    290                 295


<210> SEQ ID NO 139
<211> LENGTH: 551
<212> TYPE: PRT
<213> ORGANISM: Clausena lansium STS

<400> SEQUENCE: 139

Met Ser Thr Gln Gln Val Ser Ser Glu Asn Ile Val Arg Asn Ala Ala
1               5                   10                  15

Asn Phe His Pro Asn Ile Trp Gly Asn His Phe Leu Thr Cys Pro Ser
            20                  25                  30

Gln Thr Ile Asp Ser Trp Thr Gln Gln His His Lys Glu Leu Lys Glu
        35                  40                  45

Glu Val Arg Lys Met Met Val Ser Asp Ala Asn Lys Pro Ala Gln Arg
    50                  55                  60

Leu Arg Leu Ile Asp Thr Val Gln Arg Leu Gly Val Ala Tyr His Phe
65                  70                  75                  80

Glu Lys Glu Ile Asp Asp Ala Leu Glu Lys Ile Gly His Asp Pro Phe
                85                  90                  95

Asp Asp Lys Asp Asp Leu Tyr Ile Val Ser Leu Cys Phe Arg Leu Leu
            100                 105                 110
```

-continued

```
Arg Gln His Gly Ile Lys Ile Ser Cys Asp Val Phe Glu Lys Phe Lys
        115                 120                 125

Asp Asp Asp Gly Lys Phe Lys Ala Ser Leu Met Asn Asp Val Gln Gly
    130                 135                 140

Met Leu Ser Leu Tyr Glu Ala Ala His Leu Ala Ile His Gly Glu Asp
145                 150                 155                 160

Ile Leu Asp Glu Ala Ile Val Phe Thr Thr Thr His Leu Lys Ser Thr
                165                 170                 175

Val Ser Asn Ser Pro Val Asn Ser Thr Phe Ala Glu Gln Ile Arg His
            180                 185                 190

Ser Leu Arg Val Pro Leu Arg Lys Ala Val Pro Arg Leu Glu Ser Arg
        195                 200                 205

Tyr Phe Leu Asp Ile Tyr Ser Arg Asp Asp Leu His Asp Lys Thr Leu
    210                 215                 220

Leu Asn Phe Ala Lys Leu Asp Phe Asn Ile Leu Gln Ala Met His Gln
225                 230                 235                 240

Lys Glu Ala Ser Glu Met Thr Arg Trp Trp Arg Asp Phe Asp Phe Leu
                245                 250                 255

Lys Lys Leu Pro Tyr Ile Arg Asp Arg Val Val Glu Leu Tyr Phe Trp
            260                 265                 270

Ile Leu Val Gly Val Ser Tyr Gln Pro Lys Phe Ser Thr Gly Arg Ile
        275                 280                 285

Phe Leu Ser Lys Ile Ile Cys Leu Glu Thr Leu Val Asp Asp Thr Phe
    290                 295                 300

Asp Ala Tyr Gly Thr Phe Asp Glu Leu Ala Ile Phe Thr Glu Ala Val
305                 310                 315                 320

Thr Arg Trp Asp Leu Gly His Arg Asp Ala Leu Pro Glu Tyr Met Lys
                325                 330                 335

Phe Ile Phe Lys Thr Leu Ile Asp Val Tyr Ser Glu Ala Glu Gln Glu
            340                 345                 350

Leu Ala Lys Glu Gly Arg Ser Tyr Ser Ile His Tyr Ala Ile Arg Ser
        355                 360                 365

Phe Gln Glu Leu Val Met Lys Tyr Phe Cys Glu Ala Lys Trp Leu Asn
    370                 375                 380

Lys Gly Tyr Val Pro Ser Leu Asp Asp Tyr Lys Ser Val Ser Leu Arg
385                 390                 395                 400

Ser Ile Gly Phe Leu Pro Ile Ala Val Ala Ser Phe Val Phe Met Gly
                405                 410                 415

Asp Ile Ala Thr Lys Glu Val Phe Glu Trp Glu Met Asn Asn Pro Lys
            420                 425                 430

Ile Ile Ile Ala Ala Glu Thr Ile Phe Arg Phe Leu Asp Asp Ile Ala
        435                 440                 445

Gly His Arg Phe Glu Gln Lys Arg Glu His Ser Pro Ser Ala Ile Glu
    450                 455                 460

Cys Tyr Lys Asn Gln His Gly Val Ser Glu Glu Glu Ala Val Lys Ala
465                 470                 475                 480

Leu Ser Leu Glu Val Ala Asn Ser Trp Lys Asp Ile Asn Glu Glu Leu
                485                 490                 495

Leu Leu Asn Pro Met Ala Ile Pro Leu Pro Leu Leu Gln Val Ile Leu
            500                 505                 510

Asp Leu Ser Arg Ser Ala Asp Phe Met Tyr Gly Asn Ala Gln Asp Arg
        515                 520                 525
```

```
Phe Thr His Ser Thr Met Met Lys Asp Gln Val Asp Leu Val Leu Lys
    530                 535                 540

Asp Pro Val Lys Leu Asp Asp
545                 550


<210> SEQ ID NO 140
<211> LENGTH: 572
<212> TYPE: PRT
<213> ORGANISM: Artificial Sequence
<220> FEATURE:
<223> OTHER INFORMATION: Matricaria recutita MrBBS

<400> SEQUENCE: 140

Met Ser Thr Leu Ser Val Ser Thr Pro Ser Phe Ser Ser Ser Pro Leu
1               5                   10                  15

Ser Ser Val Asn Lys Asn Ser Thr Lys Gln His Val Thr Arg Asn Ser
            20                  25                  30

Val Ile Phe His Asp Ser Ile Trp Gly Asp Gln Phe Leu Glu Tyr Lys
        35                  40                  45

Glu Lys Phe Asn Val Ala Thr Glu Lys Gln Leu Ile Glu Glu Leu Lys
    50                  55                  60

Glu Glu Val Arg Asn Glu Leu Met Ile Arg Ala Cys Asn Glu Ala Ser
65                  70                  75                  80

Arg Tyr Ile Lys Leu Ile Gln Leu Ile Asp Val Val Glu Arg Leu Gly
                85                  90                  95

Leu Ala Tyr His Phe Glu Lys Glu Ile Glu Glu Ser Leu Gln His Ile
            100                 105                 110

Tyr Val Thr Tyr Gly His Lys Trp Thr Asn Tyr Asn Asn Ile Glu Ser
        115                 120                 125

Leu Ser Leu Trp Phe Arg Leu Leu Arg Gln Asn Gly Phe Asn Val Ser
    130                 135                 140

Ser Asp Ile Phe Glu Asn His Ile Asp Glu Lys Gly Asn Phe Gln Glu
145                 150                 155                 160

Ser Leu Cys Asn Asp Pro Gln Gly Met Leu Ala Leu Tyr Glu Ala Ala
                165                 170                 175

Tyr Met Arg Val Glu Gly Glu Ile Ile Leu Asp Lys Ala Leu Glu Phe
            180                 185                 190

Thr Lys Leu His Leu Gly Ile Ile Ser Asn Asp Pro Ser Cys Asp Ser
        195                 200                 205

Ser Leu Arg Thr Glu Ile Lys Gln Ala Leu Lys Gln Pro Leu Arg Arg
    210                 215                 220

Arg Leu Pro Arg Leu Glu Ala Val Arg Tyr Ile Ala Ile Tyr Gln Gln
225                 230                 235                 240

Lys Ala Ser His Ser Glu Val Leu Leu Lys Leu Ala Lys Leu Asp Phe
                245                 250                 255

Asn Val Leu Gln Glu Met His Lys Asp Glu Leu Ser Gln Ile Cys Lys
            260                 265                 270

Trp Trp Lys Asp Leu Asp Ile Arg Asn Lys Leu Pro Tyr Val Arg Asp
        275                 280                 285

Arg Leu Ile Glu Gly Tyr Phe Trp Ile Leu Gly Ile Tyr Phe Glu Pro
    290                 295                 300

Gln His Ser Arg Thr Arg Met Phe Leu Met Lys Thr Cys Met Trp Leu
305                 310                 315                 320

Ile Val Leu Asp Asp Thr Phe Asp Asn Tyr Gly Thr Tyr Glu Glu Leu
                325                 330                 335
```

```
Glu Ile Phe Thr Gln Ala Val Glu Arg Trp Ser Ile Thr Cys Leu Asp
            340                 345                 350

Glu Leu Pro Glu Tyr Met Lys Leu Ile Tyr His Glu Gln Phe Arg Val
        355                 360                 365

His Gln Glu Met Glu Glu Ser Leu Glu Lys Glu Gly Lys Ala Tyr Gln
    370                 375                 380

Ile His Tyr Ile Lys Glu Met Ala Lys Glu Gly Thr Arg Ser Leu Leu
385                 390                 395                 400

Leu Glu Ala Lys Trp Leu Lys Glu Gly Tyr Met Pro Thr Leu Asp Glu
                405                 410                 415

Tyr Leu Ser Asn Ser Leu Val Thr Cys Gly Tyr Ala Leu Met Thr Ala
            420                 425                 430

Arg Ser Tyr Val Ala Arg Asp Asp Gly Ile Val Thr Glu Asp Ala Phe
        435                 440                 445

Lys Trp Val Ala Thr His Pro Pro Ile Val Lys Ala Ala Cys Lys Ile
    450                 455                 460

Leu Arg Leu Met Asp Asp Ile Ala Thr His Lys Glu Glu Gln Glu Arg
465                 470                 475                 480

Gly His Ile Ala Ser Ser Ile Glu Cys Tyr Arg Lys Glu Thr Gly Ala
                485                 490                 495

Ser Glu Glu Glu Ala Cys Met Asp Phe Leu Lys Gln Val Glu Asp Gly
            500                 505                 510

Trp Lys Val Ile Asn Gln Glu Ser Leu Met Pro Thr Asp Val Pro Phe
        515                 520                 525

Pro Leu Leu Ile Pro Ala Ile Asn Leu Ala Arg Val Ser Asp Thr Leu
    530                 535                 540

Tyr Lys Asp Asn Asp Gly Tyr Asn His Ala Asp Lys Glu Val Ile Gly
545                 550                 555                 560

Tyr Ile Lys Ser Leu Phe Val His Pro Met Ile Val
                565                 570


<210> SEQ ID NO 141
<211> LENGTH: 391
<212> TYPE: PRT
<213> ORGANISM: Artificial Sequence
<220> FEATURE:
<223> OTHER INFORMATION: EGFP

<400> SEQUENCE: 141

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Tyr Pro Ala Gly Trp Arg Pro Leu Glu Met Val Glu Arg Lys Lys Leu
                245                 250                 255

Gly Val Leu Gln Pro Thr Gln Gln Cys Arg Leu Thr Val His Gln Ser
            260                 265                 270

Lys Ile Met Val Asp Ser Pro Lys Ala Leu Lys Arg Lys Ala Phe Gly
        275                 280                 285

Asp Glu Asn Phe Ser Pro Val Pro Thr Leu Ser Arg Lys Ser Ile Phe
    290                 295                 300

Glu Asp Pro Pro Thr Pro Ala Ser Lys Arg Ser Lys Leu Ser Asp Lys
305                 310                 315                 320

Val Asp Ser Ala Ile Gln Thr Asp Asn Leu Cys Cys Gly Asn Gly Gly
                325                 330                 335

Thr Glu Ile Ser Arg Gly Ser Ser Ser Ser Lys Ser Ser Ser Glu Ala
            340                 345                 350

Ser Thr Lys Ala Cys Ser Gln Lys Ser Gln Ser Gln Ser Val Leu Asp
        355                 360                 365

Met Leu Thr Ser Ala Glu Pro Asn Glu Gln Tyr Trp Gln Met Met Ala
    370                 375                 380

Ala Glu Arg Lys Ala Ala Leu
385                 390
```

<210> SEQ ID NO 142
<211> LENGTH: 410
<212> TYPE: PRT
<213> ORGANISM: Lactococcus lactis subsp. cremoris NZ9000 mvaA

<400> SEQUENCE: 142

```
Met Arg Lys Lys Phe Tyr Gln Met Ser Pro Gln Glu Arg Leu Asn Ser
1               5                   10                  15

Leu Asn Leu Ser Glu Lys Ser Gln Glu Ile Leu Ser Glu Met Ala Leu
            20                  25                  30

Asp Thr Thr Ile Leu Asp Asn Leu Ile Glu Asn Gln Ile Ser Glu Phe
        35                  40                  45

Glu Leu Pro Met Gly Ile Ala Gln Asn Phe Val Ile Asn Gly Gln Ser
    50                  55                  60

Phe Leu Ile Pro Met Val Thr Glu Glu Pro Ser Val Ile Ala Ala Ala
65                  70                  75                  80

Ser Asn Gly Ala Lys Ile Ala Gly Asn Phe Val Ala Glu Ile Lys Glu
                85                  90                  95

Arg Leu Met Arg Gly Gln Ile Val Phe Tyr Asp Val Lys Asn Ser Asp
            100                 105                 110
```

Lys Ile Ala Asn Glu Ile Leu Glu Lys Gln Glu Lys Ile Phe Glu Gln
115 120 125

Ala Glu Leu Ser Tyr Pro Ser Ile Val Lys Arg Gly Gly Gly Leu Arg
130 135 140

Glu Val Ser Ser Arg Ile Phe Ser Ser Gln Lys Phe Leu Ser Val Asp
145 150 155 160

Val Lys Val Asp Val Lys Asp Ala Met Gly Ala Asn Ile Ile Asn Ser
165 170 175

Ile Leu Glu Gly Ile Ala Glu Leu Phe Arg Arg Trp Phe Pro Asp Glu
180 185 190

Lys Ile Leu Phe Ser Ile Leu Ser Asn Tyr Ala Thr Glu Ser Leu Val
195 200 205

Lys Val Thr Cys Glu Ile Pro Val Glu Arg Leu Ser Lys Lys Ala Asp
210 215 220

Gly Tyr Glu Ile Gly Gln Lys Ile Met Ala Ala Ser Gln Tyr Ser Lys
225 230 235 240

Ile Asp Pro Tyr Arg Ala Ser Thr His Asn Lys Gly Ile Met Asn Gly
245 250 255

Ile Asn Ala Val Ile Leu Ala Thr Gly Asn Asp Thr Arg Ala Ile Ser
260 265 270

Ala Ala Ile His Ala Tyr Ala Ala Lys Asp Gly Ala Tyr Gln Gly Leu
275 280 285

Ala Asn Trp Glu Leu Gln Glu Lys Met Leu Val Gly Glu Leu Glu Phe
290 295 300

Pro Leu Pro Val Ala Thr Val Gly Gly Gly Val Lys Val Leu Pro Lys
305 310 315 320

Ala Gln Ala Ala Met Glu Ile Leu Gly Ile Ser Asp Ala Lys Glu Leu
325 330 335

Ala Lys Val Ile Ala Ala Val Gly Leu Ala Gln Asn Leu Ala Ala Leu
340 345 350

Arg Ala Leu Val Ser Glu Gly Ile Gln Gln Gly His Met Ser Leu Gln
355 360 365

Ala Arg Ser Leu Ala Leu Ser Val Gly Ala Gln Ala Asp Glu Ile Ala
370 375 380

Ile Leu Ser Gln Gln Leu Arg Lys Glu Lys Val Met Asn Gln Glu Val
385 390 395 400

Ala Gln Asn Leu Leu Lys Asn Leu Arg Lys
405 410

<210> SEQ ID NO 143
<211> LENGTH: 410
<212> TYPE: PRT
<213> ORGANISM: Artificial Sequence
<220> FEATURE:
<223> OTHER INFORMATION: Lactococcus lactis subsp. cremoris MG1363
(Hydroxymethylglutaryl-CoA reductase)

<400> SEQUENCE: 143

Met Arg Lys Lys Phe Tyr Gln Met Ser Pro Gln Glu Arg Leu Asn Ser
1 5 10 15

Leu Asn Leu Ser Glu Lys Ser Gln Glu Ile Leu Ser Glu Met Ala Leu
20 25 30

-continued

```
Asp Thr Thr Ile Leu Asp Asn Leu Ile Glu Asn Gln Ile Ser Glu Phe
        35                  40                  45

Glu Leu Pro Met Gly Ile Ala Gln Asn Phe Val Ile Asn Gly Gln Ser
    50                  55                  60

Phe Leu Ile Pro Met Val Thr Glu Glu Pro Ser Val Ile Ala Ala Ala
65                  70                  75                  80

Ser Asn Gly Ala Lys Ile Ala Gly Asn Phe Val Ala Glu Ile Lys Glu
                85                  90                  95

Arg Leu Met Arg Gly Gln Ile Val Phe Tyr Asp Val Lys Asn Ser Asp
            100                 105                 110

Lys Ile Ala Asn Glu Ile Leu Glu Lys Gln Glu Lys Ile Phe Glu Gln
        115                 120                 125

Ala Glu Leu Ser Tyr Pro Ser Ile Val Lys Arg Gly Gly Gly Leu Arg
    130                 135                 140

Glu Val Ser Ser Arg Ile Phe Ser Ser Gln Lys Phe Leu Ser Val Asp
145                 150                 155                 160

Val Lys Val Asp Val Lys Asp Ala Met Gly Ala Asn Ile Ile Asn Ser
                165                 170                 175

Ile Leu Glu Gly Ile Ala Glu Leu Phe Arg Arg Trp Phe Pro Asp Glu
            180                 185                 190

Lys Ile Leu Phe Ser Ile Leu Ser Asn Tyr Ala Thr Glu Ser Leu Val
        195                 200                 205

Lys Val Thr Cys Glu Ile Pro Val Glu Arg Leu Ser Lys Lys Ala Asp
    210                 215                 220

Gly Tyr Glu Ile Gly Gln Lys Ile Met Ala Ala Ser Gln Tyr Ser Lys
225                 230                 235                 240

Ile Asp Pro Tyr Arg Ala Ser Thr His Asn Lys Gly Ile Met Asn Gly
                245                 250                 255

Ile Asn Ala Val Ile Leu Ala Thr Gly Asn Asp Thr Arg Ala Ile Ser
            260                 265                 270

Ala Ala Ile His Ala Tyr Ala Ala Lys Asp Gly Ala Tyr Gln Gly Leu
        275                 280                 285

Ala Asn Trp Glu Leu Gln Glu Lys Met Leu Val Gly Glu Leu Glu Phe
    290                 295                 300

Pro Leu Pro Val Ala Thr Val Gly Gly Gly Val Lys Val Leu Pro Lys
305                 310                 315                 320

Ala Gln Ala Ala Met Glu Ile Leu Gly Ile Ser Asp Ala Lys Glu Leu
                325                 330                 335

Ala Lys Val Ile Ala Ala Val Gly Leu Ala Gln Asn Leu Ala Ala Leu
            340                 345                 350

Arg Ala Leu Val Ser Glu Gly Ile Gln Gln Gly His Met Ser Leu Gln
        355                 360                 365

Ala Arg Ser Leu Ala Leu Ser Val Gly Ala Gln Ala Asp Glu Ile Ala
    370                 375                 380

Ile Leu Ser Gln Gln Leu Arg Lys Glu Lys Val Met Asn Gln Glu Val
385                 390                 395                 400

Ala Gln Asn Leu Leu Lys Asn Leu Arg Lys
                405                 410
```

MARKER COMPOSITION FOR SELECTING LIVING MODIFIED ORGANISM, LIVING MODIFIED ORGANISM, AND TRANSFORMATION METHOD

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/005425 filed on May 11, 2018, which claims priority to the benefit of Korean Patent Application Nos. 10-2017-0058829 filed on May 11, 2017 and 10-2018-0054080 filed on May 11, 2018 in the Korean Intellectual Property Office, the entire contents of which are incorporated herein by reference.

TECHNICAL FIELD

The present invention relates to a marker composition for selecting a living modified organism, a living modified organism and a method of transforming an organism.

BACKGROUND ART

Recently, for industrial production of useful materials, LMOs has been mostly used. In this case, in order to enhance expressions of a metabolic pathway and a target product biosynthetic pathway, related genes are induced using various expression vectors (plasmids). In this case, the vectors have antibiotic resistance genes as a selection marker, and antibiotics are added to a culture liquid to stably maintain the plasmids in a host cell during the culture. However, when using antibiotics in the cultural process, there are problems such as an increase in production costs due to the use of expensive antibiotics, environmental pollution due to antibiotic leakage, a risk of a generation of antibiotic resistance mutations in the natural world, a need for additional separation and purification processes due to antibiotics remaining in the final product, difficulties in using antibiotic resistance gene marker-containing strains and acquiring a permission.

Further, if a cultural time is increased in a case of cultivation using antibiotics, a loss of plasmids containing antibiotic resistance genes as a selection marker occurs due to degradation and modification of antibiotics, and thereby causing a drastic decrease in productivity in the second half of the culture. The degradation and modification of the antibiotics are caused by enzymes expressed in antibiotic marker genes and by spontaneous instability of antibiotics, which result in serious problems such as a generation of secondary products in cultural processes requiring a long-term fermentation.

In order to solve these problems, there is a method of inserting foreign genes necessary for the production of the target product into chromosomes of a host organism, but this method has problems such as a decrease in an expression amount of proteins due to a reduction in an amount of genes, difficulties in introducing and expressing a number of genes into the chromosomes compared to the introduction of plasmids having a plurality of copies of the genes.

Due to the above-described reasons, developing antibiotic marker-free organisms has become an issue in the bioprocess industry in recent years. However, to date, there are no or very limited antibiotic marker-free systems that can be stably and usefully used in the industry. Although auxotrophic selection markers may be used in place of the antibiotic markers in auxotrophic selection mutant strains, there is a disadvantage that complex media, which is a commonly used industrial medium, cannot be used.

Another example is StabyExpress™, developed by Delphi Genetics. This uses ccd operons (ccdA and ccdB), which are antidote/poison systems present in bacteria. However, they are operated only in some bacteria, and are not operated frequently if an expression ratio of the ccdA/ccdB is not exactly correct.

SUMMARY

An object of the present invention is to provide a marker composition for selecting a living modified organism that can replace an antibiotic and an antibiotic resistance marker.

Another object of the present invention is to provide a transformation method that does not require use of antibiotics and antibiotic resistance markers, and a living modified organism.

1. A marker composition for selecting a living modified organism including: a plasmid into which at least one of genes encoding enzymes in an isopentenyl diphosphate or dimethylallyl diphosphate synthetic pathway is introduced.

2. The marker composition for selecting a living modified organism according to the above 1, wherein the organism inherently has the isopentenyl diphosphate or dimethylallyl diphosphate synthetic pathway.

3. The marker composition for selecting a living modified organism according to the above 1, wherein the synthetic pathway is a MEP pathway or an MVA pathway.

4. The marker composition for selecting a living modified organism according to the above 1, wherein the gene encoding enzymes in the synthetic pathway is a gene encoding one or more enzymes selected from the group consisting of 1-dioxy-D-xylulose-5-phosphate (DXP) synthase, DXP reductoisomerase, 2-C-methyl-D-erythritol-4-phosphate (MEP) cytidyltransferase, 4-diphosphocytidyl-2-C-methyl-D-erythritol kinase, 2-C-methyl-D-erythritol-2,4-cyclodiphosphate (MEcPP) synthase, 4-hydroxy-3-methyl-2-butenyl diphosphate (HMBPP) synthase, HMBPP reductase, acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and IPP isomerase.

5. The marker composition for selecting a living modified organism according to the above 1, wherein the composition is transformed into an organism in which a gene encoding the same enzyme as said gene or a complementary gene thereof is attenuated or deleted.

6. The marker composition for selecting a living modified organism according to the above 5, wherein the gene is a gene encoding enzymes in the MEP pathway, and the complementary gene is a gene encoding at least one of enzymes in the MVA pathway.

7. The marker composition for selecting a living modified organism according to the above 6, wherein the complementary gene is a gene encoding acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and IPP isomerase.

8. The marker composition for selecting a living modified organism according to the above 5, wherein the gene is a gene encoding enzymes in the MVA pathway, and the complementary gene is a gene encoding at least one of enzymes in the MEP pathway.

9. The marker composition for selecting a living modified organism according to the above 1, including at least two of the genes, and these genes are introduced into a separate plasmid, respectively.

10. The marker composition for selecting a living modified organism according to the above 1, wherein the plasmid further includes a gene introduced therein to encode enzymes in a pathway selected from the group consisting of isoprenoid, santalene, bisabolol and retinol synthetic pathways.

11. A living modified organism transformed with a plasmid in which at least one of genes encoding enzymes in an isopentenyl diphosphate or dimethylallyl diphosphate synthetic pathway is attenuated or deleted, wherein a gene encoding the same enzyme as the attenuated or deleted gene or a complementary gene thereof is introduced therein.

12. The organism according to the above 11, wherein the organism inherently has the isopentenyl diphosphate or dimethylallyl diphosphate synthetic pathway.

13. The organism according to the above 11, wherein the synthetic pathway is a MEP pathway or an MVA pathway.

14. The organism according to the above 11, wherein the gene encoding enzymes in the synthetic pathway is a gene encoding one or more enzymes selected from the group consisting of 1-dioxy-D-xylulose-5-phosphate (DXP) synthase, DXP reductoisomerase, 2-C-methyl-D-erythritol-4-phosphate (MEP) cytidyltransferase, 4-diphosphocytidyl-2-C-methyl-D-erythritol kinase, 2-C-methyl-D-erythritol-2,4-cyclodiphosphate (MEcPP) synthase, 4-hydroxy-3-methyl-2-butenyl diphosphate (HMBPP) synthase, HMBPP reductase, acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and IPP isomerase.

15. The organism according to the above 11, wherein the gene to be attenuated or deleted is a gene encoding enzymes in the MEP pathway.

16. The organism according to the above 15, wherein the gene is a gene encoding at least one of DXP synthase and DXP reductoisomerase.

17. The organism according to the above 11, wherein the gene to be attenuated or deleted is a gene encoding enzymes in the MEP pathway, and the complementary gene is a gene encoding at least one of enzymes in the MVA pathway.

18. The organism according to the above 17, wherein the complementary gene is a gene encoding acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and IPP isomerase.

19. The organism according to the above 11, wherein the attenuated or deleted gene is a gene encoding enzymes in the MVA pathway.

20. The organism according to the above 11, wherein the plasmid further includes a gene introduced therein to encode enzymes in a pathway selected from the group consisting of isoprenoid, santalene, bisabolol and retinol synthetic pathways.

21. A method of transforming an organism including: attenuating or deleting at least one of genes encoding enzymes in an isopentenyl diphosphate or dimethylallyl diphosphate synthetic pathway of an organism to be transformed; and transforming the organism with a recombinant plasmid into which a gene encoding the same enzyme as the attenuated or deleted gene or a complementary gene thereof is introduced.

22. The method of transforming an organism according to the above 21, wherein the organism inherently has the isopentenyl diphosphate or dimethylallyl diphosphate synthetic pathway.

23. The method of transforming an organism according to the above 21, wherein the transformation is performed without antibiotics.

24. The method of transforming an organism according to the above 21, wherein the synthetic pathway is a MEP pathway or an MVA pathway.

25. The method of transforming an organism according to the above 21, wherein the gene encoding enzymes in the synthetic pathway is a gene encoding one or more enzymes selected from the group consisting of 1-dioxy-D-xylulose-5-phosphate (DXP) synthase, DXP reductoisomerase, 2-C-methyl-D-erythritol-4-phosphate (MEP) cytidyltransferase, 4-diphosphocytidyl-2-C-methyl-D-erythritol kinase (IspE), 2-C-methyl-D-erythritol-2,4-cyclodiphosphate (MEcPP) synthase, 4-hydroxy-3-methyl-2-butenyl diphosphate (HMBPP) synthase, HMBPP reductase, acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and IPP isomerase.

26. The method of transforming an organism according to the above 21, wherein the attenuated or deleted gene is a gene encoding enzymes in the MEP pathway.

27. The method of transforming an organism according to the above 26, wherein the gene is a gene encoding at least one of DXP synthase and DXP reductoisomerase.

28. The method of transforming an organism according to the above 21, wherein the gene to be attenuated or deleted is a gene encoding enzymes in the MEP pathway, and the complementary gene is a gene encoding at least one of enzymes in the MVA pathway.

29. The method of transforming an organism according to the above 28, wherein the complementary gene is a gene encoding acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and IPP isomerase.

30. The method of transforming an organism according to the above 21, wherein the gene to be attenuated or deleted is a gene encoding at least one of enzymes in the MVA pathway.

31. The method of transforming an organism according to the above 21, wherein the plasmid further includes a gene encoding enzymes in a pathway selected from the group consisting of isoprenoid, santalene, bisabolol and retinol synthetic pathways.

32. The method of transforming an organism according to the above 21, wherein at least two genes are attenuated or deleted, and a strain is transformed with two plasmid including a gene encoding the same enzyme as the attenuated or deleted gene, respectively.

33. A method of producing a target product including: culturing the organism according to any one of the above 11 to 20 in a medium including a substrate.

34. The method of producing a target product according to the above 33, wherein the medium does not include antibiotics.

The marker composition for selecting a living modified organism of the present invention does not use antibiotic resistance genes. Thus, transformation is possible without the use of antibiotics and antibiotic resistance genes, thereby basically preventing many problems caused by the use of antibiotics and antibiotic resistance genes.

The marker composition for selecting a living modified organism of the present invention is less likely to disappear even when culturing the living organism (briefly, 'organism') for a long period time.

The organism of the present invention is capable of transforming and producing a target product without antibiotics and antibiotic resistance genes, thereby basically preventing many problems caused by the use of antibiotics and antibiotic resistance genes.

The transformation method of the present invention can transform an organism without antibiotics or antibiotic resistance genes.

The production method of a target product of the present invention can produce the target product in a high yield.

DETAILED DESCRIPTION

Hereinafter, the present invention will be described in detail.

The present invention provides a marker composition for selecting a living modified organism including a plasmid into which at least one of genes encoding enzymes in an isopentenyl diphosphate or dimethylallyl diphosphate synthetic pathway is introduced.

The isopentenyl diphosphate (IPP) or dimethylallyl diphosphate (DMAPP) synthetic pathway is a biosynthetic pathway which is essentially included in all living organisms. The IPP and DMAPP are metabolites in cells, and the cells cannot survive upon lacking the same. In addition, these substances are strongly negatively charged phosphorylated substances, and cannot be introduced into the cells even when they are present in a medium, such that it is necessary to be generated in the cells.

Thus, when including the plasmid into which at least one of genes encoding enzymes in the isopentenyl diphosphate or dimethylallyl diphosphate synthetic pathway introduced, it is possible to be used as a marker composition for selecting a living modified organism.

Types of the organisms according to the present invention are not limited so long as they inherently have the isopentenyl diphosphate (IPP) or dimethylallyl diphosphate (DMAPP) synthetic pathway, and may include animals, plants, and microorganisms, and specifically, the microorganisms.

Figure 1:
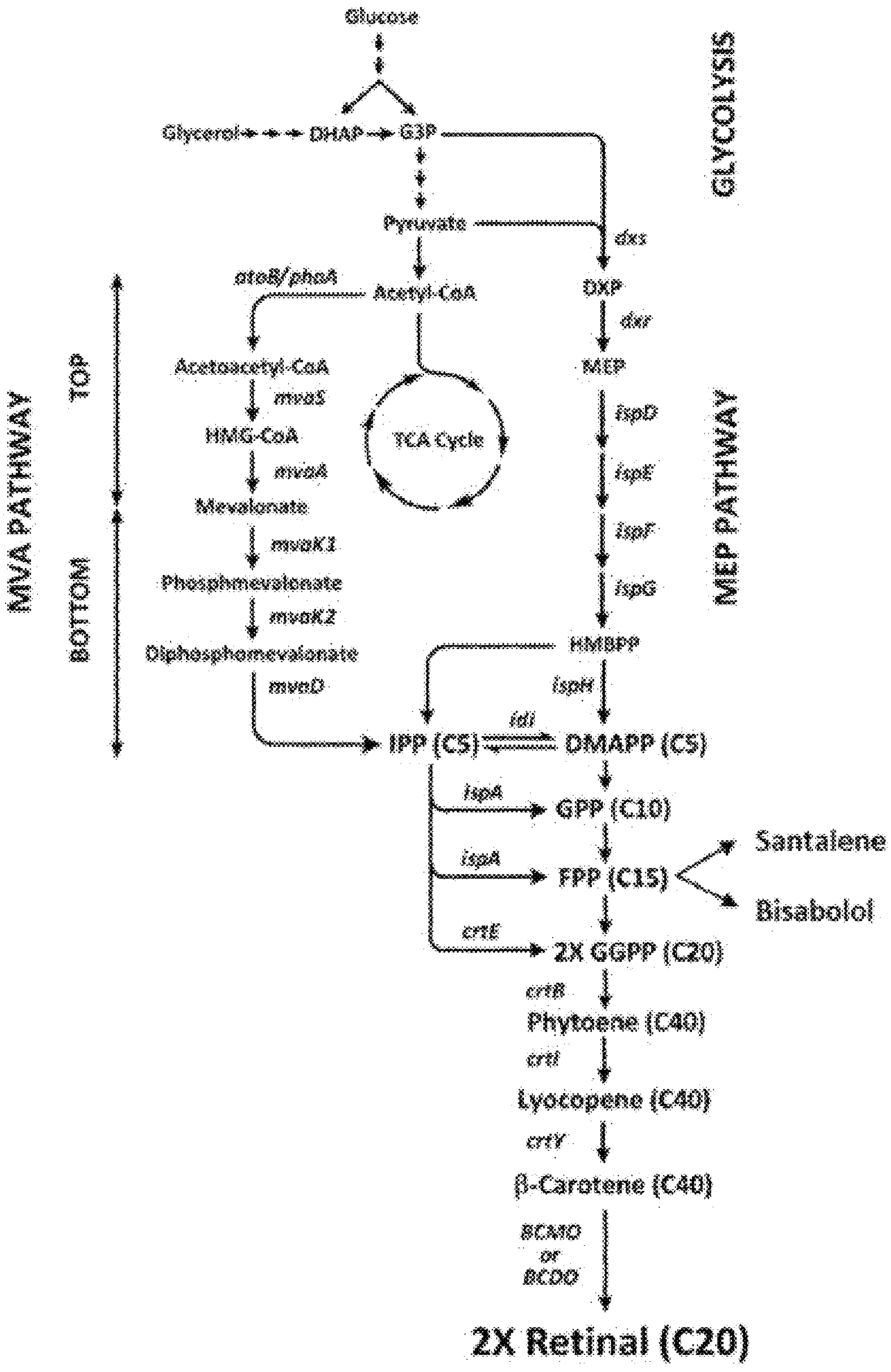
FIG. 1 is a view showing IPP and DMAPP biosynthetic pathways.

Specifically, the isopentenyl diphosphate or dimethylallyl diphosphate synthetic pathway may be an MEP pathway or MVA pathway shown in FIG. 1.

The gene encoding enzymes in the isopentenyl diphosphate or dimethylallyl diphosphate synthetic pathway may include a gene such as, for example, 1-dioxy-D-xylulose-5-phosphate (DXP) synthase of the MEP pathway, DXP reductoisomerase, 2-C-methyl-D-erythritol-4-phosphate (MEP) cytidyltransferase, 4-diphosphocytidyl-2-C-methyl-D-erythritol kinase (IspE), 2-C-methyl-D-erythritol-2,4-cyclodiphosphate (MEcPP) synthase, 4-hydroxy-3-methyl-2-butenyl diphosphate (HMBPP) synthase, HMBPP reductase, acetoacetyl-CoA synthase of the MVA pathway, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase, IPP isomerase and the like.

The marker composition for selecting a living modified organism of the present invention may be transformed into an organism in which a gene encoding the same enzyme as said gene or a complementary gene thereof is attenuated or deleted.

As described above, when the isopentenyl diphosphate and dimethylallyl diphosphate synthetic pathways are inactivated, the cells cannot survive, whereas the marker composition of the present invention includes the plasmid into which at least one of genes encoding enzymes in an isopentenyl diphosphate or dimethylallyl diphosphate synthetic pathway is introduced, thereby the organisms modified therewith can survive by activating the defective IPP/DMAPP pathways again. Therefore, it is possible to confirm the modified organism by the survival of the organism.

The organism to be transformed may be one in which a gene encoding the same enzyme as the gene of the marker composition or the complementary gene thereof is attenuated or deleted.

In a case of the gene encoding the same enzyme, the gene may be the same gene as the attenuated or deleted gene, or may be a gene encoding the same enzyme derived from other species.

As a particular example, the organism to be transformed may be one in which a gene encoding DXP reductoisomerase is attenuated or deleted, and the plasmid according to the present invention may be one into which the same gene as said gene or a gene encoding the same enzyme derived from other species (with different genes) is introduced.

The complementary gene means a gene that may activate a pathway other than the pathways inactivated by attenuation or deletion of the gene, thereby producing isopentenyl diphosphate or dimethylallyl diphosphate. For example, in a case of an organism whose gene of the MEP pathway is attenuated or deleted, the plasmid of the marker composition may be one in which a gene encoding enzymes into the entire MVA pathway is introduced, and in a case of an organism whose gene of the MVA pathway is attenuated or deleted, the plasmid of the marker composition may be one into which a gene encoding the enzymes in the entire MEP pathway is introduced.

When the composition of the present invention includes a plasmid into which at least two or more of genes encoding enzymes in the isopentenyl diphosphate or dimethylallyl diphosphate synthetic pathway is introduced, two or more genes may be introduced into one plasmid, or each gene may be introduced into separate plasmids, respectively.

When the genes are respectively introduced into the separate plasmids, the organism should be transformed with all the plasmids to survive, therefore, the organisms may be selected as an organism transformed with all the plasmids.

A particular example of the organism to be transformed may be an organism in which at least one of a gene encoding DXP synthase and a gene encoding DXP reductoisomerase is attenuated or deleted, and the composition of the present invention may include two plasmids into which the same gene as said gene or a gene encoding the same enzyme derived from other species (with different genes) is introduced In general, transformation of the organisms is performed in a culture liquid in which antibiotics are present, such that antibiotic resistance genes are used as a selection marker. However, in this case, there are problems such as an increase in production costs due to the use of expensive antibiotics, environmental pollution due to antibiotic leakage, a risk of a generation of antibiotic resistance mutant organisms and the like.

In addition, since the antibiotic resistance gene does not completely protect host cells, a damage to the host cells due to the antibiotics may occur. Further, setting and maintaining an optimal concentration of the used antibiotic to minimize the damage is recognized as a very difficult work in the industry, which may vary whenever the host cell is changed.

Furthermore, if a cultural time is increased in a case of cultivation using antibiotics, a loss of plasmids containing antibiotic resistance genes as a selection marker occurs due to degradation and modification of antibiotics, and thereby causing a drastic decrease in productivity in the second half of the cultivation. The degradation and modification of the antibiotics are caused by enzymes expressed in antibiotic marker genes and by spontaneous instability of antibiotics, which result in serious problems such as a generation of secondary products in cultural processes requiring a long-term fermentation.

However, by using the marker composition for selecting a living modified organism of the present invention, an occurrence of the above-described problems may be basically prevented, and the plasmid is safely maintained in the host organism without using antibiotics, as well as the living modified organisms may be selected.

Further, by additionally introducing genes encoding enzymes in a pathway for producing a target product into such a plasmid, it is possible to be used in stably mass-producing the target product in the host organism.

In addition, the present invention provides an organism transformed with a plasmid in which at least one of genes encoding enzymes in the isopentenyl diphosphate or dimethylallyl diphosphate synthetic pathway is attenuated or deleted, wherein a gene encoding the same enzyme as the attenuated or deleted gene or a complementary gene thereof is introduced therein.

The isopentenyl diphosphate or dimethylallyl diphosphate synthetic pathway may be the MEP pathway or the MVA pathway, and these enzymes are as described above.

The gene attenuated or deleted in the organism of the present invention may be at least one of genes encoding enzymes in the isopentenyl diphosphate or dimethylallyl diphosphate synthetic pathway, and specifically, at least one of genes encoding enzymes in the MEP pathway or the MVA pathway.

The organism of the present invention may be transformed with a plasmid into which the same gene as the attenuated or deleted gene or a gene encoding the same enzyme derived from other species is introduced.

As a particular example, it may be an organism in which at least one of genes encoding DXP synthase and DXP reductoisomerase is attenuated or deleted, or may be an organism transformed with a plasmid into which the same gene as said gene or a gene encoding the same enzyme derived from other species (with different genes) is introduced In addition, the organism of the present invention may be transformed with a plasmid into which a complementary gene of the attenuated or deleted gene is introduced.

The complementary gene means a gene that may activate a pathway other than the pathways inactivated by attenuation or deletion of the gene, thereby producing isopentenyl diphosphate or dimethylallyl diphosphate. For example, in a case of an organism whose gene of the MEP pathway is attenuated or deleted, it may be transformed with a plasmid into which a gene encoding enzymes in the entire MVA pathway is introduced, and in a case of an organism whose gene of the MVA pathway is attenuated or deleted, it may be transformed with a plasmid in which a gene encoding the enzymes in the entire MEP pathway is introduced.

The organism of the present invention may be further transformed with a gene encoding enzymes in a target product synthetic pathway for producing a target product.

The genes may be variously selected according to the target product, and examples of the target product synthetic pathway may include an isoprenoid synthetic pathway, a santalene synthetic pathway, a retinol synthetic pathway, and a bisabolol synthetic pathway, but it is not limited thereto. All of the respective synthetic pathways are known pathways, and may be transformed with genes encoding enzymes in the known pathways.

In addition, the organism of the present invention may be one in which a gene encoding enzymes in a by-product generation pathway of the target product is attenuated or deleted in the target product synthetic pathway. As a result, a yield of the target product may be further improved. An example thereof may include an enzyme for converting acetyl-CoA, which is a starting material of the MVA pathway, into acetate, lactate and ethanol of fermentation by-products, and specifically, acetaldehyde dehydrogenase (adhE), paruvate oxidase (PoxB), lactate dehydrogenase (ldhA), acetyl-COA, acetoacetyl-CoA (atoDA) synthase, and the like, but it is not limited thereto (see FIG. 7).

The organism of the present invention may not include an antibiotic resistance gene. Since the antibiotic resistance gene is not used as a marker, there is no need to include the same. Of course, after the above-described transformation, the organism may include the antibiotic resistance gene by further transforming with a plasmid into which the antibiotic resistance gene is subsequently introduced.

The present invention provides a method of transforming an organism including: attenuating or deleting at least one of genes encoding enzymes in an isopentenyl diphosphate or dimethylallyl diphosphate synthetic pathway of an organism to be transformed; and transforming the organism with a recombinant plasmid into which a gene encoding the same enzyme as the attenuated or deleted gene or a complementary gene thereof is introduced.

The gene encoding enzymes in the isopentenyl diphosphate or dimethylallyl diphosphate synthetic pathway may be a gene within the above-described range.

As described above, the transformation of organisms is usually performed in a culture liquid containing antibiotics, but since the transformation method of the present invention does not use the antibiotic resistance marker, the transformation of the present invention may be performed without antibiotics.

The attenuated or deleted gene may be at least one of genes encoding enzymes in the isopentenyl diphosphate or dimethylallyl diphosphate synthetic pathway.

Specifically, it may be a gene encoding enzymes in the MEP pathway or the MVA pathway.

During transformation, the organism may be transformed with a plasmid into which the same gene as the attenuated or deleted gene or a gene encoding the same enzyme derived from other species is introduced.

As a specific example, the organism may be transformed with a plasmid into which a gene encoding at least one of DXP synthase and DXP reductoisomerase is attenuated or deleted, and may be transformed with the plasmid into which the same gene as said gene or a gene encoding the same enzyme derived from other species (with different genes) is introduced.

In addition, the organism may be transformed with a plasmid into which the complementary gene of the attenuated or deleted gene is introduced.

The complementary gene means a gene that may activate a pathway other than the pathways inactivated by attenuation or deletion of the gene, thereby producing isopentenyl diphosphate or dimethylallyl diphosphate. For example, in a case of an organism whose gene of the MEP pathway is attenuated or deleted, it may be transformed with a plasmid into which a gene encoding enzymes in the entire MVA pathway is introduced, and in a case of an organism whose gene of the MVA pathway is attenuated or deleted, it may be transformed with a plasmid in which a gene encoding the enzymes in the entire MEP pathway is introduced.

When introducing two or more genes, these genes may be introduced into a single plasmid or may be introduced into a plurality of plasmids, respectively.

As more specific examples of the deletion and transformation methods without limitation, as described above, the organism cannot survive without the IPP and DMAPP. Therefore, by adding 2-C-methyl-D-erythritol in the medium in the absence of dxs or ispC of the MEP pathway to produce 2-C-methyl-D-erythritol-4-phosphate (MEP) which is a metabolite of ispC, the organism may be transformed with a gene encoding the same enzyme as said gene or the complementary gene thereof while maintaining the growth of the organism. In addition, the MVA lower pathway gene may be first introduced, and then attenuation or deletion of the MEP pathway gene may be performed in a medium to which mevalonic acid is added.

When deleting the MVA pathway gene, a specific method may vary according to upper or lower pathway attenuation or deletion.

As a specific example of the upper pathway deletion, the growth of organism is maintained only by the lower pathway by adding mevalonic acid to the medium, and in this state, the upper pathway gene is attenuated or deleted, then the organism may be transformed with a gene encoding the same enzyme as said gene or the complementary gene thereof.

As a specific example of the lower pathway deletion, the growth of organism is maintained by introducing all the MEP pathway genes, and in this state, the upper pathway gene is attenuated or deleted, then the organism may be transformed with a gene encoding the same enzyme as said gene or the complementary gene thereof.

The plasmid according to the present invention may further include a gene encoding enzymes in the target product generation pathway for producing a target product.

The genes may be variously selected according to the target product, and examples of the target product synthetic pathway may include an isoprenoid synthetic pathway, a santalene synthetic pathway, a retinol synthetic pathway, and a bisabolol synthetic pathway, but it is not limited thereto. All of the respective synthetic pathways are known pathways, and genes encoding enzymes of the known pathways may be further introduced.

In addition, the organism of the present invention may be one in which a gene encoding enzymes in a by-product generation pathway of the target product is attenuated or deleted in the target product synthetic pathway. As a result, a yield of the target product may be further improved. An example thereof may include an enzyme for converting acetyl-CoA, which is a starting material of the MVA pathway, into acetate, lactate and ethanol of fermentation by-products, and specifically, acetaldehyde dehydrogenase (adhE), paruvate oxidase (PoxB), lactate dehydrogenase (ldhA), acetyl-COA, acetoacetyl-CoA (atoDA) synthase, and the like, but it is not limited thereto (see FIG. 7).

In addition, the present invention provides a method of producing a target product using the organism or including the transformation method.

The method of producing a target product of the present invention includes transforming the organism with a gene encoding enzymes in the target product generation pathway to produce the target product.

The gene encoding the enzymes in the target product generation pathway may be introduced into the above-described plasmid to be transformed into the organism.

The target product may be produced by culturing the organism in a medium containing a substrate, and the cultivation may be performed under a culture condition without antibiotics.

The methods of the present invention is capable of transforming the organism and producing the target product without antibiotics and antibiotic resistance genes, thereby basically preventing the problems caused by the use of antibiotics, as well as, a loss of plasmids due to degradation and modification of the antibiotics not occur, thus it is possible to produce the target product in a higher yield than the prior art.

Hereinafter, the present invention will be described in detail with reference to examples.

Example

1. Material and Method
1) Experimental Strain and Material

Microorganisms used in experiments were purchased from the American Type Culture Collection (ATCC), the Korea Collection for Type Cultures (KCTC), and the Korea Culture Center of Microorganisms (KCCM), which are summarized in Table 1 below.

TABLE 1

| Experiment | Description | Source & Reference |
|---|---|---|
| DH5A | F−, λ−, endA1, ginV44, thi-1, recA1, relA1, gyrA96, deoR, Φ80, dlacZ Δ15, ΔlacZYA-argF) V169, hsdR17($r_K^- m_K^+$), supE44 | NEB C2987 |
| MG1655(DE3) | F- λ- ilvG rfb-50 rph-1 (DES) | KCOM 41310 |
| MG1655(DE3) DadhE ::MVA bottom | DadhE (::$P_{cTrc}$_SN12Didi-ter) | — |
| MG1655(DE3) DatoDA::MVA bottom | DatoDA (::$P_{cTrc}$_SN12Didi-ter) | |
| MG1655(DE3) DldhA::MVA bottom | DldhA (::$P_{cTrc}$_SN12Didi-ter) | |
| MG1655(DE3) DpoxB::MVA bottom | DpoxB (::$P_{cTrc}$_SN12Didi-ter) | |
| MG1655(DE3) Δdxr DadhE ::MVA bottom | Δdxr DadhE (::$P_{cTrc}$_SN12Didi-ter) | |
| MG1655(DE3) Δdxr/s DadhE ::MVA bottom | Δdxr, Δdxs, DadhE (::$P_{cTrc}$_SN12Didi-ter) | |
| E. coli EC1000 | RepA+ MC1000, KmR, carrying a single copy of the pWV01 repA gene in the glgB gene: host for pOR128-based plasmids | Leenhouts et al Mol Gen Genet. 1996 Nov. 27;253(1-2): 217-24 |
| L. lactis subsp. cremoris MG1363 | Plasmid-free derivative of L. lactis subsp. Cremoris NCD0712 | Plasmid complement of Streptococcus lactis NCD0712 and other lactic streptococci after protoplast-induced curing. J. Bacteriol. 154:1-9. |
| L. Lactis subsp. cremoris MG1363ΔmvaA | | |

DH5α(F-f80dlacZDM15D(lacZYA-argF)U169 deoR recA1 endA1 hsdR17($r_{K-}$, $m_{K+}$) phoA supE44λ−, thi-[1] gyrA96 relA1) was used in gene cloning, and MG1655 (DE3)(F−λ−ilvG rfb-50 rph-1(DE3)) was used in production of a target product. pTrc99A and pSTV28 were used as an expression vector (Table 2). Products of New England Biolabs (U.S.) were used as a restriction enzyme and other enzymes. In order to perform PCR, products of Solgent (Korea) and Thermo Scientific (U.S.) were used as Pfu-X DNA polymerase and Phusion DNA polymerase, respectively. A product of Invitrogen (U.S.) was used as a DNA size maker. Products of Promega (U.S.); Sigma (U.S.); Merck (U.S.), and Amresco (U.S.) were used as IPTG; L(+)-arabinose, glucose and lactose; acetone; and glycerol, respectively. Other products of Sigma (U.S.) were used as other reagents.

Preparation of a medium for culturing microorganisms was conducted in accordance with the recommended medium composition and Difco manual (11th edition, Difco; BD Science, U.S.) of each strain distribution institution. Reagents used to prepare the media were purchased from BD Science (U.S.) and Sigma (U.S.). Cell amounts in the culture were represented as results measured by a spectrophotometer (Shimadzu UV-1601, Japan) at an optical density (OD) of 600 nm, and pH was measured by a pH meter B-212 (HORIBA, Japan).

Ampicillin and kanamycin were used as antibiotics for maintain plasmids in gene cloning at concentrations of 100 μg/ml and 50 μg/mL, respectively.

2) Extraction and Analysis of Retinoid

Retinoids were analyzed by the following method. 50-100 μl of culture liquid was taken, and cells were recovered by centrifugation at 14,000 rpm for 40 seconds. The cells were resuspended by adding 400 μl of acetone to the recovered cells, followed by extraction at 55° C. for 15 minutes in a dark place, and again adding 600 μl of acetone thereto for 15 minutes. The extract was centrifuged at 14,000 rpm for 10 minutes, and then only a supernatant was taken for HPLC quantitative analysis. In a case of adding a heavy mineral oil layer to the retinoid culture liquid, only the heavy mineral oil layer was centrifuged at 14,000 rpm for 10 minutes, and then 5-50 μl of the heavy mineral oil layer containing the retinoid was resuspended in 1 mL of acetone. The extract was left at room temperature for 15 minutes, while vortexing the same at an interval of 5 minutes. The extract was centrifuged at 14,000 rpm for 10 minutes, and then subjected to HPLC quantitative analysis by taking only the acetone layer.

Figure 2:
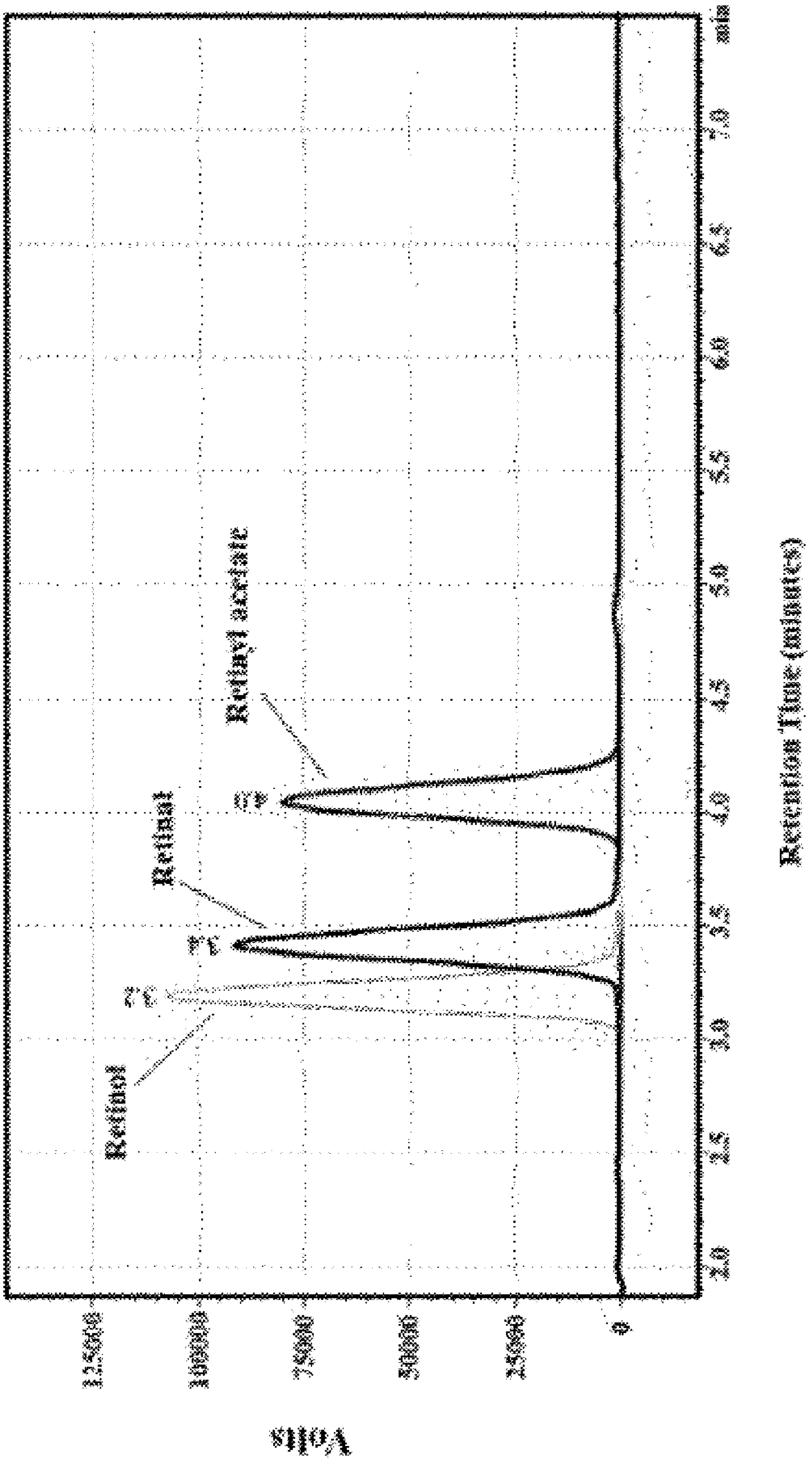
FIG. 2 is a graph showing a HPLC analysis profile of retinoid.
Figure 3:
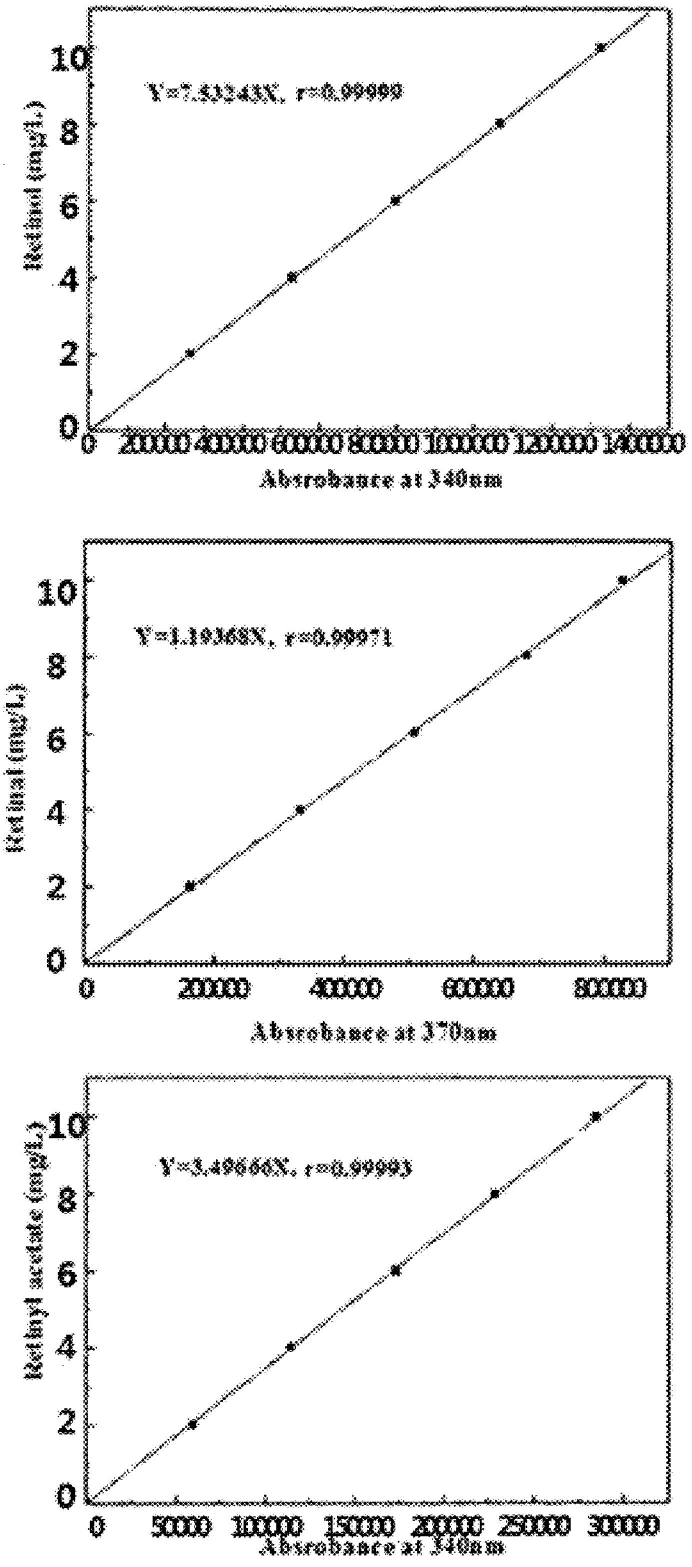
FIG. 3 is graphs showing standard curves for quantitative analysis of retinoid.

SHIMADZU LC-20A series with UV/Vis detector (Shimadzu, Kyoto, Japan) was used as a retinoid analysis system, and Symmetry C18 (250×4.6,5 μm) with Symmetry guard C18 (15×4.6, 5 μm) was used as an analysis column. A mobile phase was analyzed in a mixture solution of methanol:acetonitrile (95:5, v/v) for 15 minutes. A flow rate was set to be 1.5 mL/min, and detection wavelengths of retinal; and retinol and retinyl acetate were measured at 370 nm; and 340 nm, respectively, followed by analyzing 20 μl of sample injection amount and 40° C. of oven temperature. Retinoid standard samples were used by dissolving in ethanol. Peak retention times of the standard samples were about 3.2 minutes for retinol, about 3.4 minutes for retinal, and about 4.0 minutes for retinyl acetate (FIG. 2). Calculation was performed in such a way that the analyzed results are put into a calibration curve calculated by an area of the analyzed peak as a peak area of the standard samples and converted into a dilution factor (FIG. 3).

3) Extraction and Analysis of Santalene

Figure 4:
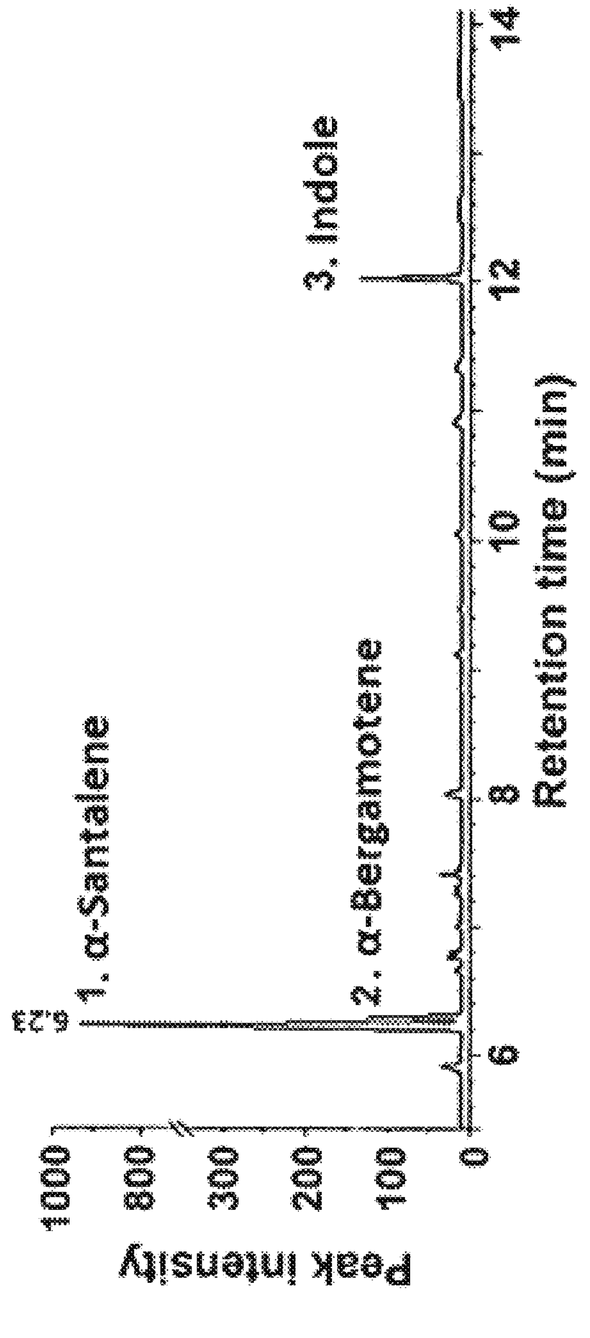
FIG. 4 is a graph showing a GC analysis profile of santalene.

For analysis of santalene produced in a two-phase culture of applying decane to a medium, a decane layer was subjected to gas chromatography (GC) and gas chromatography-mass spectrometry (GC-MS) analyses (FIG. 4). The GC analysis was performed using GC/FID (Agilent Technologies7890A) equipped with 19091N-133 HP-Innowax column (30 m; internal diameter, 0.25 mm; film thickness, 250 nm). A temperature of a column oven was raised to 250° C. at a rate of 10° C./min from an initial temperature of 80° C. for 1 minute, and held for 1 minute. Nitrogen flowed as a mobile phase gas at a pressure of 39 psi, and a detector was maintained at a temperature of 260° C. The GC-MS analysis was performed using GCMS-QP2010 Ultra (SHIMADU, Tokyo, Japan), and helium was used as the mobile phase gas.

4) Extraction and Analysis of Bisabolol

Figure 5:
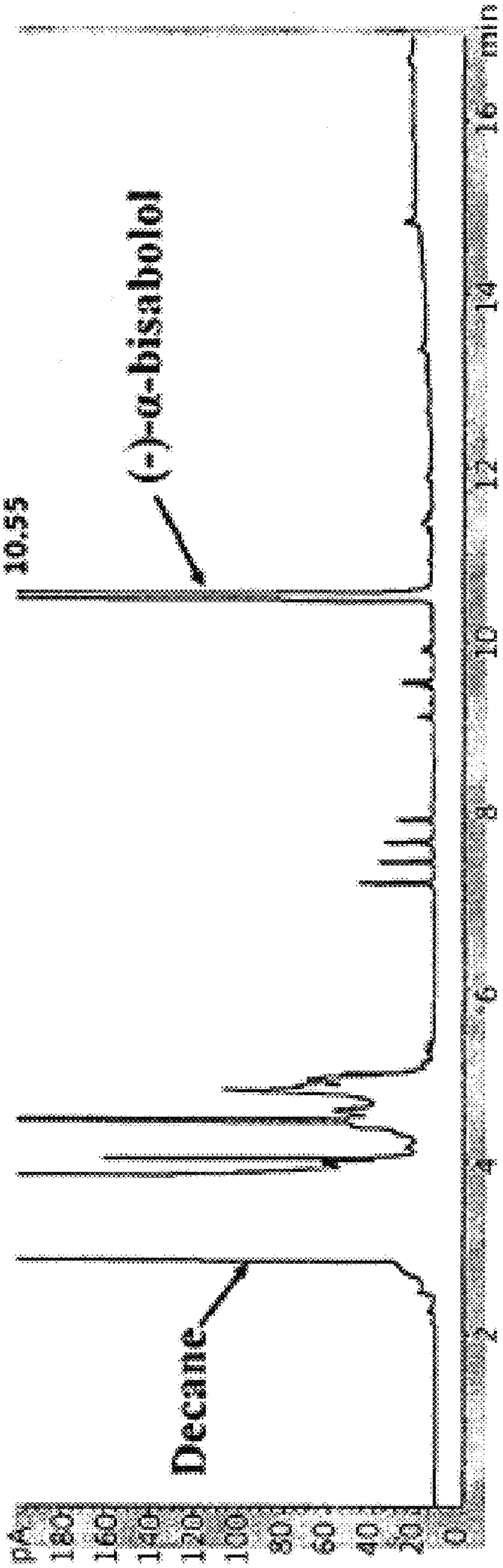
FIG. 5 is a graph showing a GC analysis profile of bisabolol.
Figure 6:
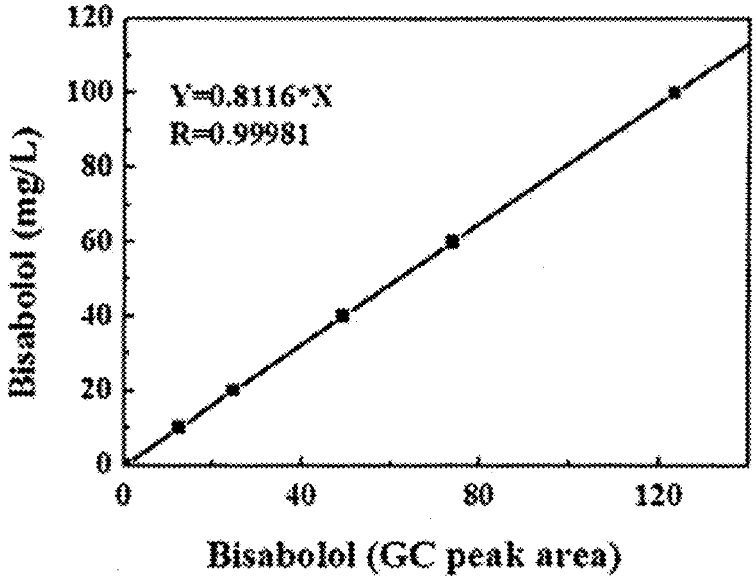
FIG. 6 is a graph showing a standard curve for quantitative analysis of bisabolol.

After the culture is completed, the decane layer was recovered by centrifugation (14,000 rpm, 10 min), and was subjected to the gas chromatography (GC) and gas chromatography-mass spectrometry (GC-MS) analyses (FIG. 5). The GC analysis was performed using GC/FID (Agilent Technologies 7890A) equipped with 19091N-133 HP-Innowax column (30 m; internal diameter, 0.25 mm; film thickness, 250 nm). The temperature of a column oven was increased at a rate of 20° C./min from an initial temperature of 50° C., and the temperature was increased at a rate of 15° C./min after reaching 90° C. After reaching 150° C., the temperature was increased to 190° C. at a rate of 20° C./min, and then allowed the temperature to reach 260° C. at a rate of 10° C./min, and maintained for 2 minutes. Nitrogen was supplied as the mobile phase gas at a pressure of 30 psi, and the detector was maintained at a temperature of 280° C. The GC-MS analysis was performed using GCMS-QP2010 Ultra (SHIMADU, Japan) and helium was used as the mobile phase gas. A peak area value of the measured bisabolol was calculated as following Equation 1 according to the calibration curve (FIG. 6) prepared in advance.

$$\alpha\text{-Bisabolol(mg/L)}=0.8116\times\text{GC Peak area}\times\text{Dilution factor} \quad \text{[Equation 1]}$$

2. Process of Constructing MEP Pathway-Defective Strain

Example of introducing MVA lower pathway gene into chromosome when constructing MEP pathway-defective strain, and performing a construction work in a mevalonic acid-added medium.

Deletion of MEP upper pathway gene

1) Insertion of Foreign MVA Lower Pathway into *E. Coli* Chromosome

Figure 7:
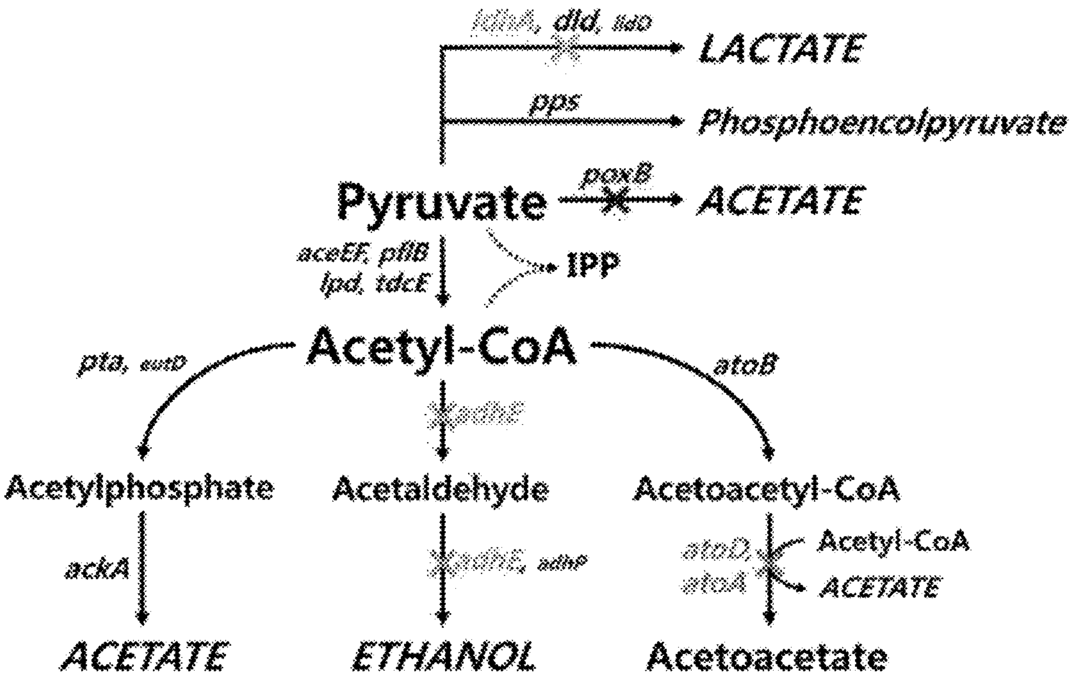
FIG. 7 is a view showing a fermentation by-product generation pathway.

Generally, there are two methods for inserting a foreign pathway into *E. coli* chromosomes: PCR-based homologous recombination method using λ-Red recombinase; and P1 transduction. In this experiment, by using the PCR-based homologous recombination method using λ-Red recombinase, a foreign MVA lower pathway was inserted into *E. coli* MG1655(DE3). In the MVA pathway, a pathway from mevalonate to DMAPP was referred to as a lower pathway (see FIG. 1). Currently, the MVA lower pathway includes: mvaK1, mvaK2, and mvaD of *Streptococcus pneumoniae*; and idi genes of *E. coli*. The gene was amplified by using primers of SEQ ID NO: 1 and SEQ ID NO: 2, and cloned into a pTFCC(DPB) vector to construct pTFCC(DPB)-SN12Didi. The MVA lower pathways were inserted into four genes including adhE, poxB, ldhA and atoDA, respectively at insertion positions. They are genes that convert acetyl-CoA, which is a starting material of the MVA pathway, into acetate, lactate and ethanol of fermentation by-products, and it is possible to improve fermentation productivity and use efficiency of carbon source by blocking the same (FIG. 7).

The experimental method is as follows. First, vectors including a promoter, a multi-cloning site, a terminator, an FRT site, and an antibiotic marker were constructed so that a pathway to be inserted into the *E. coli* chromosome is expressed in the cell, which is shown in Table 2 below.

TABLE 2

| Plasmid | Description | Genbank Grant NO. | Product | SEQ ID NO. |
|---|---|---|---|---|
| pSTV28 | p15A origin, lac promoter, lacZ, and cat | M22744 | Takara Korea (Korea) | 71 |
| pTrc99A | pMB1 origin, trc promoter, lacIq, and bla | U13872.1 | Pharmacia (U.S.) | 72 |
| pTFKC(DPB) | ColE1 origin, trc promoter without operator region, kanamycin cassette with FRT, and bla | — | | 73 |
| pTFCC(DPB) | ColE1 origin, trc promoter without operator region, chloramphenicol cassette with FRT, and bla | — | | 74 |
| pCP20 | cI8572λts, FLP, cat, and bla | — | | 75 |
| pKD46 | repA101ts, oriR101, exo, bet, gam, tL3, PBAD, araC, and bla | AY048746 | | 76 |
| pT-ispA-STS | pTrc99A vector; lacIq; Ampr; *E. coli*-derived FPP Synthase, ispA; Ptrc expression vector including Clausena lansium-derived santalene synthase, STS | — | | 77 |
| pTAS-NA | pTrc99A vector; lacIq; Ampr; IspA and idi, which are *E. coli*-derived FPP synthase; Clausena lansium-derived santalene synthase, STS; *E. faecalis*-derived mvaE and mvaS; Ptrc expression vector including *S. pneumonia*-derived mvaK1, mvaK2 and mvaD | — | In this study | 78 |
| pSNAK | pSTV28 vector; *E. faecalis*-derived lacZ; $Km^r$; mvaE and mvaS; *S. pneumonia*-d mvaK1, mvaK2 and mvaD; Plac expression vector including *E. coli*-derived idi | — | | 79 |

TABLE 2-continued

| Plasmid | Description | Genbank Grant NO. | Product | SEQ ID NO. |
|---|---|---|---|---|
| pSNAK(-E) | pSTV28 vector; lacZ; $Km^r$; *E. faecalis*-derived mvaS; *S. pneumonia*-derived mvaK1, mvaK2 and mvaD; Plac expression vector including *E. coli*-derived idi | — | In this study | 80 |
| pSNA(-E)free | pSTV28 vector; lacZ; *E. faecalis*-derived mvaS; S. pneumonia-derived mvaK1, mvaK2 and mvaD; Vector including *E. coli*-derived idi without antibiotic markers | — | In this study | 81 |
| pTEFAmvaE | pTrc99A vector; lacIq; $Amp^r$; Ptrc expression vector including *E. faecalis*-derived mvaE | — | | 82 |
| pT-DHBSRYbb0 | pTrc99A vector; lacIq; $Amp^r$; *P.agglomerans*-derived crtE, crtB and crtI; *P.ananatis*-derived vrtY; codon-optimized uncultured marine bacterium 66A03-derived SR; dxs and YbbO of *E.coli* | — | | 83 |
| pT-HBSRYbbO | pTrc99A vector; lacIq; $Amp^r$; *P.agglomerans*-derived crtE, crtB and crtI; *P.ananatis*-derived crtY; codon-optimized uncultured marine bacterium 66A03-derived SR; YbbO of *E.coli* | — | In this study | 84 |
| pT-HBSREYbbO | pTrc99A vector; lacIq; $Amp^r$; *P.agglomerans*-derived crtE, crtB and crtI; *P.ananatis*-derived crtY; codon-optimized uncultured marine bacterium 66A03-derived SR; YbbO of *E. coli; E. faecalis*-derived mvaE | — | In this study | 85 |
| pT-HBSREYbbOfree | pTrc99A vector; lacIq; *P.agglomerans*-derived crtE, crtB and crtI; *P.ananatis*-derived crtY; codon-optimized uncultured marine bacterium 66A03-derived SR; YbbO of *E. coli*; Vector including *E. faecalis*-derived mvaE without antibiotic markers | — | In this study | 86 |
| pT-dxr | pTrc99A vector; lacIq; $Amp^r$; Ptrc expression vector including *E. coli*-derived dxr | — | | 87 |
| pTAS-dxr | pTrc99A vector; lacIq; $Amp^r$; *E. coli*-derived FPP Synthases, ispA and dxr; Ptrc expression vector including STS, Clausena lansium-derived santalene synthase | — | In this study | 88 |
| pT-dxr/s | pTrc99A vector; lacIq; Ampr; Ptrc expression vector including *E. coli*-derived dxr and dxs | — | | 89 |
| pT-ispA-MrBBS | pTrc99A vector; lacIq; Ampr; *E. coli*-derived FPP Synthase, ispA; Ptrc expression vector including codon-optimized Matricaria recutita-derived α-bisabolol synthase, MrBBS | — | In this study | 90 |
| pTAS-dxs | pTrc99A vector; lacIq; Ampr; *E. coli*-derived FPP synthase, ispA and dxs; Ptrc expression vector including Clausena lansium-derived santalene synthase, STS | — | In this study | 91 |
| pTAB-idi-dxr | pTrc99A vector; lacIq; Ampr; *E. coli*-derived FPP Synthases, ispA and dxr; Ptrc expression vector including | — | In this study | 92 |

TABLE 2-continued

| Plasmid | Description | Genbank Grant NO. | Product | SEQ ID NO. |
|---|---|---|---|---|
| | codon-optimized Matricaria recutita-derived a-bisabolol synthase, MrBBS | | | |
| pSNAK(-E)-dxs | pSTV28 vector; lacZ; $Km^r$; *E. faecalis*-derived mvaS; *S.* pneumonia-derived mvaK1, mvaK2 and mvaD; Plac expression vector including *E. coli*-derived idi and dxs | — | In this study | 93 |
| pSNA(-E)-dxsfree | pSTV28 vector; lacZ; *E. faecalis*-derived MvaS; *S. pneumonia*-derived mvaK1, mvaK2 and mvaD; Vector including *E. coli*-derived idi and dxs without antibiotic markers | — | In this study | 94 |
| pT-HBSREYbb0 dxrfree | pTrc99A vector; lacIq; *P.agglomerans*-derived crtE, crtB and crtI; *P.ananatis*-derived crtY; codon-optimized uncultured marine bacterium 66A03-derived SR; YbbO and *E. coli*-derived dxr; Vector including *E. faecalis*-derived mvaE without antibiotic markers | — | In this study | 95 |
| pEGFP | pUC origin, lac promoter; EGFP, and AmpR | — | Clontech (U.S.) | 96 |
| pEGFP-dxr | pUC origin, lac promoter; EGFP, *E.coli* dxr, and AmpR | — | In this study | 97 |
| pOR119 | $Em^r$ $Ori^+$ $RepA^-$ lacZ' derivative of pORI28 | A System To Generate Chromosomal Mutations in *Lactococcus lactis* Which Allows Fast Analysis of Targeted Genes | — | 98 |
| pORI19-mvaA | pORI19-mvaA | — | In this study | 99 |
| pCI372 | *E. coli*/*L. lactis* shuttle vector, CamR | Identification of the minimal replicon of *lactococcus lactis* subsp. *lactis* UC317 plasmid pCI305 | — | 100 |
| pCIN | pCI372-FP promoter, MCS, rrnp terminator | — | In this study | 101 |
| pCIN-mvaA | pCIN-mvaA | — | In this study | 102 |
| pCIN-mvaA-EGFP | pCIN-mvaA,EGFP | — | In this study | 103 |

All the constructed vectors were used with trc promoters or used by modifying so as to express the trc promoters at all times. Therefore, the constructed pBFKC has the trc promoter, and the pTFKC (DPB) and pTFCC (DPB) have the modified trc promoters, respectively, so as to be expressed at all times. A desired pathway was inserted using a multi-cloning site of the constructed vector, and PCR was performed using each of the constructed plasmids as a template, and a primer having a homology of 50 bp with a portion into which *E. coli* is inserted. Each primer information is represented in SEQ ID NO: 3 to SEQ ID NO: 10 in Table 4. The obtained PCR product was purified, followed by performing electro-transformation to 1.8 kV through a cuvette having an interval of 1 mm on *E. coli* MG1655(DE3) competent cells containing pKD46. Thereafter, immediately adding 1 mL of SOC medium (2% of Bacto Tryptone, 0.5% of yeast extract, 10 mM of NaCl, 2.5 mM of KCl, 10 mM of $MgCl_2$, 10 mM of $MgSO_4$, and 20 mM of glucose) thereto, followed by shaking culture at 37° C. for 1 hour. After smearing it on a plate medium to which antibiotics are added to culture at 37° C., single colonies were obtained. Herein, the obtained single colonies were suspended in a small amount of distilled water, heated for 10 minutes and centrifuged, then the supernatant was used as a template to perform PCR using each primer from SEQ ID NO: 11 to SEQ ID NO: 18 to confirm whether the pathway is inserted or not. In order to remove the antibiotic marker, single colonies were obtained by transforming pCP20 plasmids into strains confirmed the foreign pathway insertion, followed by culturing at 30° C. PCR was performed through the above primers for confirmation using the obtained single colonies as a template, and consequently, it was confirmed that the antibiotic marker was removed. The confirmed colonies were cultured at 43° C. to remove the pCP20 plasmid, which is a temperature sensitive plasmid, thereby obtaining a foreign pathway-inserted strain after completion.

2) Deletion of dxr and dxs Genes in MG1655(DE3) ΔadhE::MVAbottom Strain

Deletion of gene was also performed using Datsenko and Wanner's methods to delet dxr gene in *E. coli* chromosome.

In order to replace the dxr gene with kanamycin gene which is a selection marker gene by homologous recombination, PCR primers having base sequences at upstream and downstream ends of the dxr gene while binding to the kanamycin gene of pTFKC (DPB) plasmid were prepared. A forward primer consists of a 50 bp base sequence at the upstream end of the dxr gene, followed by a 15 bp kanamycin gene binding base sequence, and a reward primer consists of a 50 bp base sequence at the downstream end of the dxr gene, followed by a 20 bp kanamycin gene binding base sequence. The primers used herein are shown in Table 7 below. PCR reaction was performed using oligonucleotides of SEQ ID NO: 19 and SEQ ID NO: 20 as a primer, and pTFKC (DPB) as a template.

The purified PCR reaction product was transformed into MG1655(DE3) ΔadhE::MVAbottom competent cells containing pKD46 (Datsenko K A and Wanner B L, 2000 Proc Natl Acad Sci U.S.A., 97(12):6640-6645). Colonies were obtained from a plate medium containing 3.3 mM mevalonate and kanamycin, and the obtained colonies were confirmed by PCR to confirm that the kanamycin gene replaced the dxr gene by the homologous recombination. In addition, it was confirmed that the MEP pathway was blocked due to the deletion of the dxr gene based on the fact that colonies could not grow by smearing on a mevalonate-free plate medium. Primers used for colony of PCR were prepared so as to be bound to a region immediately adjacent to the dxr gene on the *E. coli* MG1655(DE3) chromosome. The used primer for confirmation is a primer of oligonucleotides of SEQ ID NOs: 21, 22 and 23.

In order to remove the antibiotic marker on the chromosome, single colonies were obtained by transforming pCP20 plasmids into strains confirmed the foreign pathway insertion, followed by culturing at 30° C. PCR was performed through the above primers for confirmation using the obtained single colonies as a template, and consequently, it was confirmed that the antibiotic marker was removed. The confirmed colonies were cultured at 43° C. to remove the pCP20 plasmid, which is a temperature sensitive plasmid, thereby obtaining MG1655(DE3) Δdxr ΔadhE::MVAbottom strain after completion.

In the same manner as in the above method, the MG1655 (DE3) Δdxr ΔadhE::MVAbottom strain was subjected to deletion of the dxs gene to obtain MG1655(DE3) Δdxr/s ΔadhE::MVAbottom strain. For the homologous recombination, PCR reaction was performed using primers of SEQ ID NO: 24 and SEQ ID NO: 25, and pTFKC (DPB) as a template. Thereafter, oligonucleotides of SEQ ID NOs: 26, 27 and 28 were used as a primer for confirmation.

3. Methods of Constructing and Culturing Plasmid (MEP Pathway-Defective Strain)

Use of a strain in which a foreign MVA lower pathway is inserted into a chromosome and an MEP upper pathway gene is deleted The selection marker of the plasmid used in the MEP pathway-defective strain may be an activated MVA pathway or a deleted MEP pathway gene of the chromosome, which may complement the deleted MEP pathway. Single or plurality of plasmids may be introduced into the defective strain, and the number thereof is not particularly limited. In a single plasmid method, it is necessary to compensate for the deletion of the host's MEP pathway by the single plasmid to be introduced, and in a plurality of plasmids method, only when all the plurality of plasmids to be introduced are present, it is necessary to compensate for the deletion of the host's MEP pathway.

1) Isoprenoid Biosynthetic Plasmid Based on Foreign MVA Pathway

A. Single Plasmid Method (Example of Producing Santalene)

This is a method in which all the activated MVA pathways that complement for the deletion of the host's MEP pathway are present in the single plasmid, and it is constructed so that the MVA pathway and the biosynthetic pathway of the target product are coexisted in this plasmid.

i. Construction of Plasmid

In order to use the foreign MVA pathway as a selection marker to replace antibiotic markers in the MEP pathway-defective strain, a recombinant plasmid is constructed by introducing an MVA pathway into a plasmid for producing santalene ('santalene producing plasmid'). The defective strain may be grown when introducing recombinant plasmids to produce santalene.

Santalene producing plasmid pT-ispA-STS is formed by introducing an ispA gene which is FPP synthase of *E. coli* and STS which is a santalene synthase gene of *Clausena lansium* into pTrc99A vector. A foreign MVA pathway operon in a pSNAK plasmid was cloned using restriction enzyme sites BglII and SbfI located behind an STS gene in the plasmid. The pSNAK plasmid includes mvaK1, mvaD and mvaK2 of *Streptococcus pneumoniae*, mvaE and mvaS of *Enterococcus faecalis*, and an idi gene of *E. coli*, which are introduced therein. An MVA operon was introduced into a pT-ispA-STS vector by cleaving restriction enzymes BamHI and SbfI at both ends thereof Restriction enzymes BamHI and BglII have the same cohesive end as each other. Finally, pTAS-NA was constructed in which a santalene producing operon and the MVA pathway operon were introduced together.

In the cloning process of the plasmid above, for selection of transformants, *E. coli* DH5α or *E. coli* MG1655(DE3) Δdxr ΔadhE::MVAbottom may be used. When using *E. coli* DH5α, it is possible to select on an ampicillin plate by using an antibiotic marker present in the plasmid to be constructed. When using *E. coli* MG1655(DE3) Δdxr ΔadhE::MVAbottom, the transformants may be selected without antibiotics, because the strain is capable of growing when the MEP pathway of host *E. coli* is inactivated and a plasmid with activated MVA pathway is introduced.

ii. Introduction of Plasmid

The defective strain is capable of growing when introducing recombinant plasmids to produce santalene. The constructed plasmid pTAS-NA may be introduced into MG1655(DE3) Δdxr ΔadhE::MVAbottom strain, in which the MEP pathway is deleted, to obtain a transformant on a mevalonate-free plate, thereby selecting the recombinant strains using the foreign MVA pathway of the plasmid. Thereafter, by culturing the recombinant strain in a non-antibiotic medium to confirm the productivity of santalene, it is possible to confirm maintenance and activation abilities of the plasmid having the selection marker based on the MVA pathway.

Recombinant strain having a plasmid related to antibiotic-free santalene production was spawn cultured under a non-antibiotic condition, followed by culturing in a mixed medium of 4 mL of 2YT medium (16 g of trypton per liter, 10 g of yeast extract, and 5 g of NaCl) containing 2% (v/v) of glycerol and 0.2 mM of IPTG and 1 mL of decane, which is a production medium. For cultivation, the mixed medium is put into a tube having a groove of 15 cm in length and 25 mm in diameter and is inoculated with each of the strains, followed by culturing in a shaking incubator at 30° C. while stirring at a speed of about 250 rpm.

iii. Culture Result

Figure 8:
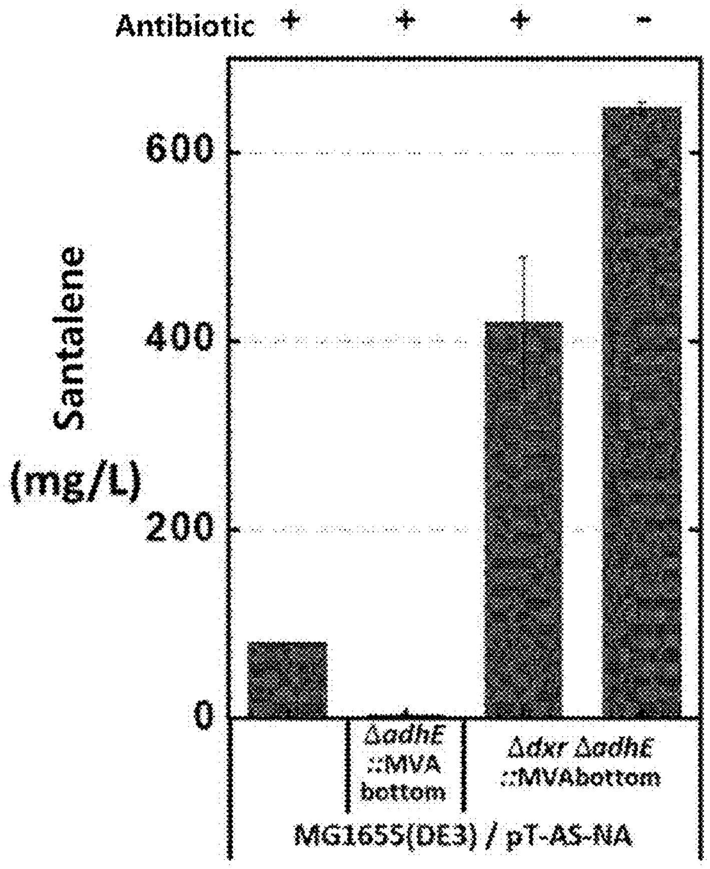
FIG. 8 is a graph showing culture results according to the presence or absence of antibiotics of santalene producing strains that do not require antibiotics (briefly, 'antibiotic-free') constructed by complementing a foreign MVA pathway in MEP pathway-defective strains.

The santalene productions were compared in MG1655 (DE3) Δdxr ΔadhE::MVAbottom, a newly constructed recombinant strain using wild type *E. coli* MG155 (DE3) strain as a control group. The culture results are shown in FIG. 8 and Table 3 below.

More specifically, the cultivation was performed in such a way that MG1655(DE3) and MG1655(DE3) ΔadhE::MVAbottom strains were cultured by adding antibiotics thereto, and MG1655(DE3) Δdxr ΔadhE::MVAbottom, to which an antibiotic-free system can be applied, was cultured by changing with or without the addition of the antibiotics. After 48 hours from the cultivation, the decane layer was recovered and the santalene production was analyzed through GC. As a result, the new recombinant strain MG1655(DE3) ΔadhE::MVAbottom strain exhibited 5 times or higher santalene production (420.2 mg/L) than strain MG1655(DE3) which produced 79.8 mg/L of santalene. In addition, the non-antibiotic culture exhibited higher santalene production (646.7 mg/L) than the case of adding the antibiotics. The same experiment as the above was performed in the MG1655(DE3) ΔadhE::MVAbottom strain to confirm the possibility that such an increase in the santalene production was caused by the MVA lower pathway additionally introduced into the chromosome. However, in this case, it exhibited an aspect that the santalene could not be produced.

TABLE 3

| Strain (48 h) | MG1655(DE3) PTAS-NA | MG1655(DE3) ΔadhE::MVAbottom PTAS-NA | MG1655(DE3) Δdxr ΔadhE::MVAbottom PTAS-NA | |
|---|---|---|---|---|
| Antibiotic addition | + | + | + | − |
| Cell growth ($OD_{600\ nm}$) | 10.9 ± 0.5 | 9.1 ± 1.0 | 10.7 ± 0.3 | 12.7 ± 0.3 |
| Santalene (mg/L) | 79.8 ± 0.9 | 2.9 ± 1.3 | 420.2 ± 69.3 | 646.7 ± 6.6 |

B. Multiple Plasmid Method (Example of Producing Retinoid)

This is a method in which the MVA pathways that compensate for the MEP pathway deletion of the host are distributed and present in a plurality of plasmids, so as to activate the MVA pathway only when all the plurality of plasmids are present. That is, it is constructed so that the MVA pathway and the biosynthetic pathway of the target product are efficiently distributed and arranged in these plasmids in consideration of a size of each plasmid and a required expression amount of constitutive genes.

i. Construction of Plasmid

As a foreign MVA pathway-based plasmid selection marker that can be used in a defective strain having the MVA lower pathway introduced therein into the chromosome, there are mvaE gene and mvaS gene, which are MVA upper pathway genes. The mvaE gene is a gene in which an atoB gene and the mvaA gene are fused, and if necessary, it may be divided into the two genes to be used as a selection marker. In this experiment, a plasmid system to maintain both plasmids under a non-antibiotic condition was constructed using pSNAK plasmid which expresses the foreign MVA pathway and pT-DHBSRYbbO which produces retinoid. The selection markers mvaE gene and mvaS gene are distributed and arranged in two plasmids so that both plasmids are introduced together to compensate for the deletion of the host's MEP pathway. Since one MVA pathway selection marker gene has to be moved from a pSNAK plasmid with a relatively low copy number and lac promoter to the pT-DHBSRYbbO plasmid with a high copy number and trc promoter, the mvaE gene, which requires higher expression amount, was transferred. That is, the mvaS gene is used as a selection marker of a plasmid expressing the MVA pathway except for mvaE, and the mvaE gene serves as a selection marker of a retinoid producing plasmid.

The restriction enzyme site HpaI of the pSNAK plasmid was used to construct a pSNAK(-E) plasmid from which the mvaE gene is removed by self-ligation after cleaving the mvaE gene. In the pSNAK(-E) plasmid, a Kanamycin antibiotic marker gene was removed by PCR using primers of SEQ ID NO: 29 and SEQ ID NO: 30 having a phosphate group at 5' end, and then pSNA(-E) free was constructed by self-ligation.

pT-DHBSRYbbO is a plasmid in which *Pantoea agglomerans*-derived crtE, crtB and crtl, *Pantoea ananatis*-derived crtY, dxs and YbbO of *E. coli*, and codon-optimized uncultured marine bacterium 66A03-derived SR gene is introduced into pTrc99A vector. In the above plasmid, the dxs gene was removed by PCR using primers of SEQ ID NOs: 31 and 32 having a phosphate group at 5' end to construct pT-HBSRYbbO.

The pTEFAmvaE plasmid is a plasmid prepared by introducing mvaE gene of *Enterococcus faecalis* into pTrc99A vector, and serves to amplify the trc promoter and mvaE gene together using the above plasmid as a template by PCR using primers of SEQ ID NOs: 33 and 34. This plasmid was cleaved with restriction enzymes NotI and SalI and inserted into the same restriction enzyme site of the pT-HBSRYbbO vector to prepare a plasmid pT-HBSREYbbO positioned between the idi gene (ipiHP1) and the crtY gene. pT-HBSREYbbOfree was constructed by introducing HindIII restriction enzyme sites after removing the ampicillin antibiotic marker through two PCRs using primers of SEQ ID NOs: 35 and 36 and SEQ ID NOs: 37 and 38 in pT-HBSREYbbO.

ii. Introduction and Culture Results of Plasmid (1) New recombinant strain that maintains the plasmid in a non-antibiotic medium was constructed by introducing new two plasmids pSNAK(-E) and pT-HBSREYbbO, from which the antibiotic marker is not removed, and pT-HBS-REYbbO together into MG1655(DE3) Δdxr ΔadhE::MVAbottom strain. Retinol production of new the recombinant strain with or without the addition of the antibiotics was confirmed using MG1655(DE3) strains containing the existing pSNAK and pT-DHBSRYbbO plasmids as a control group.

Figure 9:
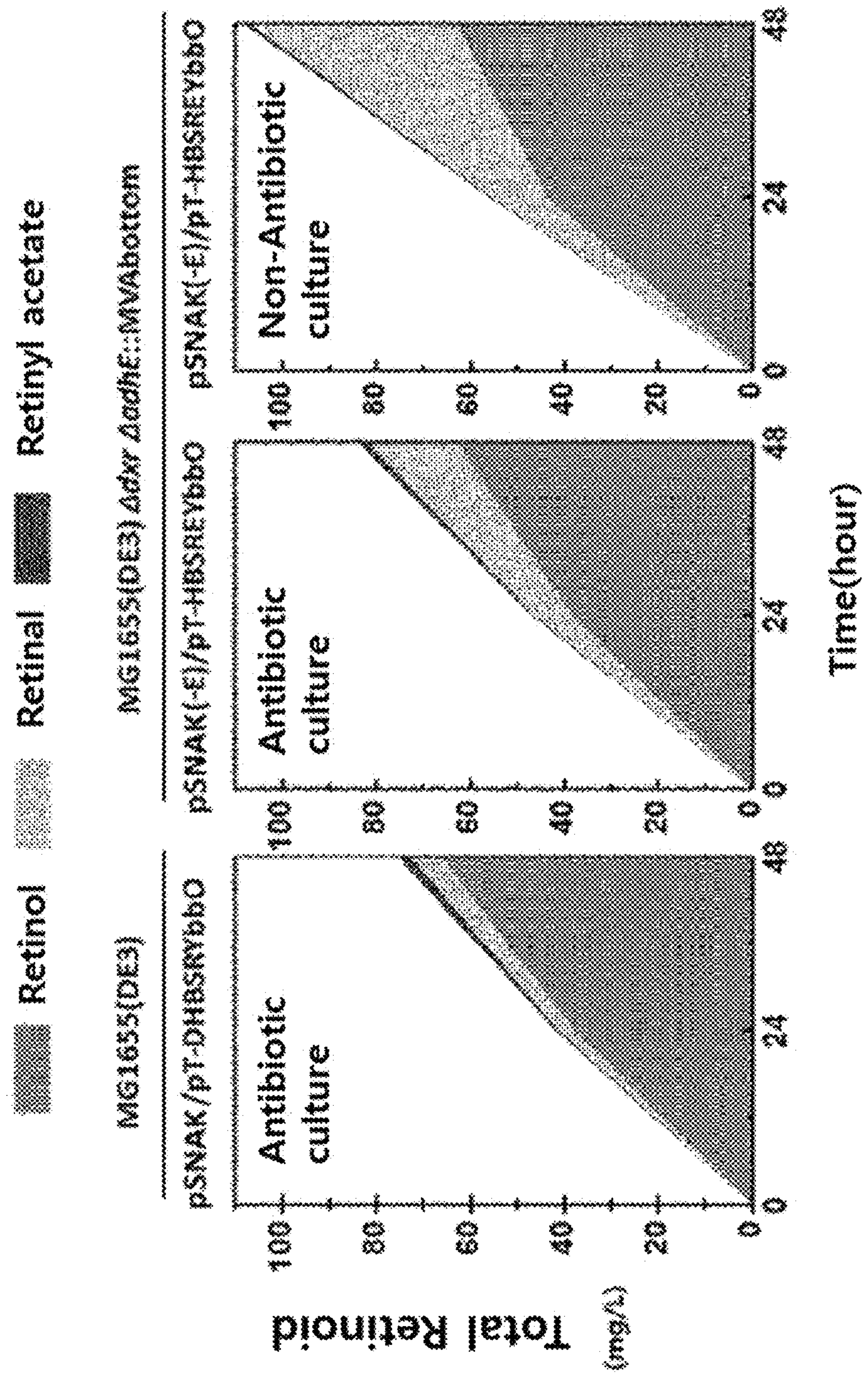
FIG. 9 is a graph showing culture results according to the presence or absence of antibiotics in the antibiotic-free retinoid producing strains constructed by dividing the foreign MVA pathway into two plasmids in the MEP pathway-defective strains.

The culture results are shown in Table 4 below and FIG. 9. More specifically, it can be seen that the production of the retinoid was increased in the new recombinant strain MG1655(DE3) Δdxr ΔadhE::MVAbottom than the existing MG1655(DE3) strain. Comparing the culture results with or without antibiotics of the new strain, cell growth in a non-antibiotice condition was slightly lower, but the production of retinoid was higher than those of the case in an antibiotice condition for 48 hours of cultivation. Front these results, it can be seen that the plasmid is well maintained and functioned with no loss thereof without a selection pressure for antibiotics, and that metabolic flow is also more directed toward the retinoid production from the cell growth. In addition, it can be seen that the difference in the production of retinoid with or without antibiotics is caused by the fact that the antibiotic resistance gene expressed in the plasmid does not completely compensate for the toxicity of the antibiotics. The antibiotics used in this cultivation are ampicillin and kanamycin, wherein the ampicillin serves to inhibit the synthesis of cell walls, and the kanamycin serves to inhibit 30 s subunits of ribosome, thereby reducing overall production of proteins. Therefore, it is determined that, in the cultivation under the non-antibiotic condition, the protein synthesis is better performed due to an absence of a factor that adversely affects the cells, thus to increase the production.

TABLE 4

| Strain (48 h) | MG1655(DE3) pSANK/pT-DHBSRYbbO | MG1655(DE3) Δdxr ΔadhE::MVAbottom pSNAK(-E)/pT-HBSREYbbO | |
|---|---|---|---|
| Antibiotic addition | + | + | − |
| Cell growth (OD $_{600\ nm}$) | 18.3 ± 0.5 | 11.4 ± 0.1 | 11.5 ± 0.2 |
| Total retinoid (mg/L) | 75.4 ± 0.1 | 83.7 ± 2 | 108 ± 1 |

(2) Further, cultivation was performed under a non-antibiotic condition by transforming plasmids from which antibiotic resistance genes were removed, pSNA(-E)free and pT-HBSREYbbOfree together into MG1655(DE3) Δdxr ΔadhE::MVAbottom strain. The cultivation was performed under a retinoid culture condition up to 72 hours which is a maximum time for test tube culture of *E. coli.*

Figure 10:
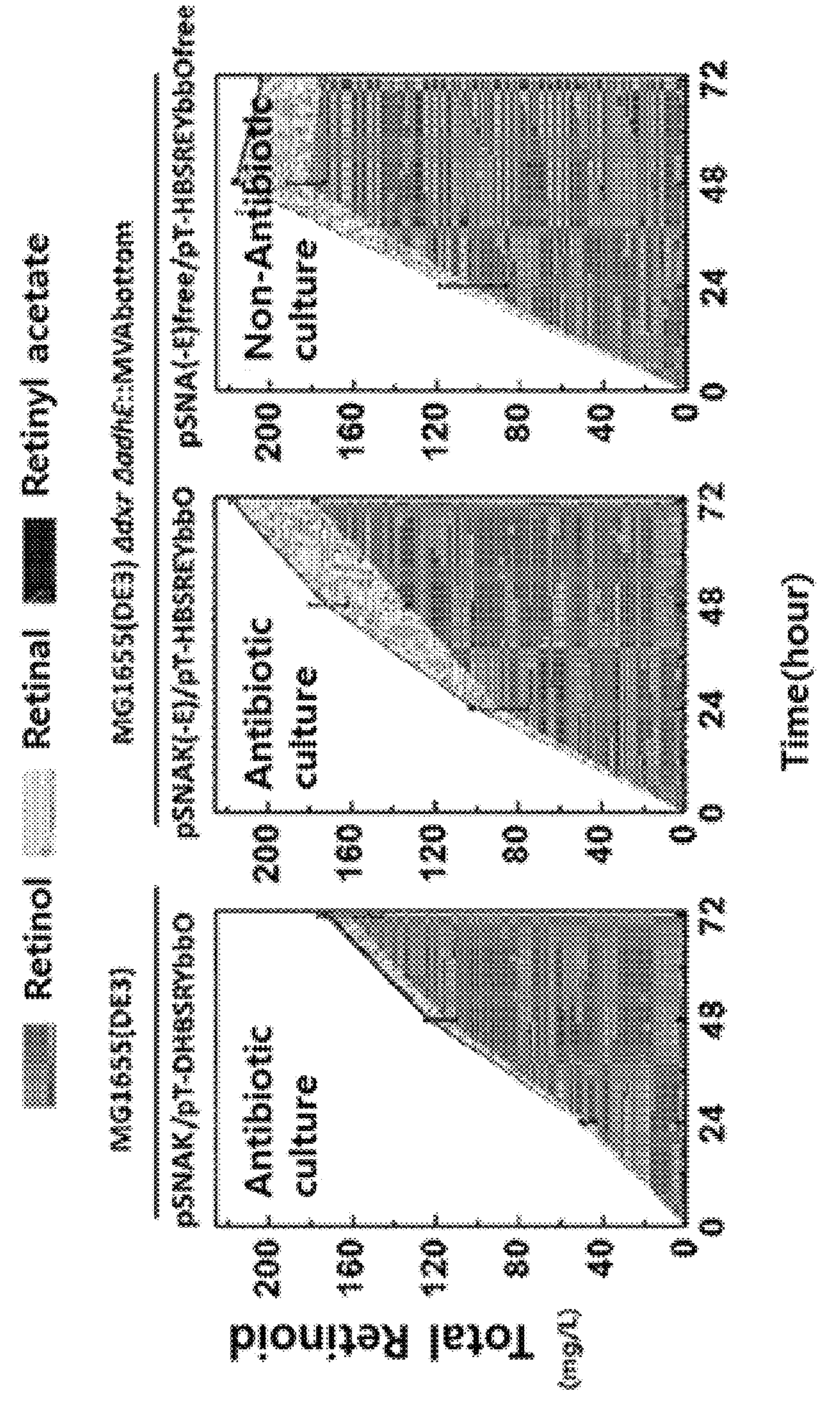
FIG. 10 is graphs showing culture results according to the presence or absence of antibiotics of the retinoid producing strains from which the antibiotic marker is removed.

The culture results are shown in Table 5 below and FIG. 10. More specifically, it can be seen that the recombinant strain including the plasmid introduced therein, from which the antibiotic marker is completely removed, exhibits the fastest production rate of retinoid, and reaches the maximum production at 48 hours, while slightly decreasing at 72 hours due to depletion of the carbon source. Therefore, it is estimated that the metabolic burden on the host cell is reduced by removing the antibiotic marker from the plasmid.

TABLE 5

| | MG1655(DE3) | MG1655(DE3) Δdxr ΔadhE::MVAbottom | |
|---|---|---|---|
| Strain (72 h) | pSANK/pT-DHBSRYbbO | pSNAK(-E)/pT-HBSREYbbO | pSNA(-E)free/pT-HBSREYbbOfree |
| Antibiotic addition | + | + | − |
| Cell growth (OD $_{600\ nm}$) | 22.1 ± 0.03 | 12.9 ± 0.08 | 13.0 ± 0.4 |
| Total retinoid (mg/L) | 173.3 ± 6 | 218.1 ± 1 | 204.2 ± 3 |

2) MEP Pathway-Based Isoprenoid Biosynthetic Plasmid Using Deleted MEP Pathway Gene of Chromosome as a Selection Marker A. Single Plasmid Method (Example of Producing Santalene)

This is a method of constructing a single plasmid having the deleted MEP pathway gene of a chromosome as a selection marker and introducing it into the host, and in this case, the host's MEP pathway deletion is complemented by the introduced plasmid.

i. Construction of Plasmid pTAS-dxr was constructed by introducing a dxr, which is the deleted MEP pathway gene in the defective strain, behind a santalene biosynthetic operon of pT-ispA-STS, which is the santalene producing plasmid. More specifically, restriction enzyme sites BglII and XhoI were introduced into both ends of the dxr gene and amplified using a pT-dxr plasmid having a dxr gene of *E. coli* introduced into pTrc99A plasmid as a template, by PCR using the primers of SEQ ID NO: 39 and SEQ ID NO: 40. Using this, a santalene producing plasmid pTAS-dxr having the deleted dxr gene was constructed by cloning with the same restriction enzyme sites BglII and SalI located behind the STS gene of the pT-ispA-STS vector. Restriction enzymes SalI and XhoI have the same cohesive end as each other.

In the cloning process of the plasmid above, for selection of transformants, *E. coli* DH5α or *E. coli* MG1655(DE3) Δdxr ΔadhE::MVAbottom may be used. When using *E. coli* DH5α, it is possible to select on an ampicillin plate by using an antibiotic marker present in the plasmid to be constructed. When using *E. coli* MG1655(DE3) Δdxr ΔadhE::MVAbottom, the transformants may be selected without antibiotics, because the strain is capable of growing when the MEP pathway of host *E. coli* is inactivated and a plasmid with activated MVA pathway is introduced.

ii. Introduction of Plasmid

The constructed plasmid pTAS-dxr was may be introduced into MG1655(DE3) Δdxr ΔadhE::MVAbottom strain, in which the MEP pathway was blocked, to obtain a strain from a mevalonate-free plate, thereby selecting an inherent MEP pathway using the dxr gene of the plasmid. Thereafter, by performing cultivation of the strain in a non-antibiotic medium to confirm the production of santalene, it is possible to confirm maintenance and activation abilities of the plasmid using the deleted MEP pathway gene.

Recombinant strain having a plasmid related to antibiotic-free santalene production was spawn cultured under a non-antibiotic condition, followed by culturing in a mixed medium of 4 mL of 2YT medium (16 g of trypton per liter, 10 g of yeast extract, and 5 g of NaCl) containing 2% (v/v) of glycerol and 0.2 mM of IPTG and 1 mL of decane, which is a production medium. For cultivation, the mixed medium is put into a tube having a groove of 15 cm in length and 25 mm in diameter and is inoculated with each of the strains, followed by culturing in a shaking incubator at 30° C. while stirring at a speed of about 250 rpm.

iii. Culture Result

Figure 11:
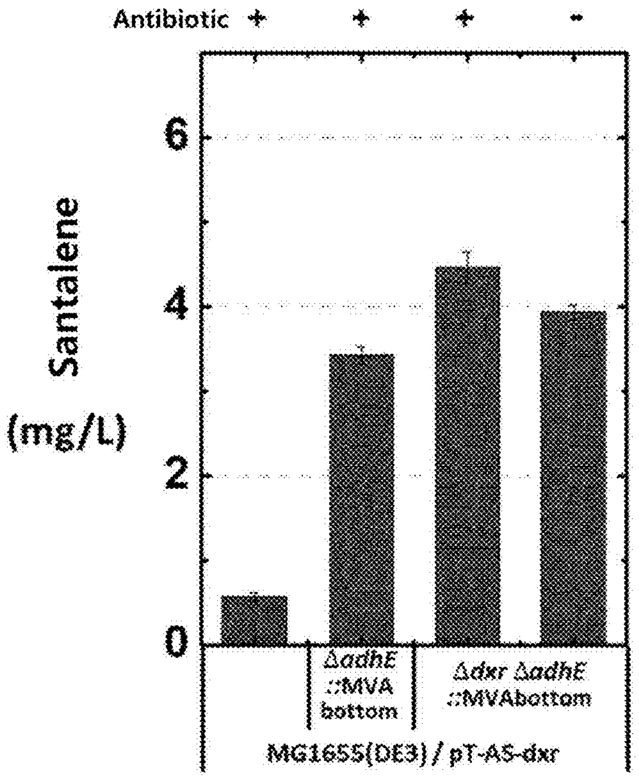
FIG. 11 is a graph showing culture results according to the presence or absence of antibiotics of the santalene producing strains using a deleted MEP pathway gene as a selection marker.

More specifically, the santalene productions were compared in MG1655(DE3) Δdxr ΔadhE::MVAbottom, a newly constructed recombinant strain using wild type *E. coli* MG155 (DE3) strain as a control group. The culture results are shown in FIG. 11 and Table 6 below. More specifically, the cultivation was performed in such a way that MG1655 (DE3) and MG1655(DE3) ΔadhE::MVAbottom strains were cultured by adding antibiotics thereto, and MG1655(DE3) Δdxr ΔadhE::MVAbottom, to which an antibiotic-free system can be applied, was cultured by changing with or without the addition of the antibiotics. After 48 hours from the cultivation, the decane layer was recovered and the santalene production was analyzed through GC. As a result, MG1655(DE3) produced 0.6 mg/L of santalene, whereas the newly constructed MG1655(DE3) Δdxr ΔadhE::MVAbottom strain produced 4.5 mg/L of santalene. The production of santalene in the MG1655(DE3) ΔadhE::MVAbottom strain was also 3.4 mg/L, which is a greater amount of the produced santalene than that of the wild type strain. The increased amount of santalene may be due to the additional introduction of the MVA lower pathway, but it is difficult to see as an increase in IPP and DMAPP through the MVA lower pathway because no mevalonate was additionally introduced. Depletion of adhE causes Acetyl-CoA to accumulate without producing ethanol of a by-product, which may alter the flow of glycolysis in the corresponding process and cause an increase in the amount of precursor G3P and Pyruvate in the MEP pathway. Therefore, the production of santalene might be increased.

TABLE 6

| Strain (48 h) | MG1655(DE3) pTAS-dxr | MG1655(DE3) ΔadhE::MVAbottom PTAS-dxr | MG1655(DE3) Δdxr ΔadhE::MVAbottom PTAS-dxr | |
|---|---|---|---|---|
| Antibiotic addition | + | + | + | − |
| Cell growth ($OD_{600\ nm}$) | 4.9 ± 0.1 | 5.5 ± 0.2 | 5.0 ± 0.2 | 4.8 ± 0.2 |
| Santalene (mg/L) | 0.6 ± 0.0 | 3.4 ± 0.1 | 4.5 ± 0.2 | 3.9 ± 0.1 |

B. Multiple Plasmid Method (Example of Producing Santalene+Bisabolol)

This is a method of constructing a plurality of plasmids having selection markers of the deleted MEP pathway genes of the chromosome and introducing into the host. In this case, to compensate for the host's MEP pathway deletion only when all the plurality of plasmids are present, it is necessary for the deleted MEP pathway genes to be evenly distributed in each plasmid. In particular, in a defective strain used as a host strain, the MEP pathway genes of the chromosome should be deleted by more than the number of plasmids to be introduced. In other words, when using two plasmids, at least two chromosome MEP pathway genes should be deleted and these genes are distributed and arranged in each plasmid having a selection marker.

i. Construction of Plasmid pTAS-dxs were constructed by introducing a dxs gene behind a santalene biosynthetic operon of pT-ispA-STS, which is the santalene producing plasmid. More specifically, restriction enzyme sites BglII and XhoI were introduced into both ends of the dxs gene and amplified using a pT-dxs/r plasmid having dxs gene and dxr gene of *E. coli* introduced into pTrc99A vector as a template, by PCR using the primers of SEQ ID NO: 41 and SEQ ID NO: 42. Using this, a santalene producing plasmid pTAS-dxs having the deleted dxr gene was constructed by cloning with the same restriction enzyme sites BglII and SalI located behind the STS gene of the pT-ispA-STS vector. Restriction enzymes SalI and XhoI have the same cohesive end as each other.

Similarly, pTAB-idi-dxr was constructed by introducing dxr gene and idi gene (b2889) behind a bisabolol biosynthetic operon of pT-ispA-MrBBS, which is the bisabolol producing plasmid including an ispA gene that is FPP Synthase of *E. coli* and MrBBS that is α-bisabolol synthase of *Matricaria recutita* into pTrc99A vector. The idi gene is able to improve the production of isoprenoid by balancing IPP and DMAPP, when the MEP pathway is enhanced by the plasmid constructed with IPP isomerase. More specifically, in the construction process, by using restriction enzyme sites BglII and SalI located behind the MrBBS gene of the pT-ispA-MrBBS vector, the PTAB-idi-dxr was constructed by introducing the idi gene amplified while introducing restriction enzyme sites BamHI and SalI by PCR using primers of SEQ ID NO: 43 and SEQ ID NO: 44 and the dxr gene amplified while introducing restriction enzyme sites SalI and HindIII by PCR using primers of SEQ ID NO: 45 and SEQ ID NO: 46 into the bisabolol producing plasmid.

In the cloning process of the plasmid above, for selection of transformants, *E. coli* MG1655(DE3) Δdxr/s ΔadhE::MVAbottom may be used. When using *E. coli* MG1655 (DE3) Δdxr/s ΔadhE::MVAbottom, the transformants may be selected without antibiotics, because the strain is capable of growing when the MEP pathway of host *E. coli* is inactivated and two plasmids respectively having the dxr gene and the dxs gene introduced therein are introduced together.

ii. Introduction of Plasmid

A recombinant strain was constructed by transforming plasmid pTAS-dxs having the constructed dxs gene as the selection marker and the plasmid pTAB-idi-dxr having the dxr gene as the selection marker together into MG1655 (DE3) Δdxr/s ΔadhE::MVAbottom strain in which both the dxr and dxs genes are deleted. Thereafter, by culturing the recombinant strain in a non-antibiotic medium environment to confirm the productions of santalene and bisabolol, it can be confirmed that each of the deleted MEP genes are operated as a selection marker of a plurality of plasmids.

The recombinant strain having the plurality of plasmids was spawn cultured under a non-antibiotic condition, followed by culturing in a mixed medium of 4 mL of 2YT medium (16 g of trypton per liter, 10 g of yeast extract, and 5 g of NaCl) containing 2% (v/v) of glycerol and 0.2 mM of IPTG and 1 mL of decane, which is a production medium. For cultivation, the mixed medium is put into a tube having a groove of 15 cm in length and 25 mm in diameter and is inoculated with each of the strains, followed by culturing in a shaking incubator at 30° C. while stirring at a speed of about 250 rpm.

iii. Culture Result

Figure 12:
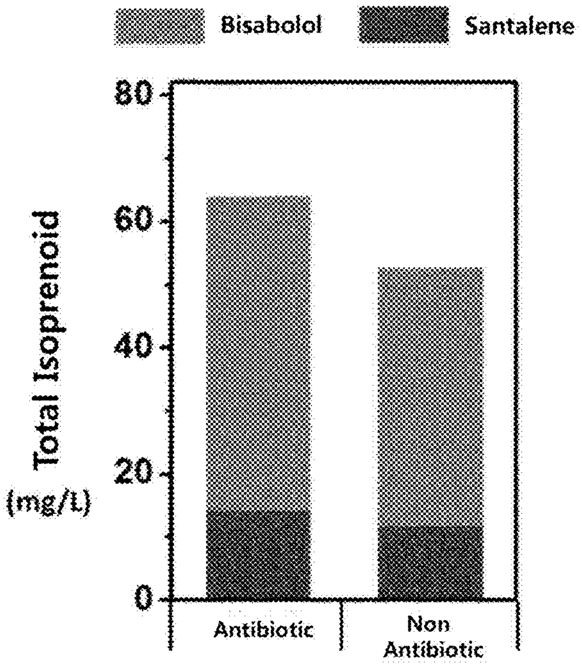
FIG. 12 is a graph showing culture results of antibiotic-free isoprenoid (santalene, and bisabolol) producing strains constructed by dividing the deleted MEP pathway gene into a plurality of plasmids.

The constructed recombinant strain was cultured using the medium with or without the addition of antibiotics. After 58 hours from the cultivation, the decane layer was recovered and productions of the santalene and bisabolol were analyzed through GC. The culture results are shown in FIG. 12 and Table 7 below. More specifically, santalene and bisabolol were produced in amounts of 7.7 mg/L and 40.7 mg/L, respectively, even in without the addition of antibiotics. Through this, it can be seen that both plasmids respectively having a santalene biosynthetic gene and a bisabolol biosynthetic gene are well maintained to express genes.

TABLE 7

| Strain (58 h) | MG1655(DE3) Δdxs/r ΔadhE::MVAbottom pTAS-dxs/pTAB-idi-dxr | |
|---|---|---|
| Antibiotic addition | + | − |
| Cell growth ($OD_{600\ nm}$) | 10.1 ± 0.8 | 10.7 ± 0.7 |
| Santalene (mg/L) | 14.3 ± 1.6 | 7.7 ± 2.5 |
| Bisabolor (mg/L) | 49.7 ± 5.0 | 40.7 ± 7.1 |

C. Method of Adding Foreign MVA Pathway (Example of Producing Retinoid)

Based on the preceding results that the introduction of foreign MVA pathways into isoprenoid production is advantageous, the present invention provides a method of using MEM pathway-defective genes as a selection marker while introducing the foreign MVA pathways into plasmids. In this case, since both the MEP and MVA pathways are activated due to the host strain, it may be expected to achieve high production of isoprenoid. However, when using a plurality of plasmids, it is necessary for the foreign MVA pathway to be additionally introduced to be evenly distributed in the used plasmids without being concentrated on any one side, so as to compensate for the host's MEP pathway deletion only when all the plurality of plasmids are present.

i. Construction of Plasmid

By using a non-antibiotic retinoid producing strain that separately expresses the constructed MVA pathway gene in two plasmids, a recombinant plasmid using the foreign MVA pathway is also constructed while using the defective gene of the MEP pathway as a selection marker. Herein, a dxr gene with a relatively small size was introduced into retinoid producing plasmid pT-HBSREYbbOfree into which the mvaE gene with the large plasmid size is introduced, and a dxs gene was introduced into plasmid pSNAK(-E) that expresses the MVA pathway except for the mvaE gene having a size margin.

BglII and XhoI were introduced into both ends of the dxs, which is an MEP upper pathway gene, and amplified, using pT-dxs/r plasmid as a template by PCR using primers of SEQ ID NO: 47 and SEQ ID NO: 48. Further, restriction enzyme sequences BglII and XhoI were introduced into both ends thereof to amplify the vector using pSNAK(-E) as a template by PCR using primers of SEQ ID NO: 49 and SEQ ID NO: 50. Two PCR products were cleaved with restriction enzymes BglII and XhoI, then the dxs gene is inserted between the idi gene (b2889) and the mvaS gene of the vector to construct pSNAK(-E)-dxs. Then, pSNA(-E)-dxsfree was constructed by removing kanamycin antibiotic resistance gene by PCR using the antibiotic removal primer.

Restriction enzymes NheI and ScaI were introduced into both ends of dxr, which is the upper MEP pathway gene, and amplified using pT-dxr plasmid as a template by PCR using primers of SEQ ID NO: 51 and SEQ ID NO: 52. Then, pT-HBSREYbbO$_{free}$ plasmid was amplified into two fragments, 7.1 kb and 5.6 kb each, using the restriction enzyme XhoI site as a starting point, through two PCRs using primers of SEQ ID NO: 36 and SEQ ID NO: 53, and SEQ ID NO: 37 and SEQ ID NO: 54. The two fragments were linked again by xhoI, and the dxr gene is cleaved with restriction enzymes ScaI and NheI and inserted into an end of the retinoid operon to construct pT-HBSREYbbOdxrfree.

ii. Introduction of Plasmid pS-HBSREYbbOdxrfree plasmid having dxr gene of MEP pathway and mvaE gene of the MVA pathway, and pSNA(-E)-dxsfree having all MVA pathway genes except for the dxs gene of the MEP pathway and mvaE gene were introduced together into E. coli MG1655(DE3) Δdxr/s ΔadhE::MVAbottom, to confirm retinol production of non-antibiotic retinol producing recombinant strain simultaneously using the MVA and MEP pathways.

iii. Culture Result

Figure 13:
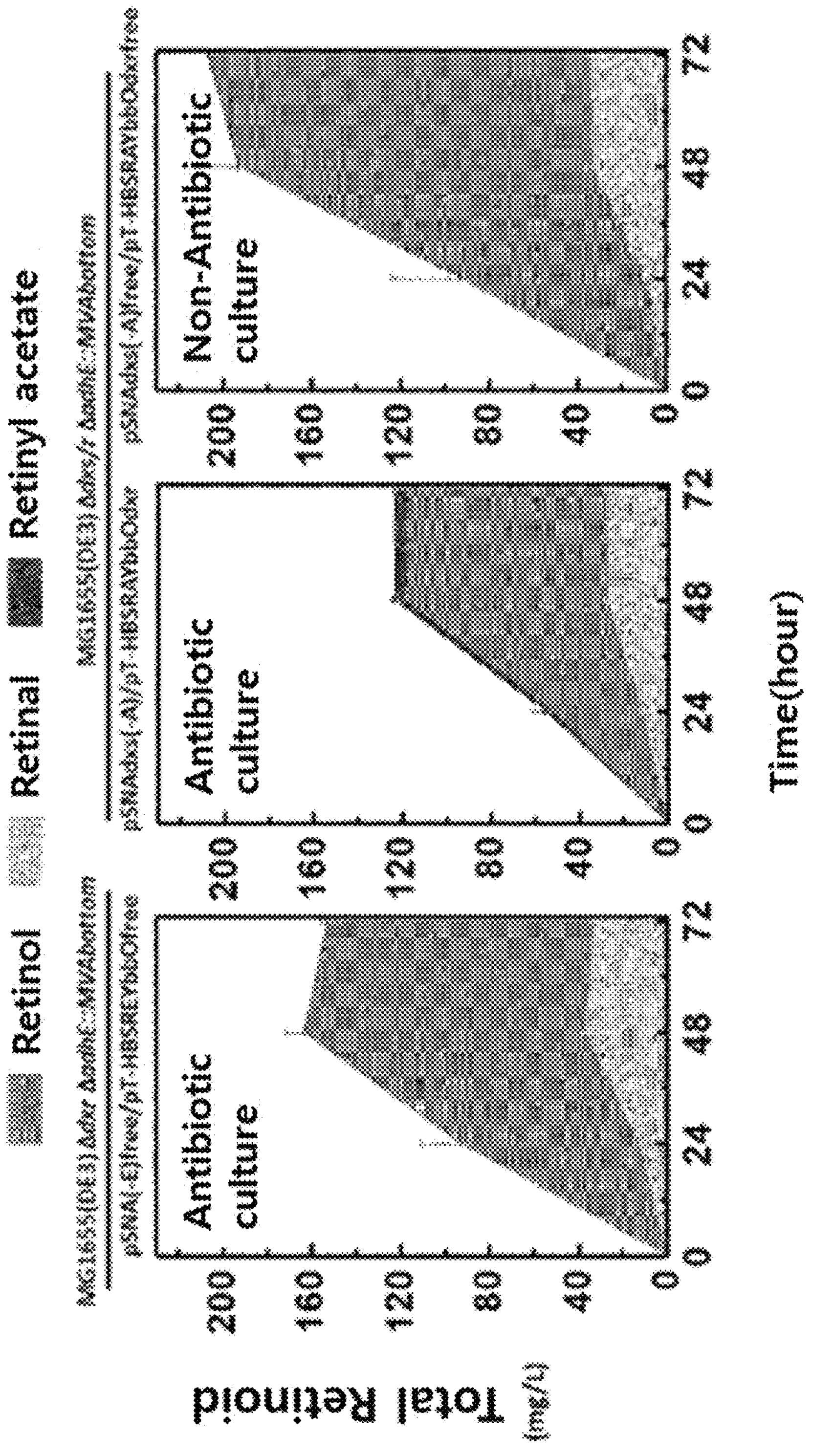
FIG. 13 is graphs showing culture results of the retinoid producing strains from which antibiotic markers having the foreign MV pathway additionally introduced together with the deleted MEP pathway gene are removed.

An antibiotic-free retinol producing recombinant strain simultaneously using the MVA pathway and the MEP pathway together with a non-antibiotic retinol producing recombinant strain using only the foreign MVA pathway in the MEP pathway-defective strain were cultured in a non-antibiotic condition, to compare the retinol production. The culture results are shown in FIG. 13 and Table 8 below. More specifically, when removing the antibiotic resistance gene by the non-antibiotic resistance retinol producing recombinant strain simultaneously using the constructed MVA and MEP pathways, a higher retinol production was shown than the retinoid producing strain in which the deletion of the MEP pathway was compensated only by the foreign MVA pathway. As a result, it was confirmed that the deleted MEP pathway gene could be used as a selection marker while additionally compensating the foreign MVA pathway.

TABLE 8

| Strain (72 h) | MG1655(DE3) Δdxr ΔadhE::MVAbottom pSNA(-E)free/pT-HBSREYbbOfree | MG1655(DE3) Δdxs/r ΔadhE::MVAbottom | |
|---|---|---|---|
| | | pSNAdxs(-A)/pT-HBSRAYbbOdxr | pSNAdxs(-A)free/pT-HBSRAYbbOdxrfree |
| Antibiotic addition | — | — | — |
| Cell growth (OD $_{600\ nm}$) | 12.7 ± 0.24 | 12.6 ± 0.28 | 12.1 ± 0.12 |
| Total retinoid (mg/L) | 153.2 ± 2 | 124.0 ± 3 | 207.2 ± 1 |

3) Plasmid for Expression of Protein Using Deleted MEP Pathway Gene in Chromosome as Selection Marker Confirmation of stability in expression of the protein using GFP protein It is not limited to the expression of a single protein but may also be used to express a variety of metabolite biosynthetic pathways.

i. Construction of Plasmid

PEGFP-dxr was constructed by introducing dxr, which is the deleted MEP pathway gene of defective strain, behind EGFP gene of vector pEGFP expressing green fluorescence. More specifically, by using restriction enzyme sites StuI and SpeI behind the EGFP gene of the vector, the dxr gene amplified by PCR using primers of SEQ ID NO: 51 and SEQ ID NO: 52 was introduced. Restriction enzyme sites ScaI and NheI are introduced into both ends of the amplified PCR product. Restriction enzymes StuI and ScaI have a blunt end, respectively, and restriction enzymes SpeI and NheI have the same cohesive end as each other. Finally, pEGFP-dxr, which is a plasmid having a dxr gene expressing green fluorescence, was constructed.

ii. Introduction of Plasmid

The constructed pEGFP-dxr plasmid is transformed into MG1655(DE3) Δdxr ΔadhE::MVAbottom strain. By smearing it on an LB plate medium without antibiotics, fluorescence was observed.

In order to ensure the expression of a target protein of the constructed recombinant strain, 1 mM of IPTG as an inducer is added and cultured. More specifically, the strain was spawn cultured under a non-antibiotic condition, and inoculated in 5 ml of LB medium which is the production medium, and cultured so as to be $OD_{600\ nm}$ 0.1. After the cultivation, 1 mM of IPTG was added thereto at the time to be $OD_{600\ nm}$ 0.6. For cultivation, the mixed medium was put into a tube having a groove of 15 cm in length and 25 mm in diameter and is inoculated with each of the strains, followed by culturing in a shaking incubator at 30° C. while stirring at a speed of about 250 rpm. The culture liquid was collected, and the stability in expression of the genes contained in the plasmid was confirmed under the non-antibiotic medium condition by SDS-PAGE and fluorescence measurement.

iii. Culture Result

Figure 14:
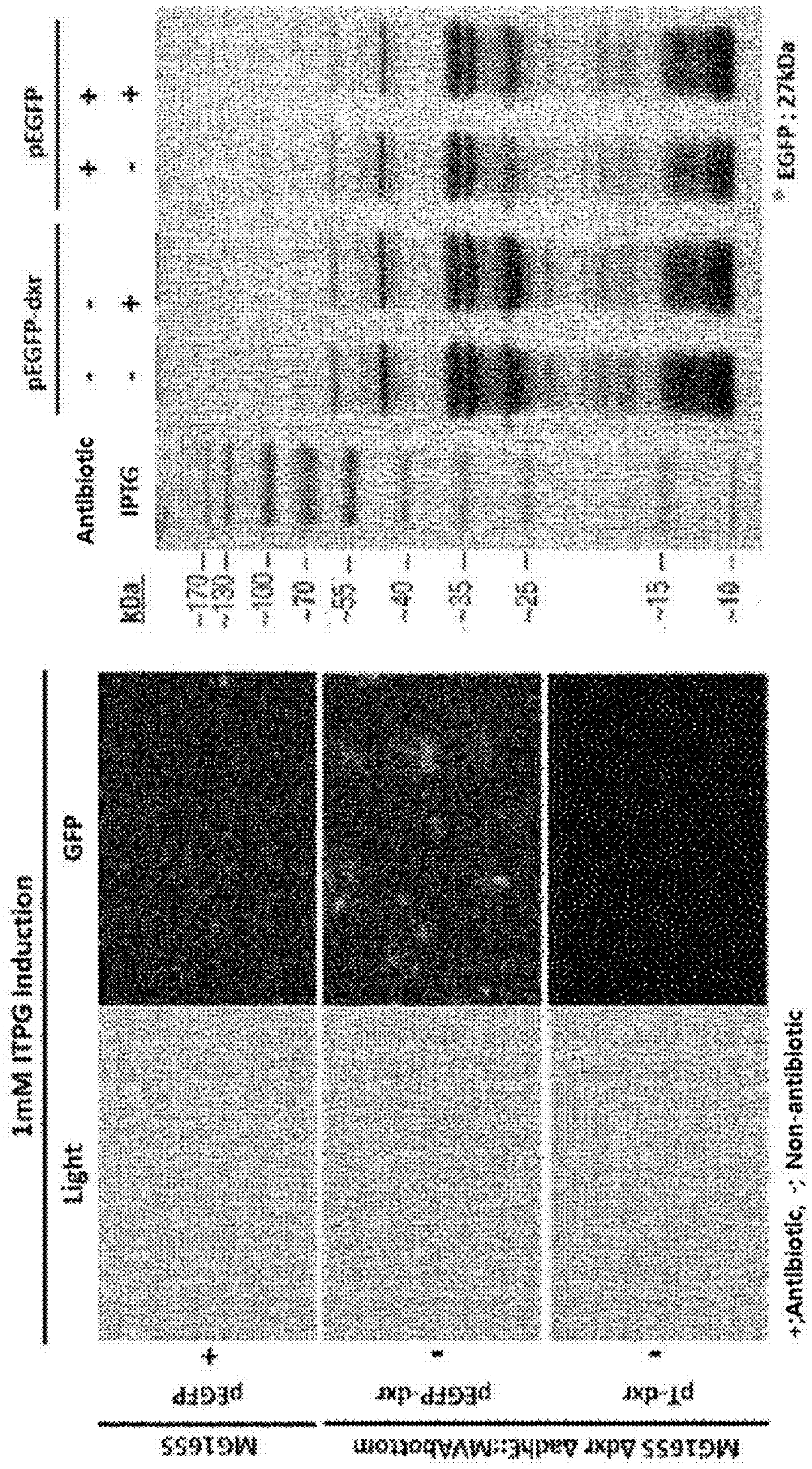
FIG. 14 is photographs showing results of fluorescent protein expression of antibiotic-free strain using the deleted MEP pathway gene as a selection marker.
Figure 15:
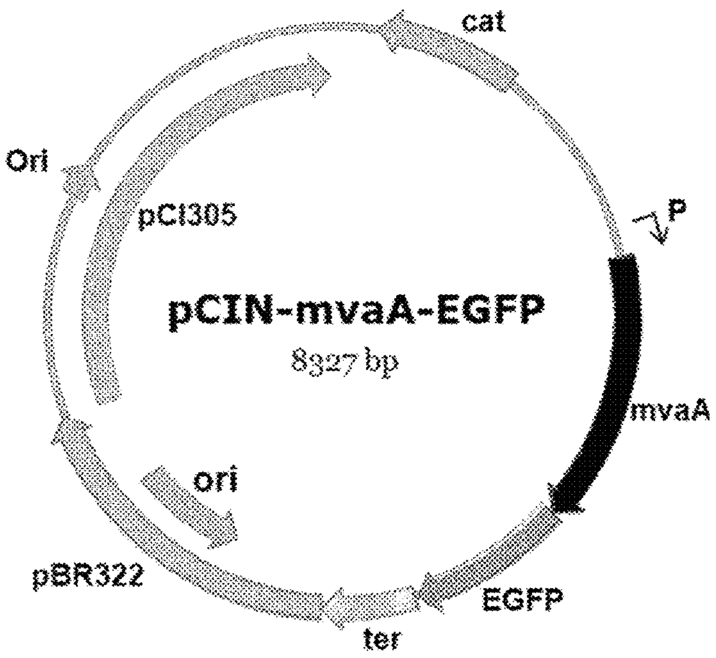
FIG. 15 is a schematic view of pCIN-mvaA-EGFP recombinant plasmid.
Figure 16:
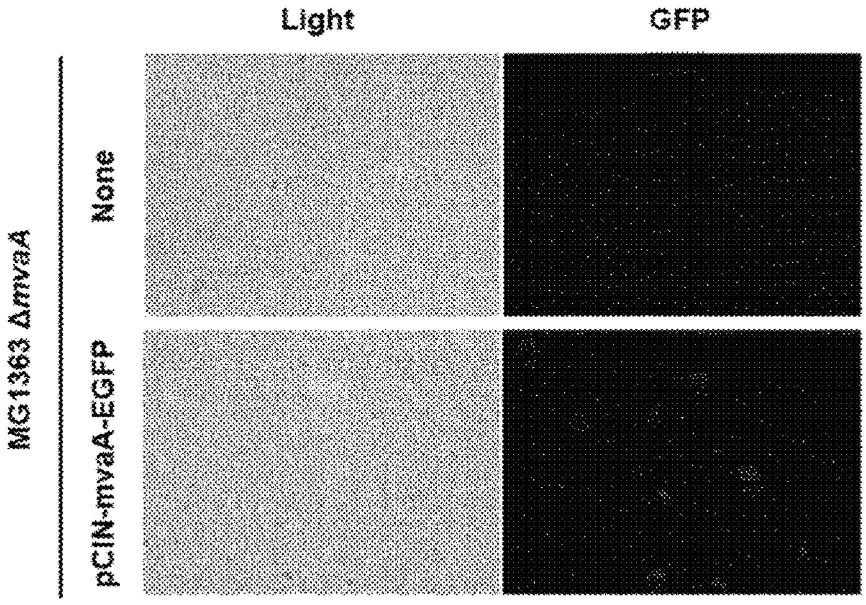
FIG. 16 is photographs showing the results of fluorescent protein expression of antibiotic-free strain using the deleted MVA pathway genes as a selection marker.

SDS-PAGE and fluorescence results are shown in FIG. 14. More specifically, as a result of observing green fluorescence by a fluorescence microscope, it was confirmed that clearer fluorescence was obtained in a case of using the deleted MEP pathway gene as the selection marker of the plasmid than the control group including the antibiotics as the selection marker. In addition, comparing the amount of protein expression through the SDS-PAGE, a larger amount of protein expression exhibited in the non-antibiotic culture of the newly constructed strain than the control group. It was confirmed that, even without treatment with an inducer such as IPTG, the plasmid was sufficiently maintained by the selection pressure of the deleted MEP pathway gene of the strain to express the gene.

4. Method of Constructing MVA Pathway Mutant

1) Inactivation of Gene Encoding *Lactobacillus* HMG-coA Reductase (mvaA)

A rate-limiting enzyme, Hydroxymethylglutaryl-CoA reductase (mvaA) gene, was inactivated using a homologous recombination system in an inherent MVA pathway of lactobacillus. For mvaA gene mutation of *Lactococcus lactis* MG1363, a front 1Kb portion of the mvaA gene in MG1363 was amplified by polymerase chain reaction (PCR) using primers of SEQ ID NO: 55 and SEQ ID NO: 56, and a rear 1Kb portion after the mvaA gene was amplified using primers of SEQ ID NO: 57 and SEQ ID NO: 58, then two PCR products were amplified using primers of SEQ ID NO: 59 and SEQ ID NO: 60 through splicing by overhang extension (SOE) PCR. In addition, pORI19 plasmid was amplified by PCR using primers of SEQ ID NO: 61 and SEQ ID NO: 62, followed by ligation of the two PCR products, then electroporation was performed on 100 μl of EC1000 competent cell through a cuvette at an interval of 2 mm under conditions of 25 μF, 200Ω and 2,500 V. After performing the electroporation, 1 ml of LB medium was added thereto, followed by culturing at 37° C. for 30 minutes, and then 100 μl thereof was smeared on an LB solid plate medium containing 300 μg/ml erythromycin antibiotic. Finally, pORI19-mvaA plasmid was obtained by culturing at 37° C. for 12 hours (Table 2).

In order to prepare a competent cell of *lactobacillus, L. lactis* MG1363 (pVE6007) strain containing plasmid pVE6007 was inoculated in 5 ml of M17 medium (5.0 g of Pancreatic Digest of Casein, 5.0 g of soy peptone, 5.0 g of beef extract, 2.5 g of yeast extract, 0.5 g of ascorbic acid, 0.25 g of magnesium sulfate, and 10.0 g of disodium-β-glycerophosphate per liter) containing 0.5% (v/v) glucose and 5 μg/ml chloramphenicol antibiotic added thereto, followed by spawn culturing at 30° C. for 16-24 hours. 1 ml of a spawn culture liquid was inoculated in 9 ml of M17 medium containing 0.5% (v/v) of glucose, 0.5 M of sucrose, 1.5% (w/v) of glycine and 5 μg/ml of chloramphenicol, followed by culturing at 30° C. for 16-24 hours. 5 ml of the spawn culture liquid was inoculated in 35 ml of the same fresh medium, followed by culturing again at 30° C. to OD 600 nm, 0.25. After cooling the spawn culture liquid on ice for 5 minutes to form the competent cell, a supernatant was removed by performing centrifugation at 4° C., 5,000 rpm for 15 minutes, and washed twice with 40 ml of wash buffer (0.5 M of sucrose, and 10% of glycerol) in the same amount as the culture liquid. The washed cells were suspended in 0.4 ml of wash buffer to obtain the competent cells.

3-5 μg of pORI19-mvaA plasmid was put into 100 ul of the obtained competent cells, and was subjected to electroporation through a cuvette at an interval of 2 mm under conditions of 25 μF, 200Ω and 2,500 V. After the electroporation, 1 ml of GM17 medium added with 5 μg/ml of chloramphenicol was added thereto, followed by culturing at 30° C. for 2 hours, and then 100 μl thereof was smeared on a GM17 solid plate medium containing 5 μg/ml of chloramphenicol and 5 μg/ml of erythromycin added thereto, to obtain MG1363 (pORI19-mvaA, pVE6007) strain.

In order to remove pVE6007 plasmid, the strains obtained above were inoculated in 5 ml of GM17 medium containing 5 μg/ml of chloramphenicol and 5 μg/ml of erythromycin added thereto, followed by culturing at 30° C. for 16-24 hours and performing cell down on 1 ml of culture liquid to wash twice with 1 ml of GM17 medium, then 10 ml of GM17 medium containing 5 μg/ml of erythromycin added thereto was inoculated in an amount of 0.1% (v/v), followed by culturing at 30° C. for 16-24 hours. After performing subculture 3 times by inoculating 0.1% (v/v) thereof in the same medium at 37° C. with an interval of 12 hours, and then diluted in $10^{5-7}$ and smeared on a GM17 solid plate medium containing 5 μg/ml of erythromycin, followed by culturing at 30° C. for 16-24 hours.

Strains in which single cross over (SCO) occurred were selected by PCR. PCR was performed using a total of three primers in which 200 colonies were additionally added with a primer of SEQ ID NO: 65 for upstream confirmation and a primer of SEQ ID NO: 66 for downstream confirmation together with primers of SEQ ID NO: 63 and SEQ ID NO: 64, respectively. When the SCO occurs in the upstream, it can be confirmed by the primers of SEQ ID NO: 63 and SEQ ID NO: 65, and when the SCO occurs in the downstream, it can be confirmed by the primers of SEQ ID NO: 64 and SEQ ID NO: 66. In addition, in a case of the wild type without SCO occurred therein, it can be confirmed by the primers of SEQ ID NO: 63 and SEQ ID NO: 64. The strains in which the SCO occurred were inoculated in 5 ml of GM17 medium containing 5 μg/ml of erythromycin, followed by culturing at 30° C. for 16-24 hours and performing cell down with 1 ml of culture liquid to wash twice with 1 ml of GM17 medium, then 10 ml of GM17 medium containing 3.3 mM of mevalonate added thereto was inoculated in an amount of 0.1% (v/v), followed by culturing at 30° C. for 16-24 hours. Mevalonate was added to the medium for growth of the mutant of gene mvaA. After performing subculture 3 times by inoculating 0.1% (v/v) thereof in the same medium at 30° C. with an interval of 12 hours, and then diluted in $10^{5-7}$ and smeared on a GM17 solid plate medium containing 3.3 mM of mevalonate, followed by culturing at 30° C. for 16-24 hours.

Strains in which single cross over (SCO) occurred were selected by PCR. 400 colonies were subjected to PCR using primers of SEQ ID NO: 63 and SEQ ID NO: 64 to construct *Lactococcus lactis* MG1363ΔmvaA strain.

5. Methods of Constructing and Culturing Plasmid (MVA Pathway Mutant Strain)

Use of strains with mutated MVA upstream pathway gene in host chromosome

1) Construction of *E. coli-Lactobacillus* Recombinant Shuttle Vector

The existing *E. coli-lactobacillus* shuttle vector pCI372 was cleaved with restriction enzymes AgeI and NheI, and a pCIN vector, into which a promoter, a multi-cloning site and a terminator were introduced, was constructed (Table 2).

2) Plasmid for Protein Expression Using Mutated MVA Pathway Gene of Chromosome as Selection Marker i. Construction of Plasmid The mvaA gene for use as a selection marker was amplified by polymerase chain reaction (PCR) using primers of SEQ ID NO: 67 and SEQ ID NO: 68 from MG1363 strain, and cleaved with restriction enzymes BamHI and XbaI, then pCIN-mvaA vector was constructed by introducing it into the same restriction enzyme site of pCIN vector. EGFP gene for confirmation of green fluorescent protein expression was amplified by polymerase chain reaction (PCR) using primers of SEQ ID NO: 69 and SEQ ID NO: 70 from pEGFP vector and cleaved with restriction enzymes SalI and SphI, then PCIN-mvaA-EGFP was constructed by introducing it into the same restriction enzyme site of pCIN-mvaA vector (FIG. 10). The above constructed vectors are shown in Table 2.

ii. Introduction of Plasmid

The pCIN-mvaA-EGFP recombinant plasmid was transformed into *L. lactis* MG1363ΔmvaA strain to prepare a lactobacillus transformant having mvaA as a selection marker.

A competent cell was prepared to transform the pCIN-mvaA-EGFP recombinant shuttle vector into *L. lactis* MG1363ΔmvaA strain. MG1363ΔmvaA strains were inoculated in 5 ml of M17 medium containing 0.5% (v/v) of glucose and 3.3 mM of mevalonate added thereto, followed by culturing at 30° C. for 16-24 hours. 1 ml of spawn culture liquid was inoculated in 9 ml of M17 medium containing 0.5% (v/v) of glucose, 0.5M of sucrose, 1.5% (w/v) of glycine and 3.3 mM of mevalonate added thereto, followed by culturing at 30° C. for 16-24 hours. 5 ml of the spawn culture liquid was inoculated in 35 ml of the same fresh medium, followed by culturing again at 30° C. to $OD_{600\ nm}$, 0.25. After cooling the spawn culture liquid on ice for 5 minutes to form the competent cell, a supernatant was removed by performing centrifugation at 4° C., 5,000 rpm for 15 minutes, and washed twice with 40 ml of wash buffer (0.5 M of sucrose, and 10% of glycerol) in the same amount as the culture liquid. The washed cells were suspended in 0.4 ml of wash buffer to obtain the competent cells.

5 μl of pCIN-mvaA-EGFP plasmid was put into 100 μl of the obtained competent cells, and was subjected to electroporation through an electroporation cuvette (at an interval of 2 mm) under conditions of 25 μF, 200Ω and 2,500 V. After electroporation, 1 ml of M17 medium added with 0.5% (v/v) of glucose was added thereto, followed by culturing at 30° C. for 1 hour. Cell samples into which pCIN-mvaA-EGFP plasmid was introduced by electroporation were diluted in $10^1$-$10^3$ and smeared on a M17 solid plate medium containing 0.5% (v/v) glucose added thereto to obtain MG1363ΔmvaA (pCIN-mvaA-EGFP) transformant.

iii. Confirmation of Stability in Expression of Protein Using GFP Protein

The constructed MG1363ΔmvaA (pCIN-mvaA-EGFP) strains were smeared on a M17 solid plate medium containing 0.5% (v/v) of glucose added thereto without antibiotics to observe fluorescence.

In order to ensure the expression of the target protein of the constructed recombinant strain, cultivation thereof was performed. More specifically, strains were spawn cultured under a non-antibiotic condition, and inoculated in 5 ml of M17 medium containing 0.5% (v/v) of glucose added thereto, which is a production medium, to culture so as to be $OD_{600\ nm}$ 0.1, followed by culturing at 30° C. This culture liquid is collected and the stability in expression of the gene contained in the plasmid under the non-antibiotic medium condition was confirmed by fluorescence measurement.

TABLE 9

| SEQ ID NO. | Primer name | SEQ ID NO. | Primer name |
|---|---|---|---|
| 1 | SN12Didi-F | 36 | RET-R |
| 2 | SN12Didi-R | 37 | RET-F |
| 3 | IS poxB-Ptrc-F | 38 | dAmp(RET)-R |
| 4 | KO poxB-R | 39 | dxr_1-F |
| 5 | IS ldhA-Ptrc-F | 40 | dxr_1-R |
| 6 | KO ldhA-R | 41 | dxs_1-F |
| 7 | IS adhE-Ptrc-F | 42 | dxs_1-R |
| 8 | KO adhE-R | 43 | idi-F |
| 9 | IS atoDA-Ptrc-F | 44 | idi-R |
| 10 | KO atoDA-R | 45 | dxr 3-F |
| 11 | KOpoxBCF-F | 46 | dxr 3-R |
| 12 | KOpoxBCF-R | 47 | dxs 2-F |
| 13 | KOldhACF-F | 48 | dxs 2-R |
| 14 | KOldhACF-R | 49 | dmvaE-F |
| 15 | KOadhECF-F | 50 | dmvaE-R |
| 16 | KOadhECF-R | 51 | dxr_2-F |
| 17 | KOatoDACF-F | 52 | dxr_2-R |
| 18 | KOatoDACF-R | 53 | RET_2-F |
| 19 | KO dxr-F | 54 | RET_2-R |
| 20 | KO dxr-R | 55 | mvaA u/s-Fwd |
| 21 | KOdxrCF-F | 56 | mvaA u/s-Rev |
| 22 | KOdxrCF-R | 57 | mvaA d/s-Fwd |
| 23 | dxrCF-R | 58 | mvaA d/s-Rev |
| 24 | KO dxs-F | 59 | mvaA ex-Fwd |
| 25 | KO dxs-R | 60 | mvaA ex-Rev |
| 26 | KOdxsCF-F | 61 | pORI19-Rev |
| 27 | KOdxsCF-R | 62 | pORI19-Fwd |
| 28 | KmCF-F | 63 | DCO-Fwd |
| 29 | dCmp(NA)-F | 64 | DCO-Rev |
| 30 | dCmp(NA)-R | 65 | SCO u/s-Rev |
| 31 | ddxs(RET)-F | 66 | SCO u/s-Fwd |
| 32 | ddxs(RET)-R | 67 | mvaA-Fwd |
| 33 | PlmvaE-F | 68 | mvaA-Rev |
| 34 | PlmvaE-R | 69 | EGFP-Fwd |
| 35 | dAmp(RET)-F | 70 | EGFP-Rev |

TABLE 10

| Gene name | Enzyme | Origin | Genbank Grant NO. | Base sequence SEQ ID NO. | Amino acid sequence SEQ ID NO. |
|---|---|---|---|---|---|
| mvaE | Acetyl-CoA Acetyltransferase/ hydroxymethylglutaryl (HMG)-CoA Reductase | *Enterococcus faecalis* | AF290092 | 104 | 124 |

TABLE 10-continued

| Gene name | Enzyme | Origin | Genbank Grant NO. | Base sequence SEQ ID NO. | Amino acid sequence SEQ ID NO. |
|---|---|---|---|---|---|
| mvaS | HMG-CoA Synthase | *Enterococcus faecalis* | AF290092 | 105 | 125 |
| mvaK 1 | Mevalonate kinase *pneumoniae* | *Streptococcus* | AF290099 | 106 | 126 |
| mvaK 2 | Phosphomevalonate Kinase *pneumoniae* | *Streptococcus* | AF290099 | 107 | 127 |
| mvaD | Mevalonate diphosphate decarboxylase | *Streptococcus pneumoniae* | AF290099 | 108 | 128 |
| Idi | IPP Isomerase | *Escherichia coli* | U00096 | 109 | 129 |
| ipiHp 1 | IPP Isoformerase | Haematococcuspluvialis | AF082325 | 110 | 130 |
| crtE | Geranylgeranyl pyrophosphate (GGPP) synthase | *pantoea agglomerans* | M87280 | 111 | 131 |
| crtB | Phytoen synthase | *pantoea agglomerans* | M87280 | 112 | 132 |
| crtI | Phytoene dehydrogenase | *pantoea agglomerans* | M87280 | 113 | 133 |
| crtY | Lycopene-β-cyclase | *pantoea ananatis* | D90087 | 114 | 134 |
| SR | β-carotene monooxygenase | unculturedmarine bacterium 66A03 | *E. coli* codon optimization 115 sequence of blh | 135 | |
| YbbO | Oxidoreductase | wild type *Escherichia coli* MG1655; taxid 511145 | 1786701 | 116 | 136 |
| dxs | 1-deoxyxylulose-5-phosphate (DXP) synthase | *Escherichia coli* | AF035440.1 | 117 | 137 |
| dxr | 1-deoxy-D-xylulose 5-phosphate reductoisomerase | *Escherichia coli* | AB013300.1 | 118 | 138 |
| ispA | Panesil Pyrophosphate Synthase | *Escherichia coli* | — | 119 | 139 |
| STS | Santalene Synthase | Clausena lansium | — | 120 | 140 |
| MrB BS | α-bisabolol synthase | Matricaria recutita | *E. coli* codon optimization sequence of KM259907.1 | 121 | 141 |
| EGFP | enhanced green fluorescent protein | Synthetic construct | KX130867.1 | 122 | 142 |
| mvaA | Hydroxymethylglutaryl-CoA reductase | *Lactococcus lactis* subsp. *cremoris* MG1363 | (WP_0118348 77.1) | 123 | 143 |

A sequence listing electronically submitted with the present application on Dec. 13, 2019 as an ASCII text file named 20191213_LC00319_TU_SEQ, created on Dec. 10, 2019 and having a size of 447,000 bytes, is incorporated herein by reference in its entirety.

The invention claimed is:

1. A method of transforming an organism, the method comprising:

attenuating or deleting at least one of the genes encoding enzymes in an isopentenyl diphosphate or dimethylallyl diphosphate synthetic pathway of an organism to be transformed;

preparing a recombinant plasmid into which (i) a selection marker gene comprising the at least one of the genes encoding the enzymes or a complementary gene thereof and (ii) a target product gene comprising a gene encoding an enzyme in a target product synthetic pathway synthesizing a target product other than the isopentenyl diphosphate or the dimethylallyl diphosphate are introduced; and transforming the organism with the recombinant plasmid.

2. The method of claim 1, wherein the transformation comprises culturing the organism in a medium that is free of an antibiotic.

3. The method of claim 1, wherein the isopentenyl diphosphate or dimethylallyl diphosphate synthetic pathway is a methylerythritol 4-phosphate (MEP) pathway or a mevalonate (MVA) pathway.

4. The method of claim 1, wherein the at least one of the genes encoding the enzymes is a gene encoding one or more enzymes selected from the group consisting of 1-dioxy-D-xylulose-5-phosphate (DXP) synthase, DXP reductoisomerase, 2-C-methyl-D-erythritol-4-phosphate (MEP) cytidyltransferase, 4-diphosphocytidyl-2-C-methyl-D-erythritol kinase (IspE), 2-C-methyl-D-erythritol-2,4-cyclodiphosphate (MEcPP) synthase, 4-hydroxy-3-methyl-2-butenyl diphosphate (HMBPP) synthase, HMBPP reductase, acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and isopentenyl pyrophosphate (IPP) isomerase.

5. The method of claim 1, wherein the attenuated or deleted gene is a gene encoding enzymes in the methylerythritol 4-phosphate (MEP) pathway.

6. The method of claim 5, wherein the attenuated or deleted gene is a gene encoding at least one of DXP synthase and DXP reductoisomerase.

7. The method of claim 1, wherein the attenuated or deleted gene is a gene encoding enzymes in the methylerythritol 4-phosphate (MEP) pathway, and the complementary gene is a gene encoding at least one of enzymes in the mevalonate (MVA) pathway.

8. The method of claim 7, wherein the complementary gene is a gene encoding acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase or isopentenyl pyrophosphate (IPP) isomerase.

9. The method of claim 1, wherein the attenuated or deleted gene is a gene encoding at least one of enzymes in the mevalonate (MVA) pathway.

10. The method of claim 1, wherein the target product synthetic pathway is selected from the group consisting of isoprenoid, santalene, bisabolol and retinol synthetic pathways.

11. The method of claim 1, wherein the attenuating or deleting comprises attenuating or deleting at least two genes, and the preparing comprises preparing two plasmids comprising a gene encoding the same enzyme as the attenuated or deleted gene, respectively.

12. The method of claim 9, wherein the complementary gene is a gene encoding 1-dioxy-D-xylulose-5-phosphate (DXP) synthase, DXP reductoisomerase, 2-C-methyl-D-erythritol-4-phosphate (MEP) cytidyltransferase, 4-diphosphocytidyl-2-C-methyl-D-erythritol kinase (IspE), 2-C-methyl-D-erythritol-2,4-cyclodiphosphate (MEcPP) synthase, 4-hydroxy-3-methyl- 2-butenyl diphosphate (HMBPP) synthase, or HMBPP reductase.

13. The method of claim 1, wherein the target product synthetic pathway is selected from the group consisting of santalene, bisabolol and retinol synthetic pathways.

14. A method of transforming an organism, the method comprising:

attenuating or deleting at least one of the genes encoding enzymes in a methylerythritol 4-phosphate (MEP) pathway of an organism to be transformed;

preparing a recombinant plasmid into which (i) a selection marker gene comprising the at least one of the genes encoding the enzymes and (ii) a target product gene comprising a gene encoding an enzyme in a target product synthetic pathway synthesizing a target product other than the isopentenyl diphosphate or the dimethylallyl diphosphate are introduced; and transforming the organism with the recombinant plasmid.

15. The method of claim 14, wherein the at least one of the genes encoding the enzymes is a gene encoding one or more enzymes selected from the group consisting of 1-dioxy-D-xylulose-5-phosphate (DXP) synthase, DXP reductoisomerase, 2-C-methyl-D-erythritol-4-phosphate (MEP) cytidyltransferase, 4-diphosphocytidyl-2-C-methyl-D-erythritol kinase (IspE), 2-C-methyl-D-erythritol-2,4-cyclodiphosphate (MEcPP) synthase, 4-hydroxy-3-methyl-2-butenyl diphosphate (HMBPP) synthase, and HMBPP reductase.

16. The method of claim 14, wherein the attenuated or deleted gene is a gene encoding at least one of DXP synthase and DXP reductoisomerase.

17. The method of claim 14, wherein the target product synthetic pathway is selected from the group consisting of isoprenoid, santalene, bisabolol and retinol synthetic pathways.

18. The method of claim 14, wherein the attenuating or deleting comprises attenuating or deleting at least two genes, and the preparing comprises preparing two plasmids comprising a gene encoding the same enzyme as the attenuated or deleted gene, respectively.

19. The method of claim 14, wherein the target product synthetic pathway is selected from the group consisting of santalene, bisabolol and retinol synthetic pathways.

20. A method of transforming an organism, the method comprising:

attenuating or deleting at least one of the genes encoding enzymes in a mevalonate (MVA) pathway of an organism to be transformed;

preparing a recombinant plasmid into which (i) a selection marker gene comprising the at least one of the genes encoding the enzymes and (ii) a target product gene comprising a gene encoding an enzyme in a target product synthetic pathway synthesizing a target product other than the isopentenyl diphosphate or the dimethylallyl diphosphate are introduced; and transforming the organism with the recombinant plasmid.

21. The method of claim 20, wherein the at least one of the genes encoding the enzymes is a gene encoding one or more enzymes selected from the group consisting of acetoacetyl-CoA synthase, 3-hydroxyl-3-methylglutary-CoA (HMG-CoA) synthase, HMG-CoA reductase, mevalonate kinase, mevalonate-5-phosphate kinase, mevalonate-5-diphosphate decarboxylase and isopentenyl pyrophosphate (IPP) isomerase.

22. The method of claim 20, wherein the target product synthetic pathway is selected from the group consisting of santalene, bisabolol and retinol synthetic pathways.

* * * * *